United States Patent
Perron et al.

(12) 
(10) Patent No.: US 6,582,703 B2
(45) Date of Patent: *Jun. 24, 2003

(54) ISOLATED NUCLEOTIDE SEQUENCES ASSOCIATED WITH MULTIPLE SCLEROSIS OR RHEUMATOID ARTHRITIS AND A PROCESS OF DETECTING

(75) Inventors: Herve Perron, Lyons (FR); Frederic Beseme, Villefontaine (FR); Frederic Bedin, Lyons (FR); Glaucia Paranhos-Baccala, Lyons (FR); Florence Komurian-Pradel, Saint Cyr au Mont d'Or (FR); Colette Jolivet-Reynaud, Bron (FR); Bernard Mandrand, Villeurbanne (FR)

(73) Assignee: Bio Merieux, Marcy l'Etoile (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,847

(22) Filed: Nov. 26, 1997

(65) Prior Publication Data

US 2003/0039664 A1 Feb. 27, 2003

Related U.S. Application Data

(63) Continuation-in-part of application No. 08/756,429, filed on Nov. 26, 1996, now abandoned.

(51) Int. Cl.[7] .......................... A61K 39/12; A61K 39/21; C07H 21/04
(52) U.S. Cl. ................................ 424/204.1; 424/187.1; 424/185.1; 435/5; 435/6; 435/69.1; 530/350; 536/23.72; 536/24.3; 536/24.32
(58) Field of Search .......................... 424/187.1, 199.1, 424/185.1, 204.1; 435/5, 235.1, 320.1, 6, 69.1; 530/350; 536/23.72, 24.3, 24.32, 24.33

(56) References Cited

U.S. PATENT DOCUMENTS

| | | | |
|---|---|---|---|
| 4,311,686 A | 1/1982 | Angers et al. | |
| 4,346,074 A | 8/1982 | Gilmour et al. | |
| 4,388,298 A | 6/1983 | Nazerian et al. | |
| 4,396,600 A | 8/1983 | Messineo et al. | |
| 4,520,113 A | 5/1985 | Gallo et al. | |
| 4,647,773 A | 3/1987 | Gallo et al. | |
| 4,708,818 A | 11/1987 | Montagnier et al. | |
| 4,900,553 A | 2/1990 | Silver et al. | |
| 5,158,976 A | 10/1992 | Rosenburg et al. | |
| 5,219,837 A | 6/1993 | Cohen et al. | |
| 5,225,352 A | 7/1993 | Zanetta et al. | |
| 5,585,262 A | 12/1996 | Perron et al. | |
| 5,650,318 A | 7/1997 | Perron et al. | 435/240.21 |
| 5,728,540 A | 3/1998 | Perron et al. | 435/23 |
| 5,800,980 A | 9/1998 | Perron et al. | 435/5 |
| 5,871,745 A | 2/1999 | Perron et al. | |
| 5,871,996 A | 2/1999 | Perron et al. | |
| 5,876,954 A | 3/1999 | Perron et al. | |
| 5,925,555 A | 7/1999 | Perron et al. | |
| 5,962,217 A | 10/1999 | Perron et al. | |
| 6,001,987 A | 12/1999 | Perron et al. | |
| 6,071,736 A | 6/2000 | Perron et al. | |
| 6,184,025 B1 | 2/2001 | Perron et al. | |
| 6,291,225 B1 | 9/2001 | Perron et al. | |
| 6,342,383 B1 | 1/2002 | Perron et al. | |

FOREIGN PATENT DOCUMENTS

| | | |
|---|---|---|
| EP | 0 222 310 | 5/1987 |
| EP | 0 326 395 | 8/1989 |
| WO | 93/07259 | 4/1993 |
| WO | 93/20188 | 10/1993 |
| WO | WO 93/23550 | 11/1993 |
| WO | WO 94/28138 | 12/1994 |
| WO | WO 95/21256 | 8/1995 |
| WO | WO95/21256 | * 8/1995 |

OTHER PUBLICATIONS

Gaudin et al , Rheumatology, 2000, vol. 39, pp. 950–954, 2000.*

P. Challoner et al., "Plaque–Associated Expression of Human Herpesvirus 6 in Multiple Sclerosis", *Proc. Natl., Acad. Sci. USA,* vol. 92, pp. 7440–7444, (Aug. 1995).

S. Haahr et al., "Increased Risk of Multiple Sclerosis After Late Epstein–Barr Virus Infection", *Acta Neurol Scand,* Suppl. 169 pp. 70–75, (1997).

K. Takeuchi, "Expression of Human Endogenous Retroviruses in Rheumatoid Arthritis" (abstract only), *Hokkaido Igaku Zasshi:,* vol. 69: No. 4, pp 821–835, (1994).

Acha–Orbea et al., "Mls—A Retrovirus Exploits the Immune System", *Immunology Today,* vol. 12, No. 10, 1991, pp. 356–361.

Asai et al., "J. of Neurochem", vol. 59, No. 1, pp. 307–317, 1992.

*ATTC Catalogue of Cell Lines and Hybridomas,* Sixth Edition, 1988, pp. 165 and 344–355.

C.R.M. Bangham et al., "PCR Analysis of DNA from Multiple Sclerosis Patients for the Presence of HTLV–I", *Science,* vol. 246, Nov. 10, 1989, pp. 821–824.

R. Baccala et al., "Genomically Imposed and Somatically Modified Human Thymocyte vb Gene Repertoires", *Proc. Natl. Acad. Sci.,* vol. 88, pp. 2908, 1991.

J. Bai et al., "Unique Long Terminal repeat U3 Sequences Distinguish Exogenous Jaagsiekte Sheep Retroviruses Associated with Ovine Pulmonary Carcinoma from Endogenous Loci in the Sheep Genome", *J. Virol.,* vol. 70, pp. 3159–3168, (1996).

(List continued on next page.)

*Primary Examiner*—Ali R. Salimi
(74) *Attorney, Agent, or Firm*—Oliff & Berridge, PLC

(57) ABSTRACT

The invention provides viral material and nucleotide fragments associated with multiple sclerosis and/or rheumatoid arthritis for use in methods of diagnosis, prophylaxis, and therapy.

5 Claims, 73 Drawing Sheets

OTHER PUBLICATIONS

Barna et al., "Human Astrocytes Proliferate in Response to Tumor Necrosis Factor Alpha", *J. Neuroimmunol.*, 30 (1990), pp. 239–243.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.*, 1988: 78, pp. 318–323.

J. I. Bell et al., "Multiple Loci for Multiple Sclerosis", *Nature Genetics*, vol. 13, pp. 377–378, (1996).

Bergamini et al., "Multiple Sclerosis. I. The Immune Pathogenetic Hypothesis", *Riv. Neurol.*, vol. 59, No. 5, Oct., 1989, pp. 176–190.

T. Bergström et al., "Isolation of Herpes Virus Type 1 During First Attack of Multiple Sclerosis.", *Annales Neurology*, vol. 26, pp. 283–285, (1989).

Bernton et al., "No Direct Neuronotoxicity by HIV–1 Virions or Culture Fluids from HIV–1 Infected T Cells or Monocytes", *Aids Research and Human Retroviruses*, vol. 8, No. 4, 1992, pp. 495–503.

Birnbaum et al., "Spinal Fluid Lymphocytes from a Sub-Group of Multiple Sclerosis Patients Respond to Mycobacterial Antigens", *Ann. Neurol.*, vol. 34, No. 1, Jul. 1993, pp. 18–24.

Bjare, "Serum–Free Cell Culture", *Pharm. Ther.*, vol. 53, 1992, pp. 355–374.

C. Bosgiraud et al., "Ultrastructural Study on Visna Virus in Sheep Plexus Choroid Cells", *Biological Abstracts*, vol. 83, No. 7, 1987.

D. Ross Boswell et al., "Sequence comparison and alignment: the measurement and interpretation of sequence similarity", *Computational Molecular Biology, Sources and Methods for Sequence Analysis*, pp. 161–178.

Boyle et al., "Cellular Immune Response in Multiple Sclerosis Plaques", *American Journal of Pathology*, vol. 137, No. 3, Sep. 1990, pp. 575–584.

Bradford, A Rapid and Sensitive Method for the Quantitation of Microgram Quantities of Protein Utilizing the Principle of Protein–Dye Binding, *Anal. Biochem.*, 72, 1976, pp. 248–254.

Brocke et al., "Induction of Relapsing Paralysis in Experimental Autoimmune Encephalomyelitis by Bacterial Superantigen", *Nature*, vol. 365, Oct. 14, 1993, pp. 642–644.

Calder, et al., "MS: A Localized Immune Disease of the Central Nervous System", *Immunology Today*, vol. 10, No. 3, 1989, pp. 99–103.

Carp et al., "Viral Etiology of Multiple Sclerosis", *Prog. Med. Virol.*, vol. 24, pp. 158–177, 1978.

Charcot, "Histologie de la sclerose en plaques [Histology of Multiple Sclerosis]", Gaz. Hop. (Paris), 1868; 41, 554–66.

Chomczynski et al., "Single–Step Method of RNA Isolation by Acid Guanidinium Thiocyanate–Phenol–Chloroform Extraction", *Anal. Biochem.*, 1987, vol. 162, pp. 156–159.

Cole et al., "The Mycoplasma Arthritidis T–Cell Mitogen, MAM: A Model Superantigen", *Immunology Today*, vol. 12, No. 8, 1991, pp. 271–276.

Cook et al., "Multiple Sclerosis and Distemper in Iceland 1966–1978", *Acta Neurol. Scandinav.* 61, 1980, pp. 244–251.

Dalgleish et al., "Do Human T–Lymphotrophic Viruses (HTLVs) and Other Enveloped Viruses Induce Autoimmunity in Multiple Sclerosis?", *Neuropath. App. Neurobiol.*, 1987, 13, pp. 241–250.

A. N. Davison et al., "Biosynthesis of Myelin and Neurotoxic Factors in the Serum of Multiple Sclerosis Patients", *Advances in Experimental Medicine and Biology*, vol. 100, pp. 19–25, 1978.

De Keyser, "Autoimmunity in Multiple Sclerosis", *Neurology*, 38, Mar. 1988, pp. 371–374.

S. Dhib–Jalbut et al., "Measles Virus Polypeptide–Specific Antibody Profile in Multiple Sclerosis", *Neurology*, vol. 40, pp. 430–435, (1990).

Dunn et al., "A Novel Method to Map Transcripts: Evidence for Homology Between an Adenovirus mRNA and Discrete Multiple Regions of the Viral Genome", *Cell*, vol. 12, Sep. 1977, pp. 23–36.

Ebers et al., "The Geography of MS Reflects Genetic Susceptibility", *Neurology*, 36, Apr. 1986, Suppl. 1, p. 108.

Elian et al., "Multiple Sclerosis Among United Kingdom–Born Children of Immigrants from the Indian Subcontinent, Africa and The West Indies", *J Neurol Neurosurg Psychiat*, 1990; 53, pp. 906–911.

Escourolle et al., "Principles Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien*, Paris, 1980; 30, pp. 2047–2053.

E. J. Field, "Immunological Treatment for Multiple Sclerosis", *The Lancet*, Jun. 3, 1989, p. 1272.

Frohman et al., "Rapid Production of Full–Length cDNAs from Rare Transcripts: Amplification Using a Single Gene–Specific Oligonucleotide Primer", *Proc. Natl. Acad. Sci. USA*, 1988, vol. 85, pp. 8998–9002.

Medline Abstract of FU et al., "Rabies virus nucleoprotein expressed in and purified from insect cells is efficacious as a vaccine," Proc Natl Acad Sci USA 88: 2001–05 (1991).

Galiana et al., "Establishment of Permanent Astroglial Cell Lines, Able to Differentiate in Vitro, From Transgenic Mice Carrying Polyoma Virus Large T Gene: An Alternative Approach to Brain Cell Immortalization", *Journal of Neuroscience Research*, 1990; 26: pp. 269–277.

M. B. Gardner et al., "Congenital Transmission of Murine Leukaemia Virus from Wild Mice Prone to Development of Lymphoma and Paralysis", *J. Natl. Cancer Inst.*, vol. 62, pp. 63–69, (1979).

M. B. Gardner, Genetic resistance to a Retroviral Neurologic Disease in Wild Mice, in "Retrovirus Infections of the Nervous System", *Oldstone M.B.A. and Koprowsky H. Eds. Current Topice in Microbiology and Immunology*, No. 160, pp. 3–10, (Springer–Verlag, Berlin, 1990).

Gay, "Is Multiple Sclerosis Caused by an Oral Spirochaete", *The Lancet*, Jul. 12, 1986, pp. 75–77.

A. Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases*, vol. 157, No. 6, Jun. 1988, pp. 1226–1234.

A. Gessain et al., Antibodies to Human T–Lymphotrophic Virus type–I in Patients with Tropical Spastic Paraparesis, *Lancet*, vol. 2, pp. 407–410, (1985).

Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769–2773.

D. Giulian et al., "Secretion of Neurotoxins by Mononuclear Phagocytes Infected with HIV–1", *Science,* vol. 250, Dec. 14, 1990, pp. 1593–1596.

Gonzalez–Scarano et al., "Multiple Sclerosis Disease Activity Correlated with Gadolinium–Enhanced Magnetic Resonance Imaging", *Annals of Neurology,* vol. 21, No. 3, Mar. 1987, pp. 300–306.

F. Gonzalez–Scarano et al., "Sequence Similarities Between Human Immunodeficiency Virus gp41 and Paramyxovirus Fusion Proteins.", *AIDS Res. Hum. Retrov.,* vol. 3, pp. 245–252, (1987).

R. Gonzalez–Quintial et al., *J. Clin. Invest.,* vol. 97, No. 5, pp. 1335–1343, 1996.

S.J. Greenberg et al., "Detection of sequences homologous to human retroviral DNA in multiple sclerosis by gene amplification", *Proc. Natl. Acad. Sci. USA,* vol. 86, Apr. 1989, pp. 2878–2882.

S. Haahr et al., "A Putative New Retrovirus Associated with Multiple Sclerosis and the Possible Involvement of Epstein–Barr Virus in this Disease", *NY Acad. Science,* vol. 724, pp. 148–156, 1994.

S. Haahr et al., "Is Multiple Sclerosis Caused by a Dual Infection with Retrovirus and Epstein–Barr Virus?", *Neuroepidemiology,* vol. 11, pp. 299–303, (1992).

S. Haahr et al., "Just Another Dubious Virus in Cells from a Patient with Multiple Sclerosis?", *The Lancet,* vol. 337, Apr. 6, 1991, pp. 863–864.

A. T. Haase, "Pathogenesis of Lentivirus Infections", *Nature,* vol. 322, Jul. 10, 1986, pp. 130–136.

Haegert et al. HLA–DRβ, –DQα, and –DQβ Restriction Fragment Length Polymorphisms in Multiple Sclerosis, *J. Neurosci. Res.,* 1989; 23, pp. 46–54.

S.L. Hauser et al., "Analysis of Human T–lymphotropic virus sequences in multiple sclerosis tissue", *Nature,* vol. 322, Jul. 10, 1986, pp. 176–178.

Hauw et al., "Aspects Anatomo–Pathologiques de la Sclerose en Plaques [Anatomopathological Aspects of Multiple Sclerosis]", *La Sclerose en Plaques [Multiple Sclerosis],* 9–47 (Rascol et al. eds., 1980).

Hirayama et al., "Serum–Mediated Oligodendrocyte Cytotoxicity in Multiple Sclerosis Patients and Controls", *Neurology* 1986, vol. 36, pp. 276–278.

Hoffman et al., "Handbook of Clinical Neurology, 12; Viral Diseases", R.R. McKendall, ed., Elsevier Science Publishing, Amsterdam, 1989, pp. 453–466.

Huang, "Defective Interfering Viruses", *Fundamental Virology,* Fields et al., eds., 1986, pp. 101–117.

Huck et al., "J. of Neurosei", vol. 4, No. 10, pp. 2650–2657, 1984.

A. W. Hugin et al., "A Virus–Encoded Superantigen in a Retrovirus–Induced Immunodeficiency Syndrome of Mice", *Science,* vol. 252, pp. 424–427, (1991).

James, "Multiple Sclerosis or Blood–Brain Barrier Disease", *The Lancet,* Jan. 7, 1989, p. 46.

Medline abstract of Jarrett et al., "Studies on vaccination against papillomaviruses: a comparison of purified virus, tumour extract and transformed cells in prophylactic vaccination," Vet Rec 126: 449–52 (1990).

Jervis et al., "Experimental Allergic Encephalomyelitis", *J. Neuropathol. Exp. Neurol.,* 1948; 7, pp. 309–320.

D. Johnson et al., "Quantitation of the Myelin–Associated Glycoprotein in Human Nervous Tissue from Controls and Multiple Sclerosis Patients", *Journal of Neurochemistry,* vol. 46, No. 4, 1986, pp. 1086–1093.

Johnson, "Viral Aspects of Multiple Sclerosis", *Handbook of Clinical Neurology,* vol. 3(47): Demyelinating Diseases, 1985, pp. 319–336.

R.T. Johnson, "Nononcogenic Retrovirus Infections as Models for Chronic and Relapsing Human Diseases: Introduction", *Reviews of Infectious Diseases,* vol. 7, No. 1, Jan.–Feb. 1985, pp. 66–67.

Juntunen et al. "Multiple Sclerosis and Occupational Exposure to Chemicals: A Co–Twin Study of a Nationwide Series of Twins", *Br. J. Int. Med.,* 1989; 46: pp. 417–419.

Karpas et al. ,"Lack of evidence for involvement of known human retroviruses in multiple sclerosis", *Nature,* vol. 322, Jul. 10, 1986, pp. 177–178.

Kent et al., "Cerebral Blood Flow, Cerebral Metabolism and Blood–Brain Barrier," *Handbook of Clinical Neurology,* vol. 56(12), 1989, pp. 79–91.

H. Koprowski et al., "Multiple sclerosis and human T–cell lymphotropic retroviruses", *Nature,* vol. 318, Nov. 14, 1985, pp. 154–160.

G. La Mantia et al., "Identification of New Human Repetitive Sequences: Characterization of the Corresponding cDNAs and their Expression in Embryonal Carcinoma Cells", *Nucleic Acids Research,* vol. 17, No. 15, 5913–5922, (1989).

G. La Mantia et al., "Identification and Characterization of Novel Human Endogenous Retroviral Sequences Preferentially Expressed in Undifferentiated Embryonal Carcinoma Cells", *Nucleic Acids Res.,* 1991, vol. 19, No. 7, pp. 1513–1520.

H. Lassmann et al., "Chronic Relapsing Experimental Allergic Encephalomyelitis–Clinicopathological Comparison with Multiple Sclerosis", Arch Neurol, vol. 36, Aug. 1979, pp. 490–497.

Medline Abstract of LEAO, "Tuberculosis: new strategies for the development of diagnostic tests and vaccines," Braz J Med Biol Res 26: 826–33 (1993).

Levi et al., Human Immunodeficiency Coat Protein gp120 Inhibits the β–adrenergic Regulation of Astroglial and Microglial Functions, *Proc. Natl. Acad. Sci. USA,* vol. 90, Feb. 1993, pp. 1541–1545.

Levine et al., "Conversion of Lytic to Persistent Alphavirus Infection by the bcl–2 Cellular Oncogene", *Nature,* vol. 361, Feb. 25, 1993, pp. 739–742.

Y.S. Lie et al., Journal of Virology, vol. 38, No. 12, Dec. 1994, pp. 7840–7849, "Chinese hamster ovary cells contain transcriptionally active full length type C provirises".

Linial et al., "Retroviral RNA Packaging: Sequence Requirements and Implications", in *Current Topics in Microbiology and Immunobiology. Retroviruses, Strategies of Replication,* Swanstrom et al., eds., vol. 157, 1990, pp. 125–152.

R. Lisak et al., "In vitro Cell–Mediated Immunity of Cerebrospinal–Fluid Lymphocytes to Myelin Basic Protein in Primary Demylinating Diseases", *The New England Journal of Medicine,* vol. 297, No. 16, Oct. 20, 1997, pp. 850–853.

Lo et al, "Newly Discovered Mycoplasma Isolated from Patients Infected with HIV", *The Lancet,* vol. 338, Dec. 7, 1991, pp. 1415–1418.

Lori et al., "Viral DNA Carried by Human Immunodeficiency Virus Type 1 Virions", *J. Virol.,* vol. 66, No. 8, Aug. 1992, pp. 5067–5074.

F. Mallet et al., "Continuous RT–PCR and tag DNA Polymerase: Characterization and Comparison to Uncoupled Procedures", *Biotechniques,* vol. 18, pp. 678–687, 1985.

Mallet et al., "Enzyme–Linked Oligosorbent Assay for Detection of Polymerase Chain Reaction–Amplified Human Immunodeficiency Virus Type I", *J. Clin. Microbiol.*, Jun. 1993, vol. 31, No. 6, pp. 1444–1449.

Marie, "Sclerosis en Plaques et Maladies Infectieuses [Multiple Sclerosis and Infectious Diseases]", *Le Progres Medical*, 1884; 12, pp. 287–289.

P. Marrack et al., "A Maternally Inherited Superantigen Encoded by a Mammary Tumor Virus", *Nature*, vol. 349, pp. 524–526, (1991).

McDonald, "The Mystery of the Origin of Multiple Sclerosis", *J. Neurol. Neurosurg. Psych.*, 1986; 49, pp. 113–123.

J. Merregaert et al., "Nucleotide Sequence of a Radiation Leukemia Virus Genome", *Virology*, vol. 158, No. 1, pp. 88–102, (1987).

Meyerhans et al., "Temporal Fluctuations in HIV Quasispecies in Vivo Are Not Reflected by Sequential HIV Isolations", *Cell*, vol. 58, Sep. 8, 1989, pp. 909–910.

J.D. Mosca et al., "Activation of human immunodeficiency virus by herpesvirus infection: Identification of a region within the long terminal repeat that responds to a trans–acting factor encoded by herpes simples virus 1", *Proceedings of the National Academy of Sciences of USA*, vol. 84, No. 21, Nov. 1987, pp. 7408–7412.

Mosmann, "Rapid Colorimetric Assay for Cellular Growth and Survival: Application to Proliferation and Cytotoxicity Assays", *Journal of Immunological Methods*, 65, 1983, pp. 55–63.

O. Narayan et al., "Lentiviral Diseases of Sheep and Goats: Chronic Pneumonia Leukoencephalomyelitis, and Arthritis", *Reviews of Infectious Diseases*, vol. 7, No. 1, Jan.–Feb. 1985, pp. 89–98.

N. Nathanson et al., "Experimental Visna in Icelandic Sheep: The Prototype Lentiviral Infection", *Reviews of Infectious Diseases*, vol. 7, No. 1, Jan.–Feb. 1985, pp. 75–82.

Newell et al., "Ligation of Major Histocompatibility Complex Class II Molecules Mediates Apoptotic Cell Death in Resting B Lymphocytes", *Proc. Natl. Acad. Sci. USA*, vol. 90, Nov. 1993, pp. 10459–10463.

Nielsen et al., "Sequence–Selective Recognition of DNA by Strand Displacement with a Thymine–Substituted Polyamide", *Science*, vol. 254, pp. 1497–1500.

Norby, "Viral Antibodies in Multiple Sclerosis", *Prog. Med. Virol.*, vol. 24 1978, pp. 1–39 (1978).

M. Ohta et al., "Sera from Patients with Multiple Sclerosis React with Human T Cell Lymphotropic Virus–I Gag Proteins but not Env Proteins—Western Blotting Analysis", The Journal of Immunology, vol. 137, No. 11, Dec. 1, 1986, pp. 3440–3443.

Medline abstract of Orlandi et al., "Characterization of the 175–kilodalton erythrocyte binding antigen of *Plasmodium falciparum*," Mol Biochem Parasitol 40: 285–94 (1990).

Ostgrove et al., "Activation of the Human Immunodeficiency Virus by Herpes Simplex Virus Type I", J Virol 61(12), Dec. 1987, pp. 3726–3732.

M. Palmerini, "The Exogenous Form of Jaagsiekte Retrovirus is Specifically Associated with a contagious Lung Cancer of Sheet", *J. Virol*, vol. 70, p. 1618–1623, (1996).

J.L. Pablos et al., "A novel retroviral POL sequence is present in patients with rheumatoid arthritis", & American College of Rheumatology 57th Annual Scientific Meeting, Nov. 7–11, 1993 San Antonio, Texas, USA, *Arthritis and Rheumatism*, vol. 36, No. 9 supl. 1993, p. S55, Abstract No. 102.

Medline abstract of PEI et al., "Identification, purification, and characterization of major antigenic proteins of *Campylobacter jejuni*," J Biol Chem 266: 16363–69 (1991).

H. Perron et al., "Isolations of an Unknown Retrovirus from CSF, Blood and Brain Cells of Patients with Multiple Sclerosis", in *Current Concepts in Multiple Sclerosis*, Wietholter et al., eds., 1991, Elsevier publ., pp. 111–116.

H. Perron et al., "Leptomeningeal cell line from multiple sclerosis with reverse transcriptase activity and viral particles", *Res. Virol.*, Nov. 1989, vol. 140(6), pp. 551–561.

H. Perron et al., "Leptomeningeal cell line from multiple sclerosis with reverse transcriptase activity and viral particles", Biological Abstracts, vol. 89, No. 9, May 1, 1990.

H. Perron et al., "Isolation of Retrovirus from Patients with Multiple Sclerosis", *The Lancet*, vol. 337, No. 8745, Apr. 6, 1991, pp. 862–863.

H. Perron et al., "Antibody to Reverse Transcriptase of Human Retrovirus in Multiple Sclerosis", Biological Abstracts, vol. 93, No. 6, Mar. 15, 1992.

H. Perron et al., "Herpes simplex virus ICP0 and ICP4 immediate early proteins strongly enhance expression of a retrovirus harboured by a leptominingeal cell line from patient with multiple sclerosis", The Journal of General Virology, vol. 74, No. 1, Jan. 1993, pp. 65–72.

H. Perron et al., "Retrovirus Isolation from Patients with Multiple Sclerosis: Epiphenomenon or Causative Factor?", *AIDS Research and Human Retroviruses*, vol. 8, No. 5, May 1992, p. 922.

H. Perron et al., "In Vitro Transmission and Antigenicity of a Retrovirus Isolated from a Multiple Sclerosis Patient", *Res. Virol.*, vol. 143, No. 5, 1992, pp. 337–350.

Perron et al., "Retroviral Reactivation by Herpesviruses in MS: Serological Arguments", Current Concepts in Multiple Sclerosis 1991, pp. 331–332.

A. Plaza et al., Theofilopoulos, A.N. New Human vβ 12DD Genes and Polymorphic Variants. J. Imm; vol. 147, No. 12, pp. 4360–4365, 1991.

Poirier et al., "La Barriere Hemato–Encaphalique. Donnees Morphologiques [The Blood–Brain Barrier. Morphological Data]", *La Revue de Medecine Interne*, vol. IV, No. 2, Jun. 1983, pp. 131–144.

J. L. Portis, "Wild Mouse Retrovirus: Pathogenesis in Retrovirus Infections of the Nervous System", Oldstone M.B.A. and Koprowsky H. Eds. Current topics in microbiology and immunology, n°160, pp. 11–27, (Springer–Verlag, Berlin, 1990).

C.M. Poser et al., "New Diagnostic Criteria for Multiple Sclerosis: Guidelines for Research Protocols, in "The diagnosis of Multiple Sclerosis"", *Thieme Stratton Inc.*, pp. 225–229, 1984.

D.N., Posnet, "Do Superantigens Play a Role in Autoimmunity?", *Semin. Immunol.*, vol. 5, pp. 65–72, 1993.

Prineas, "The Neuropathology of Multiple Sclerosis", *Handbook of Clinical Neurology*, vol. 3 (47), 1985, pp. 213–257.

Prineas et al., "Multiple Sclerosis: Remyelination of Nascent Lesions", *Annals of Neurology*, vol. 33, No. 2, Feb. 1993, pp. 137–151.

Prineas, "Pathology of the Early Lesion in Multiple Sclerosis", *Human Pathology,* vol. 6, No. 5, Sep. 1975, pp. 531–554.

Prineas et al., "Macrophages, Lymphocytes, and Plasma Cells in the Perivascular Compartment in Chronic Multiple Sclerosis", *Laboratory Investigation,* vol. 38, No. 4, 1978, pp. 409–421.

Ransohoff et al., "Heat–Shock Proteins and Autoimmunity: Implications for Multiple Sclerosis", *Annals of Neurology,* vol. 34, No. 1, Jul. 1993, pp. 5–7.

Rapoport, *Blood–Brain Barrier in Physiology and Medicine,* 129 (1976).

E.P. Reddy et al., "Amplification and Molecular Cloning of HTLV–I Sequences from DNA of Multiple Sclerosis in Patients", *Science,* vol. 243, Jan. 27, 1989, pp. 529–533.

S. S. Rhee et al., "A single Amino Acid Substitution Within the Matrix Protein of D–Type Retrovirus Converts Its Morphogenesis to that of a C–Type Retrovirus", Cell 63, pp. 77–86, (1990).

Riise et al., "Clustering of Residence of Multiple Sclerosis Patients at Age 13 to 20 Years in Hordaland, Norway", *Am. J. Epidemiol* 1991, vol. 133, No. 9, pp. 932–939.

Robbins et al., "Production of Cytotoxic Factor for Oligodendrocytes by Stimulated Astrocytes", *The Journal of Immunology,* vol. 139, No. 8, Oct. 15, 1987, pp. 2593–2597.

Rosati et al., "Incidence of Multiple Sclerosis in the Town of Sassari, Sardinia, 1965 to 1985: Evidence for Increasing Occurrence of the Disease", *Neurology* 38 (Mar. 1988), pp. 384–388.

Rudge, "Does a Retrovirally Encoded Superantigen Cause Multiple Sclerosis?", *J. Neurology Neurosurgery & Psychiatry* 1991, vol. 54, pp. 853–855.

Medline abstract of Rumschlag et al., "Immunologic characterization of a 35–kilodalton recombinant antigen of *Mycobacterium tuberculosis,*" J Clin Microbiol 28: 591–595 (1990).

Medline abstract of Sakulramrung et al., "antigenic and immunogenic characteristics of subcellular fractions and whole cells of a rough *E. coli* 0111 (J5) mutant," Immunobiology 169: 372–88 (1985).

Selmaj, et al., "Tumor Necrosis Factor Mediates Myelin and Oligodendrocyte Damage In Vitro", *Annals of Neurology,* vol. 23, No. 4, Apr. 1988, pp. 339–346.

Shih et al., "Detection of MUltiple, Novel Reverse Transcriptase Coding Sequences in Human Nucleic Acids: Relation to Primate Retroviruses", *J. Virol.,* Jan. 1989, vol. 63, No. 1, pp. 64–75.

Silberberg et al., "Tissue Culture Demyelination by Normal Human Serum", *Annals of Neurology,* vol. 15, No. 6, Jun. 1994, pp. 575–580.

M. Sommerlund et al., "Retrovirus–like particles in an Epstein–Barr virus–producing cell line derived from a patient with chronic progressive myelopathy", *Acta Neurol Scand,* 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Southern, "Detection of Specific Sequences Among DNA Fragments Separated by Gel Electrophoresis", *J. Mol. Biol.,* 1975, vol. 98, pp. 503–517.

Suzumura et al., "Serum Cytotoxicity to Oligodendrocytes in Multiple Sclerosis and Controls: Assessment by $^{51}$Cr Release Assay", *J. Neuroimmunol.,* 11 (1986), pp. 137–147.

Traugott, "Multiple Sclerosis: Relevance to Class I and Class II MHC–Expressing Cells to Lesion Development", *Journal of Neuroimmunology,* 16, 1987, pp. 283–302.

Waksman, "Mechanisms in Multiple Sclerosis", *Nature,* vol. 318, Nov. 14, 1985, pp. 104–105.

K.G. Warren et al., "Diagnostic Value of Cerebrospinal Fluid Anti–Myelin Basic Protein in Patients with Multiple Sclerosis", Annals of Neurology, vol. 20, No. 1, Jul. 1986, pp. 20–25.

Williams et al., "Molecular Regulation of Apoptosis: Genetic Controls on Cell Death", *Cell,* vol. 74, Sep. 10, 1993, pp. 777–779.

Wienfield et al., "Stress Proteins, Autoimmunity, and Autoimmune Disease", *Current Topics in Microbiology and Immunology,* vol. 167, Springer–Verlag, Berlin, 1991, pp. 161–189.

D. L. Wilkinson et al., "Evidence for a functional subclass of the RTLV–H family of human endogenous retrovirus–like sequences", *J. Virol.,* vol. 67, pp. 2981–2989, (1993).

Wollinsky et al., "Liquorpherase bein 10 Patienten mit Multiplier Sklerose [Fluid Phoresis in 10 Patients With Multiple Sclerosis]", *Verhandlungen der Deutschen Gesellschaft fur Neurologie,* vol. 7, 1992, pp. 444–445.

Woodland, et al., "An Endogenous Retrovirus Mediating Deletion of αβ T cells?", *Nature,* vol. 349, Feb. 7, 1991, pp. 529–530.

\* cited by examiner

FIG. 1

```
Consensus    GTTTAGGGAT  ANCCCTCATC  TCTTTGGTCA  GGTACTGGCC  CAAGATCTAG    50
Consensus    GCCACTTCTC  AGGTCCAGSN  ACTCTGTYCC  TTCAG  85
```

*SEQ ID NO 3 (POL MSRV-1B)*

```
Consensus    GTTCAGGGAT  AGCCCCCATC  TATTTGGCCA  GGCACTAGCT  CAATACTTGA    50
Consensus    GCCAGTTCTC  ATACCTGGAC  AYTCTYGTCC  TTCGGT  86
```

*SEQ ID NO 4 (POL MSRV-1B)*

```
Consensus    GTTCARRGAT  AGCCCCCATC  TATTTGGCCW  RGYATTAGCC  CAAGACTTGA    50
Consensus    GYCAATTCTC  ATACCTGGAC  ACTCTTGTCC  TTYRG  85
```

*SEQ ID NO 5 (POL MSRV-1B)*

```
Consensus    GTTCAGGGAT  AGCTCCCATC  TATTTGGCCT  GGCATTAACC  CGAGACTTAA    50
Consensus    GCCAGTTCTY  ATACGTGGAC  ACTCTTGTCC  TTTGG  85
```

*SEQ ID NO 6 (POL MSRV-1B)*

```
Consensus    GTGTTGCCAC  AGGGGTTTAR  RGATANCYCY  CATCTMTTTG  GYCWRGYAYT
Consensus    RRCYCRAKAY  YTRRGYCAVT  TCTYAKRYSY  RGSNAYTCTB  KYCCTTYRGT
Consensus    ACATGGATGA  C
```

*SEQ ID NO 7 (POL MSRV-1B)*

FIG. 2

CONSENSUS A  SEQ ID NO 3

```
GTTTAGGGATAGCCC    TCATCTCTTTGGTCA    GGTACTGGCCCAAGA    TCTAGGCCACTTCTC    60
 V - G - P          S S L W S          G T G P R          S R P L L
F R D S P          H L F G Q          V L A Q D          L G H F S
 L G I A L          I S L V R          Y W P K I          - A T S Q

AGGTCCAGGCACTCT    GTTCCTTCAG                                               85
 R S R H S          V P S
G P G T L          F L Q
 V Q A L C          S F
```

CONSENSUS B  SEQ ID NO 4

```
GTTCAGGGATAGCCC    CCATCTATTTGGCCA    GGCACTAGCTCAATA    CTTGAGCCAGTTCTC    60
 V Q G - P          P S I W P          G T S S I          L E P V L
F R D S P          H L F G Q          A L A Q Y          L S Q F S
 S G I A P          I Y L A R          H - L N T          - A S S H

ATACCTGGACACTCT    TGTCCTTCGGT                                              86
 I P G H S          C P S
Y L D T L          V L R
 T W T L L          S F G
```

CONSENSUS C  SEQ ID NO 5

```
GTTCAGGGATAGCCC    CCATCTATTTGGCCA    GGCATTAGCCCAAGA    CTTGAGTCAATTCTC    60
 V Q G - P          P S I W P          G I S P R          L E S I L
F R D S P          H L F G Q          A L A Q D          L S Q F S
 S G I A P          I Y L A R          H - P K T          - V N S H

ATACCTGGACACTCT    TGTCCTTCAG                                               85
 I P G H S          C P S
Y L D T L          V L Q
 T W T L L          S F
```

CONSENSUS D  SEQ ID NO 6

```
GTTCAGGGATAGCTC    CCATCTATTTGGCCT    GGCATTAACCCGAGA    CTTAAGCCAGTTCTC    60
 V Q G - L          P S I W P          G I N P R          L K P V L
F R D S S          H L F G L          A L T R D          L S Q F S
 S G I A P          I Y L A W          H - P E T          - A S S H

ATACGTGGACACTCT    TGTCCTTTGG                                               85
 I R G H S          C P L
Y V D T L          V L W
 T W T L L          S F
```

FIG. 3

| | | | | | | |
|---|---|---|---|---|---|---|
| Consensus | TTGGATCCAG | TGYTGCCACA | GGGCGCTGAA | GCCTATCGCG | TGCAGTTGCC | 50 |
| Consensus | GGATGCCGCC | TATAGCCTCT | ACGTGGATGA | CCTSCTGAAG | CTTGAG | 96 |

SEQ ID NO 11

FIG. 6

```
CAAGCCACCC  AAGAACTCTT  AAATTTCCTC  ACTACCTGTG  GCTACAAGGT   50
TTCCAAACCA  AAGGCTCAGC  TCTGCTCACA  GGAGATTAGA  TACTTAGGGT  100
TAAAATTATC  CAAAGGCACC  AGGGGCCTCA  GTGAGGAACG  TATCCAGCCT  150
ATACTGGGTT  ATCCTCATCC  CAAAACCCTA  AGCAACTAA   GAGGGTTCCT  200
TAGCATGATC  AGGTTTCTGC  CGAAAACAAG  ATTCCCAGGT  ACAACCAAAA  250
TAGCCAGACC  ATTATATACA  CTAATTAAGG  AAACTCAGAA  AGCCAATACC  300
TATTTAGTAA  GATGGACACC  TAAACAGAAG  GCTTTCCAGG  CCCTAAAGAA  350
GGCCCTAACC  CAAGCCCCAG  TGTTCAGCTT  GCCAACAGGG  CAAGATTTTT  400
CTTTATATGG  CACAGAAAAA  ACAGGAATCG  CTCTAGGAGT  CCTTACACAG  450
GTCCGAGGGA  TGAGCTTGCA  ACCCGTGGCA  TACCTGAATA  AGGAAATTGA  500
TGTAGTGGCA  AAGGGTTGGC  CTCATNGTTT  ATGGGTAATG  GNGGCAGTAG  550
CAGTCTNAGT  ATCTGAAGCA  GTTAAATAA   TACAGGGAAG  AGATCTTNCT  600
GTGTGGACAT  CTCATGATGT  GAACGGCATA  CTCACTGCTA  AAGGAGACTT  650
GTGGTTGTCA  GACAACCATT  TACTTAANTA  TCAGGCTCTA  TTACTTGAAG  700
AGCCAGTGCT  GNGACTGCGC  ACTTGTGCAA  CTCTTAAACC  C           741
```

SEQ ID NO 9 (PSJ 17)

FIG. 7

```
TCAGGGATAGCCCCCATCTATTTGGCCAGGCATTAGCCCAAGACTTGAGTC
AATTCTCATACCTGGACACTCTTGTCCTTCAGTACATGGATGATTTACTTT
TAGTCGCCCGTTCAGAAACCTTGTGCCATCAAGCCACCCAAGAACTCTTAA
CTTTCCTCACTACCTGTGGCTACAAGGTTTCCAAACCAAAGGCTCGGCTCT
GCTCACAGGAGATTAGATACTNAGGGCTAAAATTATCCAAGGCACCAGG
GCCCTCAGTGAGGAACGTATCCAGCCTATACTGGCTTATCCTCATCCCAAA
ACCCTAAAGCAACTAAGAGGGTTCCTTGGCATAACAGGTTTCTGCCGAAA
ACAGATTCCAGGTACASCCCAATAGCCAGACCATTATATACACTAATTA
NGGAAACTCAGAAAGCCAATACCTATTTAGTAAGATGGACACCTACAGAA
GTGGCTTTCCAGGCCCTAAAGAAGGCCCTAACCCAAGCCCCAGTGTTCAGC
TTGCCAACAGGGCAAGATTTTCTTTATATGCCACAGAAAAACAGGAAT
AGCTCTAGGAGTCCTTACGCAGGTCTCAGGGATGAGCTTGCAACCCGTGGT
ATACCTGAGTAAGGAAATTGATGTAGTGGCAAGGGTT
```

SEQ ID NO 8 (M003-P004)

FIG. 8

```
      10          20          30          40          50          60          70
       *           *           *           *           *           *           *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R >
─a──────a──────a──────a──────a──────a──────a─ TRANSLATION OF F11-1 (A) ─a──────a──────a──────a─

80          90         100         110         120         130         140
       *           *           *           *           *           *           *
ATT ATC AAT GAG GCT GTT CCT CTA TAC CCA GCT GTA CCT AAC CCT TAT ACA GTG CTT TCC CAA ATA CCA
 I   I   N   E   A   V   P   L   Y   P   A   V   P   N   P   Y   T   V   L   S   Q   I   P >
─a──────a──────a──────a──────a──────a──────a─ TRANSLATION OF F11-1 (A) ─a──────a──────a──────a─

150         160         170         180         190         200         210
       *           *           *           *           *           *           *
GAG GAA GCA GAG TGG TTT ACA GTC CTG GAC CTT GAC AAG GAT GCC TTT TTC TGC ATC CCT GTA CGT CCT GAC TCT
 E   E   A   E   W   F   T   V   L   D   L   D   K   D   A   F   F   C   I   P   V   R   P   D   S >
─a──────a──────a──────a──────a──────a──────a─ TRANSLATION OF F11-1 (A) ─a──────a──────a──────a─

220         230         240         250         260         270         280
       *           *           *           *           *           *           *
CAA TTC TTG TTT GCC TTT GAA GAT CCT TTG AAC CCA ACG TCT CAA CTC ACC TGG ACT GTT TTA CCC CAA GGG
 Q   F   L   F   A   F   E   D   P   L   N   P   T   S   Q   L   T   W   T   V   L   P   Q   G >
─a──────a──────a──────a──────a──────a──────a─ TRANSLATION OF F11-1 (A) ─a──────a──────a──────a─

290
  *
TTC AAG GGA
 F   K   G >
─a──────a─
```

SEQ ID NO 2 (F11-1)

FIG. 9a

```
         10              20              30              40              50              60              70
          *               *               *               *               *               *               *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
 __a___a___a___a___a___a___a___TRANSLATION OF MSRV-1 POL  *   (A)__a___a___a___a___a___a___a__>

80              90             100             110             120             130             140
          *               *               *               *               *               *               *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P>
 __a___a___a___a___a___a___a___TRANSLATION OF MSRV-1 POL  *   (A)__a___a___a___a___a___a___a__>

150             160             170    A    180             190             200             210
          *               *               *               *|              *               *               *
GAG GAA GCA GAG TGG TTT ACA GTC CTG GAC CTT AAG|GAT GCC TTT TTC TGC ATC CCT GTA CGT CCT GAC TCT
 E   E   A   E   W   F   T   V   L   D   L   K   D   A   F   F   C   I   P   V   R   P   D   S>
 __a___a___a___a___a___a___a___TRANSLATION OF MSRV-1 POL  *   (A)__a___a___a___a___a___a___a__>

220             230             240             250             260             270             280
          *               *               *               *               *               *               *
CAA TTC TTG TTT GCC TTT GAA GAT CCT TTG AAC CCA ACG TCT CAA CTC ACC TGG ACT|GTT TTA CCC CAA GGG|
 Q   F   L   F   A   F   E   D   P   L   N   P   T   S   Q   L   T   W   T  V   L   P   Q   G>
 __a___a___a___a___a___a___a___TRANSLATION OF MSRV-1 POL  *   (A)__a___a___a___a___a___a___a__>

290             300             310             320             330|  B   340             350             360
  *               *               *               *               *               *               *               *
TTC AGG GAT AGC CCC CAT CTA TTT GGC CAG GCA TTA GCC CAA|GAC TTG AGT CAA TTC TCA TAC CTG GAC ACT
 F   R   D   S   P   H   L   F   G   Q   A   L   A   Q   D   L   S   Q   F   S   Y   L   D   T>
 __a___a___a___a___a___a___a___TRANSLATION OF MSRV-1 POL  *   (A)__a___a___a___a___a___a___a__>

370             380             390             400             410             420             430
          *               *               *               *               *               *               *
CTT GTC CTT CAG|TAC ATG GAT GAT|TTA CTT TTA GTC GCC CGT TCA GAA ACC TTG TGC CAT CAA GCC ACC CAA
 L   V   L   Q  Y   M   D   D   L   L   L   V   A   R   S   E   T   L   C   H   Q   A   T   Q>
 __a___a___a___a___a___a___a___TRANSLATION OF MSRV-1 POL  *   (A)__a___a___a___a___a___a___a__>

440             450             460             470             480             490             500
          *               *               *               *               *               *               *
GAA CTC TTA ACT TTC CTC ACT ACC TGT GGC TAC AAG GTT TCC AAA CCA AAG GCT CGG CTC TGC TCA CAG GAG
 E   L   L   T   F   L   T   T   C   G   Y   K   V   S   K   P   K   A   R   L   C   S   Q   E>
 __a___a___a___a___a___a___a___TRANSLATION OF MSRV-1 POL  *   (A)__a___a___a___a___a___a___a__>

510             520             530             540             550             560             570
          *               *               *               *               *               *               *
ATT AGA TAC TNA GGG CTA AAA TTA TCC AAA GGC ACC AGG GCC CTC AGT GAG GAA CGT ATC CAG CCT ATA CTG
 I   R   Y   X   G   L   K   L   S   K   G   T   R   A   L   S   E   E   R   I   Q   P   I   L>
 __a___a___a___a___a___a___a___TRANSLATION OF MSRV-1 POL  *   (A)__a___a___a___a___a___a___a__>

580             590             600             610             620             630             640
          *               *               *               *               *               *               *
GCT TAT CCT CAT CCC AAA ACC CTA AAG CAA CTA AGA GGG TTC CTT GGC ATA ACA GGT TTC TGC CGA AAA CAG
 A   Y   P   H   P   K   T   L   K   Q   L   R   G   F   L   G   I   T   G   F   C   R   K   Q>
 __a___a___a___a___a___a___a___TRANSLATION OF MSRV-1 POL  *   (A)__a___a___a___a___a___a___a__>

650             660             670             680             690             700             710             720
  *               *               *               *               *               *               *               *
ATT CCC AGG TAC ASC CCA ATA GCC AGA CCA TTA TAT ACA CTA ATT ANG GAA ACT CAG AAA GCC AAT ACC TAT
 I   P   R   Y   X   P   I   A   R   P   L   Y   T   L   I   X   E   T   Q   K   A   N   T   Y>
 __a___a___a___a___a___a___a___TRANSLATION OF MSRV-1 POL  *   (A)__a___a___a___a___a___a___a__>

730             740             750             760             770             780             790
          *               *               *               *               *               *               *
TTA GTA AGA TGG ACA CCT ACA GAA GTG GCT TTC CAG GCC CTA AAG AAG GCC CTA ACC CAA GCC CCA GTG TTC
 L   V   R   W   T   P   T   E   V   A   F   Q   A   L   K   K   A   L   T   Q   A   P   V   F>
 __a___a___a___a___a___a___a___TRANSLATION OF MSRV-1 POL  *   (A)__a___a___a___a___a___a___a__>

800             810             820             830             840             850             860
          *               *               *               *               *               *               *
AGC TTG CCA ACA GGG CAA GAT TTT TCT TTA TAT GCC ACA GAA AAA ACA GGA ATA GCT CTA GGA GTC CTT ACG
 S   L   P   T   G   Q   D   F   S   L   Y   A   T   E   K   T   G   I   A   L   G   V   L   T>
 __a___a___a___a___a___a___a___TRANSLATION OF MSRV-1 POL  *   (A)__a___a___a___a___a___a___a__>

870             880             890             900             910             920             930
          *               *               *               *               *               *               *
CAG GTC TCA GGG ATG AGC TTG CAA CCC GTG GTA TAC CTG AGT AAG GAA ATT GAT GTA GTG GCA AAG GGT TGG
 Q   V   S   G   M   S   L   Q   P   V   V   Y   L   S   K   E   I   D   V   V   A   K   G   W>
 __a___a___a___a___a___a___a___TRANSLATION OF MSRV-1 POL  *   (A)__a___a___a___a___a___a___a__>

940             950             960             970             980             990            1000
  *               *               *               *               *               *               *
CCT CAT NGT TTA TGG GTA ATG GNG GCA GTA GCA GTC TNA GTA TCT GAA GCA GTT AAA ATA ATA CAG GGA AGA
 P   H   X   L   W   V   M   X   A   V   A   V   X   V   S   E   A   V   K   I   I   Q   G   R>
 __a___a___a___a___a___a___a___TRANSLATION OF MSRV-1 POL  *   (A)__a___a___a___a___a___a___a__>

1010            1020            1030            1040            1050            1060            1070            1080
  *               *               *               *               *               *               *               *
GAT CTT NCT GTG TGG ACA TCT CAT GAT GTG AAC GGC ATA CTC ACT GCT AAA GGA GAC TTG TGG TTG TCA GAC
 D   L   X   V   W   T   S   H   D   V   N   G   I   L   T   A   K   G   D   L   W   L   S   D>
 __a___a___a___a___a___a___a___TRANSLATION OF MSRV-1 POL  *   (A)__a___a___a___a___a___a___a__>
```

FIG. 9b

```
         1090          1100          1110          1120          1130          1140          1150
          *             *             *             *             *             *             *
AAC CAT TTA CTT AAN TAT CAG GCT CTA TTA CTT GAA GAG CCA GTG CTG NGA CTG CGC ACT TGT GCA ACT CTT
 N   H   L   L   X   Y   Q   A   L   L   L   E   E   P   V   L   X   L   R   T   C   A   T   L>
___a___a___a___a___a___a___a___TRANSLATION OF MSRV-1 POL *  (A)___a___a___a___a___a___a___a__>
AAA CCC
 K   P>
___a___>
```

SEQ ID NO 1 (MSRV-1 pol*)

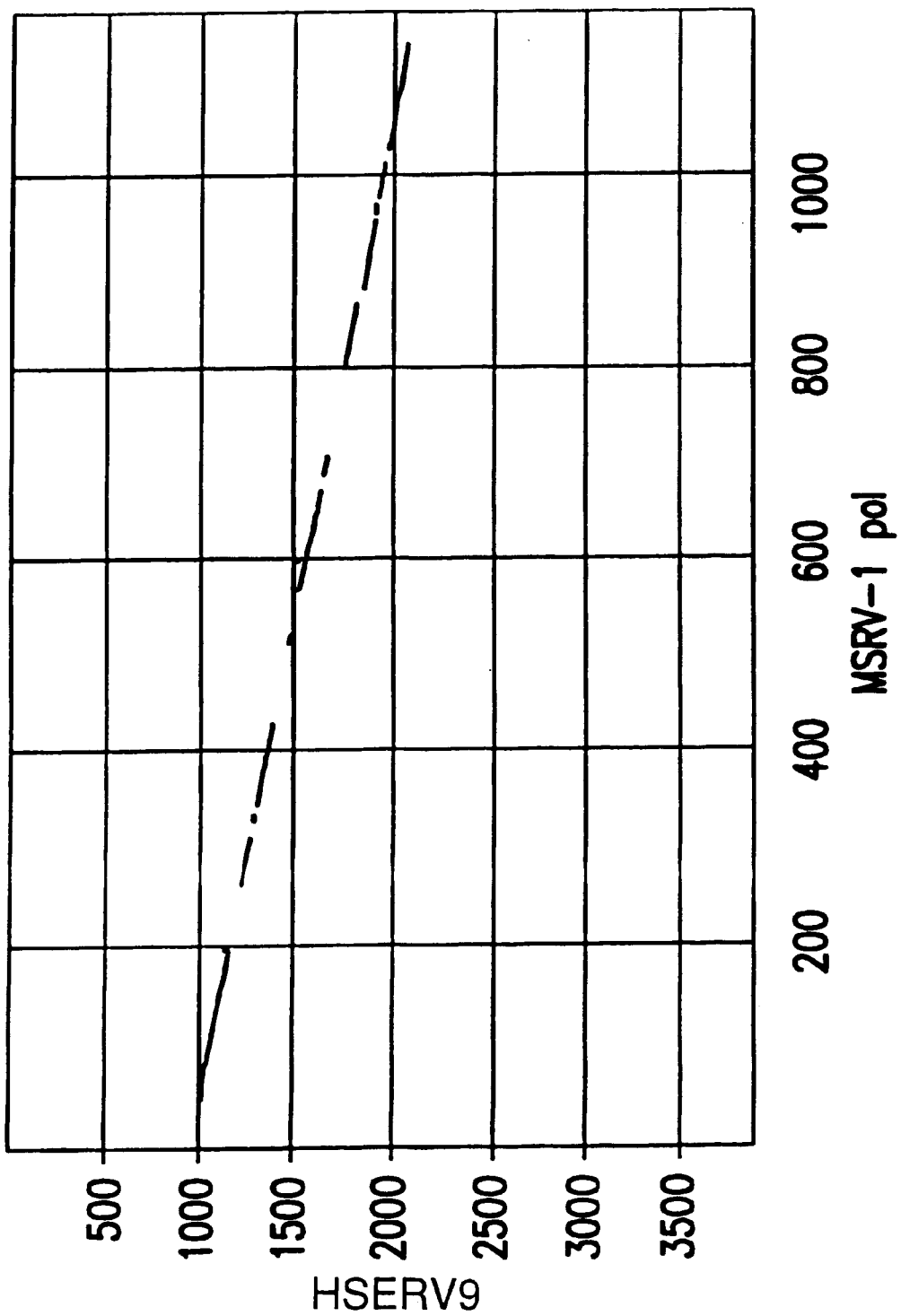

FIG. 13

```
GTGCTGATTGGTGTATTTACAATCCTTTATCTAATCCGAAATGCCCATGTTG
CAATATGGAAAGAAAGGGAGTTCCTAACCTCTGGGGGAACCCCCATTAAA
TACCACAAGTAAATCATGGAGTTATTGCACACAGTGCAAAAACTCAAGGA
GGTGGAAGTCTTACACTGCCAAAGCCATCAGAAAGGGAAGAGGGGAGAA
GAGCAGCATAAGTGGCTACAGAGGCAAGGAAAGACTAGCAGAAAGGAAA
GAGAGAAAGAGACAGAAAGTCAGAGAGAGAGAGAGGAAGAGACAGAGCA
CAAAGAGGGAGTCAGAGAGAGAGAGAGACAGAGAGTCAGAGAGAAGGAA
AGAGAGAGAGGAAGAGACAAAGAATGAATCAAACAGAGAGACAGAAAGT
CAGAGAGAGAGAGAGAGAGGAAGAGACAGAGAAAAGAGGGAGTCAGAA
AAAGAGAGACCAAAGAAGAAGTCCAAAGAGAAAGAAAGAGAGATGGAAG
TAGTAAAGGAAAAACAGTGTACCCTATTCCTTTAAAAGCCGGGGTAAATTT
AAAACCTATAATTGATAACTGAAGGTCTTCTCTGTAACCCTGTAACACTCC
AATACCACCTTGTTGTCAAGTGTAAACAAGGGCGTAGCCCAAAAGCACTG
AGGCCACTAACAACCCATAGCCTTCCTATCAAAATTCCTTAACCCAGCAGG
TTTCCTAACAGGGGATCTAAATCTTAATTAATTACCATACAATGGTCCAAC
CAGACTTAGGAGGAATTCCCTTCAGGACGGGAAGATAGATGCTTCCTCCCA
GGCGATTAAGGGAGAAAGACACAATGGGTATTCAGTAAGTGCCAAGGGA
ACACTTGTAGAAGCAAAGTTAGGAAAATTGCCAAATAATTGGTTTGCTCAA
GAGTTGTTTGCACTCAGCCAAACCTTGAAGTACTTGCAGAATCAGAAAGGA
GCCATCTATACCAATTCTAAGTTAATATGGACTGAAGGAGGTTTTATTAAT
ACCAAAGAGAAATTAAAATCCCAAACTTATAAGGTTTTCAACCAAAGTAA
AGTTTGCTAAAAGTTAACAGCGTAACATGTATTATCCTACTACCACACACT
CTCAAAGGATTTCTCAGACAGTTTGCAAGAAATAATGATATCTATCCTTAC
TCTACAATCCCAAATAGACTCTTTGGCAGCAGTGACTCTCCAAAACCGTCA
AGGCCTAGACCTCCTCACTGCTGAGAAAGGAGGACTCTGCACCTTCTTAAG
GGAAGAGTGTTGTCTTTACACTAACCAGTCAGGGATAGTATGAGATGCTGC
CCGGCATTTACAGAAAAAGGCTTCTGAAATCAGACAACGCCTTTCAAATTC
CTATACCAACCTCTGGAGTTGGGCAACATGGTTTCTTCCCTTTCTATGTCCC
ATGGCTGCCATCTTGCTATTACTCGCCTTTGGGCCCTGTATTTTTAACCTCC
TTGTCAAATTTGTTTCTTCTAGGATCGAGGCCATCAAGCTACAGATGGTCTT
ACAAATGGAACCCCAAATGAGCTCAACTATCAACTTCTACTGAGGACCCCT
AGACCAACCCCCTGGCCCTTTCACTGGCCTAAAGAGTTCCCCTCTGGAGGA
CACTACCACTGCAGGGCCCCATCTTTGCCCCTATCCAGAAGGAAGTAGCTA
GAGCAGTCATTGCCCAATTCCCAAGAGCAGCTGGGGTGTCCCGTTTAGAGT
GGGGATTGAGAGGTGAAGCCAGCTGGACTTCTGGGTCGGGTGGGGACTTG
GAGAACTTTTGTGTCTAGCTAAAGGATTGTAAATGCAACAATCAGTGCTCT
GTGTCTAGCTAAAGGATTGTAAATACACCAATCAGCAC
```

SEQ ID NO 42 (FBd3)

FIG. 15

```
GGCTGCTAAAGGAGACTTGTGGTTGTCAGACAATCGCCTACTTAGGTACCA
GGCCTTATTACTTGAGGGACTGGTGCTTCAGATGCGCACTTGTGCAGCTCT
TAACCCAAACTTATGCTGCCCAGAAGGATCTTTTAGAGGTCCCCTTAGCCA
ACCCTGACCTCAACCTATATATATACTGATGGAAGTTCGTTTGTAGAAAAG
GGATTACAAGGGNAGGATATNCCATAGGTTAGTGATAAAGCAGTACTTG
AAAGTAAGCCTCTTCCCCCCAGGGACCAGCGCCCCGTTAGCAGAACTAGT
GGCACTGACCCCGAGCCTTAGAACTTGGAAAGGGAGGAGGATAAATGTGT
ATACAGATAGCAAGTATGCTTATCTAATCCGAAATGCCCATGTTG
```

SEQ ID NO 47 (t pol)

FIG. 16

```
TCAGGGATAGCCCCCATCTATTTGGTCAGGCACTGGCCCAAGATCTAGGGA
CATGCCACTTTTAAGAGCCATTTCTCAAGTCCAGGTACTCTGGTCCTTCGGT
ATGTGGATGATTTACTTTTGGCTACCAGTTCAGTAGCCTCATGCCAGCAGG
CTACTCTAGATCTCTTGAACTTTCTAGCTAATCAAGGGTACAAGGCATCTA
GGTTGAAGGCCCAGCTTTGCCTACAGCAGGTCAAATATCTAGGCCTAATCT
TAGCCAGAGGGACCAGGGCACTCAGCAAGGAACAAATACAGCCTATACTG
GCTTATCCTCACCCTAAGACATTAAAACAGTTGCGGGGGTTCCTTGGAATC
ACTGGCTTTTTGGTGACTATGGATTCCCAGATACAGCAAGATTGGCAGGCC
CCTCTATACTGTAATCAAGGAGACTCACGAGGGCAAGTACTCATCTAGTAG
AATGGGAACTAGGGACAGAAACAGCCTTCAAAACCTTAAAGCAGGCCCTA
GTACAATCTCCAGCTTTAAGCCTTCCCACAGGACAAAACTTCTCTTTATAC
ATCACAGAGAGGGCAGAGATAGCTCTTGGTGTCCTTATTCAGACTCATGGG
ACTACCCCACAACCAGTGGCACACCTAAGTAAGGAAATTGATGTAGTAGC
AAAAGGCTGGCCTCACTGTTTATGGGTAGCTGTGGTGGTGGCTGTCTTAGT
GTCAGAAGCTATCAAAATAATACAAGGAAAGGATCTCACTGTCTGGACTA
CTCATGATGTAATGGCATACTAGGTGCCAAAAGAAGTTTATGGGTATCAGA
CAACCACCTGCTTAGATACCAGGGACTACTCCTGGAGGATTGGGCTTCAAG
TGCGTTTTTTGTGGCCTCAACCCTGCCACTTTTCCTCCAGAGGATGGAGAG
CCGCTTGAGCATGCTTGCCAACAGGTTGTAGGCCAGAATTATTCCACCCGA
GATGATCTCTTAGAGTACCCTTAGCTAATCCTGACCTTAACCTATATACCA
ATGGAAGTTCATTTGTGGAAAACGGGATATGAAGGGCAGGTTATGTCATAG
TTAGTGATGTAATCATACTTGCAAGTAAGCCTCTTACCCCAGGGGCCAGCA
CTCAGTTAGCAGAACTAGTCACACTTACCTTAACCTTAGAACTGGGAAAGG
GAAAAGAATAAATATGTATACAGATAGTAAGTATGCTTATCTAATCCTAC
ATGCCCATGCTGCAATATGGAAGGAAAGGGAGTTCCTAACCCCTGGGGGA
ACCCCCATTAAATACCACAAGGYAAATCATGGAGTTATTGCACGCAGTGC
AAAAACTCAAGGAGGTGGCAGTCTTACACTGCCGAAGCYATCAAAAAGGG
GAAGGAGAGGGGAGAACAGCAGCATAAGTGGTTGGCAGAGGCAGTGAAA
GACCAGCAGAGAGAAGGAGAGAGACAACGTCAACGACAGAAGGAAAGAA
GAGGAGGAGACAGAGAGGAAGAGACAGAGAGACAGTTAGTCCAAGAGAG
AGACAGAGAGAGGAAGAGACAGACAGAAAGTCCAAGAGAGAAGGAAAGA
GAGGAAGAGACCAAGGAGTCCNAGAGAGAGAAAGAGATAGAAGTAGTAA
AGAAAAAACATTGTACCCTATTCCTTTAAAAGCCGGGGTATATTTAAAACC
TATAATTGATAATTGAGTTCTTGCACCCTCCTCCAGGGGATYGCTGGGAGG
AAACCCTCAACCGATATGTGAAATTGTGGGTCGTCCCTATGTCTCAATTA
CCAGCCAATACCCCCTTGTTTTTAGTGTGAACGAGGGTGTAGAGCGCAGAC
AGGGAGACCTCTGACAATCCATACCCTTCCTATCCAAAATCCTTAACCCAG
CAGGTTTTCTAAAAGGGGATCTAAATCTTAATTAATTACCATACAAAGGTC
AAACCAGATCTAGGAGGAACTTCCTTCAGGACAGGATGATAGATGGTTCCT
CCCAGGCGATTAAAGAAAATAAAAGACACATGGGCAGCCAGTAAGTGAT
AAGGGAACACTAGTAGAAGCAGTTAGGAGAAGTTGCCTAATAATTGGTCT
ACTCCAAATGTGTGAGTTGTTCGCACTCAGCCCAAATCTTAAAGTACTTAC
AGAATTAGGGAGGAGCCATTTACACCAATTCTAAGTTAATATGGACTGGAT
GAGGTTTTATTAATAGCGAAGGAGAATTAAATCCTAAACTNACAAGGTTTT
CAACTAAAGTAAATTTTACTAAAAGCTAACAGTGTAACATGCATTATCCTA
CTACAACACACTCTCANAGGATTCCTCAGACAGTTTACAAGAAATAACAA
AATCTATCTGGTAAGGATAGTAACTACAATCCCAAATACATTCTTTGGCAG
CAGTGACTCTC
```

SEQ ID NO 48 (JLBc1)

FIG. 17

```
TCAGGGATAGCCCCCATCTATTTGATCAGGCACTAGCCCAAGATCTAGGCC
ACTTCTGAAGTCCAGGCATTCTAGTCCTTCAGTATGTGGATGATTTACTTTT
GGCTACCAGTTTGGAAGCCTCATGCCAGCAGGCTACTTGAGATCTCTTGAA
CTTTCTAGCTAATCAAGGGTGTATGGCATCTAAATTGAAAGTCCAGCTCTG
CCTACAACAAGTCAAATATCTAGGCCTAATCTTAGATAGAAGAACCAGGG
CCCTCAGCAAGGAATGAATAAAGCCTATGCTGGCTTATCGGCACCCTAAGA
CATTAAAACAATTGTGGGGGTTCCTTGGAATCACTGGCTTTTGCCGACTAT
GGATCCCTGGATAGAGTGAGATAGCCAGGCCCCCTCTATTACTCTTATCAA
GGAGACCCAGAGGGCAAATACTTATCTAGTATTATGGGNACCAGAGGCAG
AAAAAGCCTTCCAAACCTTAAAGGAGACCCTAGTACAAGCTCCAGCTTTAA
GCCTTCCCACAGGACAAANCTTCTCTTTATATGTCACAGAGAGAGCAGGAA
TAGCTCCTGGAGTCCTTACTCAGACTTTTGGACGACCCCACGGCCAGTGGC
RTACCTAAGTAAGGAAATTGATGTAGTAGCAAAAGGCTGGCCTCACTGTTT
ATGGGTAGTTGCGGCTGTGGCAGTCTTACTGTCAAAGGCTATCAAAATAAT
ACAAGGAAAGGATTTCACTATCTGGACTACTCATGAGGAAATGGCATATT
AGGTGCCAAAGGAAGTTTTTGGCTATCAGACAACCACCTGCTCAGATTCCA
GGCACTACTGATTGAGAGACCAGTGCTTTAAATATGTATGTGTGTGTGTGG
CCCTCAACCCTGCCACTGTTCTCCCAGAAGATGGAGAACCAATGAAGCATT
ACTGTCAACAAATTAGAGTCCAGAGTTATGCTGCCTGAGAGGATCTCTTAG
AAGTCCCCTTAGCTAATCCTGACCTTAACCTATATGCTGATGGAAGTTCAC
TTGTGGAGAATGGGATACGAAAGCACATTATGCCATAGTTAGTGAGGTA
ACAGTACTTGAAAGTAAGCCTATTCCCCCATGGACCAGAGCCCAGTTAGCA
GAACTAGTGGCACTTACCCAAGCCTTAGAACTAGGAAAGGGAAAAATAAT
AAATGTGTATACAGATAGCAAGTATGCTTATCTAATCCTACATGCCCATGC
TGCAGTATGGAAAGAAAGGGAGTTCCTAACCTCTGGGGGAACCCCCATTA
AATACCACAAGGCAAATCATGGAGTTATTGCATGTAGTGCAAAACCTCAA
GTAGGTGGCAGTTTTACACTGCCTGAAGCTATGGGGAAGGAGAGAGGAGA
ACAGCAGCATAAGTGGCTAGCAGAGGCAGCGAAAGACTAGCAGAGAGGA
GAGGTAGGGGAAAGACAGAAAGTCAAAGAAAAGAAGTCAAAGACAGACA
GAGAAAGAGACAGAGGGAGCCAGAGAGAAAGAAAAGAGAGAACGAAAGA
GACAGAATGTCAAAGAACAGAAGAGAGAGGCAGCGCCAGAAGAGTTAAG
AAAGTGAGAAAGAGAGATGGAAATAGTAAAGAAAAAACAGTGTACCCTAT
TCCTTTAAAAGCCAGGGTAAATTTAAAACGTATAATTTTATAATTGGAAGG
TCTTCTCCATAACCCTATAACATTAAAATACCACCTTGTTGTCAGTGTAAAC
AAGAGCATAGCCCAAAAGCACTGAGGCCACTGACAACCCATAGCCTTCCT
ATCAAAAATCCTTAACTCTGCAGGTTTCCTAACAGGGGATCTAAATCTCAA
CTAATCACCATACAATGGTCCGACCAGACCTAGGAGCGACTCCCCTCAGG
ACAGAAGGATGGATGGTTCCTCCCAGGCCATTAAGGGAAAGAGACACAAT
GGGTATTCAGTAAGTGATAAGGGAACTCTTGTAGAAGCAGTTAGGAAGATT
GCCTAATATTTGGTCTGCTCAAATGTGCCAGCTGTTTGCACTCAGCTAAAC
CTTAAATTACTTACAGAATTAGGAAGGAGCCATCTATACCAATTCTGAGTT
AATATGAGCTGAACAAGTTCTTATTAATAGCAAAGAATCATTGAAATCTCA
AACTTGCAAAGTTTTCAACAAAAGTAAAGTTTGCTGAAAGTTAGCAGTGTA
ACATGTATTATCCTAACTTCTAATCTTGTGGAAATCAGACCCTATCAGTGC
CCCTCAAAGCTGAAGTCCATCAGCATATGGCCATACAACTAATACCCCTAT
TTATAGGGTTAGGAATGGCCACTGCTACAGGAATGGGAGTAACAGGTTTAT
CTACTTCATTATCCTATTACCACACACTCTTAAAGGATTTCTCAGACAGTTT
ACAAGAAATAACAAAATCTATCCTTACTCTNTARTCCCAAATAGRTTCTTT
GGCAGCAGTGACTCTC
```

SEQ ID NO 49 (JLBc2)

FIG. 23

```
   1  TTCCTGAGTT  CTTGCACTAA  CCTCAAATGA  GAGAAGTGCC  GCCATAACTG  CAACCCAAGA
  61  GTTTGGCGAT  CCCTGGTATC  TCAGTCAGGT  CAATGACAGG  ATGACAACAG  AGGAAAGATA
 121  ATGATTCCCC  ACAGGCCAGC  AGGCAGTTCC  CAGTGTAGAC  CCTCATTAGG  ACACAGAATC
 181  AGAACATGGA  GATTGGTGCC  GCAGACATTT  GCTAACTTGC  GTGCTAGAAG  GACTAAGGAA
 241  AACTAGGAAG  ATATGAATTA  TTCAATGATG  TCCACTATAA  CACAGGGGAA  AGGAAGAAAA
 301  TCCTACTGCC  TTTCTGGAGA  GACTAAGGGA  GGCATTGAGG  AAGCATACCA  GGCAAGTGGA
 361  CATTGGAGGC  TCTGGAAAAG  GGAAAAGTTG  GGAAAAGTAT  ATGTCTAATA  GGGCTTGCTT
 421  CCAGTGTGGT  CTACAAGGAC  ACTTTAAAAA  AGATTGTCCA  ATAGAAATAA  GCCACCACCT
 481  CGTCCATGCC  CCTTATGTCA  AGGGAATCAC  TGGAAGGCCC  ACTGCCCCAG  GGGATGAAGG
 541  TCCTCTGAGT  CAGAAGCCAC  TAACCAGATG  ATCCAGCAGC  AGGACTGAGG  GTGCCCGGGG
 601  CAAGCGCCAG  CCCATGCCAT  CACCCTCACA  GAGCCCCAGG  TATGCTTGAC  CATTGAGGGT
 661  CAGAAGGGTA  CTGTCTCCTG  GACACTGGCG  GGCCTTCTCA  GTCTTACTTT  CCTGTCCTGG
 721  ACAACTGTCC  TCCAGATCTG  TCACTGTCCG  AGGGGTCCTA  GGACAGCCAG  TCACTAGATA
 781  CTTCTCCCAG  CCACTAAGTT  GTGACTGGGG  AACTTTACTC  TTCCACATGC  TTTTCTAATT
 841  ATGCCTGAAA  GCCCCACTCT  CTTGTTAGGG  GAGAGACATT  CTAGCAAAAG  CAGGGGCCAT
 901  TATACATGTG  AATATAGGAG  AAGGAACAAC  TGTTTGTTGT  CCCCTGCTTG  AGGAAGGAAT
 961  TAATCCTGAA  GTCCGGGCAA  CAGAAGGACA  ATATGGACAA  GCAAAGAATG  CCCGTCCTGT
1021  TCAAGTTAAA  CTAAAGGATT  CCACCTCCTT  TCCCTACCAA  AGGCAGTACC  CCCTCAGACC
1081  CGAGACCCAA  CAAGAACTCC  AAAAGATTGT  AAAGGACCTA  AAAGCCCAAG  GCCTAGTAAA
1141  ACCAAGCAAT  AGCCCTTGCA  AGACTCCAAT  TTTAGGAGTA  AGGAAACCCA  ACGGAC
```

SEQ ID NO 52 (GM3)

FIG. 27a

```
ATG ATC CAG CAG GAC NGA GGG TGC CCG GGG CAA GCG CCA CAT GCC ATC ACC CTC ACA GAG CCC CAG GTA TGC TTG ACC ATT GAG  90
 M   I   Q   Q   D   X   G   C   P   G   Q   A   P   H   A   I   T   L   T   E   P   Q   V   C   L   T   I   E

GGT CAG AAG GGT NAC CTC CTC GAC ACT GGC GCC TTC TCA TTT GAC TCC CAA CTA GTC TCC CTG CAA CCT GGA GGA TCT CAT GCT ACT 180
 G   Q   K   G   X   L   L   D   T   G   A   F   S   F   D   S   Q   L   V   S   L   Q   P   G   G   S   H   A   T

GTC CGA GGG GTC CTA GGA CAG CCC CTG CAG TAC AGA CTT GGG GGN TTC AGA AGA CCA CAT CCA TCC TTC TTA CTA ATA TTT TTT 270
 V   R   G   V   L   G   Q   P   L   Q   Y   R   L   G   G   F   R   R   P   H   P   S   F   L   L   I   F   F

CTA ATT ATG CCT GAA TGT AAA CTA AAA GAT CTT CTT GAG GGA ATT AAT CCC TAC AGC GCT CTT ATA GGA GAA GGA 360
 L   I   M   P   E   C   K   L   K   D   L   L   E   G   I   N   P   Y   S   A   L   I   G   E   G

ACA ACT GTT CAA GTT TGT TGT CCC CTG AAG GCA CAA GTC AGG AGC GTT GAT ACT AAG GAA AAT GAA AAG GAA 450
 T   T   V   Q   V   C   C   P   L   K   A   Q   V   R   S   V   D   T   K   E   N   E   K   E

CCT GTT CAA CTA GAC CTA AAA CTA AAA GCC CAA GTC AGG AGC GTT GAT ACT AAG GAA AAT GAA AAG GAA 450
```

SEQ ID NO 53 (POL)

FIG. 27b

SEQ ID NO 53 (POL)

FIG. 27c

```
CTC AAG GAG GTG GAA GTC TTA CAC TGC CAA AGC CAT CAG AAA AGG GAA GAG GAA CAG CAT AAG TGG CTA CAG CAA GGA AAG  2250
 L   K   E   V   E   V   L   H   C   Q   S   H   Q   K   R   E   E   E   Q   H   K   W   L   Q   Q   G   K

ACT AGC AGA AAG GAG AAA GAG ACA GAG GAG AGT CAG AGA GAG GAG ACA GAG CAC AAA GAG GGA GTC AGA GAG GAG AGA GAG  2340
 T   S   R   K   E   K   E   T   E   E   S   Q   R   E   E   T   E   H   K   E   G   V   R   E   R   R   E

AGA CAG GTC AGA GAG AGA GGA AGA GAC AAA GAA TGA .                                                              2391
 R   Q   V   R   E   R   G   R   D   K   E   E
```

SEQ ID NO 53 (POL)

FIG. 28

```
GATGCCTTTTTCTGCATCCCTGTACGTCCTGACTCTCAATTCTTGTTTGCCTTTGAAG
ATCCTTTGAACCCAACGTCTCAACTCACCTGGACTGTTTTACCCCAAGGGTTCAGGGA
TAGCCCCATCTATTTGGCCAGGCATTAGCCCAAGATGCCTTTTGCATCCCTGTACGTG
ACTCTCAATTCTTGTTTGCCTTTGCCTTTGAAGATGCTTTGAACCCAACGTCTCAACT
CACCTGGACTGTTTTACGCCAAGGGTTCAGGGATAGCCCCCATCTATTTGGC
CAGGCATTAGCCCAA
```

*SEQ ID NO 36*

Asp-Ala-Phe-Phe-Cys-Ile-Pro-Val-Arg-Pro-Asp-Ser-Gln-Phe-
Leu-Phe-Ala-Phe-Glu-Asp-Pro-Leu-Asn-Pro-Thr-Ser-Gln-Leu-
Thr-Trp-Thr-Val-Leu-Pro-Gln-Gly-Phe-Arg-Asp-Ser-Pro-His-
Leu-Phe-Gly-Gln-Ala-Leu-Ala-Gln

*SEQ ID NO 35* (POL2B)

| Sequence | SEQ ID NO |
|---|---|
| LFGQALAQ | 149 |
| HLFGQALA | 186 |
| PHLFGQAL | 185 |
| SPHLFGQA | 184 |
| DSPHLFGQ | 183 |
| RDSPHLFG | 182 |
| FRDSPHLF | 181 |
| GFRDSPHL | 180 |
| QGFRDSPH | 179 |
| PQGFRDSP | 178 |
| LPQGFRDS | 177 |
| VLPQGFRD | 176 |
| TVLPQGFR | 148 |
| WTVLPQGF | 175 |
| TWTVLPQG | 174 |
| LTWTVLPQ | 173 |
| QLTWTVLP | 172 |
| SQLTWTVL | 171 |
| TSQLTWTV | 170 |
| PTSQLTWT | 169 |
| NPTSQLTW | 168 |
| LNPTSQLT | 167 |
| PLNPTSQL | 166 |
| DPLNPTSQ | 165 |
| EDPLNPTS | 164 |
| FEDPLNPT | 163 |
| AFEDPLNP | 162 |
| FAFEDPLN | 40 |
| LFAFEDPL | 39 |
| FLFAFEDP | 161 |
| QFLFAFED | 160 |
| SQFLFAFE | 159 |
| DSQFLFAF | 158 |
| PDSQFLFA | 157 |
| RPDSQFLF | 147 |
| VRPDSQFL | 156 |
| PVRPDSQF | 155 |
| IPVRPDSQ | 154 |
| CIPVRPDS | 153 |
| FCIPVRPD | 146 |
| FFCIPVRP | 152 |
| AFFCIPVR | 151 |
| DAFFCIPV | 150 |

Cys-Ile-Pro-Val-Arg-Pro-Asp-Ser-Gln-Phe-Leu

*SEQ ID NO 37*

Val-Leu-Pro-Gln-Gly-Phe-Arg-Asp-Ser-Pro-His-Leu-Phe-Gly-
Gln-Ala-Leu-Ala

*SEQ ID NO 38*

Leu-Phe-Ala-Phe-Glu-Asp-Pro-Leu

*SEQ ID NO 39*

Phe-Ala-Phe-Glu-Asp-Pro-Leu-Asn

*SEQ ID NO 40*

FIG. 35

|    | 10<br>1234567890 | 20<br>1234567890 | 30<br>1234567890 | 40<br>1234567890 | 50<br>1234567890 |     |
|----|---|---|---|---|---|-----|
|    | CTTCCCCAAC<br>L P Q L<br> F P N<br>  S P T | TAATAAGGAC<br> I R T<br>. . G P<br> N K D | CCCCCTTTCA<br> P L S<br>P F Q<br> P P F N | ACCCAAACAG<br>T Q T V<br> P K Q<br>  P N S | TCCAAAAGGA<br> Q K D<br>S K R T<br> P K G | 50  |
|    | CATAGACAAA<br>I D K<br>. T K<br> H R Q R | GGAGTAAACA<br>G V N N<br> E . T<br>  S K Q | ATGAACCAAA<br> E P K<br>M N Q R<br> . T K | GAGTGCCAAT<br> S A N<br>V P I<br> E C Q Y | ATTCCCTGGT<br>I P W L<br> F P G<br>  S L V | 100 |
|    | TATGCACCCT<br> C T L<br>Y A P S<br> M H P | CCAAGCGGTG<br> Q A V<br> K R W<br>P S G G | GGAGAAGAAT<br>G E E F<br> E K N<br>  R R I | TCGGCCCAGC<br> G P A<br>S A Q P<br> R P S | CAGAGTGCAT<br>Q S A C<br> R V H<br> E C M | 150 |
|    | GTACCTTTTT<br>V P F S<br> Y L F<br>  T F F | CTCTCTCACA<br> L S H<br>L S H T<br> S L T | CTTGAAGCAA<br> L K Q<br>. S K<br>L E A N | ATTAAAATAG<br>I K I D<br> L K .<br>  . N R | ACNTAGGTNA<br> X G X<br>T . V N<br> X R X | 200 |
|    | ATTNTCAGAT<br> X S D<br> X Q I<br>I X R . | AGCCCTGATG<br>S P D G<br> A L M<br>  P . W | GYTATATTGA<br> Y I D<br>X I L M<br> L Y . | TGTTTTACAA<br>V L Q<br> F Y K<br> C F T R | GGATTAGGAC<br>G L G Q<br> D . D<br> I R T | 250 |
|    | AATCCTTTGA<br> S F D<br>N P L I<br>I L . | TCTGACATGG<br>L T W<br> . H G<br>S D M E | AGAGATATAA<br>R D I I<br> E I .<br> R Y N | TATTACTGCT<br> L L<br>Y Y C .<br> I T A | AAATCAGACG<br>N Q T<br> I R R<br>K S D A | 300 |
|    | CTAACCTCAA<br>L T S N<br> . P Q<br>N L K | ATGAGAGAAG<br> E R S<br>M R E V<br> . E K | TGCTGCCATA<br> A A I<br> L P .<br>C C H N | ACTGGAGCCC<br>T G A R<br> L E P<br>W S P | GAGAGTTTGG<br> E F G<br>E S L A<br> R V W | 350 |
|    | CAATCTCTGG<br>N L W<br> I S G<br>Q S L V | TATCTCAGTC<br>Y L S Q<br> I S V<br>S Q S | AGGTCAATGA<br> V N D<br>R S M I<br>G Q . | TAGGATGACA<br>R M T<br> G . Q<br>. D D N | ACGGAGGAAA<br>T E E R<br> R R K<br> G G K | 400 |
|    | GAGAACGATT<br> E R F<br>E N D S<br>R T I | CCCCACAGGG<br> P T G<br>P Q G<br>P H R A | CAGCAGGCAG<br>Q Q A V<br> S R Q<br> A G S | TTCCCAGTGT<br> P S V<br>F P V .<br> S Q C | AGCTCCTCAT<br> A P H<br> L L I<br>S S S L | 450 |
|    | TGGGACACAG<br>W D T E<br> G T Q<br> G H R | AATCAGAACA<br> S E H<br>N Q N M<br> I R T | TGGAGATTGG<br> G D W<br> E I G<br>W R L V | TGCCGCAGAC<br>C R R H<br> A A D<br> P Q T | ATTTA<br> L<br>I<br>F | 495 |

SEQ ID NO 55

FIG. 36

| 10<br>1234567890 | 20<br>1234567890 | 30<br>1234567890 | 40<br>1234567890 | 50<br>1234567890 | |
|---|---|---|---|---|---|
| CTTCCCCAAC<br>L P Q L | TAATAAGGAC<br>I R T | CCCCCTTTCA<br>P L S | ACCCAAACAG<br>T Q T V | TCCAAAAGGA<br>Q K D | 50 |
| CATAGACAAA<br>I D K | GGAGTAAACA<br>G V N N | ATGAACCAAA<br>E P K | GAGTGCCAAT<br>S A N | ATTCCCTGGT<br>I P W L | 100 |
| TATGCACCCT<br>C T L | CCAAGCGGTG<br>Q A V | GGAGAAGAAT<br>G E E F | TCGGCCCAGC<br>G P A | CAGAGTGCAT<br>R V H | 150 |
| GTACCTTTTT<br>V P F S | CTCTCTCACA<br>L S H | CTTGAAGCAA<br>L K Q | ATTAAAATAG<br>I K I D | ACCTAGGTAA<br>L G K | 200 |
| ATTCTCAGAT<br>F S D | AGCCCTGATG<br>S P D G | GYTATATTGA<br>Y I D | TGTTTTACAA<br>V L Q | GGATTAGGAC<br>G L G Q | 250 |
| AATCCTTTGA<br>S F D | TCTGACATGG<br>L T W | AGAGATATAA<br>R D I I | TATTACTGCT<br>L L L | AAATCAGACG<br>N Q T | 300 |
| CTAACCTCAA<br>L T S N | ATGAGAGAAG<br>E R S | TGCTGCCATA<br>A A I | ACTGGAGCCC<br>T G A R | GAGAGTTTGG<br>E F G | 350 |
| CAATCTCTGG<br>N L W | TATCTCAGTC<br>Y L S Q | AGGTCAATGA<br>V N D | TAGGATGACA<br>R M T | ACGGAGGAAA<br>T E E R | 400 |
| GAGAACGATT<br>E R F | CCCCACAGGG<br>P T G | CAGCAGGCAG<br>Q Q A V | TTCCCAGTGT<br>P S V | AGCTCCTCAT<br>A P H | 450 |
| TGGGACACAG<br>W D T E | AATCAGAACA<br>S E H | TGGAGATTGG<br>G D W | TGCCGCAGAC<br>C R R H | ATTTACAACT<br>L Q L | 500 |
| TGCGTGCTAN<br>A C X | AAGGACTNAG<br>K D X G | GAAAACTAGG<br>K L G | AAGACTANGA<br>R L X | ATTATTCAAN<br>I I Q X | 550 |
| GATGTCCACT<br>C P L | ANNCACAGG<br>X H R | GGAAAGGAAG<br>G K E E | AAAATCCTAC<br>N P T | TGCCTTTCTG<br>A F L | 600 |
| GAGAGACTAA<br>E R L R | GGGAGGCATT<br>E A L | GAGGAAGCAT<br>R K H | ACCAGGCAAG<br>T R Q V | TGGACATTGG<br>D I G | 650 |
| AGGCTCTGGA<br>G S G | AAAGGGAAAA<br>K G K S | GTTGGGCAAA<br>W A N | TTATATGCCT<br>Y M P | AATAGGGCTT<br>N R A C | 700 |
| GCTTCCAGTG<br>F Q C | CAGTCTACAA<br>S L Q | GGACGCTTTA<br>G R F R | GAAAAGATTG<br>K D C | TCCAAGTAGA<br>P S R | 750 |
| AATAAGCCGC<br>N K P P | CCCTCGTCCA<br>L V H | TGCCCCTTAT<br>A P Y | GTCAAGGGAA<br>V K G I | TCACTGGAAG<br>T G R | 800 |
| GCCTACTGCC<br>P T A | CCAGGGGACG<br>P G D E | AAGGTCCTCT<br>G P L | GAGTCAGAAG<br>S Q K | CCACTAACCT<br>P L T . | 850 |
| GA | | | | | 852 |

SEQ ID NO 82

FIG. 38a

```
          10         20         30         40         50
  1234567890 1234567890 1234567890 1234567890 1234567890
  AAGGAAACTC AGAAAGCCAA TACCCATTTA GTAAGATGGA CACCAGAAGC    50
   K  E  T  Q   K  A  N    T  H  L    V  R  W  T   P  E  A
    R  K  L    R  K  P  I   P  I  .    .  D  G   H  Q  K  Q
     G  N  S    E  S  Q    Y  P  F  S   K  M  D    T  R  S

AGAAGCAGCT TTCCAGGCCC TAAAGAAATC CCTAACCCAA GCCCCAGTGT   100
   E  A  A    F  Q  A  L   K  K  S    L  T  Q   A  P  V  L
    K  Q  L    S  R  P    .  R  N  P   .  P  K    P  Q  C
     R  S  S  F   P  G  P    K  E  I    P  N  P  S   P  S  V

TAAGCTTGCC AACGGGGCAA GACTTTTCTT TATATGTCAC AGAAAAACAG   150
    S  L  P    T  G  Q   D  F  S  L   Y  V  T    E  K  Q
   .  A  C  Q   R  G  K    T  F  L    Y  M  S  Q   K  N  R
    K  L  A    N  G  A  R   L  F  F    I  C  H    R  K  T  G

GAATAGCTCT AGGAGTCCTT ACACAGGTCC AAGGGACAAG CTTGCAACCT   200
   E  .  L  .    E  S  L    H  R  S   K  G  Q  A   C  N  L
    N  S  S    R  S  P  Y    T  G  P   R  D  K    L  A  T  C
     I  A  L    G  V  L    T  Q  V  Q   G  T  S    L  Q  P

GTGGCATACC TGAGTAAGGA AACTGATGTA NTGGCAAAGG GTTGGCCTCA   250
   W  H  T    .  V  R  K   L  M  X    W  Q  R    V  G  L  I
    G  I  P    E  .  G    N  .  C  X   G  K  G    L  A  S
   V  A  Y  L   S  K  E    T  D  V    X  A  K  G    W  P  H

TTGTTTACAG GTAGGGCAGC AGTAGCAGTC TTAGTTTCTG AAACAGTTAA   300
    V  Y  R   .  G  S     S  S  S  L   S  F  .    N  S  .
   L  F  T  G   R  A  A    V  A  V    L  V  S  E   T  V  K
    C  L  Q    V  G  Q  Q   .  Q  S    .  F  L    K  Q  L  K

AATAATACAG GGAAGAGATC TTACTGTGTG GACATCTCAT GATGTGAACG   350
   N  N  T  G   K  R  S    Y  C  V    D  I  S  .   C  E  R
    I  I  Q    G  R  D  L   T  V  W    T  S  H    D  V  N  G
    .  Y  R    E  E  I    L  L  C  G   H  L  M    M  .  T

GCATACTCAC TGCTAAAGAG GACTTGTGGC TGTCAGACAA CCATTTACTT   400
   H  T  H    C  .  R  G   L  V  A    V  R  Q    P  F  T
    I  L  T    A  K  E    D  L  W  L   S  D  N    H  L  L
   A  Y  S  L   L  K  R    T  C  G    C  Q  T  T   I  Y  L

AAATAGCAGG TTCTATTACT TGAAGTGCCA GTGCTGCGAC TGCACATTTG   450
   I  A  G    S  I  T    .  S  A  S   A  A  T    A  H  L
   K  .  Q  V   L  L  L    E  V  P    V  L  R  L   H  I  C
    N  S  R    F  Y  Y  L   K  C  Q    C  C  D    C  T  F  V

TGCAACTCTT AACCCAGCCA CATTTCTTCC AGACAATGAA GAAAAGATAG   500
   C  N  S  .   P  S  H    I  S  S    R  Q  .  R   K  D  R
   A  T  L    N  P  A  T   F  L  P    D  N  E    E  K  I  E
    Q  L  L    T  Q  P    H  F  F  Q   T  M  K    K  R  .
```

SEQ ID NO 57

FIG. 38b

| 10<br>1234567890 | 20<br>1234567890 | 30<br>1234567890 | 40<br>1234567890 | 50<br>1234567890 | |
|---|---|---|---|---|---|
| AACATAACTG<br> T . L<br>H N C<br>N I T V | TCAACAAGTA<br> S T S N<br>Q Q V<br>N K . | ATTGCTCAAA<br> C S N<br>I A Q T<br>L L K | CCTATGCTGC<br> L C C<br>Y A A<br>P M L L | TCGAGGGGAC<br> S R G P<br>R G D<br>E G T | 550 |
| CTTCTAGAGG<br> S R G<br>L L E V<br>F . R | TTCCCTTGAC<br> S L D<br>P L T<br>F P . L | TGATCCCGAC<br> . S R P<br>D P D<br>I P T | CTCAACTTGT<br> Q L V<br>L N L Y<br>S T C | ATACTGATGG<br> Y . W<br>T D G<br>I L M E | 600 |
| AAGTTCCTTG<br> K F L G<br>S S L<br>V P W | GCAGAAAAAG<br> R K R<br>A E K G<br>Q K K | GACTTTGAAA<br> T L K<br>L . K<br>D F E K | AGCGGGGTAT<br> S G V C<br>A G Y<br>R G M | GCAGTGATCA<br> S D Q<br>A V I S<br>Q . S | 650 |
| GTGATAATGG<br> . . W<br>D N G<br>V I M E | AATACTTGAA<br> N T . K<br>I L E<br>Y L K | AGTAATCGCC<br> . S P<br>S N R L<br>V I A | TCACTCCAGG<br> H S R<br>T P G<br>S L Q E | AACTAGTGCT<br> N . C S<br>T S A<br>L V L | 700 |
| CACCTGGCAG<br> P G R<br>H L A E<br>T W Q | AACTAATAGC<br> T N S<br>L I A<br>N . . P | CCTCACTTGG<br> P H L G<br>L T W<br>S L G | GCACTAGAAT<br> T R I<br>A L E L<br>H . N | TAGGAGAAGG<br> R R R<br>G E G<br>. E K E | 750 |
| AAAAAGGGTA<br> K K G K<br>K R V<br>K G . | AATATATATT<br> Y I F<br>N I Y S<br>I Y I | CAGACTCTAA<br> R L .<br>D S K<br>Q T L S | GTATGCTTAC<br> V C L P<br>Y A Y<br>M L T | CTAGTCCTCC<br> S P P<br>L V L H<br>. S S | 800 |
| ATGCCCATGC<br> C P C<br>A H A<br>M P M Q | AGCAATATGG<br> S N M E<br>A I W<br>Q Y G | AGAGAGAGGG<br> R E G<br>R E R E<br>E R G | AATTCCTAAC<br> I P N<br>F L T<br>N S . L | TTCTGAGGGA<br> F . G N<br>S E G<br>L R E | 850 |
| ACACCTATCA<br> T Y Q<br>T P I N<br>H L S | ACCATCAGGG<br> P S G<br>H Q G<br>T I R E | AAGCCATTAG<br> K P L G<br>S H .<br>A I R | GAGATTATTA<br> D Y Y<br>E I I I<br>R L L | TTGGCTGTAC<br> W L Y<br>G C T<br>L A V Q | 900 |
| AGAAACCTAA<br> R N L K<br>E T .<br>K P K | AGAGGTGGCA<br> R W Q<br>R G G S<br>E V A | GTCTTACACT<br> S Y T<br>L T L<br>V L H C | GCCAGGGTCA<br> A R V I<br>P G S<br>Q G H | TCAGGAAGAA<br> R K K<br>S G R R<br>Q E E | 950 |
| GAGGAAAGGG<br> R K G<br>G K G<br>E E R E | AAATAGAAGG<br> K . K A<br>N R R<br>I E G | CAATCGCCAA<br> I A K<br>Q S P S<br>N R Q | GCGGATATTG<br> R I L<br>G Y .<br>A D I E | AAGCAAAAAA<br> K Q K K<br>S K K<br>A K K | 1000 |

SEQ ID NO 57

FIG. 38c

|  | 10<br>1234567890 | 20<br>1234567890 | 30<br>1234567890 | 40<br>1234567890 | 50<br>1234567890 |  |
|---|---|---|---|---|---|---|
| | AGCCGCAAGG | CAGGACTCTC | CATTAGAAAT | GCTTATAGAA | GGACCCCTAG | 1050 |
| |   P  Q  G |   R  T  L | H  .  K  C |   L  .  K |   D  P  . | |
| | S  R  K  A |   G  L  S |   I  R  N | A  Y  R  R |   T  P  S | |
| | A  A  R | Q  D  S  P |   L  E  M |   L  I  E | G  P  L  V | |
| | TATGGGGTAA | TCCCCTCTGG | GAAACCAAGC | CCCAGTACTC | AGCAGGAAAA | 1100 |
| | Y  G  V  I |   P  S  G |   K  P  S |   P  S  T  Q |   Q  E  K | |
| | M  G  . | S  P  L  G | N  Q  A | P  V  L | S  R  K  N | |
| | W  G  N |   P  L  W | E  T  K  P |   Q  Y  S |   A  G  K | |
| | ATAGAATAGG | AAACCTCACA | AGGACATACT | TTCCTCCCCT | CCAGATGGCT | 1150 |
| | .  N  R | K  P  H  K |   D  I  L |   S  S  P |   P  D  G  . | |
| |   R  I  G | N  L  T | R  T  Y  F | P  P  L | Q  M  A | |
| | I  E  .  E |   T  S  Q |   G  H  T | F  L  P  S |   R  W  L | |
| | AGCCACTGAG | GAAGGAA | | | | 1167 |
| |   P  L  R | K  E | | | | |
| | S  H  .  G |   R | | | | |
| | A  T  E | E  G | | | | |

SEQ ID NO 57

FIG. 39a

|  | 10<br>1234567890 | 20<br>1234567890 | 30<br>1234567890 | 40<br>1234567890 | 50<br>1234567890 |  |
|---|---|---|---|---|---|---|
|  | AACTTGCGTG<br>N L R A<br>T C V<br>L A C | CTAGAAGGAC<br>R R T<br>L E G L<br>. K D | TAAGGAAAAC<br>K E N<br>R K T<br>. G K L | TAGGAAGACT<br>. E D Y<br>R K T<br>G R L | ATGAATTATT<br>E L F<br>M N Y S<br>. I I | 50 |
|  | CAATGATGTC<br>N D V<br>M M S<br>Q . C P | CACTATAACA<br>H Y N T<br>T I T<br>L . H | CAGGGGAAAG<br>G E R<br>Q G K G<br>R G K | GAAGAAAATC<br>K K I<br>R K S<br>E E N P | CTACTGCCTT<br>L L P F<br>Y C L<br>T A F | 100 |
|  | TCTGGAGAGA<br>W R D<br>S G E T<br>L E R | CTAAGGGAGG<br>. G R<br>K G G<br>L R E A | CATTGAGGAA<br>H . G S<br>I E E<br>L R K | GCATACCAGG<br>I P G<br>A Y Q A<br>H T R | CAAGTGGACA<br>K W T<br>S G H<br>Q V D I | 150 |
|  | TTGGAGGCTC<br>L E A L<br>W R L<br>G G S | TGGAAAAGGG<br>E K G<br>W K R E<br>G K G | AAAAGTTGGG<br>K V G<br>K L G<br>K S W A | CAAATTGAAT<br>Q I E C<br>K L N<br>N . M | GCCTAATAGG<br>L I G<br>A . . G<br>P N R | 200 |
|  | GCTTGCTTCC<br>L A S<br>L L P<br>A C F Q | AGTGCAGTCT<br>S A V Y<br>V Q S<br>C S L | ACAAGGACGC<br>K D A<br>T R T L<br>Q G R | TTTAGAAAAG<br>L E K<br>. K R<br>F R K D | ATTGTCCAAG<br>I V Q V<br>L S K<br>C P S | 250 |
|  | TAGAAATAAG<br>E I S<br>. K . A<br>R N K | CCGCCCCTCG<br>R P S<br>A P R<br>P P L V | TCCATGCCCC<br>S M P L<br>P C P<br>H A P | TTATGTCAAG<br>M S R<br>L C Q G<br>Y V K | GGAATCACTG<br>E S L<br>N H W<br>G I T G | 300 |
|  | GAAGGCTAC<br>E G L L<br>K A Y<br>R P T | TGCCCCAGGG<br>P Q G<br>C P R G<br>A P G | GACGAAGGTC<br>T K V<br>R R S<br>D E G P | CTCTGAGTCA<br>L . V R<br>S E S<br>L S Q | GAAGCCACTA<br>S H .<br>E A T N<br>K P L | 350 |
|  | ACCTGATGAT<br>P D D<br>L M I<br>T . . S | CCAGCAGCAG<br>P A A G<br>Q Q Q<br>S S R | GACTGAGGGT<br>L R V<br>D . G C<br>T E G | GCCCGGGGCA<br>P G A<br>P G Q<br>A R G K | AGTGCCAGCC<br>S A S P<br>V P A<br>C Q P | 400 |
|  | CATGCCATCA<br>C H H<br>H A I T<br>M P S | CCCTCAGAGC<br>P Q S<br>L R A<br>P S E P | CCCGGGTATG<br>P G Y V<br>P G M<br>R V C | TTTGACCATT<br>. P L<br>F D H .<br>L T I | GAGAGCCAGG<br>R A R<br>E P G<br>E S Q E | 450 |
|  | AAGTTAACTG<br>K L T V<br>S . L<br>V N C | TCTCCTGGAC<br>S W T<br>S P G H<br>L L D | ACTGGCGCAG<br>L A Q<br>W R S<br>T G A A | CCTTCTCAGT<br>P S Q S<br>L L S<br>F S V | CTTACTTTCC<br>Y F P<br>L T F L<br>L L S | 500 |

SEQ ID NO 83

FIG. 39b

|  | 10<br>1234567890 | 20<br>1234567890 | 30<br>1234567890 | 40<br>1234567890 | 50<br>1234567890 |  |
|---|---|---|---|---|---|---|
|  | TGTCCCAGAC<br>V P D<br>S Q T<br>C P R Q | AATTGTCCTC<br>N C P P<br>I V L<br>L S S | CAGATCTGTC<br>D L S<br>Q I C H<br>R S V | ACTATCCGAG<br>L S E<br>Y P R<br>T I R G | GGGTCCTAAG<br>G S .  D<br>G P K<br>V L R | 550 |
|  | ACAGCCAGTC<br>S Q S<br>T A S H<br>Q P V | ACTACATACT<br>L H T<br>Y I L<br>T T Y F | TCTCTCAGCC<br>S L S H<br>L S A<br>S Q P | ACTAAGTTGT<br>.  V V<br>T K L .<br>L S C | GACTGGGGAA<br>T G E<br>L G N<br>D W G T | 600 |
|  | CTTTACTCTT<br>L Y S F<br>F T L<br>L L F | TTCACATGCT<br>H M L<br>F T C F<br>S H A | TTTCTAATTA<br>F . L<br>S N Y<br>F L I M | TGCCTGAAAG<br>C L K A<br>A . K<br>P E S | CCCCACTCCC<br>P L P<br>P H S L<br>P T P | 650 |
|  | TTGTTAGGGA<br>C .  G<br>V R E<br>L L G R | GAGACATTTT<br>E T F .<br>R H F<br>D I L | AGCAAAAGCA<br>Q K Q<br>S K S R<br>A K A | GGGGCCATTA<br>G P L<br>G H Y<br>G A I I | TACACCTGAA<br>Y T .  T<br>T P E<br>H L N | 700 |
|  | CATAGGAAAA<br>.  E K<br>H R K R<br>I G K | GGAATACCCA<br>E Y P<br>N T H<br>G I P I | TTTGCTGTCC<br>F A V P<br>L L S<br>C C P | CCTGCTTGAG<br>C L R<br>P A .  G<br>L L E | GAAGGAATTA<br>K E L<br>R N .<br>E G I N | 750 |
|  | ATCCTGAAGT<br>I L K S<br>S .  S<br>P E V | CTGGGCAATA<br>G Q .<br>L G N R<br>W A I | GAAGGACAAT<br>K D N<br>R T I<br>E G Q Y | ATGGACAAGC<br>M D K Q<br>W T S<br>G Q A | AAAGAATGCC<br>R M P<br>K E C P<br>K N A | 800 |
|  | CGTCCTGTTC<br>V L F<br>S C S<br>R P V Q | AAGTTAAACT<br>K L N .<br>S .  T<br>V K L | AAAGGATTCT<br>R I L<br>K G F C<br>K D S | GCCTCCTTTC<br>P P F<br>L L S<br>A S F P | CCTACCAAAG<br>P T K G<br>L P K<br>Y Q R | 850 |
|  | GAAGTACCCT<br>S T L<br>E V P S<br>K Y P | CTTAGACCCG<br>L D P<br>.  T R<br>L R P E | AGGCCCTACA<br>R P Y<br>G P T<br>A L Q | AGGACTCAAA<br>D S K<br>R T Q K<br>G L K | AGATTGTTAA<br>D C .<br>I V K<br>R L L R | 900 |
|  | GGACCTAAAA<br>G P K S<br>D L K<br>T .  K | GCCCAAGGCC<br>P R P<br>A Q G L<br>P K A | TAGTAAAACC<br>S K T<br>V K P<br>.  N H | ATGCAGTAGC<br>M Q .  P<br>C S S<br>A V A | CCCTGCAATA<br>L Q Y<br>P C N T<br>P A I | 950 |
|  | CTCCAATTTT<br>S N F<br>P I L<br>L Q F . | AGGAGTAAGG<br>R S K E<br>G V R<br>E .  G | AAACCCAACG<br>T Q R<br>K P N<br>N P T | GACAGTGGAG<br>T V E<br>Q W R<br>D S G G | GTTAGTGCAA<br>V S A R<br>L V Q<br>.  C K | 1000 |

SEQ ID NO 83

FIG. 39c

```
          10         20         30         40         50
     1234567890 1234567890 1234567890 1234567890 1234567890
     GATCTCAGGA TTATTAATGA GGCTGTTTTT CCTCTATACC CAGCTGTATC    1050
       S Q D      Y . .      G C F S    S I P      S C I
     D L R I    I N E      A V F      P L Y P    A V S
     I S G      L L M R    L F F      L Y T      Q L Y L

TAGCCCTTAT ACTCTGCTTT CCCTAATACC AGAGGAAGCA GAGTAGTTTA    1100
       . P L Y    S A F      P N T      R G S R    V V Y
     S P Y      T L L S    L I P      E E A      E . F T
     A L I      L C F      P . Y Q    R K Q      S S L

CAGTCCTGGA CCTTAAGGAT GCCTCTTTCT GCATCCCTGT ACATCCTGAT    1150
       S P G      P . G C    L F L      H P C      T S . F
     V L D      L K D      A S F C    I P V      H P D
     Q S W T    L R M      P L S      A S L Y    I L I

TCTCAATTCT TGTTTGTCTT TGAAGATCCT TTGAACCCAA TGTCTCAATT    1200
       S I L      V C L      . R S F    E P N      V S I
     S Q F L    F V F      E D P      L N P M    S Q F
     L N S      C L S L    K I L      . T Q      C L N S

CACCTGGACT GTTTTACCCC AGGGGTTCCG GGATAGCCCC CATCTATTTG    1250
       H L D C    F T P      G V P      G . P P    S I W
     T W T      V L P Q    G F R      D S P      H L F G
     P G L      F Y P      R G S G    I A P      I Y L

GCCAGGCATT AGCCCAAGAC TTGAGCCAAT TCTCATACCT GGACATCTTG    1300
       P G I      S P R L    E P I      L I P      G H L V
     Q A L      A Q D      L S Q F    S Y L      D I L
     A R H .    P K T      . A N      S H T W    T S C

TCCTTCGGTA TGGGATGATT TAATTTTAGC CACCCGTTCA GAAACCTTGT    1350
       L R Y      G M I      . F . P    P V Q      K P C
     S F G M    G . F      N F S      H P F R    N L V
     P S V      W D D L    I L A      T R S      E T L C

GCCATCAAGC CACCCAAGCG TTCTTAAATT TCCTCACTCC GTGTGGCTAC    1400
       A I K P    P K R      S . I      S S L R    V A T
     P S S      H P S V    L K F      P H S      V W L Q
     H Q A      T Q A      F L N F    L T P      C G Y

AAGGTTTCCA AACCAAAGGC TCAGCTCTGC TCACAGCAGG TTAAATACTT    1450
       R F P      N Q R L    S S A      H S R      L N T .
     G F Q      T K G      S A L L    T A G      . I L
     K V S K    P K A      Q L C      S Q Q V    K Y L

AGGGTTAAAA TTATCCAAAG GCACCAGGGC CCTCTGTGAG GAATGTATCC    1500
       G . N      Y P K      A P G P    S V R      N V S
     R V K I    I Q R      H Q G      P L . G    M Y P
     G L K      L S K G    T R A      L C E      E C I Q
```

SEQ ID NO 83

FIG. 39d

```
         10         20         30         40         50
 1234567890 1234567890 1234567890 1234567890 1234567890
 AACCTGTACT GGCTTATCTT CATCCCAAAA CCCTAAAGCA ACTAAGAAGG          1550
 N  L  Y  W  L  I  F    I  P  K    P  .  S  N    .  E  G
  T  C  T    G  L  S  S    S  Q  N    P  K  A    T  K  K  V
   P  V  L    A  Y  L    H  P  K  T    L  K  Q    L  R  R

TCCTTGGCAT AACAGGTTTC TGCCGAA                                  1577
 P  W  H    N  R  F  L  P
  L  G  I    T  G  F    C  R
   S  L  A  .  Q  V  S    A  E
```

SEQ ID NO 83

FIG. 40

|  | 10<br>1234567890 | 20<br>1234567890 | 30<br>1234567890 | 40<br>1234567890 | 50<br>1234567890 |  |
|---|---|---|---|---|---|---|
|  | TCCAGCAGCA<br>S  S  S  R | GGACTGAGGG<br>T  E  G | TGCCCGGGGC<br>A  R  G | AAGTGCCAGC<br>K  C  Q  P | CCATGCCATC<br>M  P  S | 50 |
|  | ACCCTCAGAG<br>P  S  E | CCCCGGGTAT<br>P  R  V  C | GTTTGACCAT<br>L  T  I | TGAGAGCCAG<br>E  S  Q | GAAGTTAACT<br>E  V  N  C | 100 |
|  | GTCTCCTGGA<br>L  L  D | CACTGGCGCA<br>T  G  A | GCCTTCTCAG<br>A  F  S  V | TCTTACTTTC<br>L  L  S | CTGTCCCAGA<br>C  P  R | 150 |
|  | CAATTGTCCT<br>Q  L  S  S | CCAGATCTGT<br>R  S  V | CACTATCCGA<br>T  I  R | GGGGTCCTAA<br>G  V  L  R | GACAGCCAGT<br>Q  P  V | 200 |
|  | CACTACATAC<br>T  T  Y | TTCTCTCAGC<br>F  S  Q  P | CACTAAGTTG<br>L  S  C | TGACTGGGGA<br>D  W  G | ACTTTACTCT<br>T  L  L  F | 250 |
|  | TTTCACATGC<br>S  H  A | TTTTCTAATT<br>F  L  I | ATGCCTGAAA<br>M  P  E  S | GCCCCACTCC<br>P  T  P | CTTGTTAGGG<br>L  L  G | 300 |
|  | AGAGACATTT<br>R  D  I  L | TAGCAAAAGC<br>A  K  A | AGGGGCCATT<br>G  A  I | ATACACCTGA<br>I  H  L  N | ACATAGGAAA<br>I  G  K | 350 |
|  | AGGAATACCC<br>G  I  P | ATTTGCTGTC<br>I  C  C  P | CCCTGCTTGA<br>L  L  E | GGAAGGAATT<br>E  G  I | AATCCTGAAG<br>N  P  E  V | 400 |
|  | TCTGGGCAAT<br>W  A  I | AGAAGGACAA<br>E  G  Q | TATGGACAAG<br>Y  G  Q  A | CAAAGAATGC<br>K  N  A | CCGTCCTGTT<br>R  P  V | 450 |
|  | CAAGTTAAAC<br>Q  V  K  L | TAAAGGATTC<br>K  D  S | TGCCTCCTTT<br>A  S  F | CCCTACCAAA<br>P  Y  Q  R | GGAAGTACCC<br>K  Y  P | 500 |
|  | TCTTAGACCC<br>L  R  P | GAGGCCCTAC<br>E  A  L  Q | AAGGACTCAA<br>G  L  K | AAGATTGTTA<br>R  L  L | AGGACCT<br>R  T | 547 |

SEQ ID NO 84

FIG. 44

```
PAN-UO        5'-ltggaaagtgttacccc-3'  (SEQ ID NO: 187)
                   c g  a PAN-UI        5'-lagtgttacccaagg-3'   (SEQ ID NO: 188)
                   c g a  g
                                                               c    g g
PAN-DI                                                 3'-atgtacctactgtgac-5'
                                                (SEQ ID NO: 189)

HTLV-1   tggaaagtactacccaagg gtttaaaatagtcccaccctgttcgaaatgcagctggccatatcctgcagccattcggcaagcttcccccaatgactattcttcag  tacatgatgacattctc
         W K V L P Q  G  F K N S P T L F E M Q L A H I L Q P I R Q A F P Q C T I L Q                                     Y M D D I L
                                                     (SEQ ID NO: 190)

HIV-1    tacaatgtgcttccacaggg atggaaggatcacccagcaatattccaagtgcatgacaaagtagcattagagccttttaaaaaatccagacatagttatctatcaa  tacatgatgatttgtat
         Y N V L P Q  G  W K G S P A I F Q S S M T K I L E P F K K Q N P D I V I Y Q                                     Y M D D L Y
                                                     (SEQ ID NO: 191)

MoMLV    tggaccagactcccacaggg tttcaaaaacagtcccacccctgtttgatgaggcactgcacagagacttacggcagatccagcactcgatcctgctacag        tacgtgatgactactg
         W T R L P Q  G  F K N S P T L F D E A L H R D L L A D F R I Q H P D L I L Q                                     Y V D D L L
                                                     (SEQ ID NO: 192)

MPMV     tggaaggttttaccacaagg tatggccaacagtcctacttatgtgccacagccataacaataatgcttagacatgtatattatacat                       tacatgatgacatcca
         W K V L P Q  G  M A N S P T L C Q K Y V A T A I H K V R H A W K Q M Y I I H                                     Y M D D I L
                                                     (SEQ ID NO: 193)

ERV9     tggatggtcttgccccaagg gtttagggatagccctcatctgttggtcaggccctagccaaagatctagccacttctcaagtccagc-----actctgtccttcaa   tatgttgatgattactt
         W M V L P Q  G  F R D S P H L F G Q A L A K D L G H F S S P G - - T L V L Q                                     Y V D D L L
                                                     (SEQ ID NO: 194)

MSRV-cpol                    gttcagggatagcccccatatttggccaggcattagccagacttgagcccaagattctcatatctggac-----actcttgtccttcag
                             F R D S P H L F G Q A L A Q D L S Q F S Y L D - - T L V L Q
                                                     K                              Y                                            R
                                                                                                                                  W
                                                     (SEQ ID NO: 195)

DpV1     Perox-5'-catctittggicaggcaitagc-3'  (SEQ ID NO: 196)

CpV1B    5'-cttgagccagttctcatacctgga-3'  (SEQ ID NO: 197)
```

FIG. 46A

```
          TCCAGCAGCA GGACTGAGGG TGCCCGGGGC AAGTGCCAGC CCATGCCATC    50
                          G    A  R  G    K  C  Q  P    M  P  S
P
R         GCCCTCAGAG CCCCGGGTAT GTTTGACCAT TGAGAGCCAG GAAGTTAACT   100
O          P  S  E    P  R  V  C  L  T  I  E  S  Q    E  V  N  C
T
E         GTCTCCTGGA CACTGGCGCA GCCTTCTCAG TCTTACTTTC CTGTCCCAGA   150
A          L  L  D   T  G  A    A  F  S    V  L  L  S  C  P  R
S
E         CAATTATCCT CCAGATCTGT CACTATCCGA GGGGTCCTAG GACAGCCAGT   200
           Q  L  S  S    R  S  V   T  I  R    G  V  L  G  Q  P  V

CACTACATAC TTCTCTCAGC CACTAAGTTG TGACTGGGGA ACTTTACTCT   250
           T  T  Y    F  S  Q  P    L  S  C    D  W  G    T  L  L  F

TTTCACATGC TTTTCTAATT ATGCCTGAAA GCCCCACTCC CTTGTTAGGG   300
           S  H  A    F  L  I    M  P  E  S    P  T  P    L  L  G

AGAGACATTC TAGCAAAAGC AGGGGCCATT ATACACCTGA ACATAGGAAA    350
           R  D  I  L    A  K  A    G  A  I    I  H  L  N│ I  G  K
         ┌─────────────────────────────────────────────────┤
         │AGGAATACCC ATTTGCTGTC CCTGCTTGA GGAAGGAATT AATCCTGAAG   400
         │ G  I  P    I  C  C    P  L  L  E    E  G  I    N  P  E  V

│TCTGGGCAAT AGAAGGACAA TATGGACAAG CAAAGAATGC CCGTCCTGTT   450
         │  W  A  I    E  G  Q    Y  G  Q    K  N  A    R  P  V

│CAAGTTAAAC TAAAGGATTC TGCCTCCTTT CCCTACCAAA GGAAGTACCC   500
         │Q  V  K  L    K  D  S    A  S  F    P  Y  Q  R    K  Y  P

│TCTTAGACCC GAGGCCCTAC AAGGANCTCA AAAGATTGTT AAGGACCTAA   550
         │ L  R  P    E  A  L  Q    G  X  Q    K  I  V    K  D  L  K

│AAGCCCAAGG CCTAGTAAAA CCATGCAGTA GCCCCTGCAA TACTCCAATT   600
         │  A  Q  G    L  V  K    P  C  S  S    P  C  N    T  P  I
         │      ┌──────→
         │TT AGGAGTAA GGAAACCCAA CGGACAGTGG AGGTTAGTGC AAGATCTCAG   650
         │L │ G  V  R    K  P  N    G  Q  W    R  L  V  Q    D  L  R
         │  │region A
         │GATTATTAAT GAGGCTGTTT TTCCTCTATA CCCAGCTGTA TCTAGCCCTT   700
         │  I  I  N    E  A  V  F    P  L  Y    P  A  V    S  S  P  Y │ATACTCTGCT TTCCCTAATA CCAGAGGAAG CAGAGTGGTT TACAGTCCTG   750
         │  T  L  L    S  L  I    P  E  E  A    E  W  F    T  V  L │GACCTTAAGG ATGCCTTTTT CTGCATCCCT GTACGTCCTG ACTCTCAATT   800
         │ D  L  K  D    A  F  F    C  I  P    V  R  P  D    S  Q  F │CTTGTTTGCC TTTGAAGATC CTTTGAACCC AACGTCTCAA CTCACCTGGA   850
         │ L  F  A    F  E  D  P    L  N  P    T  S  Q    L  T  W  T │CTGTTTTACC CCAAGGGTTC AGGGATAGCC CCCATCTATT TGGCCAGGCA   900
         │  V  L  P  Q  G  F    R  D  S  P    H  L  F    G  Q  A │TTAGCCCAAG ACTTGAGTCA ATTCTCATAC CTGGACACTC TTGTCCTTCA   950
         │L  A  Q  D    L  S  Q    F  S  Y    L  D  T  L    V  L  Q │GTACGTGGAT GATTTACTTT TAGTCGCCCG TTCAGAAACC TTGTGCCATC  1000
         │ Y  V  D    D  L  L    L  V  A  R    S  E  T    L  C  H  Q │AAGCCACCCA AGAACTCTTA ACTTTCCTCA CTACCTGTGG CTACAAGGTT  1050
         │ A  T  Q    E  L  L    T  F  L  T    T  C  G    Y  K  V
```

PROTEASE

REVERSE-TRANSCRIPTASE & RnaseH

FIG. 46B

```
TCCAAACCAA AGGCTCGGCT CTGCTCACAG GAGATTAGAT ACTTAGGGCT    1100
 S  K  P  K   A  R  L   C  S  Q    E  I  R  Y   L  G  L
AAAATTATCC AAAGGCACCA GGGCCCTCAG TGAGGAACGT ATCCAGCCTA    1150
 K  L  S   K  G  T  R   A  L  S   E  E  R   I  Q  P  I
           region B
TACTGGCTTA TCCTCATCCC AAAACCCTAA AGCAACTAAG AGGGTTCCTT    1200
 L  A  Y    P  H  P   K  T  L  K   Q  L  R   G  F  L
GGCATAACAG GTTTCTGCCG AAAACAGATT CCCAGGTACA CCCCAATAGC    1250
 G  I  T  G   F  C  R   K  Q  I   P  R  Y  T   P  I  A
            region A
CAGACCATTA TATACACTAA TTAGGGAAAC TCAGAAAGCC AATACCTATT    1300
 R  P  L   Y  T  L  I   R  E  T   Q  K  A   N  T  Y  L
TAGTAAGATG GACACCTACA GAAGTGGCTT TCCAGGCCCT AAAGAAGGCC    1350
  V  R  W   T  P  T   E  V  A  F   Q  A  L   K  K  A
CTAACCCAAG CCCCAGTGTT CAGCTTGCCA ACAGGGCAAG ATTTTCTTT     1400
 L  T  Q  A   P  V  F   S  L  P   T  G  Q  D   F  S  L
ATATGCCACA GAAAAAACAG GAATAGCTCT AGGAGTCCTT ACGCAGGTCT    1450
 Y  A  T   E  K  T   G  I  A  L   G  V  L   T  Q  V  S
CAGGGATGAG CTTGCAACCC GTGGTATACC TGAGTAAGGA AATTGATGTA    1500
 G  M  S   L  Q  P   V  V  Y  L   S  K  E   I  D  V
GTGGCAAAGG GTTGGCCTCA TTGTTTATGG GTAATGGCGG CAGTAGCAGT    1550
 V  A  K  G   W  P  H   C  L  W   V  M  A  A   V  A  V
CTTAGTATCT GAAGCAGTTA AAATAATACA GGGAAGAGAT CTTACTGTGT    1600
 L  V  S   E  A  V  K   I  I  Q   G  R  D   L  T  V  W
GGACATCTCA TGATGTGAAC GGCATACTCA CTGCTAAAGG AGACTTGTGG    1650
 T  S  H   D  V  N   G  I  L  T   A  K  G   D  L  W
TTGTCAGACA ACCATTTACT TAATTATCAG GCTCTATTAC TTGAAGAGCC    1700
 L  S  D  N   H  L  L   N  Y  Q   A  L  L   E  E  P
AGTGCTGAGA CTGCGCACTT GTGCAACTCT TAAACCCGCC ACATTCTTC     1750
 V  L  R   L  R  T   C  A  T  L   K  P   A   T  F  L  P
                                  region B
CAGACAATGA AGAAAAGATA GAACATAACT GTCAACAAGT AATTGCTCAA    1800
 D  N  E   E  K  I   E  H  N  C   Q  Q  V   I  A  Q
ACCTATGCTG CTCGAGGGGA CCTTCTAGAG GTTCCCTTGA CTGATCCCGA    1850
 T  Y  A  A   R  G  D   L  L  E   V  P  L  T   D  P  D
                 →RNase H
CCTCAACTTG TATACTGATG GAAGTTCCTT GGCAGAAAAA GGACTTCGAA    1900
 L  N   L   Y  T  D   G  S  S   L  A  E  K   G  L  R  K
AAGCGGGGTA TGCAGTGATC AGTGATAATG GAATACTTGA AAGTAATCGC    1950
 A  G  Y   A  V  I   S  D  N  G   I  L  E   S  N  R
CTCACTCCAG GAACTAGTGC TCACCTGGCA GAACTAATAG CCCTCACTTG    2000
 L  T  P  G   T  S  A   H  L  A   E  L  I  A   L  T  W
GGCACTAGAA TTAGGAGAAG GAAAAAGGGT AAATATATAT TCAGACTCTA    2050
 A  L  E   L  G  E  G   K  R  V   N  I  Y   S  D  S  K
AGTATGCTTA CCTAGTCCTC CATGCCCATG CAGCAATATG GAGAGAGAGG    2100
  Y  A  Y   L  V  L   H  A  H  A   A  I  W   R  E  R
GAATTCCTAA CTTCTGAGGG AACACCTATC AACCATCAGG AAGCCATTAG    2150
 E  F  L  T   S  E  G   T  P  I   N  H  Q   E  A  I  R
```

FIG. 46C

```
GAGATTATTA TTGGCTGTAC AGAAACCTAA AGAGGTGGCA GTCTTACACT    2200
  R  L  L    L  A  V  Q    K  P  K    E  V  A    V  L  H  C

GCCAGGGTCA TCAGGAAGAA GAGGAAAGGG AAATAGAAGG CAATCGCCAA    2250
  Q  G  H    Q  E  E    E  E  R  E    I  E  G    N  R  Q

GCGGATATTG AAGCAAAAAA AGCCGCAAGG CAGGACTCTC CATTAGAAAT    2300
  A  D  I  E    A  K  K    A  A  R    Q  D  S    P  L  E  M

GCTT                                                      2304
  L
```

(SEQ ID NO: 87)

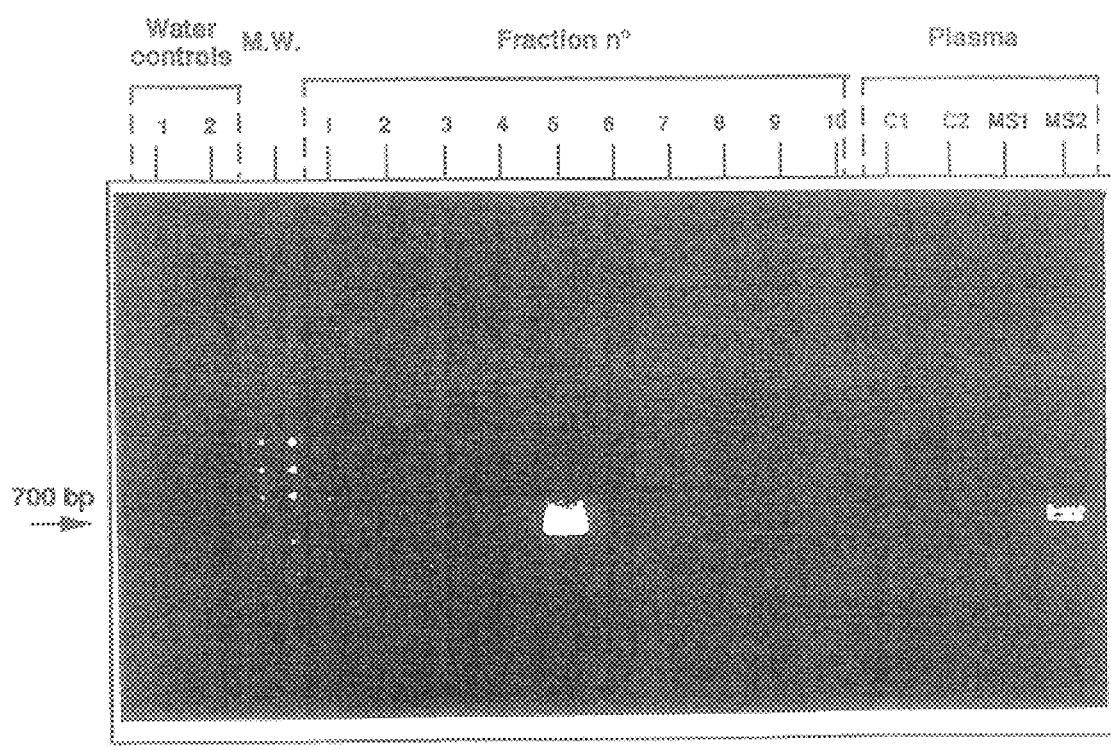

FIG 48A

|             10 |             20 |             30 |             40 |             50 |     |
|----------------|----------------|----------------|----------------|----------------|-----|
|     1234567890 |     1234567890 |     1234567890 |     1234567890 |     1234567890 |     |
| ATGATCCAGC     | AGCAGGACNG     | AGGGTGCCCG     | GGGCAAGCGC     | CAGCCCATGC     | 50  |
|  M  I  Q  Q    |  Q  D  X       |  G  C  P       |  G  Q  A  P    |  A  H  A       |     |
| CATCACCCTC     | ACAGAGCCCC     | AGGTATGCTT     | GACCATTGAG     | GGTCAGAAGG     | 100 |
|  I  T  L       |  T  E  P  Q    |  V  C  L       |  T  I  E       |  G  Q  K  G    |     |
| GTNACTGTCT     | CCTGGACACT     | GGCGGNGCCT     | TCTCAGTCTT     | ACTTTCCTGT     | 150 |
|  X  C  L       |  L  D  T       |  G  G  A  F    |  S  V  L       |  L  S  C       |     |
| CCTGGACAAC     | TGTCCTCCAG     | ATCTGTCACT     | GTCCGAGGGG     | TCCTAGGACA     | 200 |
|  P  G  Q  L    |  S  S  R       |  S  V  T       |  V  R  G  V    |  L  G  Q       |     |
| GCCAGTCACT     | AGATACTTCT     | CCCAGCCACT     | AAGTTGTGAC     | TGGGGAACTT     | 250 |
|  P  V  T       |  R  Y  F  S    |  Q  P  L       |  S  C  D       |  W  G  T  L    |     |
| TACTCTTCCC     | ACATGCTTTT     | CTAATTATGC     | CTGAAAGCCC     | CACTCTCTTG     | 300 |
|  L  F  P       |  H  A  F       |  L  I  M  P    |  E  S  P       |  T  L  L       |     |
| TTGGGGAGAG     | ACATTCTAGC     | AAAAGCAGGG     | GCCATTATAC     | ATGTGAATAT     | 350 |
|  L  G  R  D    |  I  L  A       |  K  A  G       |  A  I  I  H    |  V  N  I       |     |
| AGGAGAAGGA     | ACAACTGTTT     | GTTGTCCCCT     | GCTTGAGGAA     | GGAATTAATC     | 400 |
|  G  E  G       |  T  T  V  C    |  C  P  L       |  L  E  E       |  G  I  N  P    |     |
| CTGAAGTCCG     | GGCAACAGAA     | GGACAATATG     | GACAAGCAAA     | GAATGCCCGT     | 450 |
|  E  V  R       |  A  T  E       |  G  Q  Y  G    |  Q  A  K       |  N  A  R       |     |
| CCTGTTCAAG     | TTAAACTAAA     | GGATTCCACC     | TCCTTTCCCT     | ACCAAAGGCA     | 500 |
|  P  V  Q  V    |  K  L  K       |  D  S  T       |  S  F  P  Y    |  Q  R  Q       |     |

(SEQ ID NO: 88)

FIG 48B

|          10 |          20 |          30 |          40 |          50 |      |
|-------------|-------------|-------------|-------------|-------------|------|
|  1234567890 |  1234567890 |  1234567890 |  1234567890 |  1234567890 |      |
| GTACCCCTC   | AGACCCGAGA  | CCCAACAAGA  | ACTCCAAAAG  | ATTGTAAAGG  |  550 |
|  Y  P  L    |  R  P  E  T |  Q  Q  E    |  L  Q  K    |  I  V  K  D |      |
| ACCTAAAAGC  | CCAAGGCCTA  | GTAAAACCAA  | GCAATAGCCC  | TTGCAAGACT  |  600 |
|  L  K  A    |  Q  G  L    |  V  K  P  S |  N  S  P    |  C  K  T    |      |
| CCAATTTTAG  | GAGTAAGGAA  | ACCCAACGGA  | CAGTGGAGGT  | TAGTGCAAGA  |  650 |
|  P  I  L  G |  V  R  K    |  P  N  G    |  Q  W  R  L |  V  Q  E    |      |
| ACTCAGGATT  | ATCAATGAGG  | CTGTTGTTCC  | TCTATACCCA  | GCTGTACCTA  |  700 |
|  L  R  I    |  I  N  E  A |  V  V  P    |  L  Y  P    |  A  V  P  N |      |
| ACCCTTATAC  | AGTGCTTTCC  | CAAATACCAG  | AGGAAGCAGA  | GTGGTTTACA  |  750 |
|  P  Y  T    |  V  L  S    |  Q  I  P  E |  E  A  E    |  W  F  T    |      |
| GTCCTGGACC  | TTAAGGATGC  | CTTTTTCTGC  | ATCCCTGTAC  | GTCCTGACTC  |  800 |
|  V  L  D  L |  K  D  A    |  F  F  C    |  I  P  V  R |  P  D  S    |      |
| TCAATTCTTG  | TTTGCCTTTG  | AAGATCCTTT  | GAACCCAACG  | TCTCAACTCA  |  850 |
|  Q  F  L    |  F  A  F  E |  D  P  L    |  N  P  T    |  S  Q  L  T |      |
| CCTGGACTGT  | TTTACCCCAA  | GGGTTCAGGG  | ATAGCCCCCA  | TCTATTTGGC  |  900 |
|  W  T  V    |  L  P  Q    |  G  F  R  D |  S  P  H    |  L  F  G    |      |
| CAGGCATTAG  | CCCAAGACTT  | GAGTCAATTC  | TCATACCTGG  | ACACTCTTGT  |  950 |
|  Q  A  L  A |  Q  D  L    |  S  Q  F    |  S  Y  L  D |  T  L  V    |      |
| CCTTCAGTAC  | ATGGATGATT  | TACTTTTAGT  | CGCCCGTTCA  | GAAACCTTGT  | 1000 |
|  L  Q  Y    |  M  D  D  L |  L  L  V    |  A  R  S    |  E  T  L  C |      |

(SEQ ID NO: 88)

FIG 48C

| 10<br>1234567890 | 20<br>1234567890 | 30<br>1234567890 | 40<br>1234567890 | 50<br>1234567890 | |
|---|---|---|---|---|---|
| GCCATCAAGC<br>H Q A | CACCCAAGAA<br>T Q E | CTCTTAACTT<br>L L T F | TCCTCACTAC<br>L T T | CTGTGGCTAC<br>C G Y | 1050 |
| AAGGTTTCCA<br>K V S K | AACCAAAGGC<br>P K A | TCGGCTCTGC<br>R L C | TCACAGGAGA<br>S Q E I | TTAGATACTN<br>R Y X | 1100 |
| AGGGCTAAAA<br>G L K | TTATCCAAAG<br>L S K G | GCACCAGGGC<br>T R A | CCTCAGTGAG<br>L S E | GAACGTATCC<br>E R I Q | 1150 |
| AGCCTATACT<br>P I L | GGCTTATCCT<br>A Y P | CATCCCAAAA<br>H P K T | CCCTAAAGCA<br>L K Q | ACTAAGAGGG<br>L R G | 1200 |
| TTCCTTGGCA<br>F L G I | TAACAGGTTT<br>T G F | CTGCCGAAAA<br>C R K | CAGATTCCCA<br>Q I P R | GGTACASCCC<br>Y X P | 1250 |
| AATAGCCAGA<br>I A R | CCATTATATA<br>P L Y T | CACTAATTAN<br>L I X | GGAAACTCAG<br>E T Q | AAAGCCAATA<br>K A N T | 1300 |
| CCTATTTAGT<br>Y L V | AAGATGGACA<br>R W T | CCTACAGAAG<br>P T E V | TGGCTTTCCA<br>A F Q | GGCCCTAAAG<br>A L K | 1350 |
| AAGGCCCTAA<br>K A L T | CCCAAGCCCC<br>Q A P | AGTGTTCAGC<br>V F S | TTGCCAACAG<br>L P T G | GGCAAGATTT<br>Q D F | 1400 |
| TTCTTTATAT<br>S L Y | GCCACAGAAA<br>A T E K | AAACAGGAAT<br>T G I | AGCTCTAGGA<br>A L G | GTCCTTACGC<br>V L T Q | 1450 |
| AGGTCTCAGG<br>V S G | GATGAGCTTG<br>M S L | CAACCCGTGG<br>Q P V V | TATACCTGAG<br>Y L S | TAAGGAAATT<br>K E I | 1500 |

(SEQ ID NO: 88)

FIG 48D

```
         10           20           30           40           50
1234567890   1234567890   1234567890   1234567890   1234567890
GATGTAGTGG   CAAAGGGTTG   GCCTCATNGT   TTATGGGTAA   TGGNGGCAGT   1550
 D  V  V  A    K  G  W     P  H  X     L  W  V  M    X  A  V

AGCAGTCTNA   GTATCTGAAG   CAGTTAAAAT   AATACAGGGA   AGAGATCTTN   1600
 A  V  X     V  S  E  A    V  K  I      I  Q  G     R  D  L  X

CTGTGTGGAC   ATCTCATGAT   GTGAACGGCA   TACTSRCTGC   TAAAGGAGAC   1650
 V  W  T     S  H  D      V  N  G  I    L  X  A     K  G  D

TTGTGGTTGT   CAGACAACCA   TTTACTTAAN   TAYCAGGCYY   TATTACTTGA   1700
 L  W  L  S    D  N  H      L  L  X     Y  Q  A  L     L  L  E

AGAGCCAGTG   CTGNGACTGC   GCACTTGTCC   AACTCTTAAA   CCCAAACTTA   1750
 E  P  V       L  X  L  R    T  C  P     T  L  K     P  K  L  M

TGCTGCCCAG   AAGGATCTTT   NTAGAGGTCC   CCTTAGCCAA   CCCTGACCTC   1800
 L  P  R       R  I  F      X  E  V  P    L  A  N     P  D  L

AACTATATAT   ATACTGATGG   AAGTTCGTTT   GTAGAAAAGG   GATTACAAAG   1850
 N  Y  I  Y    T  D  G      S  S  F      V  E  K  G     L  Q  R

GGNAGGATAT   NCCATAGGTG   TTAGTGATAA   AGCAGTACTT   GAAAGTAAGC   1900
 X  G  Y       X  I  G  V    S  D  K     A  V  L      E  S  K  P

CTCTTCCCCC   CCAGGGACCA   GCGCCCCGT    TAGCAGAACT   AGTGGCACTG   1950
 L  P  P       Q  G  P      A  P  P  L    A  E  L     V  A  L

ACCCCGCGAG   CCTTAGAACT   TTGGAAAGGG   AGGAGGATAA   ATGTGTATAC   2000
 T  P  R  A    L  E  L      W  K  G      R  R  I  N    V  Y  T
```

(SEQ ID NO: 88)

FIG 48E

|  | 10<br>1234567890 | 20<br>1234567890 | 30<br>1234567890 | 40<br>1234567890 | 50<br>1234567890 |  |
|---|---|---|---|---|---|---|
| | AGATAGCAAG<br>D S K | TATGCTTATC<br>Y A Y L | TAATCCGAAA<br>I R N | TGCCCATGTT<br>A H V | GCAATATGGA<br>A I W K | 2050 |
| | AAGAAAGGGA<br>E R E | GTTCCTAACC<br>F L T | TCTGGGGGAA<br>S G G T | CCCCCATTAA<br>P I K | ATACCACAAG<br>Y H K | 2100 |
| | TTAATCATGG<br>L I M E | AGTTATTGCA<br>L L H | CACAGTGCAA<br>T V Q | AAACTCAAGG<br>K L K E | AGGTGGAAGT<br>V E V | 2150 |
| | CTTACACTGC<br>L H C | CAAAGCCATC<br>Q S H Q | AGAAAAGGGA<br>K R E | AAGAGGGGAA<br>R G E | GAGCAGCATA<br>E Q H K | 2200 |
| | AGTGGCTACA<br>W L Q | GAGGCAAGGA<br>R Q G | AAGACTAGCA<br>K T S R | GAAAGGAAAG<br>K E R | AGAGAAAGAG<br>E K E | 2250 |
| | ACAGAAAGTC<br>T E S Q | AGAGAGAGAG<br>R E R | AGAGGAAGAG<br>E E E | ACAGAGCACA<br>T E H K | AAGAGGGAGT<br>E G V | 2300 |
| | CAGAGAGAGA<br>R E R | GAGAGACAGA<br>E R Q R | GAGTCAGAGA<br>V R E | GAAGGAAAGA<br>K E R | GAGAGAGGAA<br>E R G R | 2350 |
| | GAGACAAAGA<br>D K E | ATGA<br>• | | | | 2364 |

(SEQ ID NO: 88)

FIG 49A

| | | | | | | | |
|---|---|---|---|---|---|---|---|
| Complement of 8/46-7 propre (SEQ ID NO: 132) | GACTTGAGCC | AGTCCTCATA | CCTGGACATT | CTTGTTCTTC | AGTATAGGGA | 50 |
| 1 /46-7 propre (SEQ ID NO: 136) | GACTTGAGCC | AGTCCTCATA | CCTGGACATT | CTTGTTCTTC | AGTATGGGGA | 50 |
| Complement of c15 propre 46-7 (SEQ ID NO: 138) | GACTTGAGCC | AGTCCTCATA | CCTGGACATT | CTTGTTCCTC | AGTATGGGGA | 50 |
| Consensus (SEQ ID NO: 135) | GACTTGAGCC | AGTCCTCATA | CCTGGACATT | CTTGTTCYTC | AGTATRGGGA | 50 |

| | | | | | | |
|---|---|---|---|---|---|---|
| Complement of 8/46-7 propre | TGATTTAATT | ATAGCCACCC | ATTCAGAAAC | CTTGTGGCAT | CAAGCCACCC | 100 |
| 1 /46-7 propre | TGACTTAATT | ATAGCCACCC | ATTCAGAAAC | CTTGTGGCAT | CAAGCCACCC | 100 |
| Complement of c15 propre 46-7 | TGATTTAATT | ATAGCCACCC | ATTCAGAAAC | CTTGTGGCAC | CAAGCCACCC | 100 |
| Consensus | TGAYTTAATT | ATAGCCACCC | ATTCAGAAAC | CTTGTGGCAY | CAAGCCACCC | 100 |

| | | | | | | |
|---|---|---|---|---|---|---|
| Complement of 8/46-7 propre | AAGTGCTCTT | AAATTTCCTC | GCTACCTGTG | GCTCCAAACA | AAGGGCTCAG | 150 |
| 1 /46-7 propre | AAGCGCTCTT | AAATTTCCTT | GCTACCTGTG | GCTCCAAACA | AAAGGCTCAC | 150 |
| Complement of c15 propre 46-7 | AAGCGCTCTT | AAATTTCCTC | GCTACCTGTG | GCTCCAAACA | AAAGGCTCAG | 150 |
| Consensus | AAGYGCTCTT | AAATTTCCTY | GCTACCTGTG | GCTCCAAACA | AARGGCTCAS | 150 |

| | | | | | | |
|---|---|---|---|---|---|---|
| Complement of 8/46-7 propre | CTCTGCTCAC | AGCAGGTTAA | ATACTTAGGG | CTAAAATTAT | CCAAAGTCGC | 200 |
| 1 /46-7 propre | CTCTGCTCAC | ACCAGGTTAA | ATACTTAGGG | CTAAAATTAT | CCAAAGTCAC | 200 |
| Complement of c15 propre 46-7 | CTCTGCTCAC | AGCAGGTTAA | ATACTTAGGG | CTAAAATTAT | CCAAAGTCAC | 200 |
| Consensus | CTCTGCTCAC | ASCAGGTTAA | ATACTTAGGG | CTAAAATTAT | CCAAAGTCRC | 200 |

| | | | | | | |
|---|---|---|---|---|---|---|
| Complement of 8/46-7 propre | CAGGGCCCTC | AGAGAGGAAC | GTATCCAGCG | TATACTGGAT | TATCCTCATC | 250 |
| 1 /46-7 propre | CAGGGCCCTC | AGAGAGGAAC | GTATCCAGCG | TATACTGGCT | TATCCTCATC | 250 |
| Complement of c15 propre 46-7 | CAGGGCCCTC | AGAGAGGAAC | GTATCCAGCG | TATACTGGCT | TATCCCCATC | 250 |
| Consensus | CAGGGCCCTC | AGAGAGGAAC | GTATCCAGCG | TATACTGGMT | TATCCYCATC | 250 |

| | | | | | | |
|---|---|---|---|---|---|---|
| Complement of 8/46-7 propre | CCAAAACCAT | AAAGCAACTA | AGACGGTTCC | TTGGCATAAC | AGCCTTCTGC | 300 |
| 1 /46-7 propre | CCATAACCCT | AAAGCAACTA | AGAGGGTTCC | TTGGCATATC | AGCCTTCTGC | 300 |
| Complement of c15 propre 46-7 | CCAAAACCCT | AAAGCAACTA | AGARGGTTCC | TTGGCATAAC | AGCCTTCTGC | 300 |
| Consensus | CCAWAACCMT | AAAGCAACTA | AGARGGTTCC | TTGGCATAWC | AGCCTTCTGC | 300 |

| | | | | | | |
|---|---|---|---|---|---|---|
| Complement of 8/46-7 propre | CGAATATGGA | TTCCCCGATA | CAGTGAAATA | GCCAGGCCAT | TATGTACATT | 350 |
| 1 /46-7 propre | CGAATATGGA | TTCCCGGATA | CAGTGAAATA | GCCAGGCCAT | TATGTACATT | 350 |
| Complement of c15 propre 46-7 | CGAATATGGA | TTCCCAGATA | CAGCGAAATA | GCCAGGCCAT | TATGTACATT | 350 |
| Consensus | CGAATATGGA | TTCCCVGATA | CAGYGAAATA | GCCAGGCCAT | TATGTACATT | 350 |

| | | | | | | |
|---|---|---|---|---|---|---|
| Complement of 8/46-7 propre | AGTTAAGGAA | ACTCAGAAAG | CCAATACCCA | TATAGTAAGA | TGGACACCTG | 400 |
| 1 /46-7 propre | AATTAAGGAA | ACTCAGAAAG | CCAATACCCA | TATAGTAAGA | TGGACACCTG | 400 |
| Complement of c15 propre 46-7 | ATCTAAGGAA | ACTCAGAAAG | CCAATACCCA | TATAGTAAGA | TGGACACCTG | 400 |
| Consensus | ADYTAAGGAA | ACTCAGAAAG | CCAATACCCA | TATAGTAAGA | TGGACACCTG | 400 |

| | | | | |
|---|---|---|---|---|
| Complement of 8/46-7 propre | AGACAGAAGT | GGCTTTCCAG | GCCCTAAAG | 429 |
| 1 /46-7 propre | AAACAGAAGT | GGCTTTCCAG | GCCCTAAAG | 429 |
| Complement of c15 propre 46-7 | AAACAGAAGT | GGCTTTCCAG | GCCCTAAAG | 429 |
| Consensus | ARACAGAAGT | GGCTTTCCAG | GCCCTAAAG | 429 |

FIG 49B

| | | | | | | | |
|---|---|---|---|---|---|---|---|
| Trans of 1 /46-7 pr (SEQ ID NO: 139) | DLSQSSYLDI | LVLQYGDDLI | IATHSETLWH | QATQALLNFL | ATCGSKQKAH | | 50 |
| Trans of Complement-2 (8) (SEQ ID NO: 140) | DLSQSSYLDI | LVLQYRDDLI | IATHSETLWH | QATQVLLNFL | ATCGSKQRAQ | | 50 |
| Trans of Complement (5) (SEQ ID NO: 141) | DLSQSSYLDI | LVPQYGDDLI | IATHSETLWH | QATQALLNFL | ATCGSKQKAQ | | 50 |
| Consensus | DLSQSSYLDI | LVLQYGDDLI | IATHSETLWH | QATQALLNFL | ATCGSKQKAQ | | 50 |
| Trans of 1 /46-7 pr | LCSHQVKYLG | LKLSKVIRAL | REERIQRILA | YPHPITLKQL | RGFLGISAFC | | 100 |
| Trans of Complement-2 | LCSQQVKYLG | LKLSKVARAL | REERIQRILD | YPHPKTIKQL | RGFLGIIAFC | | 100 |
| Trans of Complement | LCSQQVKYLG | LKLSKVIRAL | REERIQRILA | YPHPKTLKQL | RKFLGIIAFC | | 100 |
| Consensus | LCSQQVKYLG | LKLSKVIRAL | REERIQRILA | YPHPKTLKQL | RGFLGIIAFC | | 100 |
| Trans of 1 /46-7 pr | RIWIPGYSEI | ARPLCTLIKE | TQKANTHIVR | WTPETEVAFQ | ALK | | 143 |
| Trans of Complement-2 | RIWIPRYSEI | ARPLCTLVKE | TQKANTHIVR | WTPETEVAFQ | ALK | | 143 |
| Trans of Complement | RIWIPRYSEI | ARPLCTLSKE | TQKANTHIVR | WTPETEVAFQ | ALK | | 143 |
| Consensus | RIWIPRYSEI | ARPLCTL.KE | TQKANTHIVR | WTPETEVAFQ | ALK | | 143 |

FIG 50A

| | | | | | | | |
|---|---|---|---|---|---|---|---|
| 41/68-1 propre (SEQ ID NO: 129) | GACTTGAGCC | AGTCCTCATA | CCTGGACACT | CTTGTCCTTC | GGTACATGGA | | 50 |
| cl43 propre 68-1 (SEQ ID NO: 131) | GACTTGAGCC | AGTCYTCATA | CCTGGACAYT | CTTGTCCTTC | GGTACATGGA | | 50 |
| 42/68-1 propre (SEQ ID NO: 130) | GACTTGAGCC | AGTCCTCATA | CCTGGACACT | CTTGTCCTTC | GGTACATGGA | | 50 |
| Consensus (SEQ ID NO: 128) | GACTTGAGCC | AGTCYTCATA | CCTGGACAYT | CTTGTCCTTC | GGTACATGGA | | 50 |
| 41/68-1 propre | TGATTTACTT | TTAGCCACCC | ATTCAGAAAC | CTTGTGCCAT | CAAGCCACCC | | 100 |
| cl43 propre 68-1 | TGATTTACTT | TTAGCCACCC | ATTCAGAAAC | CTTGTGCCAT | CAAGCCACCC | | 100 |
| 42/68-1 propre | TGATTTACTT | TTAGCCACCC | ATTCAGAAAC | CTTGTGCCAT | CAAGCCACCC | | 100 |
| Consensus | TGATTTACTT | TTAGCCACCC | ATTCAGAAAC | CTTGTGCCAT | CAAGCCACCC | | 100 |
| 41/68-1 propre | AAGCACTCTT | AAATTTCCTT | GCTACCTGTG | GCTACAAGGT | TTCCAAACCA | | 150 |
| cl43 propre 68-1 | AAGCACTCTT | AAATTTCCTT | GCTACCTGTG | GCTACAAGGT | TTCCAAACCA | | 150 |
| 42/68-1 propre | AAGCACTCTT | AAATTTCCTT | GCTACCTGTG | GCTACAAGGT | TTCCAAACCA | | 150 |
| Consensus | AAGCACTCTT | AAATTTCCTT | GCTACCTGTG | GCTACAAGGT | TTCCAAACCA | | 150 |
| 41/68-1 propre | AAGGCTCAGC | TCTGCTCACA | GCAGGTTAAA | TACTTAGGGC | TAAAATTATC | | 200 |
| cl43 propre 68-1 | AAGGCTCAGC | TCTGCTCACA | GCAGGTTAAA | TACTTAGGGC | TAAAATTATC | | 200 |
| 42/68-1 propre | AAGGCTCAGC | TCTGCTCACA | GCAGGTTAAA | TACTTAGGGC | TAAAATTATC | | 200 |
| Consensus | AAGGCTCAGC | TCTGCTCACA | GCAGGTTAAA | TACTTAGGGC | TAAAATTATC | | 200 |
| 41/68-1 propre | CAAAGGCACC | AGAACCCTCA | GTGAGGAACG | TATCCAGCCT | ATACTGGGTT | | 250 |
| cl43 propre 68-1 | CAAAGGCACC | AGAACCCTCA | GTGAGGAACG | TATCCAGCCT | ATACTGGGTT | | 250 |
| 42/68-1 propre | CAAAGGCACC | AGAACCCTCA | GTGAGGAACG | TATCCAGCCT | ATACTGGGTT | | 250 |
| Consensus | CAAAGGCACC | AGAACCCTCA | GTGAGGAACG | TATCCAGCCT | ATACTGGGTT | | 250 |
| 41/68-1 propre | ATCCTCATCC | CAAAACCCTA | AAGCAACTAA | CAGCGTTCCT | TGGCATAACA | | 300 |
| cl43 propre 68-1 | ATCCTCATCC | CAAAACCCTA | AAGCAACTAA | CAGCGTTCCT | TGGCATAACA | | 300 |
| 42/68-1 propre | ATCCTCATCC | CAAAACCCTA | AAGCAACTAA | CAGCGTTCCT | TGGCATAACA | | 300 |
| Consensus | ATCCTCATCC | CAAAACCCTA | AAGCAACTAA | CAGCGTTCCT | TGGCATAACA | | 300 |
| 41/68-1 propre | GGTTTCTGCC | AAATATGGAT | TCCCAGGTAC | AGCAAGATAG | CCAGACCATT | | 350 |
| cl43 propre 68-1 | GGTTTCTGCC | AAATATGGAT | TCCCAGGTAC | AGCAAAATAG | CCAGACCATT | | 350 |
| 42/68-1 propre | GGTTTCTGCC | AAATATGGAT | TCCCAGGTAC | AGCAAGTAG | CCAGACCATT | | 350 |
| Consensus | GGTTTCTGCC | AAATATGGAT | TCCCAGGTAC | AGCAARRTAG | CCAGACCATT | | 350 |
| 41/68-1 propre | AAATACACGA | ATTAAGGAAA | CTCAAAAAGC | CAATACCCAT | TTAGTAAGAT | | 400 |
| cl43 propre 68-1 | AAATACACGA | ATTAAGGAAA | CTCAAAAAGC | CAATACCCAT | TTAGTAAGAT | | 400 |
| 42/68-1 propre | AAATACACGA | ATTAAGGAAA | CTCAAAAAGC | CAGTACCCAT | TTAGTAAGAT | | 400 |
| Consensus | AAATACACGA | ATTAAGGAAA | CTCAAAAAGC | CARTACCCAT | TTAGTAAGAT | | 400 |
| 41/68-1 propre | GGACACCTGA | AGCAGAAGTG | GCTTTCCAGG | CCCTAAAG | | | 438 |
| cl43 propre 68-1 | GGACAICTGA | AGCAGAAGTG | GCTTTCCAGG | CCCTAAAG | | | 438 |
| 42/68-1 propre | GGACACCTGA | AGCAGAAGTG | GCTTTCCAGG | CCCTAAAG | | | 438 |
| Consensus | GGACAYCTGA | AGCAGAAGTG | GCTTTCCAGG | CCCTAAAG | | | 438 |

FIG 50B

| | | | | | | |
|---|---|---|---|---|---|---|
| Trans of c143 propr (SEQ ID NO: 134) | DLSQSSYLDX | LVLRYMDDLL | LATHSETLCH | QATQALLNFL | ATCGYKVSKP | 50 |
| Trans of 42/68-1 pr (SEQ ID NO: 133) | DLSQSSYLDT | LVLRYMDDLL | LATHSETLCH | QATQALLNFL | ATCGYKVSKP | 50 |
| Trans of 41/68-1 pr (SEQ ID NO: 132) | DLSQSSYLDT | LVLRYMDDLL | LATHSETLCH | QATQALLNFL | ATCGYKVSKP | 50 |
| Consensus | DLSQSSYLDT | LVLRYMDDLL | LATHSETLCH | QATQALLNFL | ATCGYKVSKP | 50 |
| Trans of c143 propr | KAQLCSQQVK | YLGLKLSKGT | RTLSEERIQP | ILGYPHPKTL | KQLTAFLGIT | 100 |
| Trans of 42/68-1 pr | KAQLCSQQVK | YLGLKLSKGT | RTLSEERIQP | ILGYPHPKTL | KQLTAFLGIT | 100 |
| Trans of 41/68-1 pr | KAQLCSQQVK | YLGLKLSKGT | RTLSEERIQP | ILGYPHPKTL | KQLTAFLGIT | 100 |
| Consensus | KAQLCSQQVK | YLGLKLSKGT | RTLSEERIQP | ILGYPHPKTL | KQLTAFLGIT | 100 |
| Trans of c143 propr | GFCQIWIPRY | SKIARPLNTR | IKETQKANTH | LVRWTSEAEV | AFQALK | 146 |
| Trans of 42/68-1 pr | GFCQIWIPRY | SKVARPLNTR | IKETQKASTH | LVRWTPEAEV | AFQALK | 146 |
| Trans of 41/68-1 pr | GFCQIWIPRY | SKIARPLNTR | IKETQKANTH | LVRWTPEAEV | AFQALK | 146 |
| Consensus | GFCQIWIPRY | SKIARPLNTR | IKETQKANTH | LVRWTPEAEV | AFQALK | 146 |

FIG 51A

```
MSRV pol          ATTATGCCTG AAAGCCCCAC TCCCTTGTTA GGGAGAGACA TTTTAGCAAA  50
(SEQ ID NO: 205)
    cons DNA 1,5,8 ---------- ---------- ---------- ---------- ----------
(SEQ ID NO: 135)
    Consensus     ATTATGCCTG AAAGCCCCAC TCCCTTGTTA GGGAGAGACA TTTTAGCAAA  50
(SEQ ID NO: 206)

MSRV pol          AGCAGGGGCC ATTATACACC TGAACATAGG AAAAGGAATA CCCATTTGCT 100
    cons DNA 1,5,8 ---------- ---------- ---------- ---------- ----------
    Consensus     AGCAGGGGCC ATTATACACC TGAACATAGG AAAAGGAATA CCCATTTGCT 100

MSRV pol          GTCCCCTGCT TGAGGAAGGA ATTAATCCTG AAGTCTGGGC AATAGAAGGA 150
    cons DNA 1,5,8 ---------- ---------- ---------- ---------- ----------
    Consensus     GTCCCCTGCT TGAGGAAGGA ATTAATCCTG AAGTCTGGGC AATAGAAGGA 150

MSRV pol          CAATATGGAC AAGCAAAGAA TGCCCGTCCT GTTCAAGTTA AACTAAAGGA 200
    cons DNA 1,5,8 ---------- ---------- ---------- ---------- ----------
    Consensus     CAATATGGAC AAGCAAAGAA TGCCCGTCCT GTTCAAGTTA AACTAAAGGA 200

MSRV pol          TTCTGCCTCC TTTCCCTACC AAAGGAAGTA CCCTCTTAGA CCCGAGGCCC 250
    cons DNA 1,5,8 ---------- ---------- ---------- ---------- ----------
    Consensus     TTCTGCCTCC TTTCCCTACC AAAGGAAGTA CCCTCTTAGA CCCGAGGCCC 250

MSRV pol          TACAAGGANC TCAAAAGATT GTTAAGGACC TAAAAGCCCA AGGCCTAGTA 300
    cons DNA 1,5,8 ---------- ---------- ---------- ---------- ----------
    Consensus     TACAAGGANC TCAAAAGATT GTTAAGGACC TAAAAGCCCA AGGCCTAGTA 300

MSRV pol          AAACCATGCA GTAGCCCCTG CAATACTCCA ATTTTAGGAG TAAGGAAACC 350
    cons DNA 1,5,8 ---------- ---------- ---------- ---------- ----------
    Consensus     AAACCATGCA GTAGCCCCTG CAATACTCCA ATTTTAGGAG TAAGGAAACC 350

MSRV pol          CAACGGACAG TGGAGGTTAG TGCAAGATCT CAGGATTATT AATGAGGCTG 400
    cons DNA 1,5,8 ---------- ---------- ---------- ---------- ----------
    Consensus     CAACGGACAG TGGAGGTTAG TGCAAGATCT CAGGATTATT AATGAGGCTG 400

MSRV pol          TTTTTCCTCT ATACCCAGCT GTATCTAGCC CTTATACTCT GCTTTCCCTA 450
    cons DNA 1,5,8 ---------- ---------- ---------- ---------- ----------
    Consensus     TTTTTCCTCT ATACCCAGCT GTATCTAGCC CTTATACTCT GCTTTCCCTA 450

MSRV pol          ATACCAGAGG AAGCAGAGTG GTTTACAGTC CTGGACCTTA AGGATGCCTT 500
    cons DNA 1,5,8 ---------- ---------- ---------- ---------- ----------
    Consensus     ATACCAGAGG AAGCAGAGTG GTTTACAGTC CTGGACCTTA AGGATGCCTT 500

MSRV pol          TTTCTGCATC CCTGTACGTC CTGACTCTCA ATTCTTGTTT GCCTTTGAAG 550
    cons DNA 1,5,8 ---------- ---------- ---------- ---------- ----------
    Consensus     TTTCTGCATC CCTGTACGTC CTGACTCTCA ATTCTTGTTT GCCTTTGAAG 550

MSRV pol          ATCCTTTGAA CCCAACGTCT CAACTCACCT GGACTGTTTT ACCCCAAGGG 600
    cons DNA 1,5,8 ---------- ---------- ---------- ---------- ----------
    Consensus     ATCCTTTGAA CCCAACGTCT CAACTCACCT GGACTGTTTT ACCCCAAGGG 600

MSRV pol          TTCAGGGATA GCCCCCATCT ATTTGGCCAG GCATTAGCCC AAGACTTGAG 650
    cons DNA 1,5,8 ---------- ---------- ---------- ---------- --GACTTGAG   8
    Consensus     TTCAGGGATA GCCCCCATCT ATTTGGCCAG GCATTAGCCC AAGACTTGAG 650

MSRV pol          TCAATTCTCA TACCTGGACA CTCTTGTCCT TCAGTACGTG GATGATTTAC 700
    cons DNA 1,5,8 CCAGTCCTCA TACCTGGACA TTCTTGTTCY TCAGTATRGG GATGAYTTAA  58
    Consensus     YCARTYCTCA TACCTGGACA YTCTTGTYCY TCAGTAYRKG GATGAYTTAM 700

MSRV pol          TTTTAGTCGC CCGTTCAGAA ACCTTGTGCC ATCAAGCCAC CCAAGAACTC 750
    cons DNA 1,5,8 TTATAGCCAC CCATTCAGAA ACCTTGTGGC AYCAAGCCAC CCAAGYGCTC 108
    Consensus     TTWTAGYCRC CCRTTCAGAA ACCTTGTGSC AYCAAGCCAC CCAAGHRCTC 750

MSRV pol          TTAACTTTCC TCACTACCTG TGGCTACAAG GTTTCCAAAC CAAAGGCTCG 800
    cons DNA 1,5,8 TTAAWTTTCC TYGCTACCTG TGGCT----- ----CCAAAC AAARGGCTCA 149
    Consensus     TTAAMTTTCC TYRCTACCTG TGGCTACAAG GTTTCCAAAC MAARGGCTCR 800
```

FIG 51B

```
    MSRV pol        GCTCTGCTCA CAGGAGATTA GATACTTAGG GCTAAAATTA TCCAAAGGCA   850
(SEQ ID NO: 205)
    cons DNA 1,5,8  SCTCTGCTCA CASCAGGTTA AATACTTAGG GCTAAAATTA TCCAAAGTCR   199
(SEQ ID NO: 135)
    Consensus       SCTCTGCTCA CASSAGRTTA RATACTTAGG GCTAAAATTA TCCAAAGKCR   850
(SEQ ID NO: 206)

MSRV pol        CCAGGGCCCT CAGTGAGGAA CGTATCCAGC CTATACTGGC TTATCCTCAT    900
    cons DNA 1,5,8  CCAGGGCCCT CAGAGAGGAA CGTATCCAGC GTATACTGGM TTATCCYCAT    249
    Consensus       CCAGGGCCCT CAGWGAGGAA CGTATCCAGC STATACTGGM TTATCCYCAT    900

MSRV pol        CCCAAAACCC TAAAGCAACT AAGAGGGTTC CTTGGCATAA CAGGTTTCTG    950
    cons DNA 1,5,8  CCCAWAACCM TAAAGCAACT AAGARGGTTC CTTGGCATAW CAGCCTTCTG    299
    Consensus       CCCAWAACCM TAAAGCAACT AAGARGGTTC CTTGGCATAW CAGSYTTCTG    950

MSRV pol        CCGAAAACAG ATTCCCAGGT ACACCCCAAT AGCCAGACCA TTATATACAC   1000
    cons DNA 1,5,8  CCGAATATAG ATTCCCVGAT ACAGYGAAAT AGCCAGGCCA TTATGTACAT    349
    Consensus       CCGAAWAYRG ATTCCCVGRT ACASYSMAAT AGCCAGRCCA TTATRTACAY   1000

MSRV pol        TAATTAGGGA AACTCAGAAA GCCAATACCT ATTTAGTAAG ATGGACACCT   1050
    cons DNA 1,5,8  TADYTAAGGA AACTCAGAAA GCCAATACCC ATATAGTAAG ATGGACACCT    399
    Consensus       TADYTARGGA AACTCAGAAA GCCAATACCY ATWTAGTAAG ATGGACACCT   1050

MSRV pol        ---ACAGAAG TGGCTTTCCA GGCCCTAAAG AAGGCCCTAA CCCAAGCCCC   1097
    cons DNA 1,5,8  GARACAGAAG TGGCTTTCCA GGCCCTAAAG ---------- ----------    429
    Consensus       GARACAGAAG TGGCTTTCCA GGCCCTAAAG AAGGCCCTAA CCCAAGCCCC   1100

MSRV pol        AGTGTTCAGC TTGCCAACAG GGCAAGATTT TTCTTTATAT GCCACAGAAA   1147
    cons DNA 1,5,8  ---------- ---------- ---------- ---------- ----------    429
    Consensus       AGTGTTCAGC TTGCCAACAG GGCAAGATTT TTCTTTATAT GCCACAGAAA   1150

MSRV pol        AAACAGGAAT AGCTCTAGGA GTCCTTACGC AGGTCTCAGG GATGAGCTTG   1197
    cons DNA 1,5,8  ---------- ---------- ---------- ---------- ----------    429
    Consensus       AAACAGGAAT AGCTCTAGGA GTCCTTACGC AGGTCTCAGG GATGAGCTTG   1200

MSRV pol        CAACCCGTGG TATACCTGAG TAAGGAAATT GATGTAGTGG CAAAGGGTTG   1247
    cons DNA 1,5,8  ---------- ---------- ---------- ---------- ----------    429
    Consensus       CAACCCGTGG TATACCTGAG TAAGGAAATT GATGTAGTGG CAAAGGGTTG   1250

MSRV pol        GCCTCATTGT TTATGGGTAA TGGCGGCAGT AGCAGTCTTA GTATCTGAAG   1297
    cons DNA 1,5,8  ---------- ---------- ---------- ---------- ----------    429
    Consensus       GCCTCATTGT TTATGGGTAA TGGCGGCAGT AGCAGTCTTA GTATCTGAAG   1300

MSRV pol        CAGTTAAAAT AATACAGGGA AGAGATCTTA CTGTGTGGAC ATCTCATGAT   1347
    cons DNA 1,5,8  ---------- ---------- ---------- ---------- ----------    429
    Consensus       CAGTTAAAAT AATACAGGGA AGAGATCTTA CTGTGTGGAC ATCTCATGAT   1350

MSRV pol        GTGAACGGCA TACTCACTGC TAAAGGAGAC TTGTGGTTGT CAGACAACCA   1397
    cons DNA 1,5,8  ---------- ---------- ---------- ---------- ----------    429
    Consensus       GTGAACGGCA TACTCACTGC TAAAGGAGAC TTGTGGTTGT CAGACAACCA   1400

MSRV pol        TTTACTTAAT TATCAGGCTC TATTACTTGA AGAGCCAGTG CTGAGACTGC   1447
    cons DNA 1,5,8  ---------- ---------- ---------- ---------- ----------    429
    Consensus       TTTACTTAAT TATCAGGCTC TATTACTTGA AGAGCCAGTG CTGAGACTGC   1450

MSRV pol        GCACTTGTGC AACTCTTAAA CCCGCCACAT TTCTTCCAGA CAATGAAGAA   1497
    cons DNA 1,5,8  ---------- ---------- ---------- ---------- ----------    429
    Consensus       GCACTTGTGC AACTCTTAAA CCCGCCACAT TTCTTCCAGA CAATGAAGAA   1500

MSRV pol        AAGATAGAAC ATAACTGTCA ACAAGTAATT GCTCAAACCT ATGCTGCTCG   1547
    cons DNA 1,5,8  ---------- ---------- ---------- ---------- ----------    429
    Consensus       AAGATAGAAC ATAACTGTCA ACAAGTAATT GCTCAAACCT ATGCTGCTCG   1550

MSRV pol        AGGGGACCTT CTAGAGGTTC CCTTGACTGA TCCCGACCTC AACTTGTATA   1597
    cons DNA 1,5,8  ---------- ---------- ---------- ---------- ----------    429
    Consensus       AGGGGACCTT CTAGAGGTTC CCTTGACTGA TCCCGACCTC AACTTGTATA   1600
```

FIG 51C

| | | | | | | |
|---|---|---|---|---|---|---|
| Trans of MSRV pol (SEQ ID NO: 198) | IMPESPTPLL | GRDILAKAGA | IIHLNIGKGI | PICCPLLEEG | INPEVWAIEG | 50 |
| cons prot 1,5,8 (SEQ ID NO: 199) | ---------- | ---------- | ---------- | ---------- | ---------- | |
| Consensus (SEQ ID NO: 200) | .......... | .......... | .......... | .......... | .......... | 50 |
| Trans of MSRV pol | QYGQAKNARP | VQVKLKDSAS | FPYQRKYPLR | PEALQGXQKI | VKDLKAQGLV | 100 |
| cons prot 1, 5, 8 | ---------- | ---------- | ---------- | ---------- | ---------- | |
| Consensus | .......... | .......... | .......... | .......... | .......... | 100 |
| Trans of MSRV pol | KPCSSPCNTP | ILGVRKPNGQ | WRLVQDLRII | NEAVFPLYPA | VSSPYTLLSL | 150 |
| cons prot 1, 5, 8 | ---------- | ---------- | ---------- | ---------- | ---------- | |
| Consensus | .......... | .......... | .......... | .......... | .......... | 150 |
| Trans of MSRV pol | IPEEAEWFTV | LDLKDAFFCI | PVRPDSQFLF | AFEDPLNPTS | QLTWTVLPQG | 200 |
| cons prot 1, 5, 8 | ---------- | ---------- | ---------- | ---------- | ---------- | |
| Consensus | .......... | .......... | .......... | .......... | .......... | 200 |
| Trans of MSRV pol | FRDSPHLFGQ | ALAQDLSQRS | YLDILVLQYV | DDLLLVARSE | TLCHQATQEL | 250 |
| cons prot 1, 5, 8 | ---------- | ----DLSQSS | YLDILVLQYG | DDLIIATHSE | TLWHQATQAL | 36 |
| Consensus | .......... | ....DLSQ.S | YLD.LVLQY. | DDL.....SE | TL.HQATQ.L | 250 |
| Trans of MSRV pol | LIFLITCGYK | VSKPKARLCS | QEIRYLGLKL | SKGTRALSEE | RIQPILAYPH | 300 |
| cons prot 1, 5, 8 | LNFLATCGSK | ---QKAQLCS | QDVKYLGLKL | SKMTRALREE | RIQRILAYPH | 83 |
| Consensus | L.EL.TCG.K | ....KA.LCS | Q...YLGLKL | SK.TRAL.EE | RIQ.ILAYPH | 300 |
| Trans of MSRV pol | PKTLKQLRGF | LGITGFCRKQ | IPRYTPIARP | LYTLIRETQK | ANTYLVRWTP | 350 |
| cons prot 1, 5, 8 | PKTLKQLRGF | LGITAFCRIW | IPRYSEIARP | LCTLKKETQK | ANTHIVRWTP | 133 |
| Consensus | PKTLKQLRGF | LGIT.ECR.. | IPRY..IARP | L.TL..ETQK | ANT..VRWTP | 350 |
| Trans of MSRV pol | -TEVAFQALK | KALTQAPVFS | LPTGQDFSLY | ATEKTGIALG | VLTQVSGMSL | 399 |
| cons prot 1, 5, 8 | ETEVAFQALK | ---------- | ---------- | ---------- | ---------- | 143 |
| Consensus | .TEVAFQALK | .......... | .......... | .......... | .......... | 400 |
| Trans of MSRV pol | QPVVYLSKEI | DVVAKGWPHC | LWVMAAVAVL | VSEAVKIIQG | RDLTVWTSHD | 449 |
| cons prot 1, 5, 8 | ---------- | ---------- | ---------- | ---------- | ---------- | 143 |
| Consensus | .......... | .......... | .......... | .......... | .......... | 450 |
| Trans of MSRV pol | VNGILTAKGD | LWLSDNHLLN | YQALLLEEPV | LRLRTCATLK | PATFLPDNEE | 499 |
| cons prot 1, 5, 8 | ---------- | ---------- | ---------- | ---------- | ---------- | 143 |
| Consensus | .......... | .......... | .......... | .......... | .......... | 500 |
| Trans of MSRV pol | KIEHNCQQVI | AQTYAARGDL | LEVPLTDPDL | NLYTDGSSLA | EKGLRKAGYA | 549 |
| cons prot 1, 5, 8 | ---------- | ---------- | ---------- | ---------- | ---------- | 143 |
| Consensus | .......... | .......... | .......... | .......... | .......... | 550 |
| Trans of MSRV pol | VISDNGILES | NRLTPGTSAH | LAELIALTWA | LELGEGKRVN | IYSDSKYAYL | 599 |
| cons prot 1, 5, 8 | ---------- | ---------- | ---------- | ---------- | ---------- | 143 |
| Consensus | .......... | .......... | .......... | .......... | .......... | 600 |
| Trans of MSRV pol | VLHAHAAIWR | EREFLTSEGT | PINHQEAIRR | LLLAVQKPKE | VAVLHCQGHQ | 649 |
| cons prot 1, 5, 8 | ---------- | ---------- | ---------- | ---------- | ---------- | 143 |
| Consensus | .......... | .......... | .......... | .......... | .......... | 650 |
| Trans of MSRV pol | EEEEREIEGN | RQADIEAKKA | ARQDSPLEML | IEGP | | 683 |
| cons prot 1, 5, 8 | ---------- | ---------- | ---------- | ---- | | 143 |
| Consensus | .......... | .......... | .......... | .... | | 684 |

FIG 52A

```
        MSRV pol        ATTATGCCTG  AAAGCCCCAC  TCCCTTGTTA  GGGAGAGACA  TTTTAGCAAA   50
(SEQ ID NO: 205)
        cons DNA 41,42,43  ----------  ----------  ----------  ----------  ----------
(SEQ ID NO: 128)
        Consensus       ATTATGCCTG  AAAGCCCCAC  TCCCTTGTTA  GGGAGAGACA  TTTTAGCAAA   50
(SEQ ID NO: 207)

MSRV pol        AGCAGGGGCC  ATTATACACC  TGAACATAGG  AAAAGGAATA  CCCATTTGCT  100
        cons DNA 41,42,43  ----------  ----------  ----------  ----------  ----------
        Consensus       AGCAGGGGCC  ATTATACACC  TGAACATAGG  AAAAGGAATA  CCCATTTGCT  100

MSRV pol        GTCCCCTGCT  TGAGGAAGGA  ATTAATCCTG  AAGTCTGGGC  AATAGAAGGA  150
        cons DNA 41,42,43  ----------  ----------  ----------  ----------  ----------
        Consensus       GTCCCCTGCT  TGAGGAAGGA  ATTAATCCTG  AAGTCTGGGC  AATAGAAGGA  150

MSRV pol        CAATATGGAC  AAGCAAAGAA  TGCCCGTCCT  GTTCAAGTTA  AACTAAAGGA  200
        cons DNA 41,42,43  ----------  ----------  ----------  ----------  ----------
        Consensus       CAATATGGAC  AAGCAAAGAA  TGCCCGTCCT  GTTCAAGTTA  AACTAAAGGA  200

MSRV pol        TTCTGCCTCC  TTTCCCTACC  AAAGGAAGTA  CCCTCTTAGA  CCCGAGGCCC  250
        cons DNA 41,42,43  ----------  ----------  ----------  ----------  ----------
        Consensus       TTCTGCCTCC  TTTCCCTACC  AAAGGAAGTA  CCCTCTTAGA  CCCGAGGCCC  250

MSRV pol        TACAAGGANC  TCAAAAGATT  GTTAAGGACC  TAAAAGCCCA  AGGCCTAGTA  300
        cons DNA 41,42,43  ----------  ----------  ----------  ----------  ----------
        Consensus       TACAAGGANC  TCAAAAGATT  GTTAAGGACC  TAAAAGCCCA  AGGCCTAGTA  300

MSRV pol        AAACCATGCA  GTAGCCCCTG  CAATACTCCA  ATTTTAGGAG  TAAGGAAACC  350
        cons DNA 41,42,43  ----------  ----------  ----------  ----------  ----------
        Consensus       AAACCATGCA  GTAGCCCCTG  CAATACTCCA  ATTTTAGGAG  TAAGGAAACC  350

MSRV pol        CAACGGACAG  TGGAGGTTAG  TGCAAGATCT  CAGGATTATT  AATGAGGCTG  400
        cons DNA 41,42,43  ----------  ----------  ----------  ----------  ----------
        Consensus       CAACGGACAG  TGGAGGTTAG  TGCAAGATCT  CAGGATTATT  AATGAGGCTG  400

MSRV pol        TTTTTCCTCT  ATACCCAGCT  GTATCTAGCC  CTTATACTCT  GCTTTCCCTA  450
        cons DNA 41,42,43  ----------  ----------  ----------  ----------  ----------
        Consensus       TTTTTCCTCT  ATACCCAGCT  GTATCTAGCC  CTTATACTCT  GCTTTCCCTA  450

MSRV pol        ATACCAGAGG  AAGCAGAGTG  GTTTACAGTC  CTGGACCTTA  AGGATGCCTT  500
        cons DNA 41,42,43  ----------  ----------  ----------  ----------  ----------
        Consensus       ATACCAGAGG  AAGCAGAGTG  GTTTACAGTC  CTGGACCTTA  AGGATGCCTT  500

MSRV pol        TTTCTGCATC  CCTGTACGTC  CTGACTCTCA  ATTCTTGTTT  GCCTTTGAAG  550
        cons DNA 41,42,43  ----------  ----------  ----------  ----------  ----------
        Consensus       TTTCTGCATC  CCTGTACGTC  CTGACTCTCA  ATTCTTGTTT  GCCTTTGAAG  550

MSRV pol        ATCCTTTGAA  CCCAACGTCT  CAACTCACCT  GGACTGTTTT  ACCCCAAGGG  600
        cons DNA 41,42,43  ----------  ----------  ----------  ----------  ----------
        Consensus       ATCCTTTGAA  CCCAACGTCT  CAACTCACCT  GGACTGTTTT  ACCCCAAGGG  600

MSRV pol        TTCAGGGATA  GCCCCCATCT  ATTTGGCCAG  GCATTAGCCC  AAGACTTGAG  650
        cons DNA 41,42,43  ----------  ----------  ----------  ----------  --GACTTGAG    8
        Consensus       TTCAGGGATA  GCCCCCATCT  ATTTGGCCAG  GCATTAGCCC  AAGACTTGAG  650

MSRV pol        TCAATTCTCA  TACCTGGACA  CTCTTGTCCT  TCAGTACGTG  GATGATTTAC  700
        cons DNA 41,42,43  CCAGTCYTCA  TACCTGGACA  YTCTTGTCCT  TCGGTACATG  GATGATTTAC   58
        Consensus       YCARTYYTCA  TACCTGGACA  YTCTTGTCCT  TCRGTACRTG  GATGATTTAC  700

MSRV pol        TTTTAGTCGC  CCGTTCAGAA  ACCTTGTGCC  ATCAAGCCAC  CCAAGAACTC  750
        cons DNA 41,42,43  TTTTAGCCAC  CCATTCAGAA  ACCTTGTGCC  ATCAAGCCAC  CCAAGCACTC  108
        Consensus       TTTTAGYCRC  CCRTTCAGAA  ACCTTGTGCC  ATCAAGCCAC  CCAAGMACTC  750

MSRV pol        TTAACTTTCC  TCACTACCTG  TGGCTACAAG  GTTTCCAAAC  CAAAGGCTCG  800
        cons DNA 41,42,43  TTAAATTTCC  TTGCTACCTG  TGGCTACAAG  GTTTCCAAAC  CAAAGGCTCA  158
        Consensus       TTAAMTTTCC  TYRCTACCTG  TGGCTACAAG  GTTTCCAAAC  CAAAGGCTCR  800
```

FIG 52B

```
                        1         2         3         4         5
MSRV pol                GCTCTGCTCA CAGGAGATTA GATACTTAGG GCTAAAATTA TCCAAAGGCA    850
(SEQ ID NO: 205)
cons DNA 41,42,43       GCTCTGCTCA CAGCAGGTTA AATACTTAGG GCTAAAATTA TCCAAAGGCA    208
(SEQ ID NO: 128)
Consensus               GCTCTGCTCA CAGSAGRTTA RATACTTAGG GCTAAAATTA TCCAAAGGCA    850
(SEQ ID NO: 207)

MSRV pol                CCAGGGCCCT CAGTGAGGAA CGTATCCAGC CTATACTGGC TTATCCTCAT    900
cons DNA 41,42,43       CCAGAACCCT CAGTGAGGAA CGTATCCAGC CTATACTGGG TTATCCTCAT    258
Consensus               CCAGRRCCCT CAGTGAGGAA CGTATCCAGC CTATACTGGS TTATCCTCAT    900

MSRV pol                CCCAAAACCC TAAAGCAACT AAGAGGGTTC CTTGGCATAA CAGGTTTCTG    950
cons DNA 41,42,43       CCCAAAACCC TAAAGCAACT AACAGCGTTC CTTGGCATAA CAGGTTTCTG    308
Consensus               CCCAAAACCC TAAAGCAACT AASAGSGTTC CTTGGCATAA CAGGTTTCTG    950

MSRV pol                CCGAAAACAG ATTCCAGGT ACACCCAAT AGCCAGACCA TTATATACAC    1000
cons DNA 41,42,43       CCAAATATGG ATTCCCAGGT ACAGCMMRRT AGCCAGACCA TTAAATACAC    358
Consensus               CCRAAWAYRG ATTCCCAGGT ACASCMMRRT AGCCAGACCA TTAWATACAC    1000

MSRV pol                TAATTAGGGA AACTCAGAAA GCCAATACCT ATTTAGTAAG ATGGACACCT    1050
cons DNA 41,42,43       GAATTAAGGA AACTCAAAAA GCCARTACCC ATTTAGTAAG ATGGACAYCT    408
Consensus               KAATTARGGA AACTCARAAA GCCARTACCY ATTTAGTAAG ATGGACAYCT    1050

MSRV pol                --A-CAGAAG TGGCTTTCCA GGCCCTAAAG AAGGCCCTAA CCCAAGCCCC    1097
cons DNA 41,42,43       GAAGCAGAAG TGGCTTTCCA GGCCCTAAAG ---------- ----------    438
Consensus               GAAGCAGAAG TGGCTTTCCA GGCCCTAAAG AAGGCCCTAA CCCAAGCCCC    1100

MSRV pol                AGTGTTCAGC TTGCCAACAG GGCAAGATTT TTCTTTATAT GCCACAGAAA    1147
cons DNA 41,42,43       ---------- ---------- ---------- ---------- ----------    438
Consensus               AGTGTTCAGC TTGCCAACAG GGCAAGATTT TTCTTTATAT GCCACAGAAA    1150

MSRV pol                AAACAGGAAT AGCTCTAGGA GTCCTTACGC AGGTCTCAGG GATGAGCTTG    1197
cons DNA 41,42,43       ---------- ---------- ---------- ---------- ----------    438
Consensus               AAACAGGAAT AGCTCTAGGA GTCCTTACGC AGGTCTCAGG GATGAGCTTG    1200

MSRV pol                CAACCCGTGG TATACCTGAG TAAGGAAATT GATGTAGTGG CAAAGGGTTG    1247
cons DNA 41,42,43       ---------- ---------- ---------- ---------- ----------    438
Consensus               CAACCCGTGG TATACCTGAG TAAGGAAATT GATGTAGTGG CAAAGGGTTG    1250

MSRV pol                GCCTCATTGT TTATGGGTAA TGGCGGCAGT AGCAGTCTTA GTATCTGAAG    1297
cons DNA 41,42,43       ---------- ---------- ---------- ---------- ----------    438
Consensus               GCCTCATTGT TTATGGGTAA TGGCGGCAGT AGCAGTCTTA GTATCTGAAG    1300

MSRV pol                CAGTTAAAAT AATACAGGGA AGAGATCTTA CTGTGTGGAC ATCTCATGAT    1347
cons DNA 41,42,43       ---------- ---------- ---------- ---------- ----------    348
Consensus               CAGTTAAAAT AATACAGGGA AGAGATCTTA CTGTGTGGAC ATCTCATGAT    1350

MSRV pol                GTGAACGGCA TACTCACTGC TAAAGGAGAC TTGTGGTTGT CAGACAACCA    1397
cons DNA 41,42,43       ---------- ---------- ---------- ---------- ----------    438
Consensus               GTGAACGGCA TACTCACTGC TAAAGGAGAC TTGTGGTTGT CAGACAACCA    1400

MSRV pol                TTTACTTAAT TATCAGGCTC TATTACTTGA AGAGCCAGTG CTGAGACTGC    1447
cons DNA 41,42,43       ---------- ---------- ---------- ---------- ----------    438
Consensus               TTTACTTAAT TATCAGGCTC TATTACTTGA AGAGCCAGTG CTGAGACTGC    1450

MSRV pol                GCACTTGTGC AACTCTTAAA CCCGCCACAT TTCTTCCAGA CAATGAAGAA    1497
cons DNA 41,42,43       ---------- ---------- ---------- ---------- ----------    438
Consensus               GCACTTGTGC AACTCTTAAA CCCGCCACAT TTCTTCCAGA CAATGAAGAA    1500

MSRV pol                AAGATAGAAC ATAACTGTCA ACAAGTAATT GCTCAAACCT ATGCTGCTCG    1547
cons DNA 41,42,43       ---------- ---------- ---------- ---------- ----------    438
Consensus               AAGATAGAAC ATAACTGTCA ACAAGTAATT GCTCAAACCT ATGCTGCTCG    1550

MSRV pol                AGGGGACCTT CTAGAGGTTC CCTTGACTGA TCCCGACCTC AACTTGTATA    1597
cons DNA 41,42,43       ---------- ---------- ---------- ---------- ----------    438
Consensus               AGGGGACCTT CTAGAGGTTC CCTTGACTGA TCCCGACCTC AACTTGTATA    1600
```

FIG 52C

```
Trans of MSRV pol      IMPESPTPLL  GRDILAKAGA  IIHLNIGKGI  PICCPLLEEG  INPEVWAIEG   50
(SEQ ID NO: 208)
cons prot 41,42,43     ----------  ----------  ----------  ----------  ----------
(SEQ ID NO: 209)
Consensus              ..........  ..........  ..........  ..........  ..........   50
(SEQ ID NO: 210)

Trans of MSRV pol      QYGQAKNARP  VQVKLKDSAS  FPYQRKYPLR  PEALQGXQKI  VKDLKAQGLV  100
cons prot 41,42,43     ----------  ----------  ----------  ----------  ----------
Consensus              ..........  ..........  ..........  ..........  ..........  100

Trans of MSRV pol      KPCSSPCNTP  ILGVRKPNGQ  WRLVQDLRII  NEAVFPLYPA  VSSPYTLLSL  150
cons prot 41,42,43     ----------  ----------  ----------  ----------  ----------
Consensus              ..........  ..........  ..........  ..........  ..........  150

Trans of MSRV pol      IPEEAEWFTV  LDLKDAFFCI  PVRPDSQFLF  AFEDPLNPTS  QLTWTVLPQG  200
cons prot 41,42,43     ----------  ----------  ----------  ----------  ----------
Consensus              ..........  ..........  ..........  ..........  ..........  200

Trans of MSRV pol      FRDSPHLFGQ  ALAQDLSQFS  YLDTLVLQYV  DDLLLVARSE  TLCHQATQEL  250
cons prot 41,42,43     ----------  ----DLSQSS  YLDTLVLRYM  DDLLLATHSE  TLCHQATQAL   36
Consensus              ..........  ....DLSQ.S  YLDTLVL.Y.  DDLLL...SE  TLCHQATQ.L  250

Trans of MSRV pol      LIFLITCGYK  VSKPKARLCS  QEIRYLGLKL  SKGTRALSEE  RIQPILAYPH  300
cons prot 41,42,43     LNFLATCGYK  VSKPKAQLCS  QQVKYLGLKL  SKGTRILREE  RIQPILGYPH   86
Consensus              L.FL.TCGYK  VSKPKA.LCS  Q...YLGLKL  SKGTR.LSEE  RIQPIL.YPH  300

Trans of MSRV pol      PKTLKQLRGF  LGITGFCRKQ  IPRYTPIARP  LYTLIRETQK  ANTYLVRWTP  350
cons prot 41,42,43     PKTLKQLTAF  LGITGFCQIW  IPRYSKIARP  LNTRIKETQK  ANTHLVRWTP  136
Consensus              PKTLKQL..F  LGITGFC...  IPRY..IARP  L.T.I.ETQK  ANT.LVRWTP  350

Trans of MSRV pol      TEVAFQALKK  ALTQAPVFSL  PTGQDFSLYA  TEKTGIALGV  LTQVSGMSLQ  400
cons prot 41,42,43     ----------  ----------  ----------  ----------  ----------  136
Consensus              ..........  ..........  ..........  ..........  ..........  400

Trans of MSRV pol      PVVYLSKEID  VVAKGWPHCL  WVMAAVAVLV  SEAVKIIQGR  DLTVWTSHDV  450
cons prot 41,42,43     -------EAE  V---------  ----------  ----------  ----------  140
Consensus              .......E..  V.........  ..........  ..........  ..........  450

Trans of MSRV pol      NGILTAKGDL  WLSDNHLLNY  QALLLEEPVL  RLRTCATLKP  ATFLPDNEEK  500
cons prot 41,42,43     ----------  --------AF  QALK------  ----------  ----------  146
Consensus              ..........  ..........  QAL.......  ..........  ..........  500

Trans of MSRV pol      IEHNCQQVIA  QTYAARGDLL  EVPLTDPDLN  LYTDGSSLAE  KGLRKAGYAV  550
cons prot 41,42,43     ----------  ----------  ----------  ----------  ----------  146
Consensus              ..........  ..........  ..........  ..........  ..........  550

Trans of MSRV pol      ISDNGILESN  RLTPGTSAHL  AELIALTWAL  ELGEGKRVNI  YSDSKYAYLV  600
cons prot 41,42,43     ----------  ----------  ----------  ----------  ----------  146
Consensus              ..........  ..........  ..........  ..........  ..........  600

Trans of MSRV pol      LHAHAAIWRE  REFLTSEGTP  INHQEAIRRL  LLAVQKPKEV  AVLHCQGHQE  650
cons prot 41,42,43     ----------  ----------  ----------  ----------  ----------  146
Consensus              ..........  ..........  ..........  ..........  ..........  650

Trans of MSRV pol      EEEREIEGNR  QADIEAKKAA  RQDSPLEMLI  EGP                     683
cons prot 41,42,43     ----------  ----------  ----------  ---                     146
Consensus              ..........  ..........  ..........  ...                     683
```

FIG 53A

```
cons DNA 41,42,43    GACTTGAGCC  AGTCYTCATA  CCTGGACAYT  CTTGTCCTTC  GGTACATGGA   50
(SEQ ID NO: 128)
cons DNA 1,5,8       GACTTGAGCC  AGTCCTCATA  CCTGGACATT  CTTGTTCYTC  AGTATRGGA    50
(SEQ ID NO: 135)
Consensus            GACTTGAGCC  AGTCYTCATA  CCTGGACAYT  CTTGTYCYTC  RGTAYRKGGA   50
(SEQ ID NO: 201)

cons DNA 41,42,43    TGATTTACTT  TTAGCCACCC  ATTCAGAAAC  CTTGTGCCAT  CAAGCCACCC  100
cons DNA 1,5,8       TGAMTTAATT  ATAGCCACCC  ATTCAGAAAC  CTTGTGGCAY  CAAGCCACCC  100
Consensus            TGAMTTAMTT  WTAGCCACCC  ATTCAGAAAC  CTTGTGBCAY  CAAGCCACCC  100 cons DNA 41,42,43    AAGCACTCTT  AAATTTCCTT  GCTACCTGTG  GCTACAAGGT  TTCCAAACCA  150
cons DNA 1,5,8       AAGYGCTCTT  AAATTTCCTY  GCTACCTGTG  GC--------  -TCCAAACAA  141
Consensus            AAGYRCTCTT  AAATTTCCTY  GCTACCTGTG  GCTACAAGGT  TCCAAACCMA  150 cons DNA 41,42,43    AAGGCTCAGC  TCTGCTCACA  GCAGGTTAAA  TACTTAGGGC  TAAAATTATC  200
cons DNA 1,5,8       ARGGCTCASC  TCTGCTCACA  SCAGGTTAAA  TACTTAGGGC  TAAAATTATC  191
Consensus            ARGGCTCASC  TCTGCTCACA  SCAGGTTAAA  TACTTAGGGC  TAAAATTATC  200 cons DNA 41,42,43    CAAAGGCACC  AGAACCCTCA  GTGAGGAACG  TATCCAGCCT  ATACTGGGTT  250
cons DNA 1,5,8       CAAAGTCRCC  AGGGCCCTCA  GAGAGGAACG  TATCCAGCGT  ATACTGGMTT  241
Consensus            CAAAGKCRCC  AGRRCCCTCA  GWGAGGAACG  TATCCAGCST  ATACTGGVTT  250 cons DNA 41,42,43    ATCCTCATCC  CAAAACCCTA  AAGCAACTAA  CAGCGTTCCT  TGGCATAACA  300
cons DNA 1,5,8       ATCCYCATCC  CAWAACCMTA  AAGCAACTAA  GARGGTTCCT  TGGCATAWCA  291
Consensus            ATCCYCATCC  CAWAACCMTA  AAGCAACTAA  SARSGTTCCT  TGGCATAWCA  300 cons DNA 41,42,43    GGTTTCTGCC  AAATATGGAT  TCCCAGGTAC  AGCAARRTAG  CCAGACCATT  350
cons prot 1,5,8      GCCTTCTGCC  GAATATGGAT  TCCCVGATAC  AGYGAAATAG  CCAGGCCATT  341
Consensus            GSYTTCTGCC  RAATATGGAT  TCCCVGRTAC  AGYRARRTAG  CCAGRCCATT  350 cons DNA 41,42,43    AAAATACACGA ATTAAGGAAA  CTCAAAAAGC  CARTACCCAT  TTAGTAAGAT  400
cons DNA 1,5,8       ATGTACATTA  DYTAAGGAAA  CTCAGAAAGC  CAATACCCAT  ATAGTAAGAT  391
Consensus            AWRTACAYKA  DYTAAGGAAA  CTCARAAAGC  CARTACCCAT  WTAGTAAGAT  400 cons DNA 41,42,43    GGACAYCTGA  AGCAGAAGTG  GCTTTCCAGG  CCCTAAAG                438
cons DNA 1,5,8       GGACACCTGA  RACAGAAGTG  GCTTTCCAGG  CCCTAAAG                429
Consensus            GGACAYCTGA  RRCAGAAGTG  GCTTTCCAGG  CCCTAAAG                438
```

FIG 53B

```
cons prot 41,42,43   DLSQSSYLDT  LVLRYMDDLL  LATHSETLCH  QATQALLNFL  ATCGYKVSKP   50
(SEQ ID NO: 202)
cons prot 1,5,8      DLSQSSYLDI  LVLCYGDDLI  LATHSETLWH  QATQALLNFL  ATCGSK---Q   47
(SEQ ID NO: 203)
Consensus            DLSQSSYLD.  LVL.Y.DDL.  .ATHSETL.H  QATQALLNFL  ATCG.K....   50
(SEQ ID NO: 204)

cons prot 41,42,43   KAQLCSQQVK  YLGLKLSKGT  RIDSEERIQP  TLGYPHPKTL  KQLTAFLGIT  100
cons prot 1, 5, 8    KAQLCSQQVK  YLGLKLSKVT  RALREERIQR  ILAYPHPKTL  KQLRGFLGIT   97
Consensus            KAQLCSQQVK  YLGLKLSK.T  R.L.EERIQ.  IL.YPHPKTL  KQL..FLGIT  100 cons prot 41,42,43   GFCCIWIPRY  SKIARPLNTR  IKETQKANTH  LVRWTPEAEV  AFQALK      146
cons prot 1, 5, 8    AFCRIWIPRY  SEIARPLCTL  XKETQKANTH  IVRWTPEIEV  AFQALK      143
Consensus            .FC.IWIPRY  S.IARPL.T.  .KETQKANTH  .VRWTPE.EV  AFQALK      146
```

ISOLATED NUCLEOTIDE SEQUENCES ASSOCIATED WITH MULTIPLE SCLEROSIS OR RHEUMATOID ARTHRITIS AND A PROCESS OF DETECTING

This application is a continuation-in-part of U.S. application Ser. No. 08/756,429, filed Nov. 26, 1996, now abandoned.

Multiple sclerosis (MS) is a demyelinating disease of the central nervous system (CNS), the cause of which remains as yet unknown.

"Multiple sclerosis (MS) is the most common neurological disease of young adults with a prevalence in Europe and North America of between 20 and 200 per 100,000. It is characterized clinically by a relapsing/remitting or chronic progressive course, frequently leading to severe disability. Current knowledge suggests that MS is associated with autoimmunity, that genetic background has an important influence and that "infectious" agent(s) may be involved. Indeed, many viruses have been proposed as possible candidates but as yet, none of them has been shown to play an aetiological role.

Many studies have supported the hypothesis of a viral aetiology of the disease, but none of the known viruses tested has proved to be the causal agent sought: a review of the viruses sought for several years in MS has been compiled by E. Norrby (1) and R. T. Johnson (2).

The discovery of pathogenic retroviruses in man (HTLVs and HIVs) was followed by great interest in their ability to impair the immune system and to provoke central nervous system inflammation and/or degeneration. In the case of HTLV-1, its association with a chronic inflammatory demyelinating disease in man (48) led to extensive investigations to search for an HTLV1-like retrovirus in MS patients. However, despite initial claims, the presence of HTLV-1 or HTLV-like retroviruses was not confirmed.

Recently, a retrovirus different from the known human retroviruses has been isolated in patients suffering from MS (3, 4, and 5).

In 1989, the authors described the production of extracellular virions, associated with reverse transcriptase (RT) activity, by a culture of leptomeningeal cells (LM7) obtained from the cerebrospinal fluid of a patient with MS (3). This was followed by similar findings in monocyte cultures from a series of MS patients (5). Neither viral particles nor viral RT-activity were found in control individuals. Furthermore, the authors were able to transfer the LM7 virus to non-infected leptomeningeal cells in vitro (26). The molecular characterization of the "LM7" retrovirus was a prerequisite for further evaluation of its possible role in MS. Considerable difficulties arose from the absence of continuously productive retroviral cultures and from the low levels of expression in the few transient cultures. The strategy described here focused on RNA from extracellular virions, in order to avoid non-specific detection of cellular RNA and of endogenous elements from contaminating human DNA. A specific retroviral sequence associated with virions produced by cell cultures from several MS patients has been identified. The entire sequence of this novel retroviral genome is currently being obtained using RT-PCR on RNA from extracellular virions. The retrovirus previously called "LM7 virus" corresponds to an oncovirus and is now designated MSRV (Multiple Sclerosis-associated RetroVirus).

The authors were also able to show that this retrovirus could be transmitted in vitro, that patients suffering from MS produced antibodies capable of recognizing proteins associated with the infection of leptomeningeal cells by this retrovirus, and that the expression of the latter could be strongly stimulated by the immediate-early genes of some herpesviruses (6).

All these results point to the role in MS of at least one unknown retrovirus or of a virus having reverse transcriptase activity which is detectable according to the method published by H. Perron (3) and qualified as "LM7-like RT" activity. The content of the publication identified by (3) is incorporated in the present description by reference.

Recently, the Applicant's studies have enabled two continuous cell lines infected with natural isolates originating from two different patients suffering from MS to be obtained by a culture method as described in the document WO-A-93/20188, the content of which is incorporated in the present description by reference. These two lines, derived from human choroid plexus cells, designated LM7PC and PLI-2, were deposited with the ECACC on Jul. 22, 1992 and Jan. 8, 1993, respectively, under numbers 92072201 and 93010817, in accordance with the provisions of the Budapest Treaty. Moreover, the viral isolates possessing LM7-like RT activity were also deposited with the ECACC under the overall designation of "strains". The "strain" or isolate harboured by the PLI-2 line, designated POL-2, was deposited with the ECACC on Jul. 22, 1992 under No. V92072202. The "strain" or isolate harboured by the LM7PC line, designated MS7PG, was deposited with the ECACC on Jan. 8, 1993 under No. V93010816.

Starting from the cultures and isolates mentioned above, characterized by biological and morphological criteria, the next step was to endeavour to characterize the nucleic acid material associated with the viral particles produced in these cultures.

The portions of the genome which have already been characterized have been used to develop tests for molecular detection of the viral genome and iunmunoserological tests, using the amino acid sequences encoded by the nucleotide sequences of the viral genome, in order to detect the immune response directed against epitopes associated with the infection and/or viral expression.

These tools have already enabled an association to be confirmed between MS and the expression of the sequences identified in the patents cited later. However, the viral system discovered by the Applicant is related to a complex retroviral system. In effect, the sequences to be found encapsidated in the extracellular viral particles produced by the different cultures of cells of patients suffering from MS show clearly that there is coencapsidation of retroviral genomes which are related but different from the "wild-type" retroviral genome which produces the infective viral particles. This phenomenon has been observed between replicative retroviruses and endogenous retroviruses belonging to the same family, or even heterologous retroviruses. The notion of endogenous retroviruses is very important in the context of our discovery since, in the case of MSRV-1, it has been observed that endogenous retroviral sequences comprising sequences homologous to the MSRV-1 genome exist in normal human DNA. The existence of endogenous retroviral elements (ERV) related to MSRV-1 by all or part of their genome explains the fact that the expression of the MSRV-1 retrovirus in human cells is able to interact with closely related endogenous sequences. These interactions are to be found in the case of pathogenic and/or infectious endogenous retroviruses (for example some ecotropic strains of the murine leukaemia virus), and in the case of exogenous retroviruses whose nucleotide sequence may be found partially or wholly, in the form of ERVs, in the host animal's genome (e.g. mouse exogenous mammary tumor virus transmitted via the milk). These interactions consist mainly of (i) a trans-activation or coactivation of ERVs by the replicative retrovirus (ii) and "illegitimate" encapsidation of RNAs related to ERVS, or of ERVs—or even of cellular RNAs—simply possessing compatible encapsidation sequences, in the retroviral particles produced by the expression of the replicative strain, which are sometimes transmissible and sometimes with a pathogenicity of their own, and (iii) more or less substantial recombinations between the coencapsidated genomes, in particular in the phases of reverse transcription, which lead to the formation of hybrid genomes, which are sometimes transmissible and sometimes with a pathogenicity of their own.

Thus, (i) different sequences related to MSRV-1 have been found in the purified viral particles; (ii) molecular analysis of the different regions of the MSRV-1 retroviral genome should be carried out by systematically analyzing the coencapsidated, interfering and/or recombined sequences which are generated by the infection and/or expression of MSRV-1; furthermore, some clones may have defective sequence portions produced by the retroviral replication and template errors and/or errors of transcription of the reverse transcriptase; (iii) the families of sequences related to the same retroviral genomic region provide the means for an overall diagnostic detection which may be optimized by the identification of invariable regions among the clones expressed, and by the identification of reading frames responsible for the production of antigenic and/or pathogenic polypeptides which may be produced only by a portion, or even by just one, of the clones expressed, and, under these conditions, the systematic analysis of the clones expressed in the region of a given gene enables the frequency of variation and/or of recombination of the MSRV-1 genome in this region to be evaluated and the optimal sequences for the applications, in particular diagnostic applications, to be defined; (iv) the pathology caused by a retrovirus such as MSRV-1 may be a direct effect of its expression and of the proteins or peptides produced as a result thereof, but also an effect of the activation, the encapsidation or the recombination of related or heterologous genomes and of the proteins or peptides produced as a result thereof; thus, these genomes associated with the expression of and/or infection by MSRV-1 are an integral part of the potential pathogenicity of this virus, and hence constitute means of diagnostic detection and special therapeutic targets. Similarly, any agent associated with or cofactor of these interactions responsible for the pathogenesis in question, such as MSRV-2 or the gliotoxic factor which are described in the patent application published under No. FR-2,716,198, may participate in the development of an overall and very effective strategy for the diagnosis, prognosis, therapeutic monitoring and/or integrated therapy of MS in particular, but also of any other disease associated with the same agents.

In this context, a parallel discovery has been made in another autoimmune disease, rheumatoid arthritis (RA), which has been described in the French Patent Application filed under No. 95/02960. This discovery shows that, by applying methodological approaches similar to the ones which were used in the Applicant's work on MS, it was possible to identify a retrovirus expressed in RA which shares the sequences described for MSRV-1 in MS, and also the coexistence of an associated MSRV-2 sequence also described in MS. As regards MSRV-1, the sequences detected in common in MS and RA relate to the pol and gag genes. In the current state of knowledge, it is possible to associate the gag and pol sequences described with the MSRV-1 strains expressed in these two diseases.

The present patent application relates to various results which are additional to those already protected by the following French Patent Applications:

No. 92/04322 of 03.04.1992, published under No. 2,689,519;

No. 92/13447 of 03.11.1992, published under No. 2,689,521;

No. 92/13443 of 03.11.1992, published under No. 2,689,520;

No. 94/01529 of 04.02.1994, published under No. 2,715,936;

No. 94/01531 of 04.02.1994, published under No. 2,715,939;

No. 94/01530 of 04.02.1994, published under No. 2,715,936;

No. 94/01532 of 04.02.1994, published under No. 2,715,937;

No. 94/14322 of 24.11.1994, published under No. 2,727,428;

and No. 94/15810 of 23.12.1994; published under No. 2,728,585.

SUMMARY OF THE INVENTION

The present invention relates, in the first place, to a viral material, in the isolated or purified state, which may be recognized or characterized in different ways:

its genome comprises a nucleotide sequence chosen from the group including the sequences SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83, their complementary sequences and their equivalent sequences, in particular nucleotide sequences displaying, for any succession of 100 contiguous monomers, at least 50% and preferably at least 70% homology with the said sequences SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83, respectively, and their complementary sequences;

the region of its genome comprising the env and pol genes and a portion of the gag gene, excluding the subregion having a sequence identical or equivalent to SEQ ID NO:1, codes for any polypeptide displaying, for any contiguous succession of at least 30 amino acids, at least 50% and preferably at least 70% homology with a peptide sequence encoded by any nucleotide sequence chosen from the group including SEQ ID NO:42, SEQ ID NO:47, SEQ ID NO:48, SEQ ID NO:49, SEQ ID NO:52, SEQ ID NO:54, SEQ ID NO:55, SEQ ID NO:56, SEQ ID NO:57, SEQ ID NO:83 and their complementary sequences;

the pol gene comprises a nucleotide sequence partially or totally identical or equivalent to SEQ ID NO:53 or SEQ ID NO:87, excluding SEQ ID NO:1.

the gag gene comprises a nucleotide sequence partially or totally identical or equivalent to SEQ ID NO:82.

As indicated above, according to the present invention, the viral material as defined above is associated with MS. And as defined by reference to the pol or gag gene of MSRV-1, and more especially to the sequences SEQ ID NOS 47, 52, 53, 55, 56, 57, 82, 83, 87, 128, 129, 130, 131, 135, 136, 137 and 138, this viral material is associated with RA.

The present invention also relates to a nucleic material, in the isolated or purified state, having at least one of the following definitions:

a nucleic material comprising a nucleotide sequence selected from the group including sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences and their equivalent sequences, in particular nucleotide sequences displaying, for any succession of 100 contiguous monomers, at least 50% and preferably at least 60% homology with said sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, and their complementary sequences, excluding HSERV-9 (or ERV-9); advantageously, the nucleotide sequence of said nucleic material is selected from the group including sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences and their equivalent sequences, in particular nucleotide sequences displaying, for any succession of 100 contiguous monomers, at least 70% and preferably at least 80% homology with said sequences SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, and their complementary sequences;

a nucleic material, in the isolated or purified state, coding for any polypeptide displaying, for any contiguous succession of at least 30 amino acids, at least 50%, preferably at least 60 %, and most preferably at least 70% homology with a peptide sequence encoded by any nucleotide sequence selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138 and their complementary sequences;

a nucleic material, in the isolated or purified state, of retroviral type, comprising a nucleotide sequence identical or similar to at least part of the pol gene of an isolated retrovirus associated with multiple sclerosis or rheumatoid arthritis; advantageously, said nucleotide sequence is 80% similar to said at least part of the gene pol;

a nucleic material comprising a nucleotide sequence identical or similar to at least part of the pol gen of an isolated virus encoding a reverse transcriptase having a enzymatic site comprised between the amino acid domains LPQG-YXDD, having a phylogenic distance with HSERV-9 of 0.063±0.1, and preferably 0.063±0.05; the phylogenic distances are calculated on the basis of a reference sequence according to UPGM tree option of the Geneworks™ Software (INTELLIGENETICS); By enzymatic site, we understand the amino acids domain(s) conferring the specific activity of a given enzyme.

The present invention also relates to different nucleotide fragments each comprising a nucleotide sequence chosen from the group including:

(a) all the genomic sequences, partial and total, of the pol gene of the MSRV-1 virus, except for the total sequence of the nucleotide fragment defined by SEQ ID NO:1;

(b) all the genomic sequences, partial and total, of the env gene of MSRV-1;

(c) all the partial genomic sequences of the gag gene of MSRV-1;

(d) all the genomic sequences overlapping the pol gene and the env gene of the MSRV-1 virus, and overlapping the pol gene and the gag gene;

(e) all the sequences, partial and total, of a clone chosen from the group including the clones FBd3 (SEQ ID NO:42), t pol (SEQ ID NO:47), JLBc1 (SEQ ID NO:48), JLBc2 (SEQ ID NO:49) and GM3 (SEQ ID NO:52), FBd13 (SEQ ID NO:54), LB19 (SEQ ID NO:55), LTR-GAG12 (SEQ ID NO:56), FP6 (SEQ ID NO:57), G+E+A (SEQ ID NO:83), excluding any nucleotide sequence identical to or lying within the sequence defined by SEQ ID NO:1;

(f) sequences complementary to the said genomic sequences;

(g) sequences equivalent to the said sequences (a) to (e), in particular nucleotide sequences displaying, for any succession of 100 contiguous monomers, at least 50% and preferably at least 70% homology with the said sequences (a) to (d), provided that this nucleotide fragment does not comprise or consist of the sequence ERV-9 as described in LA MANTIA et al. (18).

The term genomic sequences, partial or total, includes all sequences associated by coencapsidation or by coexpression, or recombined sequences.

Preferably, such a fragment comprises:

either a nucleotide sequence identical to a partial or total genomic sequence of the pol gene of the MSRV-1 virus, except for the total sequence of the nucleotide fragment defined by SEQ ID NO:1, or identical to any sequence equivalent to the said partial or total genomic sequence, in particular one which is homologous to the latter;

or a nucleotide sequence identical to a partial or total genomic sequence of the env gene of the MSRV-1 virus, or identical to any sequence complementary to the said nucleotide sequence, or identical to any sequence equivalent to the said nucleotide sequence, in particular one which is homologous to the latter.

In particular, the invention relates to a nucleotide fragment comprising a coding nucleotide sequence which is partially or totally identical to a nucleotide sequence chosen from the group including:

the nucleotide sequence defined by SEQ ID NO:36, SEQ ID NO:58 or SEQ ID NO:83;

sequences complementary to SEQ ID NO:36, SEQ ID NO:58 or SEQ ID NO:83;

sequences equivalent, and in particular homologous to SEQ ID NO:36, SEQ ID NO:58 or SEQ ID NO:83;

sequences coding for all or part of the peptide sequence defined by SEQ ID NO:35, SEQ ID NO:59 or SEQ ID NO:84;

sequences coding for all or part of a peptide sequence equivalent, in particular homologous to SEQ ID NO:35, SEQ ID NO:59 or SEQ ID NO:84, which is capable of being recognized by sera of patients infected with the MSRV-1 virus, or in whom the MSRV-1 virus has been reactivated.

The invention also relates to a nucleotide fragment (called fragment I) having at least one of the following definitions:

a nucleotide fragment comprising a nucleotide sequence selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences, and their equivalent sequences, in particular nucleotide sequences displaying, for any succession of 100 contiguous monomers, at least 50% and preferably at least 60% homology with said sequences and their complementary sequences, said group excluding SEQ ID NO:1, said nucleotide fragment not comprising nor consisting of the sequence HSERV-9 (or ERV-9); preferably the nucleotide sequence of said fragment is selected from the group including SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138, their complementary sequences, and their equivalent sequences, in particular nucleotide sequences displaying, for any succession of 100 contiguous monomers, at least 70% and preferably at least 80% homology with said sequences and their complementary sequences;

a nucleotide fragment comprising a coding nucleotide sequence which is partially or totally identical to a nucleotide sequence selected from the group including:

SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138; their complementary sequences; their equivalent sequences, in particular homologous to SEQ ID NO:87, SEQ ID NO:88, SEQ ID NO:128, SEQ ID NO:129, SEQ ID NO:130, SEQ ID NO:131, SEQ ID NO:135, SEQ ID NO:136, SEQ ID NO:137, SEQ ID NO:138;

sequences encoding all or parts of the peptide sequence defined by SEQ ID NO:89, SEQ ID NO:132, SEQ ID NO:133, SEQ ID NO:134, SEQ ID NO:139, SEQ ID NO:140, SEQ ID NO:141;

sequences encoding all or parts of a peptide sequence equivalent, in particular homologous to SEQ ID NO:89, SEQ ID NO:132, SEQ ID NO:133, SEQ ID NO:134, SEQ ID NO:139, SEQ ID NO:140, SEQ ID NO:141, which is capable of being recognized by sera of patients infected with the MSRV-1 virus, or in whom the MSRV-1 virus has been reactivated.

The invention also relates to any nucleic acid probe for the detection of virus associated with MS and/or rheumatoid arthritis (RA), which is capable of hybridizing specifically with any fragment such as is defined above, belonging or lying within the genome of the said pathogenic agent. It relates, in addition, to any nucleic acid probe for detection of a pathogenic and/or infective agent associated with RA, which is capable of hybridizing specifically with any fragment as defined above by reference to the pol and gag genes, and especially with respect to the sequences SEQ ID NOS 36, 47, 52, 55, 56, 57, 58, 83 and SEQ ID NOS 35, 59 and 84.

The invention also relates to a primer for the amplification by polymerization of an RNA or a DNA of a viral material, associated with MS and/or RA, comprising a nucleotide sequence identical or equivalent to at least one portion of the nucleotide sequence of any fragment such as is defined above, in particular a nucleotide sequence displaying, for any succession of at least 10 contiguous monomers, preferably 15 contiguous monomers, more preferably 18 contiguous monomers and even most preferably 20 contiguous monomers, at least 70% homology with at least the said portion of the said fragment. Preferably, the nucleotide sequence of such a primer is identical to any one of the sequences selected from the group including SEQ ID NO:15 to SEQ ID NO:18, SEQ ID NO:43 to SEQ ID NO:46, SEQ ID NO:51, SEQ ID NO:60, SEQ ID NO:72, SEQ ID NO:76, SEQ ID NO:80, SEQ ID NO:93 to SEQ ID NO:99, SEQ ID NO:142, SEQ ID NO:143, SEQ ID NO:144, and SEQ ID NO:145.

Generally speaking the invention also encompasses any RNA or DNA, and in particular replication vector, comprising a genomic fragment of the viral material such as is defined above, or a nucleotide fragment such as is defined above.

The invention also relates to the different peptides encoded by any open reading frame belonging to a nucleotide fragment such as is defined above, in particular any polypeptide, for example any oligopeptide forming or comprising an antigenic determinant recognized by sera of patients infected with the MSRV-1 virus and/or in whom the MSRV-1 virus has been reactivated. Preferably, this polypeptide is antigenic, and is encoded by the open reading frame beginning, in the 5'-3' direction, at nucleotide 181 and ending at nucleotide 330 of SEQ ID NO:1.

The invention also encompasses the following polypeptides:

a)

a polypeptide encoded by any open reading frame belonging to a nucleotide fragment, fragment I, as defined above;

a polypeptide, characterized in that the open reading frame encoding it, is comprised, in the 5'-3' direction, between nucleotide 18 and nucleotide 2304 of SEQ ID NO:87;

a polypeptide, having a peptide sequence comprising a sequence partially or totally identical to SEQ ID NO:89;

b)

a polypeptide, recombinant or synthetic, having a peptide sequence which comprises a sequence identical or equivalent to SEQ ID NO:90; in particular said polypeptide exhibits an enzymatic activity consisting of proteolytic activity;

a polypeptide, recombinant or synthetic, characterized in that the open reading frame encoding it begins, in the 5'-3' direction, at nucleotide 18 and ends at nucleotide 340 of SEQ ID NO:87;

a polypeptide having an inhibitory activity on the proteolytic activity of a polypeptide as defined according to b);

c)

a polypeptide, recombinant or synthetic, having a peptide sequence which comprises a sequence identical or equivalent to SEQ ID NO:91; in particular said polypeptide exhibits a reverse transcriptase activity;

a polypeptide having a peptide sequence which comprises a sequence identical or equivalent to SEQ ID NO:92; in particular said polypeptide exhibits a ribonuclease activity;

a polypeptide, recombinant or synthetic, characterized in that the open reading frame encoding it begins, in the 5'-3' direction, at nucleotide 341 and ends at nucleotide 2304 of SEQ ID NO:87;

a polypeptide, recombinant or synthetic, characterized in that the open reading frame encoding it begins, in the 5'-3' direction, at nucleotide 1858 and ends at nucleotide 2304 of SEQ ID NO:87.

a polypeptide having an inhibitory activity on the reverse transcriptase activity of a polypeptide as defined according to c) or on the ribonuclease H activity of a polypeptide as defined according to c).

In particular, the invention relates to an antigenic polypeptide recognized by the sera of patients infected with the MSRV-1 virus, and/or in whom the MSRV-1 virus has been reactivated, whose peptide sequence is partially or totally identical or is equivalent to the sequence defined by SEQ ID NO:35, SEQ ID NO:59, SEQ ID NO:81, SEQ ID NO:89, SEQ ID NO:90, SEQ ID NO:91, SEQ ID NO:92, SEQ ID NO:132, SEQ ID NO:133, SEQ ID NO:134, SEQ ID NO:139, SEQ ID NO:140 and SEQ ID NO:141; such a sequence is identical, for example, to any sequence selected from the group including the sequences SEQ ID NO:37 to SEQ ID NO:40, SEQ ID NO:59 and SEQ ID NO:81.

The present invention also encompasses mono- or polyclonal antibodies directed against the MSRV-1 virus, which are obtained by the immunological reaction of a human or animal body or cells to an immunogenic agent consisting of an antigenic polypeptide such as is defined above.

The invention next relates to:

reagents for detection of the MSRV-virus, or of an exposure to the latter, comprising, at least one reactive substance selected from the group consisting of a probe of the present invention, a polypeptide, in particular an antigenic peptide, such as is defined above, or an anti-ligand, in particular an antibody to the said polypeptide;

all diagnostic, prophylactic or therapeutic compositions comprising one or more peptides, in particular antigenic peptides, such as are defined above, or one or more anti-ligands, in particular antibodies to the peptides, discussed above; such a composition is preferably, and by way of example, a vaccine composition.

The invention also relates to any diagnostic, prophylactic or therapeutic composition, in particular for inhibiting the expression of at least one virus associated with MS or RA, and/or the enzymatic activities of the proteins of said virus, comprising a nucleotide fragment such as is defined above or a polynucleotide, in particular oligonucleotide, whose sequence is partially identical to that of the said fragment, except for that of the fragment having the nucleotide sequence SEQ ID NO:1. Likewise, it relates to any diagnostic, prophylactic or therapeutic composition, in particular for inhibiting the expression of at least one pathogenic and/or infective agent associated with RA, comprising a nucleotide fragment such as is defined above by reference to the pol and gag genes, and especially with respect to the sequences SEQ ID NOS 36, 47, 52, 55, 56, 57, 58 and 83.

According to the invention, these same fragments or polynucleotides, in particular oligonucleotides, may participate in all suitable compositions for detecting, according to any suitable process or method, a pathological and/or infective agent associated with MS and with RA, respectively, in a biological sample. In such a process, an RNA and/or a DNA presumed to belong or originating from the said pathological and/or infective agent, and/or their complementary RNA and/or DNA, is/are brought into contact with such a composition.

The present invention also relates to any process for detecting the presence or exposure to such a pathological and/or infective agent, in a biological sample, by bringing this sample into contact with a peptide, in particular an antigenic peptide such as is defined above, or an anti-ligand, in particular an antibody to this peptide, such as is defined above.

In practice, and for example, a device for detection of the MSRV-1 virus comprises a reagent such as is defined above, supported by a solid support which is immunologically compatible with the reagent, and a means for bringing the biological sample, for example a sample of blood or of cerebrospinal fluid, likely to contain anti-MSRV-1 antibodies, into contact with this reagent under conditions permitting a possible immunological reaction, the foregoing items being accompanied by means for detecting the immune complex formed with this reagent.

Lastly, the invention also relates to the detection of anti-MSRV-1 antibodies in a biological sample, for example a sample of blood or of cerebrospinal fluid, according to which this sample is brought into contact with a reagent such as is defined above, consisting of an antibody, under conditions permitting their possible immunological reaction, and the presence of the immune complex thereby formed with the reagent is then detected.

Definitions

Before describing the invention in detail, different terms used in the description and the claims are now defined:

strain or isolate is understood to mean any infective and/or pathogenic biological fraction containing, for example, viruses and/or bacteria and/or parasites, generating pathogenic and/or antigenic power, harbored by a culture or a living host; as an example, a viral strain according to the above definition can contain a coinfective agent, for example a pathogenic protist, the term "MSRV" used in the present description denotes any pathogenic and/or infective agent associated with MS, in particular a viral species, the attenuated strains of the said viral species or the defective-interfering particles or particles containing coencapsidated genomes, or alternatively genomes recombined with a portion of the MSRV-1 genome, derived from this species. Viruses, and especially viruses containing RNA, are known to have a variability resulting, in particular, from relatively high rates of spontaneous mutation (7), which will be borne in mind below for defining the notion of equivalence, human virus is understood to mean a virus capable of infecting, or of being harbored by human beings, in view of all the natural or induced variations and/or recombination which may be encountered when implementing the present invention, the subjects of the latter, defined above and in the claims, have been expressed including the equivalents or derivatives of the different biological materials defined below, in particular of the homologous nucleotide or peptide sequences, the variant of a virus or of a pathogenic and/or infective agent according to the invention comprises at least one antigen recognized by at least one antibody directed against at least one corresponding antigen of the said virus and/or said pathogenic and/or infective agent, and/or a genome any part of which is detected by at least one hybridization probe and/or at least one nucleotide amplification primer specific for the said virus and/or pathogenic and/or infective agent, such as, for example, for the MSRV-1 virus, the primers and probes having a nucleotide sequence chosen from SEQ ID NO:15 to SEQ ID NO:21, SEQ ID NO:23, SEQ ID NO:27 to SEQ ID NO:29, SEQ ID NO:41, SEQ ID NO:43, SEQ ID NO:44, SEQ ID NO:45, SEQ ID NO:46, and their complementary sequences, under particular hybridization conditions well known to a person skilled in the art, according to the invention, a nucleotide fragment or an oligonucleotide or polynucleotide is an arrangement of monomers, or a biopolymer, characterized by the informational sequence of the natural nucleic acids, which is capable of hybridizing with any other nucleotide fragment under predetermined conditions, it being possible for the arrangement to contain monomers of different chemical structures and to be obtained from a molecule of natural nucleic acid and/or by genetic recombination and/or by chemical synthesis; a nucleotide fragment may be identical to a genomic fragment of the MSRV-1 virus discussed in the present invention, in particular a gene of this virus, for example pol or env in the case of the said virus, thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or the nucleotide can be modified in at least one of the three constituent elements; as an example, the modification can occur in the bases, generating modified bases such as inosine, 5-methyldeoxycytidine, deoxyuridine, 5-(dimethylamino)deoxyuridine, 2,6-diaminopurine, 5-bromodeoxyuridine and any other modified base promoting hybridization; in the sugar, the modification can consist of the replacement of at least one deoxyribose by a polyamide (8), and in the phosphate group, the modification can consist of its replacement by esters chosen, in particular, from diphosphate, alkyl- and arylphosphonate and phosphorothioate esters, "informational sequence" is understood to mean any ordered succession of monomers whose chemical nature and order in a reference direction constitute an item of functional information of the same quality as that of the natural nucleic acids, hybridization is understood to mean the process during which, under suitable working conditions, two nucleotide fragments having sufficiently complementary sequences pair to form a complex structure, in particular double or triple, preferably in the form of a helix, a probe comprises a nucleotide fragment synthesized chemically or obtained by digestion or enzymatic cleavage of a longer nucleotide fragment, comprising at least six monomers, advantageously from 10 to 1000 monomers, preferably 10 to 30 monomers and more preferably 18 to 30, and possessing a specificity of hybridization under particular conditions; preferably, a probe possessing fewer than 10 monomers, but preferably fewer than 15 monomers is not used alone, but is used in the presence of other probes of equally short size or otherwise; under certain special conditions, it may be useful to use probes of size greater than 100 monomers; a probe may be used, in particular, for diagnostic purposes, such molecules being, for example, capture and/or detection probes, the capture probe may be immobilized on a solid support by any suitable means, that is to say directly or indirectly, for example by covalent bonding or passive adsorption, the detection probe may be labelled by means of a label chosen, in particular, from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogues and biotin, the probes used for diagnostic purposes of the invention may be employed in all known hybridization techniques, and in particular the techniques termed "DOT-BLOT" (9), "SOUTHERN BLOT" (10), "NORTHERN BLOT", which is a technique identical to the "SOUTHERN BLOT" technique but which uses RNA as target, and the SANDWICH technique (11); advantageously, the SANDWICH technique is used in the present invention, comprising a specific capture probe and/or a specific detection probe, on the understanding that the capture probe and the detection probe must possess an at least partially different nucleotide sequence, any probe according to the present invention can hybridize in vivo or in vitro with RNA and/or with DNA in order to block the phenomena of replication, in particular translation and/or transcription, and/or to degrade the said DNA and/or RNA, a primer is a probe comprising at least six monomers, and advantageously from 10 to 30 monomers, and preferably from 18 to 25 monomers, possessing a specificity of hybridization under particular conditions for the initiation of an enzymatic polymeirzation, for example in an amplification technique such as PCR (polymerase chain reaction), in an elongation process such as sequencing, in a method of reverse transcription or the like, two nucleotide or peptide sequences are termed equivalent or derived with respect to one another, or with respect to a reference sequence, if functionally the corresponding biopolymers can perform substantially the same role, without being identical, as regards the application or use in question, or in the technique in which they participate; two sequences are, in particular, equivalent if they are obtained as a result of natural variability, in particular spontaneous mutation of the species from which they have been identified, or induced variability, as are two homologous sequences, homology being defined below, "variability" is understood to mean any spontaneous or induced modification of a sequence, in particular by substitution and/or insertion and/or deletion of nucleotides and/or of nucleotide fragments, and/or extension and/or shortening of the sequence at one or both ends; an unnatural variability can result from the genetic engineering techniques used, for example the choice of synthesis primers, degenerate or otherwise, selected for amplifying a nucleic acid; this variability can manifest itself in modifications of any starting sequence, considered as reference, and capable of being expressed by a degree of homology relative to the said reference sequence, homology characterizes the degree of identity of two nucleotide or peptide fragments compared; it is measured by the percentage identity which is determined, in particular, by direct comparison of nucleotide or peptide sequences, relative to reference nucleotide or peptide sequences, this percentage identity has been specifically determined for the nucleotide fragments, clones in particular, dealt with in the present invention, which are homologous to the fragments identified, for the MSRV-1 virus, by SEQ ID NO:1 to NO:9, SEQ ID NO:42, SEQ ID NO:47 to SEQ ID NO:49, SEQ ID NO:36, SEQ ID NO:52, SEQ ID NO:53 and SEQ ID NO:87, as well as for the probes and primers homologous to the probes and primers identified by SEQ ID NO:17 to SEQ ID NO:21, SEQ ID NO:23, SEQ ID NO:15, SEQ ID NO:16, SEQ ID NO:27 to SEQ ID NO:29, SEQ ID NO:41, SEQ ID NO:43, SEQ ID NO:44, SEQ ID NO:45, SEQ ID NO:46, SEQ ID NO:51, SEQ ID NO:36, SEQ ID NO:52, SEQ ID NO:53, SEQ ID NO:72, SEQ ID NO:76, and SEQ ID NO:93 to SEQ ID NO:99; as an example, the smallest percentage identity observed between the different general consensus sequences of nucleic acids obtained from fragments of MSRV-1 viral RNA, originating from the LM7PC and PLI-2 lines according to a protocol detailed later, is 67% in the region described in FIG. 1, any nucleotide fragment is termed equivalent or derived from a reference fragment if it possesses a nucleotide sequence equivalent to the sequence of the reference fragment; according to the above definition, the following in particular are equivalent to a reference nucleotide fragment:

a) any fragment capable of hybridizing at least partially with the complement of the reference fragment, b) any fragment whose alignment with the reference fragment results in the demonstration of a larger number of identical contiguous bases than with any other fragment originating from another taxonomic group, c) any fragment resulting, or capable of resulting, from the natural variability of the species from which it is obtained, d) any fragment capable of resulting from the genetic engineering techniques applied to the reference fragment, e) any fragment containing at least eight contiguous nucleotides encoding a peptide which is homologous or identical to the peptide encoded by the reference fragment, f) any fragment which is different from the reference fragment by insertion, deletion or substitution of at least one monomer, or extension or shortening at one or both of its ends; for example, any fragment corresponding to the reference fragment flanked at one or both of its ends by a nucleotide sequence not coding for a polypeptide, polypeptide is understood to mean, in particular, any peptide of at least two amino acids, in particular an oligopeptide, or protein, and for example an enzyme, extracted, separated or substantially isolated or synthesized through human intervention, in particular those obtained by chemical synthesis or by expression in a recombinant organism, polypeptide partially encoded by a nucleotide fragment is understood to mean a polypeptide possessing at least three amino acids encoded by at least nine contiguous monomers lying within the said nucleotide fragment, an amino acid is termed analogous to another amino acid when their respective physicochemical properties, such as polarity, hydrophobicity and/or basicity and/or acidity and/or neutrality are substantially the same; thus, a leucine is analogous to an isoleucine.

any polypeptide is termed equivalent or derived from a reference polypeptide if the polypeptides compared have substantially the same properties, and in particular the same antigenic, immunological, enzymological and/or molecular recognition properties; the following in particular are equivalent to a reference polypeptide:

a) any polypeptide possessing a sequence in which at least one amino acid has been replaced by an analogous amino acid, b) any polypeptide having an equivalent peptide sequence, obtained by natural or induced variation of the said reference polypeptide and/or of the nucleotide fragment coding for the said polypeptide, c) a mimotope of the said reference polypeptide, d) any polypeptide in whose sequence one or more amino acids of the L series are replaced by an amino acid of the D series, and vice versa, e) any polypeptide into whose sequence a modification of the side chains of the amino acids has been introduced, such as, for example, an acetylation of the amine functions, a carboxylation of the thiol functions, an esterification of the carboxyl functions, f) any polypeptide in whose sequence one or more peptide bonds have been modified, such as, for example, carba, retro, inverso, retro-inverso, reduced and methylenoxy bonds, (g) any polypeptide at least one antigen of which is recognized by an antibody directed against a reference polypeptide, the percentage identity characterizing the homology of two peptide fragments compared is, according to the present invention, at least 50% and preferably at least 70%.

In view of the fact that a virus possessing reverse transcriptase enzymatic activity may be genetically characterized equally well in RNA and in DNA form, both the viral DNA and RNA will be referred to for characterizing the sequences relating to a virus possessing such reverse transcriptase activity, termed MSRV-1 according to the present description.

The expressions of order used in the present description and the claims, such as "first nucleotide sequence", are not adopted so as to express a particular order, but so as to define the invention more clearly.

Detection of a substance or agent is understood below to mean both an identification and a quantification, or a separation or isolation, of the said substance or said agent.

BRIEF DESCRIPTION OF THE DRAWINGS

A better understanding of the invention will be gained on reading the detailed description which follows, prepared with reference to the attached figures, in which:

FIG. 1 shows general consensus sequences of nucleic acids of the MSRV-1B clones amplified by the PCR technique in the "pol" region defined by Shih (12), from viral DNA originating from the LM7PC and PLI-2 lines, and identified under the references SEQ ID NO:3, SEQ ID NO:4, SEQ ID NO:5 and SEQ ID NO:6, and the common consensus with amplification primers bearing the reference SEQ ID NO:7;

FIG. 2 gives the definition of a functional reading frame for each MSRV-1B/"PCR pol" type family, the said families A to D being defined, respectively, by the nucleotide sequences SEQ ID NO:3, SEQ ID NO:4, SEQ ID NO:5 and SEQ ID NO:6 described in FIG. 1;

FIG. 3 gives an example of consensus of the MSRV-2B sequences, identified by SEQ ID NO:11;

FIG. 6 shows the nucleotide sequence of the clone PSJ17 (SEQ ID NO:9);

FIG. 7 shows the nucleotide sequence SEQ ID NO:8 of the clone designated M003-P004;

FIG. 8 shows the nucleotide sequence SEQ ID NO:2 of the clone F11-1; the portion located between the two arrows in the region of the primer corresponds to a variability imposed by the choice of primer which was used for the cloning of F11-1; in this same Figure, the translation into amino acids is shown;

FIG. 9, split into FIGS. 9a and 9b, shows the nucleotide sequence SEQ ID NO:1, and a possible functional reading frame of SEQ ID NO:1 in terms of amino acids; on this sequence, the consensus sequences of the pol gene are underlined;

FIG. 12 gives a representation in matrix form of the homology between SEQ ID NO:1 of MSRV-1 and that of an endogenous retrovirus designated HSERV9; this homology of at least 65% is demonstrated by a continuous line, the absence of a line meaning a homology of less than 65%;

FIG. 13 shows the nucleotide sequence SEQ ID NO:42 of the clone FBd3;

FIG. 15 shows the nucleotide sequence SEQ ID NO:47 of the clone t pol;

FIGS. 16 and 17 show, respectively, the nucleotide sequences SEQ ID NO:48 and SEQ ID NO:49 of the clones JLBc1 and JLBc2, respectively;

FIG. 23 shows the nucleotide sequence SEQ ID NO:52 of the clone GM3;

FIG. 27, split into three successive FIGS. 27a–27c, shows a possible reading frame covering the whole of the pol gene;

FIG. 28 shows, according to SEQ ID NO:36, the nucleotide sequence coding for the peptide fragment POL2B, having the amino acid sequence identified by SEQ ID NO:35;

FIGS. 31 to 33 show the results obtained (relative intensity of the spots) for 43 overlapping octapeptides covering the amino acid sequence 61–110, according to the Spotscan technique, respectively with a pool of MS sera, with a pool of control sera and with the pool of MS sera after deduction of a background corresponding to the maximum signal detected on at least one octapeptide with the control serum (intensity=1), on the understanding that these sera were diluted to 1/50. The bar at the far right-hand end represents a graphic scale standard unrelated to the serological test;

FIG. 34 shows the SEQ ID NO:37 and SEQ ID NO:38 of two polypeptides comprising immunodominant regions, while SEQ ID NO:39 and 40 represent immunoreactive polypeptides specific to MS;

FIG. 35 shows the nucleotide sequence SEQ ID NO:55 of the clone LB19 and three potential reading frames of SEQ ID NO:55 in terms of amino acids;

FIG. 36 shows the nucleotide sequence SEQ ID NO:82 (GAG*) and a potential reading frame of SEQ ID NO:82 in terms of amino acids;

FIG. 38, split into FIGS. 38a–38c, shows the nucleotide sequence SEQ ID NO:57 of the clone FP6 and three potential reading frames of SEQ ID NO:57 in terms of amino acids;

FIG. 39, split into FIGS. 39a–39d, shows the nucleotide sequence SEQ ID NO:83 of the clone G+E+A and three potential reading frames of SEQ ID NO:83 in terms of amino acids;

FIG. 40 shows a reading frame found in the region E and coding for an MSRV-1 retroviral protease identified by SEQ ID NO:84;

FIG. 44 shows the nucleotide and amino acid alignment of the conserved pol regions of viruses detected in the study (cf Example 18) by the "Pan-retrovirus" PCR. "Deletions" are represented by dashes and standard single-letter abbreviations are used to designate amino acids and nucleotides (i=inosine). The most highly conserved VLPQG and YXDD regions are shown as separate blocks in bold type at the end of each sequence. Amino acids which are present in all or in all but one of the sequences are underlined. PCR primers (modified from (12)) PAN-UO and PAN-UI are orientated 5' to 3' (sense) whereas primer PAN-DI is 3' to 5' (antisense). Degeneracies are shown above (PAN-UO & PAN-DI) or below (PAN-UI) the PCR primer sequences. "I" denotes the nine base 5' extension cttggatcc, "-I" denotes the nine base 5' extension ctcaagctt. The capture and detector probes DpV1 and CpV1b used in the ELOSA assay are shown below a representative MSRV-cpol sequence. At three positions below the translated MSRV-cpol sequence alternative amino acids (representing "non-silent" nucleic acid variations) are shown in italics—K and Y substitutions were only observed in PLI-1 derived clones whereas R and W were encoded by a significant proportion of the clones irrespective of derivation. Note that DpV1 is peroxidase labelled and that CpV1 b may be biotinylated at the 5' end if streptavidin coated plates are used. The name of each sequence is indicated at the left of the figure.

HTLV1: Human Leukaemia Virus type 1; HIV1: Human Immunodeficiency Virus type 1; MoMLV: Moloney-Murine Leukaemia Virus; MPMV: Mason-Pfizer Monkey Virus. ERV9: Endogenous Retrovirus 9. MSRV-cpol: Multiple Sclerosis associated RetroVirus conserved pol region.

Figure 45:
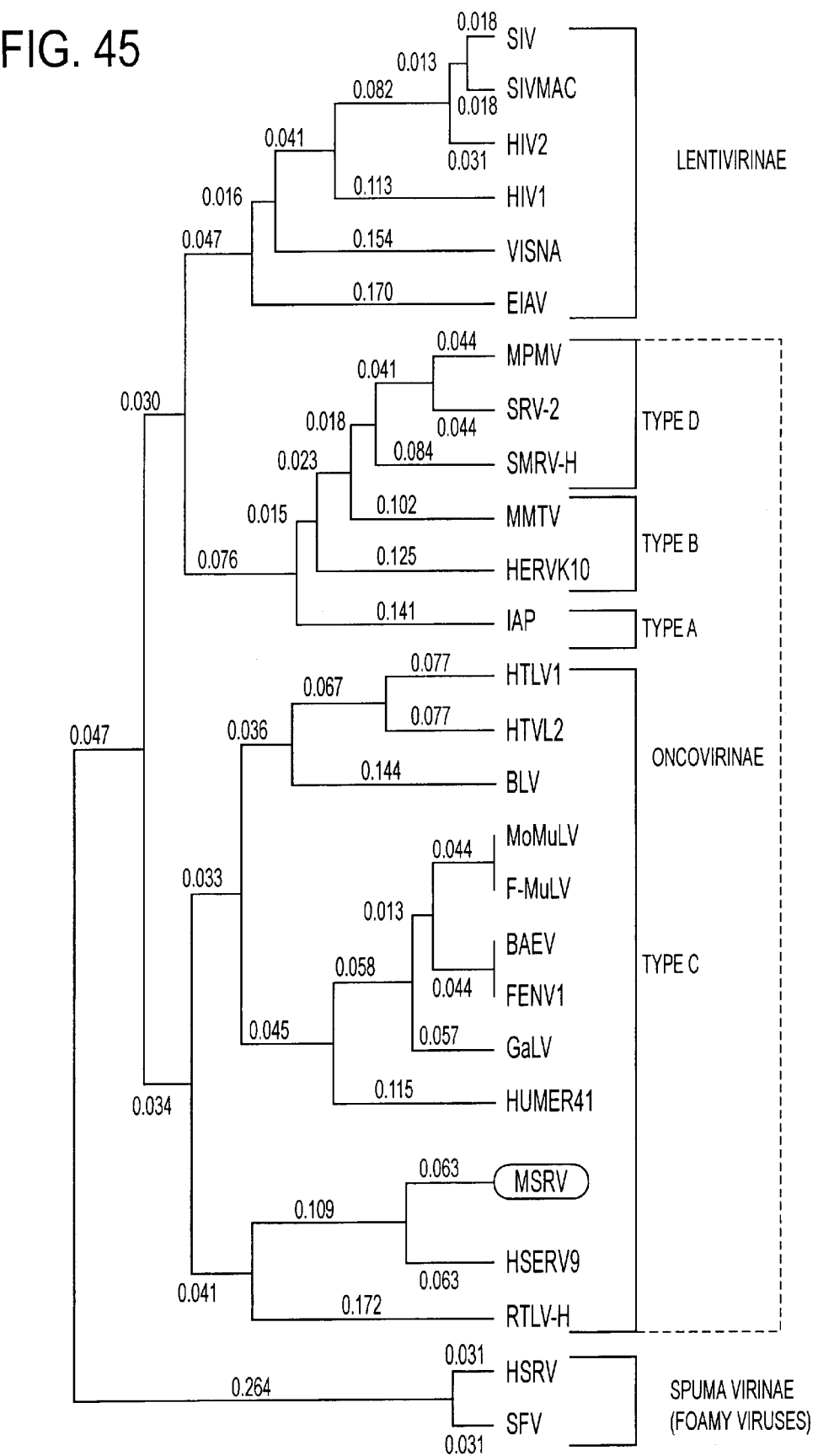

FIG. 45 shows a phylogenic tree which is based on the conserved amino acid region encoded by the pol gene of MSRV and of representative endogenous and exogenous retroviruses and DNA viruses with reverse transcriptase. It was generated by the U.P.G.M.A. tree program of Geneworks® software.

HSRV: Human Spumaretrovirus. EIAV: Equine Infectious Aenemia Virus. BLV: Bovine Leukaemia Virus. HIV1, HIV2: Human Immunodeficiency Viruses type 1 and 2. HTLV1 and HTLV2: Human Leukaemia Viruses type 1 and 2. F-MULV: Friend-Murine Leukaemia Virus. MoMLV: Moloney-Murine Leukaemia Virus. BAEV: Baboon Endogenous Virus. GaLV/Gibbon Ape Leukaemia Virus. HUMER41: Human Endogenous Retroviral sequence, clone 41. IAP: Intracisternal A-type Particle. MPMV: Mason-Pfizer Monkey Virus. HERVK10: Human Endogenous Retrovirus K10. MMTV: Mouse Mammary tumour Virus. HSERV9 (ERV9 database sequence): Human sequence of Endogenous Retrovirus 9. MSRV: Multiple Sclerosis associated RetroVirus. SIV: Simian Imunodeficiency Virus; RTLV-H: Reverse Transcriptase-Like Viral sequence H; SFV: Simian Foamy Virus; VISNA: Visna retrovirus; SIV1: Simian Immunodeficiency Virus type 1; SRV-2: Simian Retrovirus type 2; SMRV-H: Squirrel Monkey Retrovirus H.

FIG. 46 shows the MSRV sequence in the Protease and Reverse-Transcriptase regions of the pol gene. The aminoacid translation is aligned under the corresponding nucleotide sequence. The region corresponding to the Protease ORF cloned in a recombinant vector and expressed in *E. coli*, is boxed. The regions corresponding to the A and B fragments amplified on plasma samples from MS patients are indicated by brackets. The Reverse-Transcriptase (RT) and RNase H (RNH) region is boxed with dotted line. The highly conserved aminoacids and/or active sites of enzyme activities of both PRT and RT (including RNH) are shown underlined.

Figure 47B:
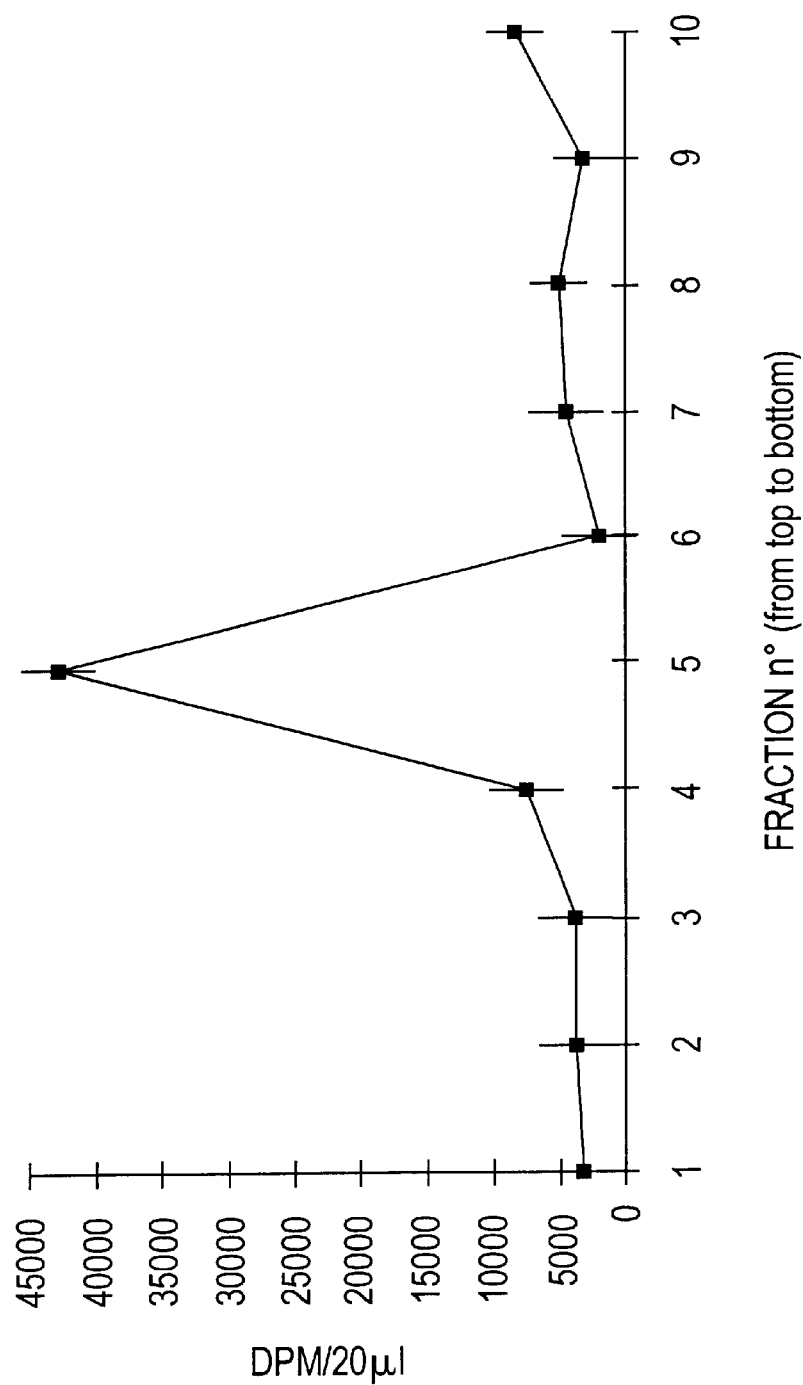

FIG. 47A illustrates the specific detection of MSRV-pol RNA sequence by RT-PCR in the sucrose density fraction associated with RT-activity and in MS plasma; FIG. 47B shows the RT-activity profile on a sucrose density gradient obtained with extracellular virion pelleted from an MS choroid-plexus culture. The photograph below shows an agarose gel loaded with PCR products amplified from round 1 (ST1.1) RT-PCR products with the ST1.2 primer set. From left to right: water control 1 from RT-PCR step with ST1.1 set; water control 2 amplified from water control 1 with ST1.2 nested primers; Molecular weight markers; Fraction n°1 to 10 corresponding to the RT-activity profile shown above; Plasma samples C1 and C2 from healthy blood donors. Plasma samples MS1 and MS2 from two MS patients.

Figure 25:
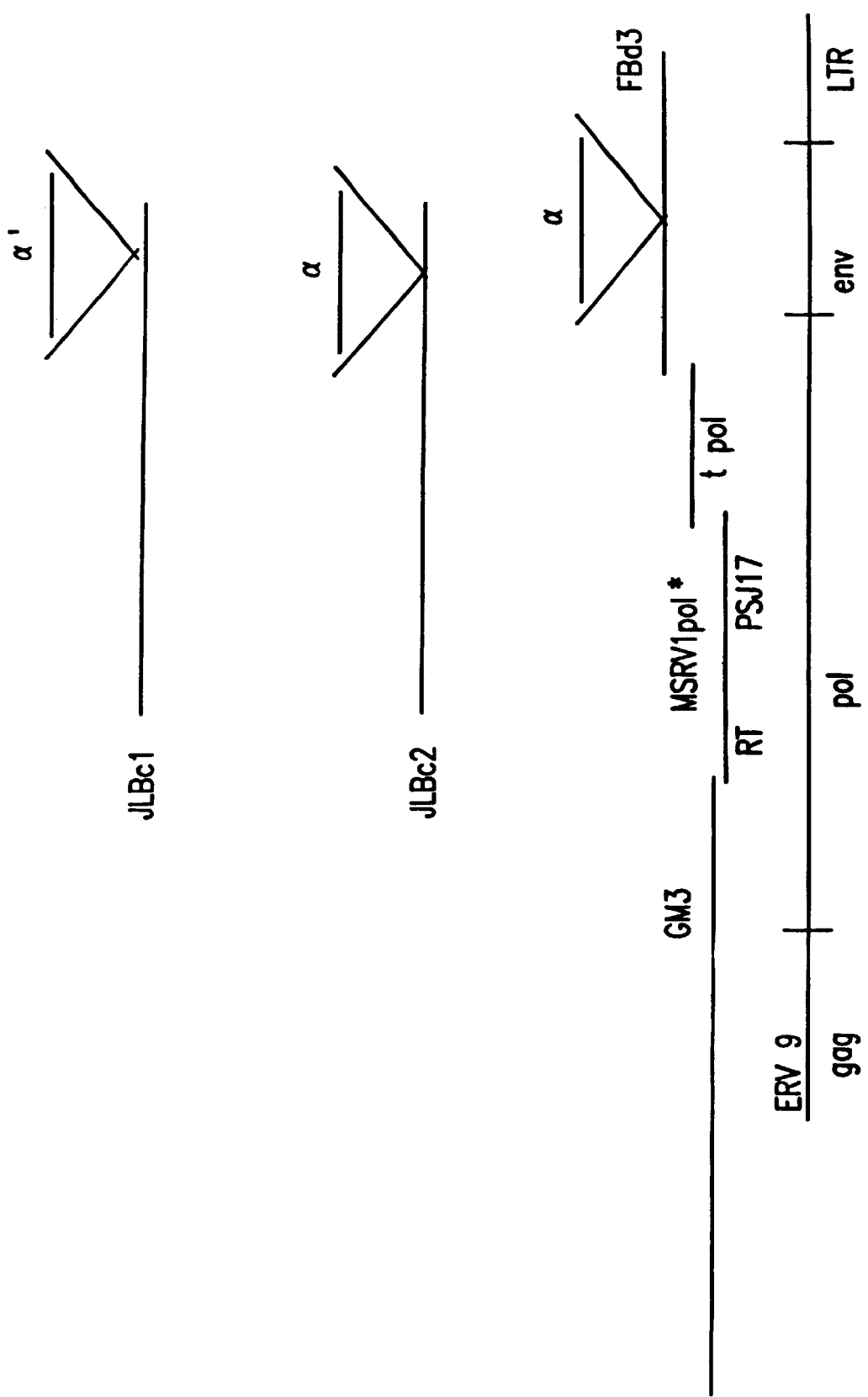
FIG. 25 shows the localization of the different clones studied, relative to the genome of the known retrovirus ERV9.

FIG. 48, split into FIGS. 48a–48e, shows an example of a variant and/or recombined sequence in the region of the pol gene defined by homology with the overlapping regions described in FIG. 25, as GM3, MSRV-1 pol*, t pol and FBd3.

FIG. 49 shows the nucleotide (FIG. 49A) and amino acid (FIG. 49B) alignments of the pol region between clones 1, 5 and 8 of the same patient (Experiment 46-7).

FIG. 50 shows the nucleotide (FIG. 50A) and amino acid (FIG. 50B) alignments of the pol region between clones 41, 43 and 42 of the same patient (Experiment 68-1).

FIG. 51 shows the nucleotide ( split into FIGS. 51A and 51B) and amino acid (FIG. 51C) alignments of the pol region between the consensus sequence (SEQ ID NO: 135) of clones 1, 5 and 8 of the same patient (Experiment 46-7) and SEQ ID NO:1, and between their corresponding peptide sequences.

FIG. 52 shows the nucleotide (split into FIGS. 52A and 52B) and amino acid (FIG. 52C) alignments of the pol region between the consensus sequence (SEQ ID NO: 128) of clones 41, 43 and 42 of the same patient (Experiment 68-1) and SEQ ID NO:1, and between their corresponding peptide sequences.

FIG. 53 shows the nucleotide (FIG. 53A) and amino acid (FIG. 53B) alignments of the pol region between the consensus sequence (SEQ ID NO: 135) of clones 1, 5 and 8 of the same patient (Experiment 46-7) and the consensus sequence (SEQ ID NO: 128) of clones 41, 43 and 42 of the same patient (Experiment 68-1).

Table 5 (at the end of the description) shows the sequences obtained by RT-PCR with degenerate pol primers on sucrose density gradient fractions containing the peak of RT-activity or its negative control (cf Example 18); and Table 6 (at the end of the description) shows the clinical data and results of MSRV-cpol detection by "Pan-retro" PCR with specific ELOSA assay, on CSF from MS and control patients (cf Example 18).

DETAILED DESCRIPTION OF PREFERRED EMBODIMENTS

EXAMPLE 1

Obtaining Clones Designated MSRV-1B and MSRV-2B, Defining, Respectively, a Retrovirus MSRV-1 and a Coinfective Agent MSRV2, by "Nested" PCR Amplification of the Conserved POL Regions of Retroviruses on Virion Preparations Originating from the LM7PC and PLI-2 Lines A PCR technique derived from the technique published by Shih (12) was used. This technique enables all trace of contaminant DNA to be removed by treating all the components of the reaction medium with DNase. It concomitantly makes it possible, by the use of different but overlapping primers in two successive series of PCR amplification cycles, to increase the chances of amplifying a cDNA synthesized from an amount of RNA which is small at the outset and further reduced in the sample by the spurious action of the DNAse on the RNA. In effect, the DNase is used under conditions of activity in excess which enable all trace of contaminant DNA to be removed before inactivation of this enzyme remaining in the sample by heating to 85° C. for 10 minutes. This variant of the PCR technique described by Shih (12) was used on a cDNA synthesized from the nucleic acids of fractions of infective particles purified on a sucrose gradient according to the technique described by H. Perron (13) from the "POL-2" isolate (ECACC No. V92072202) produced by the PLI-2 line (ECACC No. 92072201) on the one hand, and from the MS7PG isolate (ECACC No. V93010816) produced by the LM7PC line (ECACC No. 93010817) on the other hand. These cultures were obtained according to the methods which formed the subject of the patent applications published under Nos WO 93/20188 and WO 93/20189.

After cloning the products amplified by this technique with the TA Cloning Kit™ and analysis of the sequence using an Applied Biosystems model 373A Automatic Sequencer, the sequences were analysed using the Geneworks® software on the latest available version of the GenBank™ data bank.

The sequences cloned and sequenced from these samples correspond, in particular, to two types of sequence: a first type of sequence, to be found in the majority of the clones (55% of the clones originating from the POL-2 isolates of the PLI-2 culture, and 67% of the clones originating from the MS7PG isolates of the LM7PC cultures), which corresponds to a family of "pol" sequences closely similar to, but different from, the endogenous human retrovirus designated ERV-9 or HSERV-9, and a second type of sequence which corresponds to sequences very strongly homologous to a sequence attributed to another infective and/or pathogenic agent designated MSRV-2.

The first type of sequence, representing the majority of the clones, consists of sequences whose variability enables four subfamilies of sequences to be defined. These subfamilies are sufficiently similar to one another for it to be possible to consider them to be quasi-species originating from the same retrovirus, as is well known for the HIV-1 retrovirus (14), or to be the outcome of interference with several endogenous proviruses coregulated in the producing cells. These more or less defective endogenous elements are sensitive to the same regulatory signals possibly generated by a replicative provirus, since they belong to the same family of endogenous retroviruses (15). This new family of endogenous retroviruses, or alternatively this new retroviral species from which the generation of quasi-species has been obtained in culture, and which contains a consensus of the sequences described below, is designated MSRV-1B.

FIG. 1 presents the general consensus sequences of the sequences of the different MSRV-1B clones sequenced in this experiment, these sequences being identified, respectively, by SEQ ID NO:3, SEQ ID NO:4, SEQ ID NO:5 and SEQ ID NO:6. These sequences display a homology with respect to nucleic acids ranging from 70% to 88% with the HSERV9 sequence referenced X57147 and M37638 in the GenBank® data base. Four "consensus" nucleic acid sequences representative of different quasi-species of a possibly exogenous retrovirus MSRV-1B, or of different subfamilies of an endogenous retrovirus MSRV-1B, have been defined. These representative consensus sequences are presented in FIG. 2, with the translation into amino acids. A functional reading frame exists for each subfamily of these MSRV-1B sequences, and it can be seen that the functional open reading frame corresponds in each instance to the amino acid sequence appearing on the second line under the nucleic acid sequence. The general consensus of the MSRV-1B sequence, identified by SEQ ID NO:7 and obtained by this PCR technique in the "pol" region, is presented in FIG. 1.

The second type of sequence representing the majority of the clones sequenced is represented by the sequence MSRV-2B presented in FIG. 3 and identified by SEQ ID NO:11. The differences observed in the sequences corresponding to the PCR primers are explained by the use of degenerate primers in mixture form used under different technical conditions.

The MSRV-2B sequence (SEQ ID NO:11) is sufficiently divergent from the retroviral sequences already described in the data banks for it to be suggested that the sequence region in question belongs to a new infective agent, designated MSRV-2. This infective agent would, in principle, on the basis of the analysis of the first sequences obtained, be related to a retrovirus but, in view of the technique used for obtaining this sequence, it could also be a DNA virus whose genome codes for an enzyme which incidentally possesses reverse transcriptase activity, as is the case, for example, with the hepatitis B virus, HBV (12). Furthermore, the random nature of the degenerate primers used for this PCR amplification technique may very well have permitted, as a result of unforeseen sequence homologies or of conserved sites in the gene for a related enzyme, the amplification of a nucleic acid originating from a prokaryotic or eukaryotic pathogenic and/or coinfective agent (protist).

EXAMPLE 2

Figure 4:
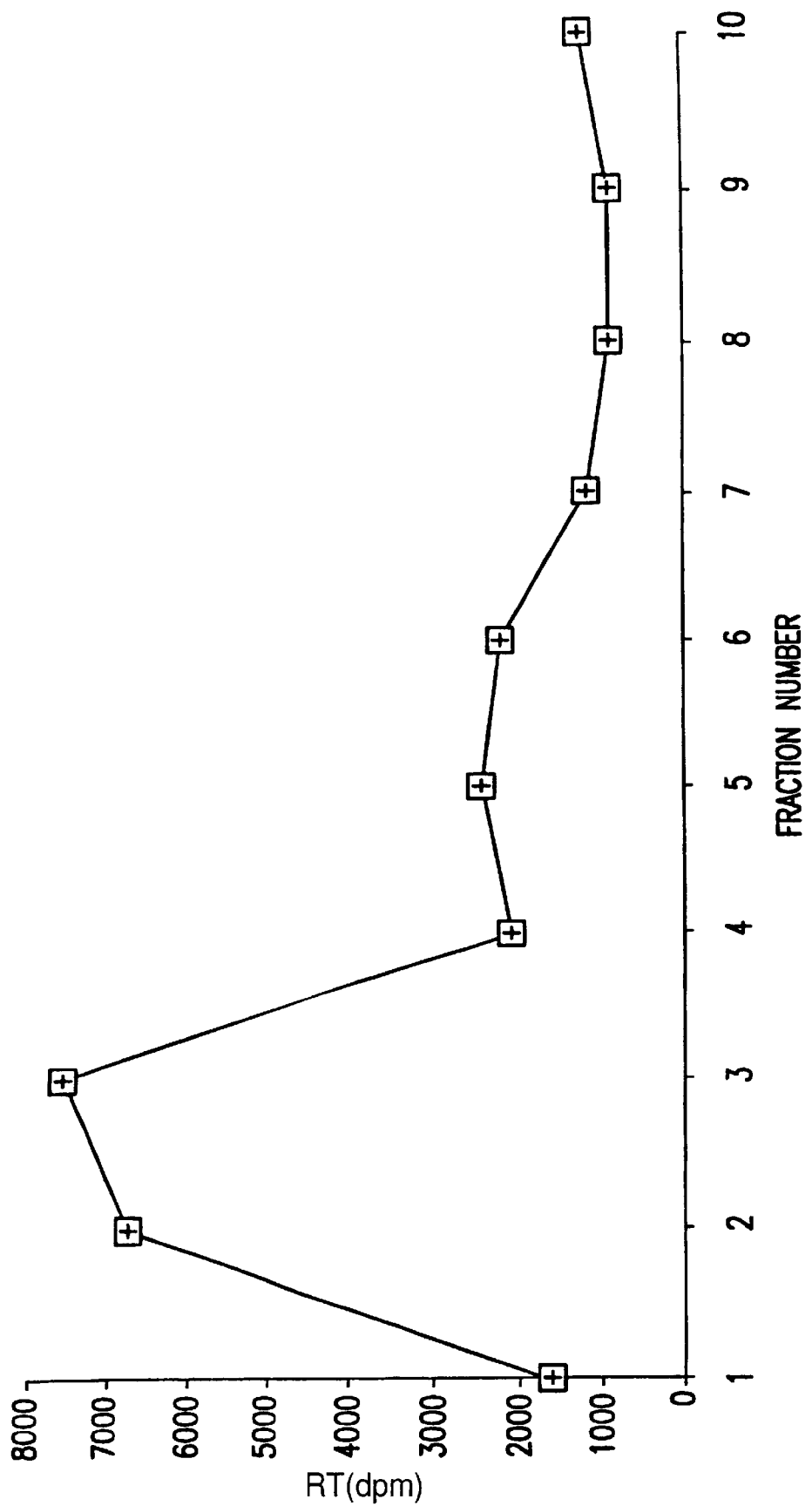
FIG. 4 is a representation of the reverse transcriptase (RT) activity in dpm (disintegrations per minute) in the sucrose fractions taken from a purification gradient of the virions produced by the B lymphocytes in culture from a patient suffering from MS.
Figure 5:
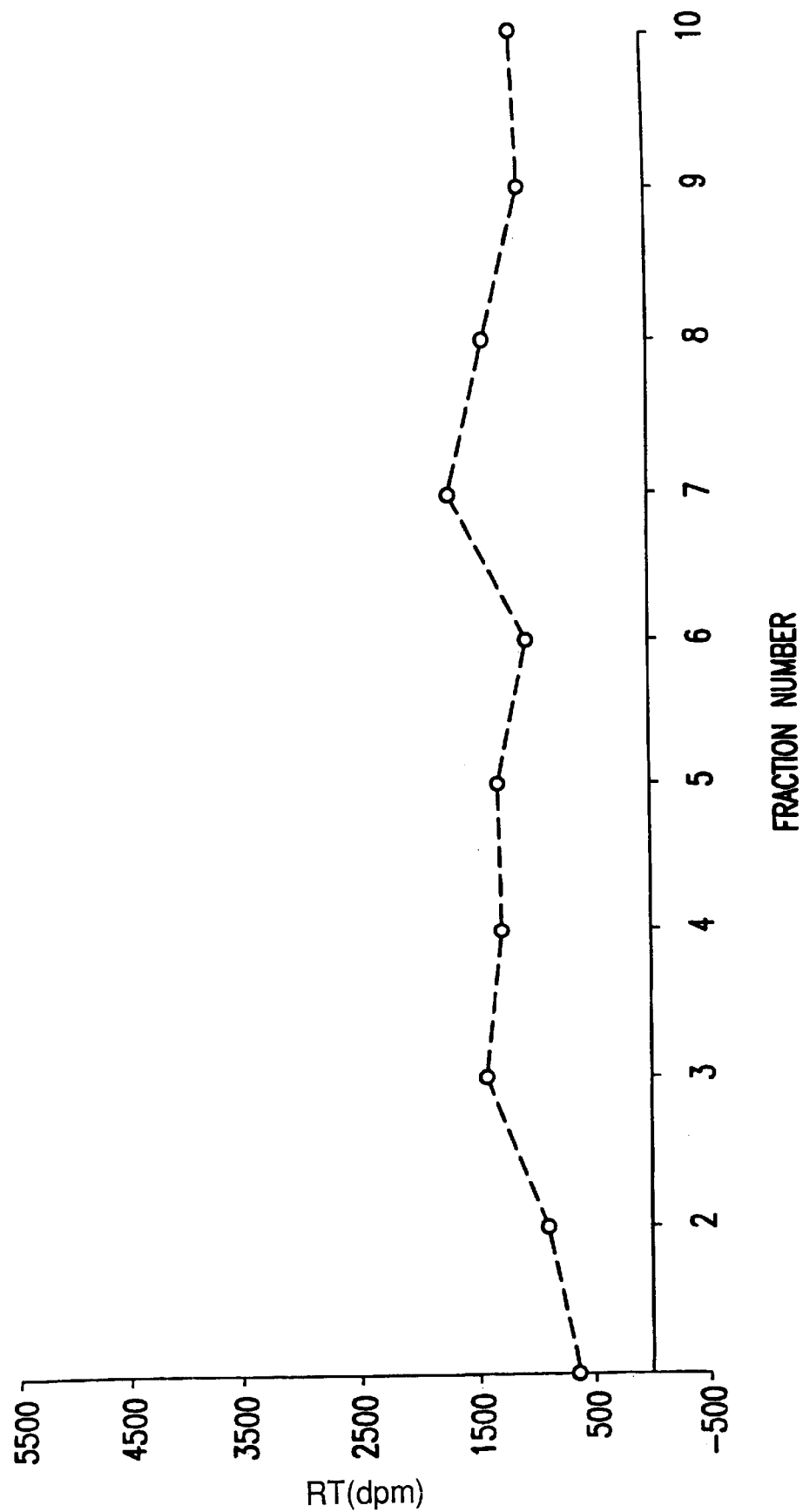
FIG. 5 gives, under the same experimental conditions as in FIG. 4, the assay of the reverse transcriptase activity in the culture of a B lymphocyte line obtained from a control free from MS.

Obtaining Clones Designated MSRV-1B and MSRV-2B, Defining a Family MSRV-1 and MSRV-2, by "Nested" PCR Amplification of the Conserved Pol Regions of Retroviruses on Preparations of B Lymphocytes from a New Case of MS The same PCR technique, modified according to the technique of Shih (12), was used to amplify and sequence the RNA nucleic acid material present in a purified fraction of virions at the peak of "LM7-like" reverse transcriptase activity on a sucrose gradient according to the technique described by H. Perron (13), and according to the protocols mentioned in Example 1, from a spontaneous lymphoblastoid line obtained by self-immortalization in culture of B lymphocytes from an MS patient who was seropositive for the Epstein-Barr virus (EBV), after setting up the blood lymphoid cells in culture in a suitable culture medium containing a suitable concentration of cyclosporin A. A representation of the reverse transcriptase activity in the sucrose fractions taken from a purification gradient of the virions produced by this line is presented in FIG. 4. Similarly, the culture supernatants of a B line obtained under the same conditions from a control free from MS were treated under the same conditions, and the assay of reverse transcriptase activity in the sucrose gradient fractions proved negative throughout (background), and is presented in FIG. 5. Fraction 3 of the gradient corresponding to the MS B line and the same fraction without reverse transcriptase activity of the non-MS control gradient were analysed by the same RT-PCR technique as before, derived from Shih (12), followed by the same steps of cloning and sequencing as described in Example 1.

It is particularly noteworthy that the MSRV-1 and MSRV-2 type sequences are to be found only in the material associated with a peak of "LM7-like" reverse transcriptase activity originating from the MS B lymphoblastoid line. These sequences were not to be found with the material from the control (non-MS) B lymphoblastoid line in 26 recombinant clones taken at random. Only Mo-MuLV type contaminant sequences, originating from the commercial reverse transcriptase used for the cDNA synthesis step, and sequences without any particular retroviral analogy were to be found in this control, as a result of the "consensus" amplification of homologous polymerase sequences which is produced by this PCR technique. Furthermore, the absence of a concentrated target which competes for the amplification reaction in the control sample permits the amplification of dilute contaminants. The difference in results is manifestly highly significant (chi-squared, p<0.001).

EXAMPLE 3
Obtaining a Clone PSJ17, Defining a Retrovirus MSRV-1, by Reaction of Endogenous Reverse Transcriptase with a Virion Preparation Originating from the PLI-2 Line This approach is directed towards obtaining reverse-transcribed DNA sequences from the supposedly retroviral RNA in the isolate using the reverse transcriptase activity present in this same isolate. This reverse transcriptase activity can theoretically function only in the presence of a retroviral RNA linked to a primer tRNA or hybridized with short strands of DNA already reverse-transcribed in the retroviral particles (16). Thus, the obtaining of specific retroviral sequences in a material contaminated with cellular nucleic acids was optimized according to these authors by means of the specific enzymatic amplification of the portions of viral RNAs with a viral reverse transcriptase activity. To this end, the authors determined the particular physico-chemical conditions under which this enzymatic activity of reverse transcription on RNAs contained in virions could be effective in vitro. These conditions correspond to the technical description of the protocols presented below (endogenous RT reaction, purification, cloning and sequencing).

The molecular approach consisted in using a preparation of concentrated but unpurified virion obtained from the culture supernatants of the PLI-2 line, prepared according to the following method: the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virion. This concentrated but unpurified viral sample was used to perform a so-called endogenous reverse transcription reaction, as described below.

A volume of 200 ml of virion purified according to the protocol described above, and containing a reverse transcriptase activity of approximately 1–5 million dpm, is thawed at 37° C. until a liquid phase appears, and then placed on ice. A 5-fold concentrated buffer was prepared with the following components: 500 mM Tris-HCl pH 8.2; 75 mM NaCl; 25 mM $MgCl_2$; 75 mM DTT and 0.10% NP 40; 100 ml of 5×buffer+25 ml of a 100 mM solution of dATP+25 ml of a 100 mM solution of dTTP+25 ml of a 100 mM solution of dGTP+25 ml of a 100 mM solution of dCTP+100 ml of sterile distilled water+200 ml of the virion suspension (RT activity of 5 million DPM) in PBS were mixed and incubated at 42° C. for 3 hours. After this incubation, the reaction mixture is added directly to a buffered phenol/chloroform/isoamyl alcohol mixture (Sigma ref. P 3803); the aqueous phase is collected and one volume of sterile distilled water is added to the organic phase to re-extract the residual nucleic acid material. The collected aqueous phases are combined, and the nucleic acids contained are precipitated by adding 3M sodium acetate pH 5.2 to 1/10 volume+2 volumes of ethanol+1 ml of glycogen (Boehringer-Mannheim ref. 901 393) and placing the sample at −20° C. for 4 h or overnight at +4° C. The precipitate obtained after centrifugation is then washed with 70% ethanol and resuspended in 60 ml of distilled water. The products of this reaction were then purified, cloned and sequenced according to the protocol which will now be described: blunt-ended DNAs with unpaired adenines at the ends were generated: a "filling-in" reaction was first performed: 25 ml of the previously purified DNA solution were mixed with 2 ml of a 2.5 mM solution containing, in equimolar amounts, dATP+dGTP+dTTP+dCTP/1 ml of T4 DNA polymerase (Boehringer-Mannheim ref. 1004 786)/5 ml of 10×"incubation buffer for restriction enzyme" (Boehringer-Mannheim ref. 1417 975)/1 ml of a 1% bovine serum albumin solution/16 ml of sterile distilled water. This mixture was incubated for 20 minutes at 11° C. 50 ml of TE buffer and 1 ml of glycogen (Boehringer-Mannheim ref. 901 393) were added thereto before extraction of the nucleic acids with phenol/chloroform/isoamyl alcohol (Sigma ref. P 3803) and precipitation with sodium acetate as described above. The DNA precipitated after centrifugation is resuspended in 10 ml of 10 mM Tris buffer pH 7.5. 5 ml of this suspension were then mixed with 20 ml of 5×Taq buffer, 20 ml of 5 mM dATP, 1 ml (5 U) of Taq DNA polymerase (AmplitaqTM) and 54 ml of sterile distilled water. This mixture is incubated for 2 h at 75° C. with a film of oil on the surface of the solution. The DNA suspended in the aqueous solution drawn off under the film of oil after incubation is precipitated as described above and resuspended in 2 ml of sterile distilled water. The DNA obtained was inserted into a plasmid using the TA CloningTM kit. The 2 ml of DNA solution were mixed with 5 ml of sterile distilled water, 1 ml of a 10-fold concentrated ligation buffer "10×LIGATION BUFFER", 2 ml of "pCR™ VECTOR" (25 ng/ml) and 1 ml of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA cloning™ kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

Discriminating analysis on the computerized data banks of the sequences cloned from the DNA fragments present in the reaction mixture enabled a retroviral type sequence to be revealed. The corresponding clone PSJ17 was completely sequenced, and the sequence obtained, presented in FIG. 6 and identified by SEQ ID NO:9, was analysed using the "Geneworks®" software on the updated "GenBank™" data banks. An identical sequence already described could not be found by analysis of the data banks. Only a partial homology with some known retroviral elements was to be found. The most useful relative homology relates to an endogenous retrovirus designated ERV-9, or HSERV-9, according to the references (18).

EXAMPLE 4
PCR Amplification of the Nucleic Acid Sequence Contained Between the 5' Region Defined by the Clone "POL MSRV-1B" and the 3' Region Defined by the Clone PSJ17

Five oligonucleotides, M001, M002-A, M003-BCD, P004 and P005, were defined in order to amplify the RNA originating from purified POL-2 virions. Control reactions were performed so as to check for the presence of contaminants (reaction with water). The amplification consists of an RT-PCR step according to the protocol described in Example 2, followed by a "nested" PCR according to the PCR protocol described in the document EP-A-0,569,272. In the first RT-PCR cycle, the primers M001 and P004 or P005 are used. In the second PCR cycle, the primers M002-A or M003-BCD and the primer P004 are used. The primers are positioned as follows:

Their composition is:
primer M001: GGTCITICCICAIGG (SEQ ID NO:19)
primer M002-A: TTAGGGATAGCCCTCATCTCT (SEQ ID NO:20)
primer M003-BCD: TCAGGGATAGCCCCCATCTAT (SEQ ID NO:17)
primer P004: AACCCTTTGCCACTACATCAATTT (SEQ ID NO:18)
primer P005: GCGTAAGGACTCCTAGAGCTATT (SEQ ID NO:21)

The "nested" amplification product obtained, and designated M003-P004, is presented in FIG. 7, and corresponds to the sequence SEQ ID NO:8.

EXAMPLE 5
Amplification and Cloning of a Portion of the MSRV-1 Retroviral Genome Using a Sequence Already Identified, in a Sample of Virus Purified at the Peak of Reverse Transcriptase Activity A PCR technique derived from the technique published by Frohman (19) was used. The technique derived makes it possible, using a specific primer at the 3' end of the genome to be amplified, to elongate the sequence towards the 5' region of the genome to be analyzed. This technical variant is described in the documentation of the firm "Clontech Laboratories Inc.", (Palo-Alto Calif., USA) supplied with its product "5'-AmpliFINDER™ RACE Kit", which was used on a fraction of virion purified as described above.

The specific 3' primers used in the kit protocol for the synthesis of the cDNA and the PCR amplification are, respectively, complementary to the following MSRV-1 sequences:

cDNA: TCATCCATGTACCGAAGG (SEQ ID NO:22)

amplification: ATGGGGTTCCCAAGTTCCCT (SEQ ID NO:23)

The products originating from the PCR were obtained after purification on agarose gel according to conventional methods (17), and then resuspended in 10 $\mu$l of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 $\mu$l of DNA solution were mixed with 5 ml of sterile distilled water, 1 $\mu$l of a 10-fold concentrated ligation buffer "10×LIGATION BUFFER", 2 $\mu$l of "pCR™ VECTOR" (25 ng/ml) and 1 $\mu$l of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer model 373 A" apparatus according to the manufacturer's instructions.

This technique was applied first to two fractions of virion purified as described below on sucrose from the "POL-2" isolate produced by the PLI-2 line on the one hand, and from the MS7PG isolate produced by the LM7PC line on the other hand. The culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virions. The concentrated virus is then applied to a sucrose gradient in sterile PBS buffer (15 to 50% weight/weight) and ultracentrifuged at 35,000 rpm (100,000 g) for 12 h at +4° C. in a swing-out rotor. 10 fractions are collected, and 20 ml are withdrawn from each fraction after homogenization to assay the reverse transcriptase activity therein according to the technique described by H. Perron (3). The fractions containing the peak of "LM7-like" RT activity are then diluted in sterile PBS buffer and ultracentrifuged for one hour at 35,000 rpm (100,000 g) to sediment the viral particles. The pellet of purified virion thereby obtained is then taken up in a small volume of a buffer which is appropriate for the extraction of RNA. The cDNA synthesis reaction mentioned above is carried out on this RNA extracted from purified extracellular virion. PCR amplification according to the technique mentioned above enabled the clone F1-11 to be obtained, whose sequence, identified by SEQ ID NO:2, is presented in FIG. 8.

This clone makes it possible to define, with the different clones previously sequenced, a region of considerable length (1.2 kb) representative of the "pol" gene of the MSRV-1 retrovirus, as presented in FIG. 9. This sequence, designated SEQ ID NO:1, is reconstituted from different clones overlapping one another at their ends, correcting the artefacts associated with the primers and with the amplification or cloning techniques which would artificially interrupt the reading frame of the whole. This sequence will be identified below under the designation "MSRV-1 pol* region". Its degree of homology with the HSERV-9 sequence is shown in FIG. 12.

In FIG. 9, the potential reading frame with its translation into amino acids is presented below the nucleic acid sequence.

EXAMPLE 6

Detection of Specific MSRV-1 and MSRV-2 Sequences in Different Samples of Plasma Originating from Patients Suffering from MS or From Controls A PCR technique was used to detect the MSRV-1 and MSRV-2 genomes in plasmas obtained after taking blood samples from patients suffering from MS and from non-MS controls onto EDTA.

Extraction of the RNAs from plasma was performed according to the technique described by P. Chomzynski (20), after adding one volume of buffer containing guanidinium thiocyanate to 1 ml of plasma stored frozen at −80° C. after collection.

For MSRV-2, the PCR was performed under the same conditions and with the following primers:

5' primer, identified by SEQ ID NO:14
5' GTAGTTCGATGTAGAAAGCG 3';
3' primer, identified by SEQ ID NO:13
5' GCATCCGGCAACTGCACG 3'.

However, similar results were also obtained with the following PCR primers in two successive amplifications by "nested" PCR on samples of nucleic acids not treated with DNase.

The primers used for this first step of 40 cycles with a hybridization temperature of 48° C. are the following:

5' primer, identified by SEQ ID NO:24
5' GCCGATATCACCCGCCATGG 3', corresponding to a 5' MSRV-2 PCR primer, for a first PCR on samples from patients,
3' primer, identified by SEQ ID NO:13
5' GCATCCGGCAACTGCACG 3', corresponding to a 3' MSRV-2 PCR primer, for a first PCR on samples from patients.

After this step, 10 ml of the amplification product are taken and used to carry out a second, so-called "nested" PCR amplification with primers located within the region already amplified. This second step takes place over 35 cycles, with a primer hybridization ("annealing") temperature of 50° C. The reaction volume is 100 ml.

The primers used for this second step are the following:

5' primer, identified by SEQ ID NO:25
5 CGCGATGCTGGTTGGAGAGC 3', corresponding to a 5' MSRV-2 PCR primer, for a nested PCR on samples from patients,
3' primer, identified by SEQ ID NO:26
5' TCTCCACTCCGAATATTCCG 3', corresponding to a 3' MSRV-2 PCR primer, for a nested PCR on samples from patients.

For MSRV-1, the amplification was performed in two steps. Furthermore, the nucleic acid sample is treated beforehand with DNase, and a control PCR without RT (AMV reverse transcriptase) is performed on the two amplification steps so as to verify that the RT-PCR amplification comes exclusively from the MSRV-1 RNA. In the event of a positive control without RT, the initial aliquot sample of RNA is again treated with DNase and amplified again.

The protocol for treatment with DNase lacking RNAse activity is as follows: the extracted RNA is aliquoted in the presence of "RNAse inhibitor" (Boehringer-Mannheim) in water treated with DEPC at a final concentration of 1 mg in 10 ml; to these 10 ml, 1 ml of "RNAse-free DNAse" (Boehringer-Mannheim) and 1.2 ml of pH 5 buffer containing 0.1 M/1 sodium acetate and 5 MM/1 $MgSO_4$ is added; the mixture is incubated for 15 min at 20° C. and brought to 95° C. for 1.5 min in a "thermocycler".

The first MSRV-1 RT-PCR step is performed according to a variant of the RNA amplification method as described in Patent Application No. EP-A-0,569,272. In particular, the cDNA synthesis step is performed at 42° C. for one hour; the PCR amplification takes place over 40 cycles, with a primer hybridization ("annealing") temperature of 53° C. The reaction volume is 100 µl.

The primers used for this first step are the following:

5' primer, identified by SEQ ID NO:15
5' AGGAGTAAGGAAACCCAACGGAC 3';
3' primer, identified by SEQ ID NO:16
5' TAAGAGTTGCACAAGTGCG 3'.

After this step, 10 ml of the amplification product are taken and used to carry out a second, so-called "nested" PCR amplification with primers located within the region already amplified. This second step takes place over 35 cycles, with a primer hybridization ("annealing") temperature of 53° C. The reaction volume is 100 µl.

The primers used for this second step are the following:

5' primer, identified by SEQ ID NO:17
5' TCAGGGATAGCCCCCATCTAT 3';
3' primer, identified by SEQ ID NO:18
5' AACCCTTTGCCACTACATCAATTT 3'.

Figure 10:
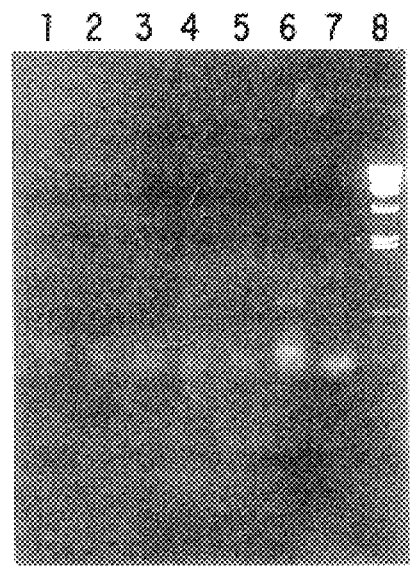
FIGS. 10 and 11 give the results of a PCR, in the form of a photograph under ultraviolet light of an ethidium bromide-impregnated agarose gel, of the amplification products obtained from the primers identified by SEQ ID NO:15, SEQ ID NO:16, SEQ ID NO:17 and SEQ ID NO:18.
Figure 11:
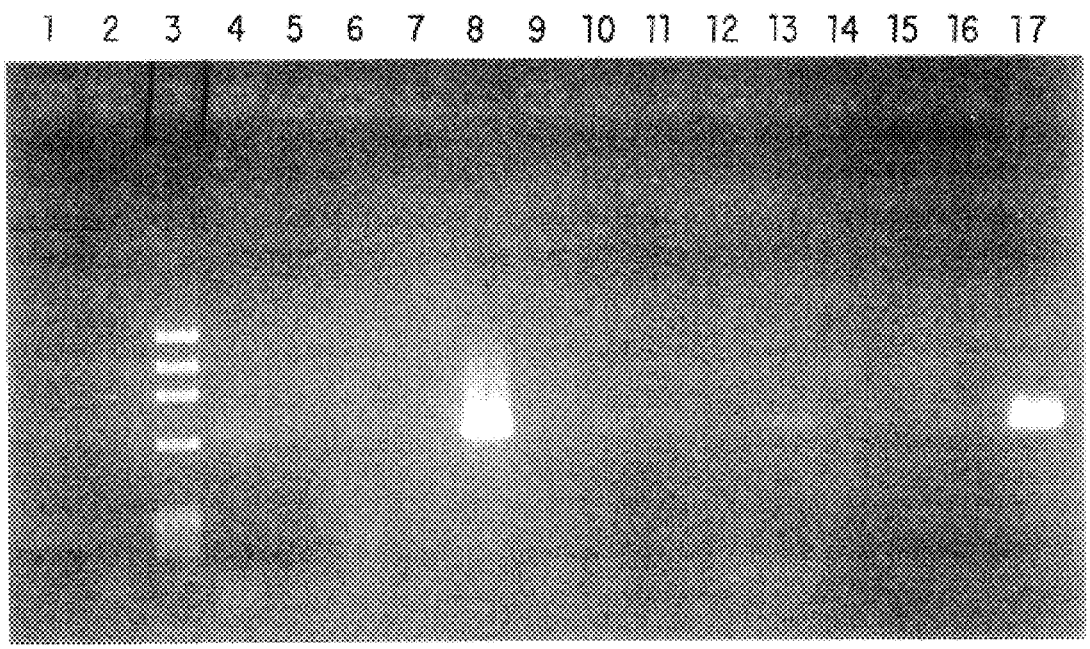

FIGS. 10 and 11 present the results of PCR in the form of photographs under ultraviolet light of ethidium bromide-impregnated agarose gels, in which an electrophoresis of the PCR amplification products applied separately to the different wells was performed.

The top photograph (FIG. 10) shows the result of specific MSRV-2 amplification.

Well number 8 contains a mixture of DNA molecular weight markers, and wells 1 to 7 represent, in order, the products amplified from the total RNAs of plasmas originating from 4 healthy controls free from MS (wells 1 to 4) and from 3 patients suffering from MS at different stages of the disease (wells 5 to 7).

In this series, MSRV-2 nucleic acid material is detected in the plasma of one case of MS out of the 3 tested, and in none of the 4 control plasmas. Other results obtained on more extensive series confirm these results.

The bottom photograph (FIG. 11) shows the result of specific amplification by MSRV-1 "nested" RT-PCR:

well No. 1 contains the PCR product produced with water alone, without the addition of AMV reverse transcriptase; well No. 2 contains the PCR product produced with water alone, with the addition of AMV reverse transcriptase; well number 3 contains a mixture of DNA molecular weight markers; wells 4 to 13 contain, in order, the products amplified from the total RNAs extracted from sucrose gradient fractions (collected in a downward direction), on which gradient a pellet of virion originating from a supernatant of a culture infected with MSRV-1 and MSRV-2 was centrifuged to equilibrium according to the protocol described by H. Perron (13); to well 14 nothing was applied; to wells 15 to 17, the amplified products of RNA extracted from plasmas originating from 3 different patients suffering from MS at different stages of the disease were applied.

The MSRV-1 retroviral genome is indeed to be found in the sucrose gradient fraction containing the peak of reverse transcriptase activity measured according to the technique described by H. Perron (3), with a very strong intensity (fraction 5 of the gradient, placed in well No. 8). A slight amplification has taken place in the first fraction (well No. 4), probably corresponding to RNA released by lysed particles which floated at the surface of the gradient; similarly, aggregated debris has sedimented in the last fraction (tube bottom), carrying with it a few copies of the MSRV-1 genome which have given rise to an amplification of low intensity.

Of the 3 MS plasmas tested in this series, MSRV-1 RNA turned up in one case, producing a very intense amplification (well No. 17).

In this series, the MSRV-1 retroviral RNA genome, probably corresponding to particles of extracellular virus present in the plasma in extremely small numbers, was detected by "nested" RT-PCR in one case of MS out of the 3 tested. Other results obtained on more extensive series confirm these results.

Furthermore, the specificity of the sequences amplified by these PCR techniques may be verified and evaluated by the "ELOSA" technique as described by F. Mallet (21) and in the document FR-A-2,663,040.

For MSRV-1, the products of the nested PCR described above may be tested in two ELOSA systems enabling a consensus A and a consensus B+C+D of MSRV-1 to be detected separately, corresponding to the subfamilies described in Example 1 and FIGS. 1 and 2. In effect, the sequences closely resembling the consensus B+C+D are to be found essentially in the RNA samples originating from MSRV-1 virions purified from cultures or amplified in extracellular biological fluids of MS patients, whereas the sequences closely resembling the consensus A are essentially to be found in normal human cellular DNA.

The ELOSA/MSRV-1 system for the capture and specific hybridization of the PCR products of the subfamily A uses a capture oligonucleotide cpV1A with an amine bond at the 5' end and a biotinylated detection oligonucleotide dpV1A having as their sequence, respectively:

cpV1A identified by SEQ ID NO:27
5' GATCTAGGCCACTTCTCAGGTCCAGS 3', corresponding to the ELOSA capture oligonucleotide for the products of MSRV-1 nested PCR performed with the primers identified by SEQ ID NO:15 and SEQ ID NO:16, optionally followed by amplification with the primers identified by SEQ ID NO:17 and SEQ ID NO:18 on samples from patients;

dpV1A identified by SEQ ID NO:28;
5' CATCTITTTGGICAGGCAITAGC 3', corresponding to the ELOSA capture oligonucleotide for the subfamily A of the products of MSRV-1 "nested" PC R performed with the primers identified by SEQ ID NO:15 and SEQ ID NO:16, optionally followed by amplification with the primers identified by SEQ ID NO:17 and SEQ ID NO:18 on samples from patients.

The ELOSA/MSRV-1 system for the capture and specific hybridization of the PCR products of the subfamily B+C+D uses the same biotinylated detection oligonucleotide dpV1A and a capture oligonucleotide cpV1B with an amine bond at the 5' end having as its sequence:

dpV1B identified by SEQ ID NO:29
5° CTTGAGCCAGTTCTCATACCTGGA 3', corresponding to the ELOSA capture oligonucleotide for the subfamily B+C+D of the products of MSRV-1 "nested" PCR performed with the primers identified by SEQ ID NO:15 and SEQ ID NO;16, optionally followed by amplification with the primers identified by SEQ ID NO:17 and SEQ ID NO:18 on samples from patients.

This ELOSA detection system enabled it to be verified that none of the PCR products thus amplified from DNase-treated plasmas of MS patients contained a sequence of the subfamily A, and that all were positive with the consensus of the subfamilies B, C and D.

For MSRV-2, a similar ELOSA technique was evaluated on isolates originating from infected cell cultures, using the following PCR amplification primers, 5' primer, identified by SEQ ID NO:30
5' AGTGYTRCCMCARGGCGCTGAA 3', corresponding to a 5' MSRV-2 PCR primer, for PCR on samples from cultures, 3' primer, identified by SEQ ID NO:31
5' GMGGCCAGCAGSAKGTCATCCA 3', corresponding to a 3' MSRV-2 PCR primer, for PCR on samples from cultures, and the capture oligonucleotides with an amine bond at the 5' end cpV2 and the biotinylated detection oligonucleotide dpV2 having as their respective sequences:

cpV2 identified by SEQ ID NO:32
5 GGATGCCGCCTATAGCCTCTAC 3', corresponding to an ELOSA capture oligonucleotide for the products of MSRV-2 PCR performed with the primers SEQ ID NO:34 and SEQ ID NO:35, or optionally with the degenerate primers defined by Shih (12).

dpV2 identified by SEQ ID NO:33
5' AAGCCTATCGCGTGCAGTTGCC 3', corresponding to an ELOSA detection oligonucleotide for the products of MSRV-2 PCR performed with the primers SEQ ID NO:30 and SEQ ID NO:31, or optionally with the degenerate primers defined by Shih (12).

This PCR amplification system with a pair of primers different from those which were described previously for amplification on the samples from patients made it possible to confirm the infection with MSRV-2 of in vitro cultures and of samples of nucleic acids used for the molecular biology studies.

All things considered, the first results of PCR detection of the genome of pathogenic and/or infective agents show that it is possible that free "virus" may circulate in the blood stream of patients in an acute, virulent phase, outside the nervous system. This is compatible with the almost invariable presence of "gaps" in the blood-brain barrier of patients in an active phase of MS.

EXAMPLE 7

Obtaining Sequences of the "env" Gene of the MSRV-1 Retroviral Genome

As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analysed. This technical variant is described in the documentation of "Clontech Laboratories Inc., (Palo-Alto Calif., USA) supplied with its product "5'-AmpliFINDER™ RACE Kit", which was used on a fraction of virion purified as described above.

In order to carry out an amplification of the 3' region of the MSRV-1 retroviral genome encompassing the region of the "env" gene, a study was carried out to determine a consensus sequence in the LTR regions of the same type as those of the defective endogenous retrovirus HSERV-9 (18, 24), with which the MSRV-1 retrovirus displays partial homologies.

The same specific 3' primer was used in the kit protocol for the synthesis of the cDNA and the PCR amplification; its sequence is as follows:

GTGCTGATTGGTGTATTTACAATCC (SEQ ID NO 41)

Synthesis of the complementary DNA (cDNA) and uni-directional PCR amplification with the above primer were carried out in one step according to the method described in Patent EP-A-0,569,272.

The products originating from the PCR were extracted after purification of agarose gel according to conventional methods (17), and then resuspended in 10 μl of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 μl of DNA solution were mixed with 5 μl of sterile distilled water, 1 μl of a 10-fold concentrated ligation buffer "10×LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer, model 373 A" apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone FBd3 to be obtained, whose sequence, identified by SEQ ID NO:42, is presented in FIG. 13.

Figure 14:
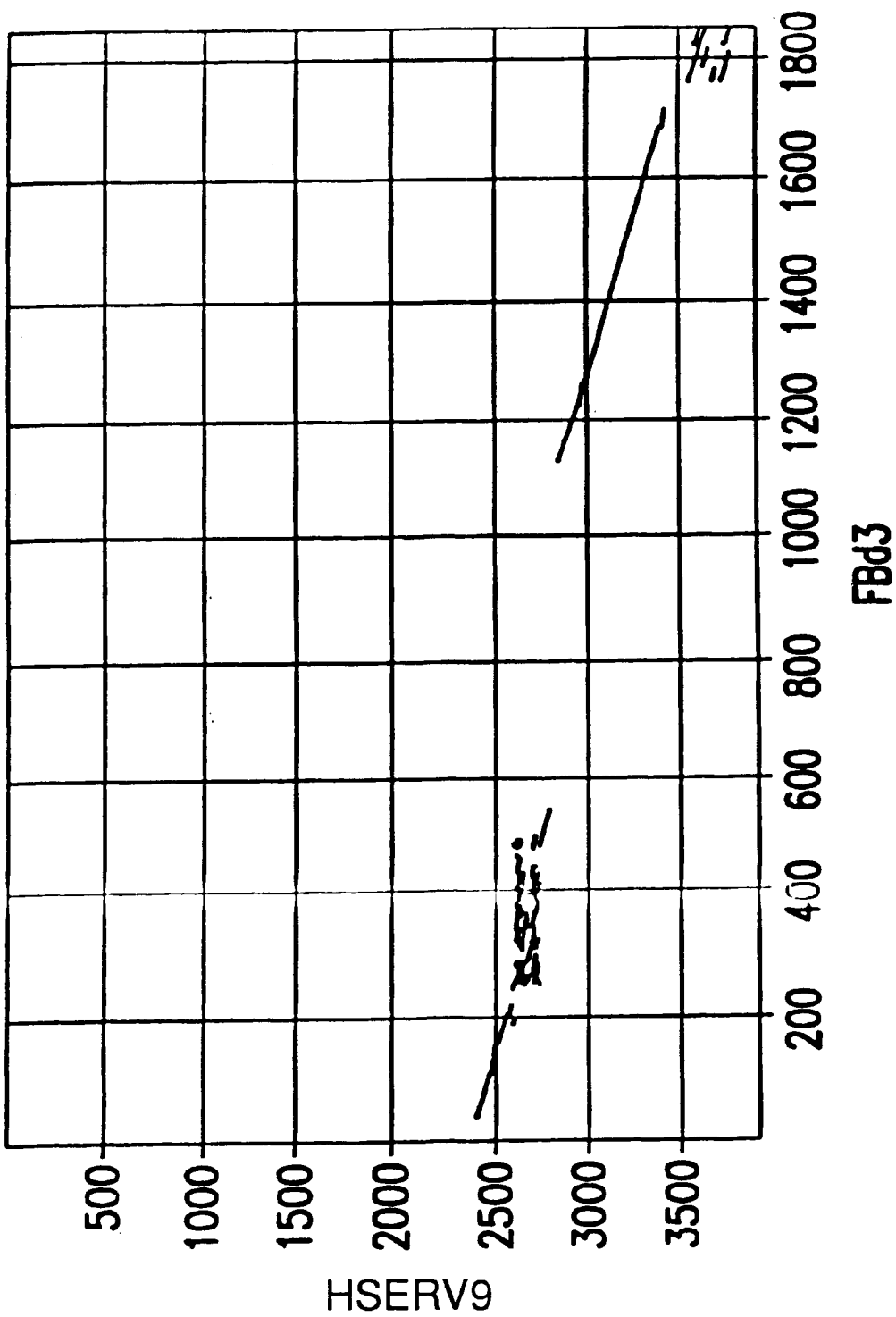
FIG. 14 shows the sequence homology between the clone FBd3 and the HSERV-9 retrovirus.

In FIG. 14, the sequence homology between the clone FBd3 and the HSERV-9 retrovirus is shown on the matrix chart by a continuous line for any partial homology greater than or equal to 65%. It can be seen that there are homologies in the flanking regions of the clone (with the pol gene at the 5' end and with the env gene and then the LTR at the 3' end), but that the internal region is totally divergent and does not display any homology, even weak, with the "env" gene of HSERV9. Furthermore, it is apparent that the clone FBd3 contains a longer "env" region than the one which is described for the defective endogenous HSERV-9; it may thus be seen that the internal divergent region constitutes an "insert" between the regions of partial homology with the HSERV-9 defective genes.

EXAMPLE 8
Amplification, Cloning and Sequencing of the Region of the MSRV-1 Retroviral Genome Located Between the Clones PSJ17 and FBd3

Four oligonucleotides, F1, B4, F6 and B1, were defined for amplifying RNA originating from concentrated virions of the strains POL2 and MS7PG. Control reactions were performed so as to check for the presence of contaminants (reaction with water). The amplification consists of a first step of RT-PCR according to the protocol described in Patent Application EP-A-0,569,272, followed by a second step of PCR performed on 10 μl of product of the first step with primers internal to the amplified first region ("nested" PCR). In the first RT-PCR cycle, the primers F1 and B4 are used. In the second PCR cycle, the primers F6 and the primer B1 are used. The primers are positioned as follows:

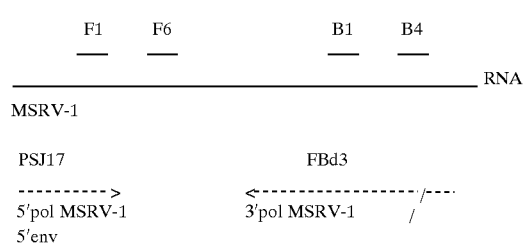

Their composition is:
primer F1: TGATGTGAACGGCATACTCACTG (SEQ ID NO:43)
primer B4: CCCAGAGGTTAGGAACTCCCTTTC (SEQ ID NO 44)
primer F6: GCTAAAGGAGACTTGTGGTTGTCAG (SEQ ID NO 45)
primer B1: CAACATGGGCATTTCGGATTAG (SEQ ID NO 46)

The product of "nested" amplification obtained and designated "t pol" is presented in FIG. 15, and corresponds to the sequence SEQ ID NO:47.

EXAMPLE 9
Obtaining New Sequences, Expressed as RNA in Cells in Culture Producing MSRV-1, and Comprising an "env" Region of the MSRV-1 Retroviral Genome A library of cDNA was produced according to the procedure described by the manufacturer of the "cDNA synthesis module, cDNA rapid adaptator ligation module, cDNA rapid cloning module and lambda gt10 in vitro packaging module" kits (Amersham, ref RPN1256Y/Z, RPN1712, RPN1713, RPN1717, N334Z), from the messenger RNA extracted from cells of a B lymphoblastoid line such as is described in Example 2, established from the lymphocytes of a patient suffering from MS and possessing reverse transcriptase activity which is detectable according to the technique described by Perron et al. (3).

Oligonucleotides were defined for amplifying the cDNA cloned into the nucleic acid library between the 3' region of the clone PSJ17 (pol) and the 5'(LTR) region of the clone FBd3. Control reactions were performed so as to check for the presence of contaminants (reaction with water). PCR reactions performed on the nucleic acids cloned into the library with different pairs of primers enabled a series of clones linking pol sequences to the MSRV-1 type env or LTR sequences to be amplified.

Two clones are representative of the sequences obtained in the cellular cDNA library:
the clone JLBc1, whose sequence SEQ ID NO:48 is presented in FIG. 16;
the clone JLBc2, whose sequence SEQ ID NO:49 is presented in FIG. 17.

Figure 18:
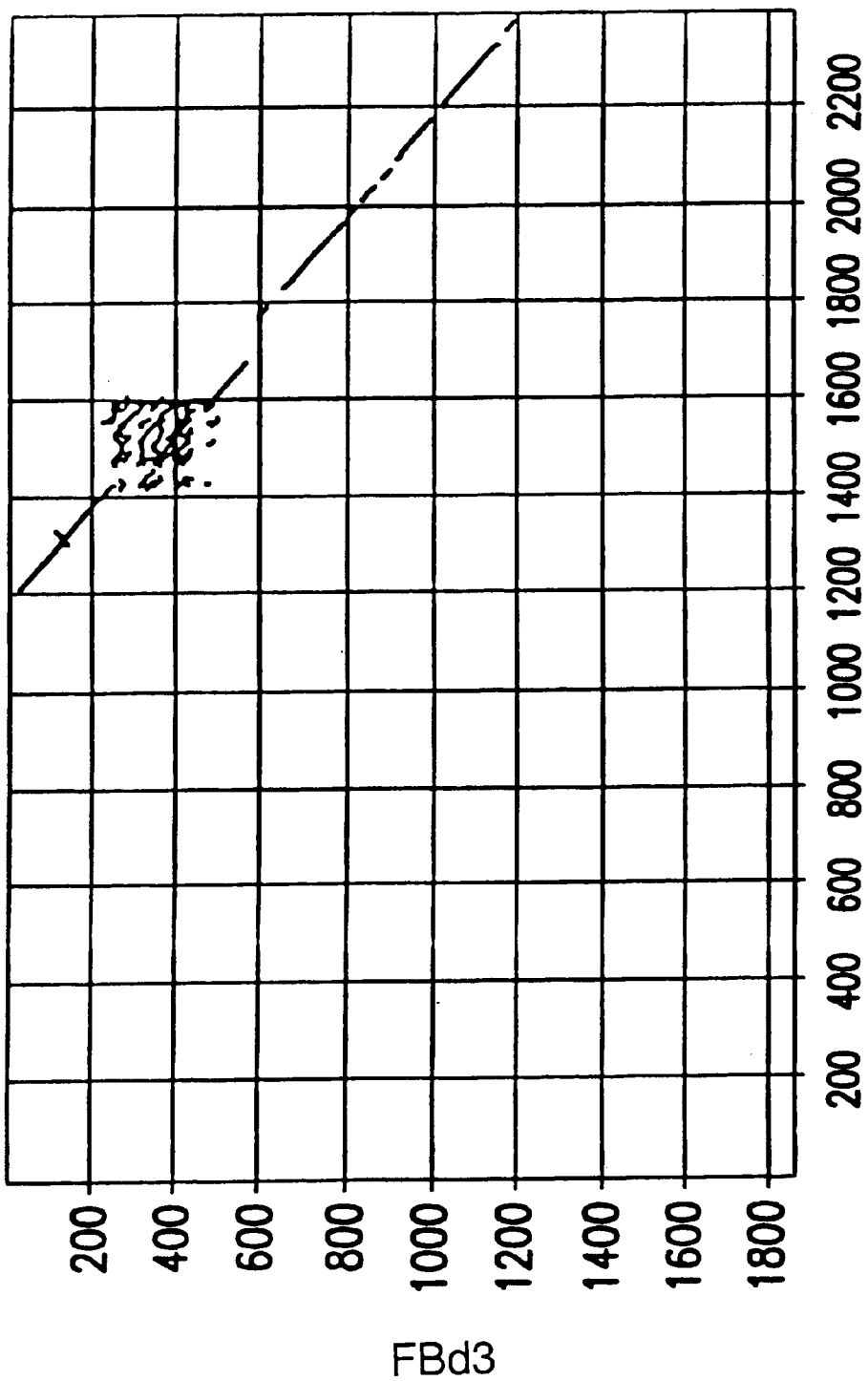
FIG. 18 shows the sequence homology between the clone JLBc1 and the clone FBd3.
Figure 19:
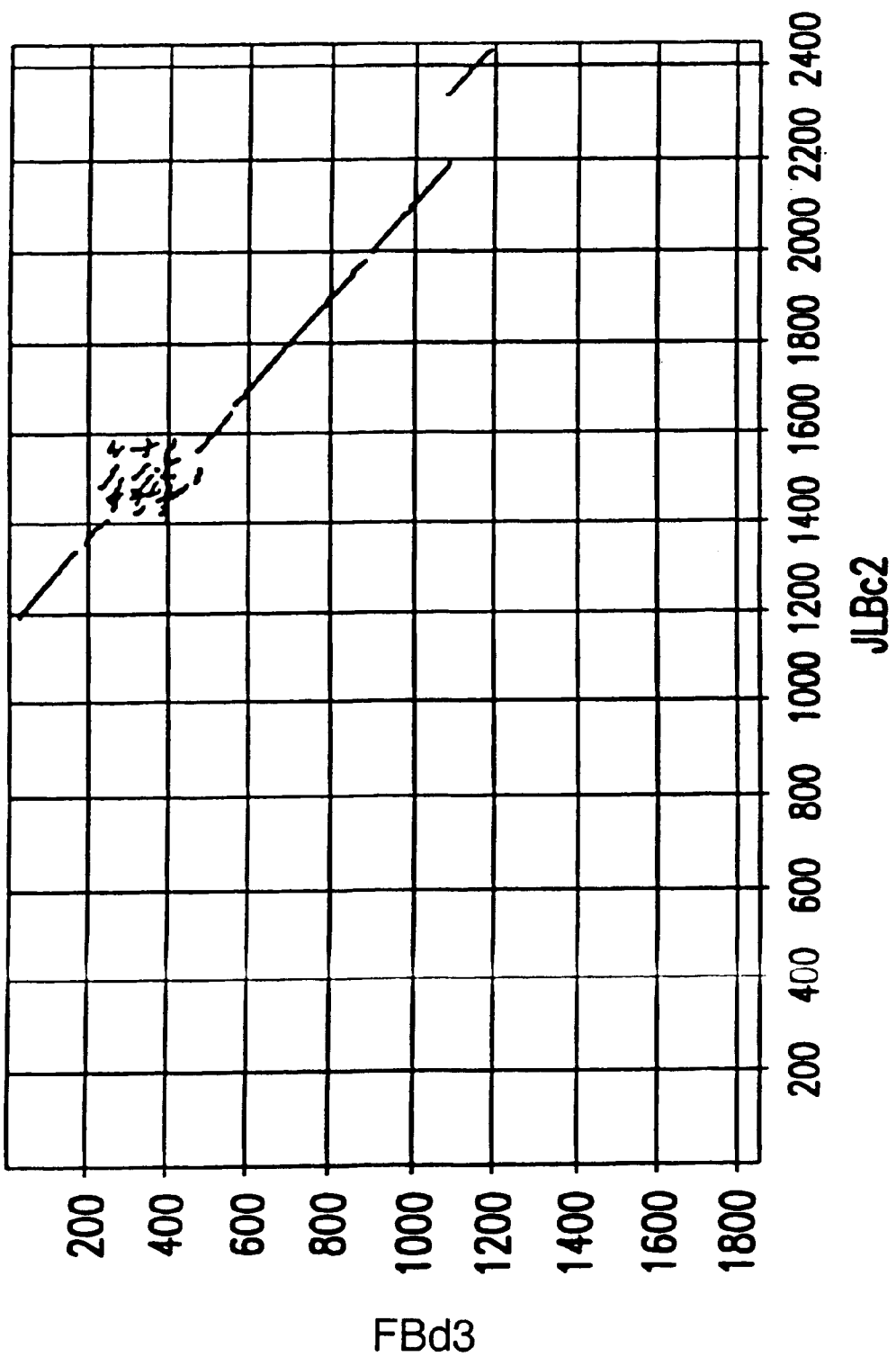
FIG. 19 shows the sequence homology between the clone JLBc2 and the clone FBd3.
Figure 20:
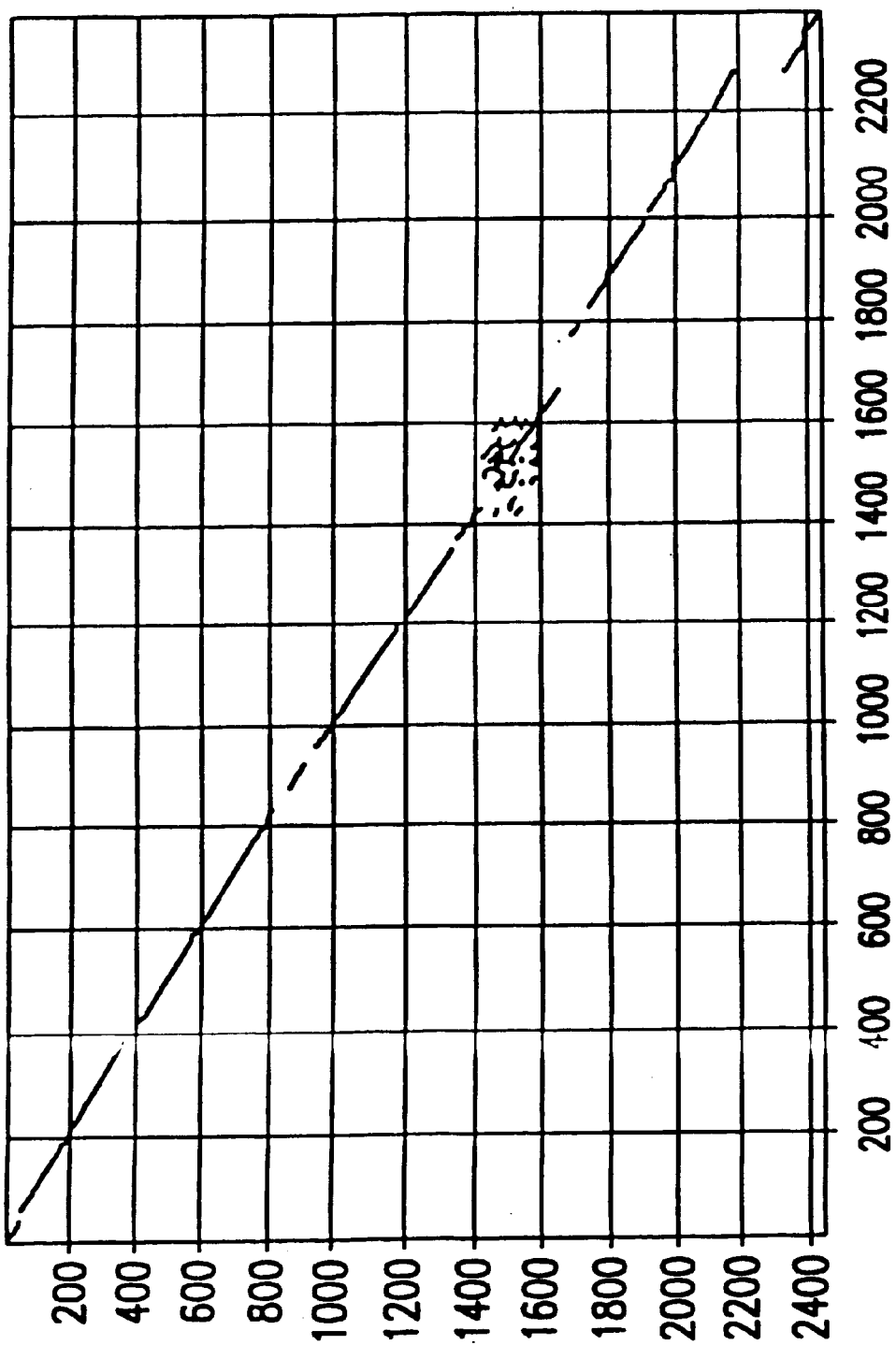
FIG. 20 shows the sequence homology between the clones JLBc1 and JLBc2.

The sequences of the clones JLBc1 and JLBc2 are homologous to that of the clone FBd3, as is apparent in FIGS. 18 and 19. The homology between the clone JLBc1 and the clone JLBc2 is shown in FIG. 20.

Figure 21:
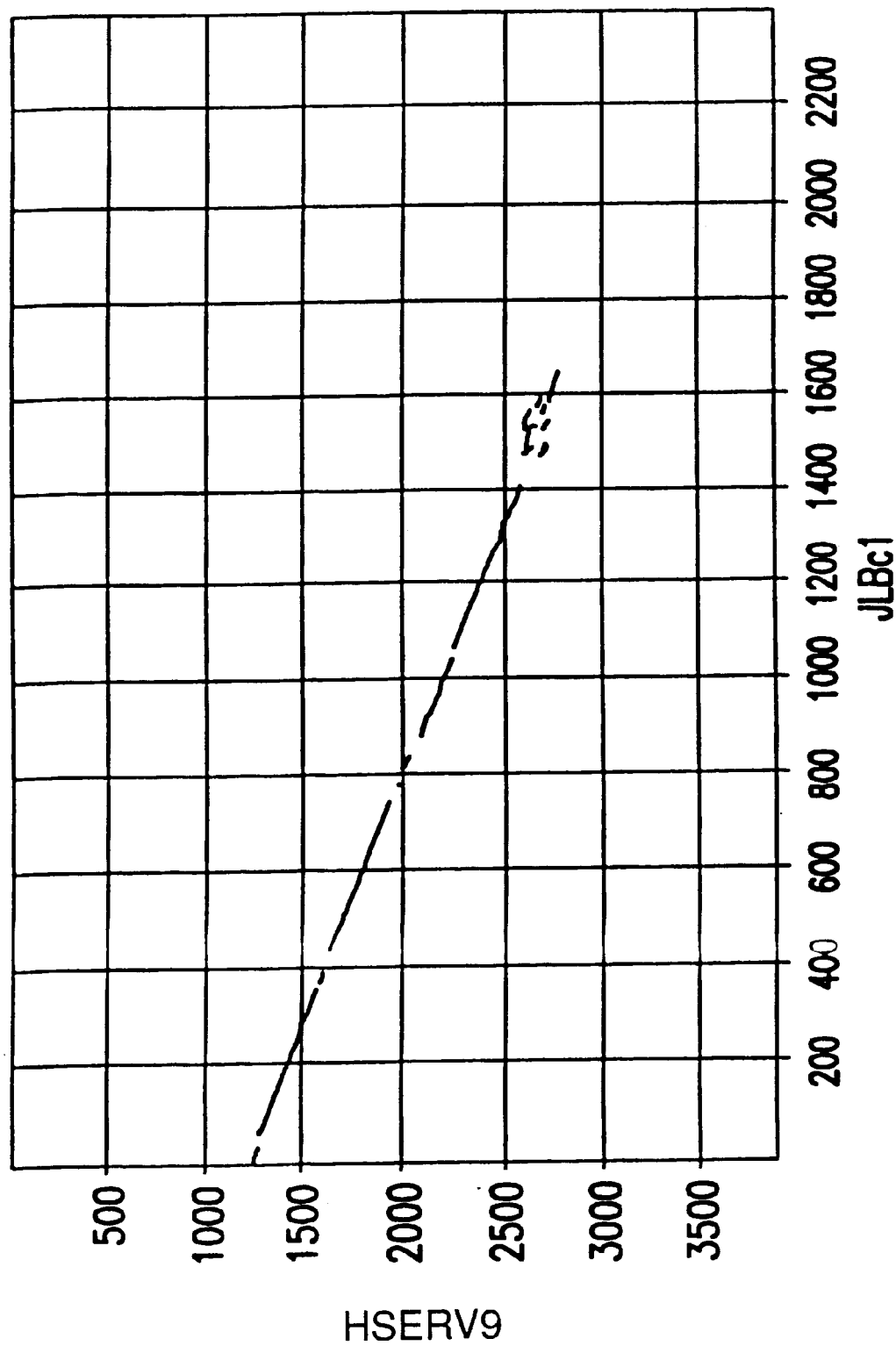
FIGS. 21 and 22 show the sequence homology between the HSERV-9 retrovirus and the clones JLBc1 and JLBc2, respectively.
Figure 22:
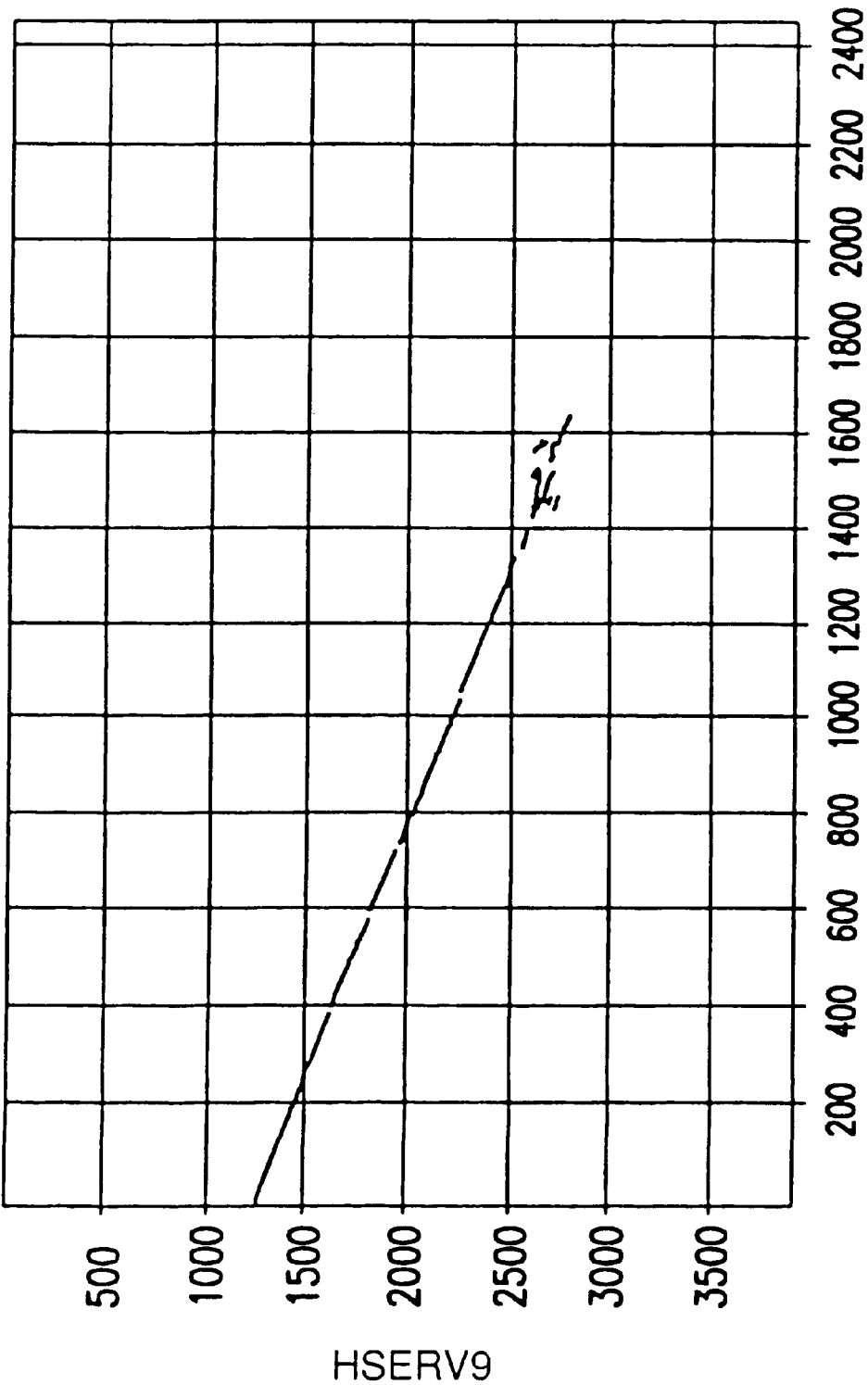

The homologies between the clones JLBc1 and JLBc2 on the one hand and the HSERV9 sequence on the other hand are presented, respectively, in FIGS. 21 and 22.

It will be noted that the region of homology between JLB1, JLB2 and FBd3 comprises, with a few sequence and size variations of the "insert", the additional sequence absent ("inserted") in the HSERV-9 env sequence, as described in Example 8.

It will also be noted that the cloned "pol" region is very homologous to HSERV-9, does not possess a reading frame (bearing in mind the sequence errors induced by the techniques used, including even the automatic sequencer) and diverges from the MSRV-1 sequences obtained from virions. In view of the fact that these sequences were cloned from the RNA of cells expressing MSRV-1 particles, it is probable that they originate from endogenous retroviral elements related to the ERV9 family; this is all the more likely for the fact that the pol and env genes are present on the same RNA which is clearly not the MSRV-1 genomic RNA. Some of these ERV9 elements possess functional LTRs which can be activated by replicative viruses coding for homologous or heterologous transactivators. Under these conditions, the relationship between MSRV-1 and HSERV-9 makes probable the transactivation of the defective (or otherwise) endogenous ERV9 elements by homologous, or even identical, MSRV-1 transactivating proteins.

Such a phenomenon may induce a viral interference between the expression of MSRV-1 and the related endogenous elements. Such an interference generally leads to a so-called "defective-interfering" expression, some features of which were to be found in the MSRV-1-infected cultures studied. Furthermore, such a phenomenon does not lack generation of the expression of polypeptides, or even of endogenous retroviral proteins which are not necessarily tolerated by the immune system. Such a scheme of aberrant expression of endogenous elements related to MSRV-1 and induced by the latter is liable to multiply the aberrant antigens, and hence to contribute to the induction of autoimmune processes such as are observed in MS.

It is, however, essential to note that the clones JLBc1 and JLBc2 differ from the ERV9 or HSERV9 sequence already described, in that they possess a longer env region comprising an additional region totally divergent from ERV9. Their kinship with the endogenous ERV9 family may hence be defined, but they clearly constitute novel elements never hitherto described. In effect, interrogation of the data banks of nucleic acid sequences available in version No. 15 (1995) of the "Entrez" software (NCBI, NIH, Bethesda, USA) did not enable a known homologous sequence in the env region of these clones to be identified.

EXAMPLE 10

Obtaining Sequences Located in the 5' pol and 3' gag Region of the MSRV-1 Retroviral Genome As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analyzed. This technical variant is described in the documentation of the firm Clontech Laboratories Inc., (Palo-Alto Calif., USA) supplied with its product "5'-AmpliFINDER™ RACE Kit", which was used on a fraction of virion purified as described above.

In order to carry out an amplification of the 5' region of the MSRV-1 retroviral genome starting from the pol sequence already sequenced (clone F11-1) and extending towards the gag gene, MSRV-1 specific primers were defined.

The specific 3' primers used in the kit protocol for the synthesis of the cDNA and the PCR amplification are, respectively, complementary to the following MSRV-1 sequences:

cDNA: (SEQ ID NO:50)
CCTGAGTTCTTGCACTAACCC
amplification: (SEQ ID NO:51)
GTCCGTTGGGTTTCCTTACTCCT The products originating from the PCR were extracted after purification on agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 ml of DNA solution were mixed with 5 ml of sterile distilled water, 1 ml of a 10-fold concentrated ligation buffer "10×LIGATION BUFFER", 2 ml of "pCR™ VECTOR" (25 ng/ml) and 1 ml of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning™ Kit. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer model 373 A" apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone GM3 to be obtained, whose sequence, identified by SEQ ID NO 52, is presented in FIG. 23.

Figure 24:
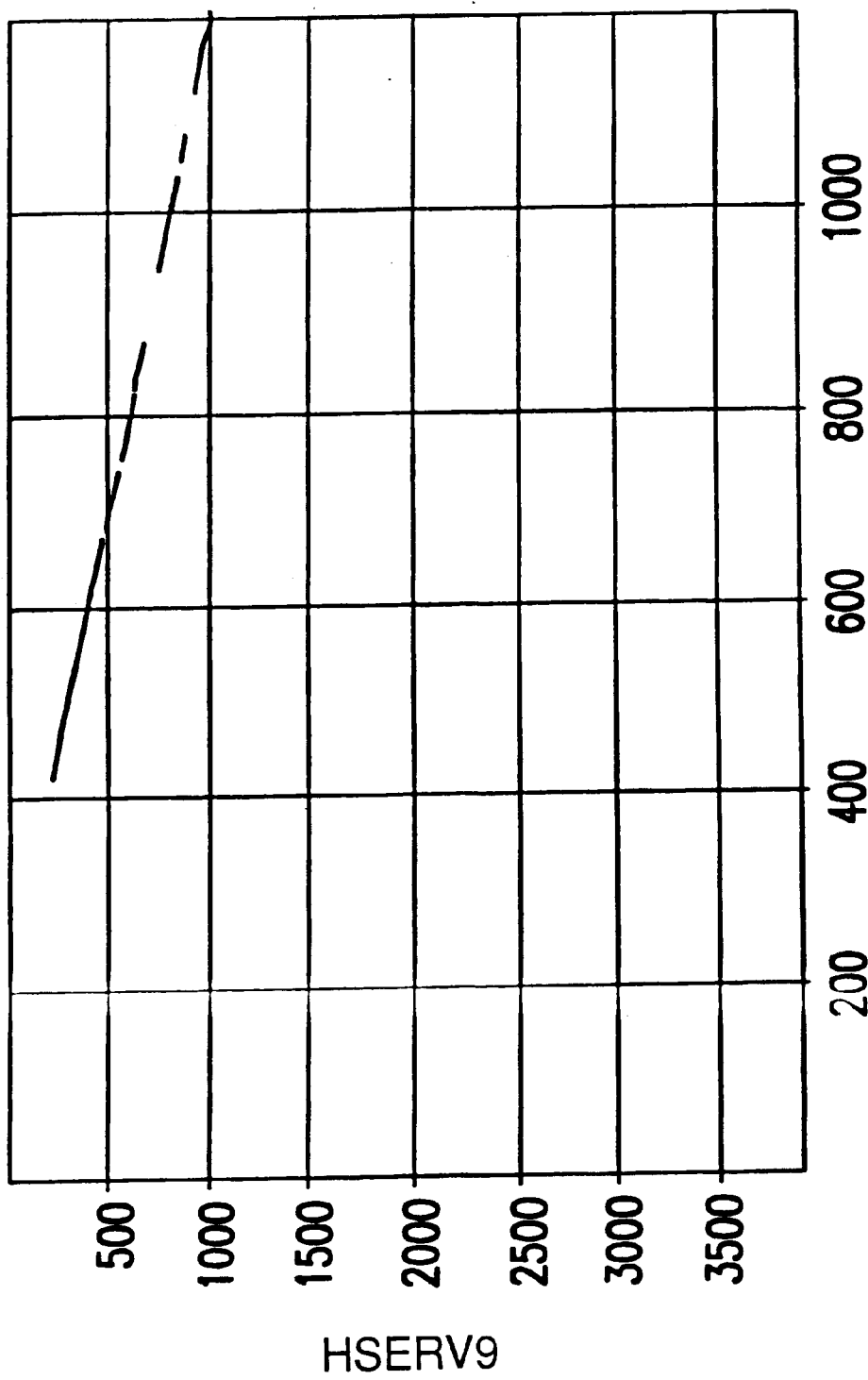
FIG. 24 shows the sequence homology between the HSERV-9 retrovirus and the clone GM3.

In FIG. 24, the sequence homology between the clone GMP3 and the HSERV-9 retrovirus is shown on the matrix chart by a continuous line, for any partial homology greater than or equal to 65%.

Figure 26:
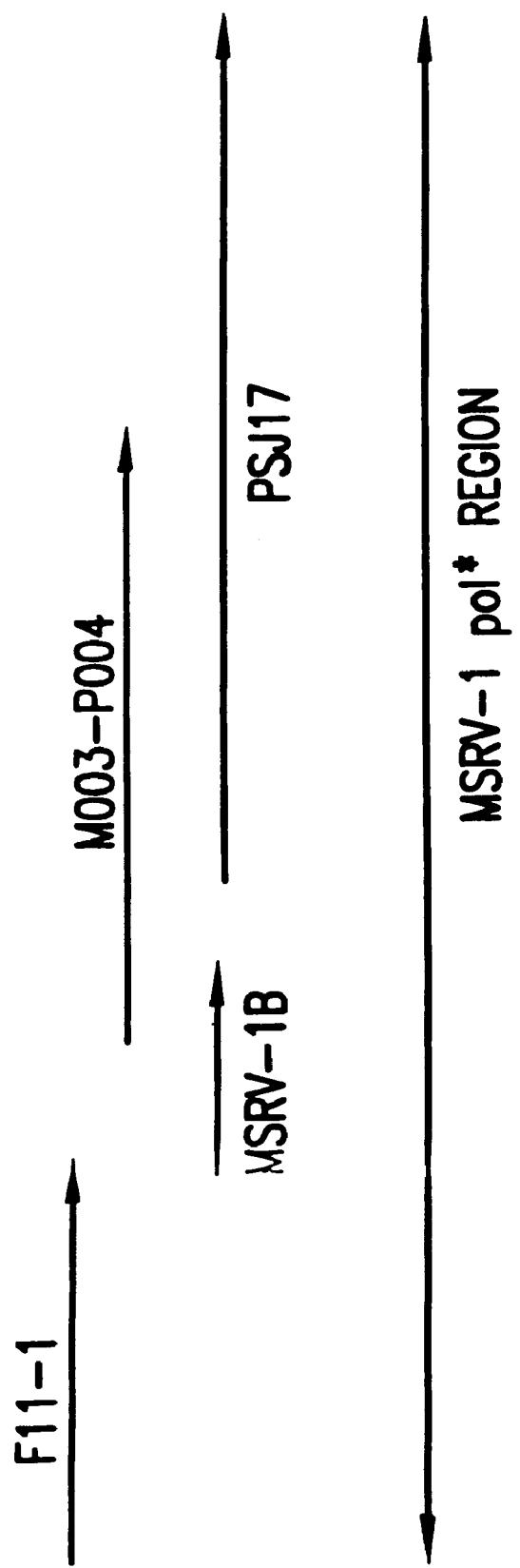
FIG. 26 shows the position of the clones F11-1, M003-P004, MSRV-1B and PSJ17 in the region hereinafter designated MSRV-1 pol*.

In summary, FIG. 25 shows the localization of the different clones studied above, relative to the known ERV9 genome. In FIG. 25, since the MSRV-1 env region is longer than the reference ERV9 env gene, the additional region is shown above the point of insertion according to a "V", on the understanding that the inserted material displays a sequence and size variability between the clones shown (JLBc1, JLBc2, FBd3). And FIG. 26 shows the position of different clones studied in the MSRV-1 pol* region.

Figure 27B:
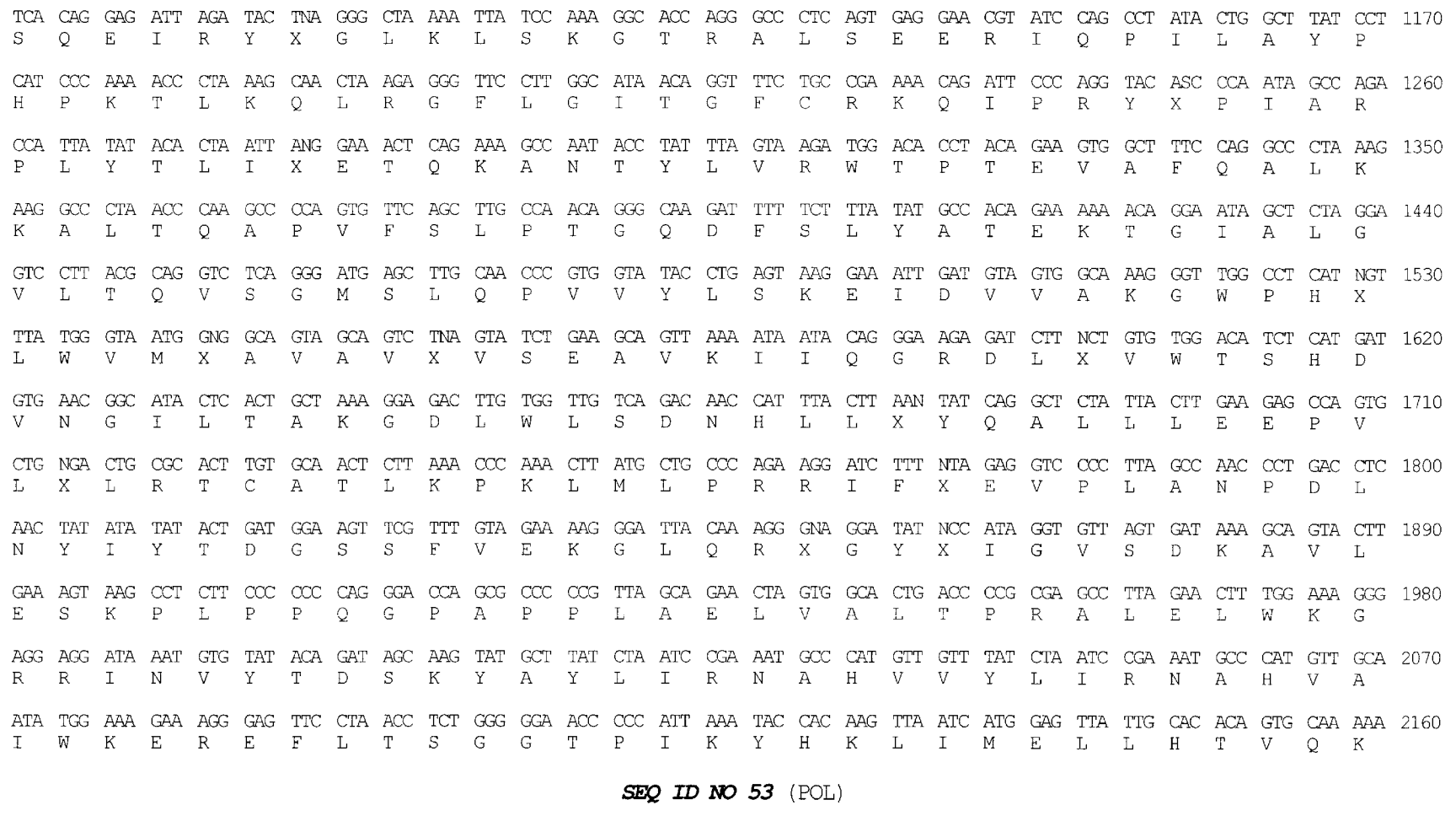

By means of the clone GM3 described above, a possible reading frame could be defined, covering the whole of the pol gene, referenced according to SEQ ID NO:57, shown in the successive FIGS. 27a to 27c.

EXAMPLE 11

Detection of Anti-MSRV-1 Specific Antibodies in Human Serum

Identification of the sequence of the pol gene of the MSRV-1 retrovirus and of an open reading frame of this gene enabled the amino acid sequence SEQ ID NO:35 of a region of the said gene, referenced SEQ ID NO:36, to be determined (see FIG. 28).

Different synthetic peptides corresponding to fragments of the protein sequence of MSRV-1 reverse transcriptase encoded by the pol gene were tested for their antigenic specificity with respect to sera of patients suffering from MS and of healthy controls.

The peptides were synthesized chemically by solid-phase synthesis according to the Merrifield technique (Barany G, and Merrifielsd R. B, 1980, In the Peptides, 2, 1–284, Gross E and Meienhofer J, Eds., Academic Press, New York). The practical details are those described below.

a) Peptide synthesis:

The peptides were synthesized on a phenylacetamidomethyl (PAM)/polystyrene/divinylbenzene resin (Applied Biosystems, Inc. Foster City, Calif.), using an "Applied Biosystems 430A" automatic synthesizer. The amino acids are coupled in the form of hydroxybenzotriazole (HOBT) esters. The amino acids used are obtained from Novabiochem (Läuflerlfingen, Switzerland) or Bachem (Bubendorf, Switzerland).

The chemical synthesis was performed using a double coupling protocol with N-methylpyrrolidone (NMP) as solvent. The peptides were cut from the resin, as well as the side-chain protective groups, simultaneously, using hydrofluoric acid (HF) in a suitable apparatus (type I cleavage apparatus, Peptide Institute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDACr C18 analytical column (250×4.6 mm) at a flow rate of 1 ml/min. Fractions having the same retention time are pooled and lyophilized. The preponderant fraction is then analysed by analytical high performance liquid chromatography with the system described above. The peptide which is considered to be of acceptable purity manifests itself in a single peak representing not less than 95% of the chromatogram.

The purified peptides are then analyzed with the object of monitoring their amino acid composition, using an Applied Biosystems 420H automatic amino acid analyzer. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated POL2B to be selected, whose sequence is shown in FIG. 28 in the identifier SEQ ID NO:35, below, encoded by the pol gene of MSRV-1 (nucleotides 181 to 330).

b) Antigenic properties:

The antigenic properties of the POL2B peptide were demonstrated according to the ELISA protocol described below.

The lyophilized POL2B peptide was dissolved in sterile distilled water at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 1 microgram/ml. 100 microliters of this dilution are placed in each well of microtitration plates ("high-binding" plastic, COSTAR ref: 3590). The plates are covered with a "plate-sealer" type adhesive and kept overnight at +4° C. for the phase of adsorption of the peptide to the plastic. The adhesive is removed and the plates are washed three times with a volume of 300 microliters of a solution A (1×PBS, 0.05% Tween 20r), then inverted over an absorbent tissue. The plates thus drained are filled with 200 microliters per well of a solution B (solution A+10% of goat serum), then covered with an adhesive and incubated for 45 minutes to 1 hour at 37° C. The plates are then washed three times with the solution A as described above.

The test serum samples are diluted beforehand to 1/50 in the solution B, and 100 microliters of each dilute test serum are placed in the wells of each microtitration plate. A negative control is placed in one well of each plate, in the form of 100 microliters of buffer B. The plates covered with an adhesive are then incubated for 1 to 3 hours at 37° C. The plates are then washed three times with the solution A as described above. In parallel, a peroxidase-labelled goat antibody directed against human IgG (Sigma Immunochemicals ref. A6029) or IgM (Cappel ref. 55228) is diluted in the solution B (dilution 1/5000 for the anti-IgG and 1/1000 for the anti-IgM). 100 microliters of the appropriate dilution of the labelled antibody are then placed in each well of the microtitration plates, and the plates covered with an adhesive are incubated for 1 to 2 hours at 37° C. A further washing of the plates is then performed as described above. In parallel, the peroxidase substrate is prepared according to the directions of the "Sigma fast OPD kit" (Sigma Immunochemicals, ref. P9187). 100 microliters of substrate solution are placed in each well, and the plates are placed protected from light for 20 to 30 minutes at room temperature.

When the color reaction has stabilized, the plates are placed immediately in an ELISA plate spectrophotometric reader, and the optical density (OD) of each well is read at a wavelength of 492 nm. Alternatively, 30 microliters of 1N HCl are placed in each well to stop the reaction, and the plates are read in the spectrophotometer within 24 hours.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20r, 10% goat serum).

c) Detection of anti-MSRV-1 IgG antibodies by ELISA:

The technique described above was used with the POLB2 peptide to test for the presence of anti-MSRV-1 specific IgG antibodies in the serum of 29 patients for whom a definite or probable diagnosis of MS was established according to the criteria of Poser (23), and of 32 healthy controls (blood donors).

Figure 29:
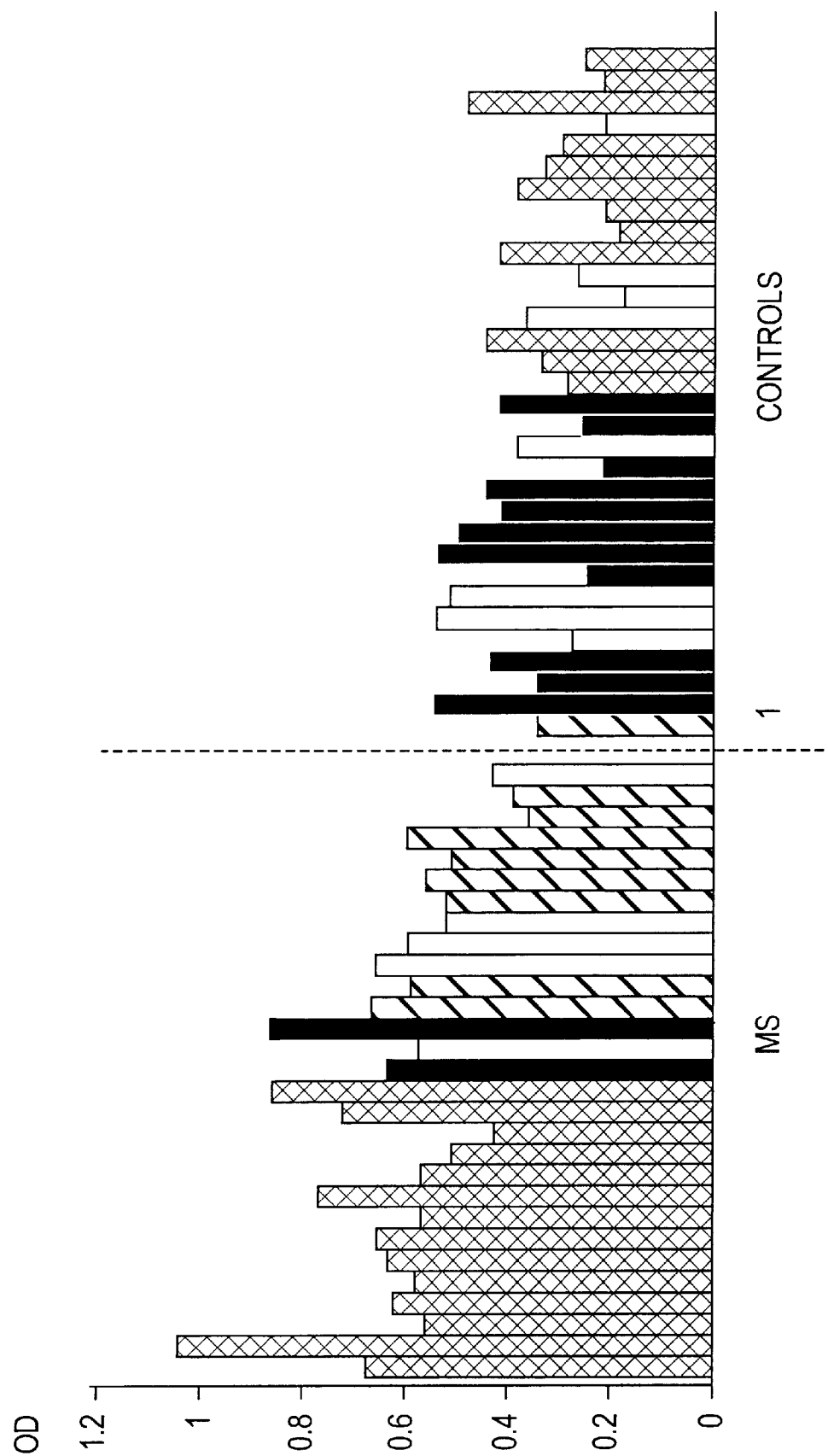
FIG. 29 shows the OD values (ELISA tests) at 492 nm obtained for 29 sera of MS patients and 32 sera of healthy controls tested with an anti-IgG antibody.

FIG. 29 shows the results for each serum tested with an anti-IgG antibody. Each vertical bar represents the net optical density (OD at 492 nm) of a serum tested. The ordinate axis gives the net OD at the top of the vertical bars. The first 29 vertical bars lying to the left of the vertical broken line represent the sera of 29 cases of MS tested, and the 32 vertical bars lying to the right of the vertical broken line represent the sera of 32 healthy controls (blood donors).

The mean of the net OD values for the MS sera tested is 0.62. The diagram enables 5 controls to be revealed whose net OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.36. Without the 5 controls whose net OD values are greater than or equal to 0.5, the mean of the "negative" controls is 0.33. The standard deviation of the negative controls is 0.10. A theoretical threshold of positivity may be calculated according to the formula:

threshold value (mean of the net OD values of the seronegative controls)+(2 or 3×standard deviation of the net OD values of the seronegative controls).

In the first case, there are considered to be symptomless seropositives, and the threshold value is equal to 0.33+(2× 0.10)=0.53. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.36+ (2×0.116)=0.59.

According to this analysis, the test is specific for MS. In this respect, it is seen that the test is specific for MS, since, as shown in Table 1, no control has a net OD above this threshold. In fact, this result reflects the fact that the antibody titers in patients suffering from MS are, for the most part, higher than in healthy controls who have been in contact with MSRV-1.

TABLE 1

|  | MS | CONTROLS |
|---|---|---|
|  | 0.681 | 0.3515 |
|  | 1.0425 | 0.56 |
|  | 0.5675 | 0.3565 |
|  | 0.63 | 0.449 |
|  | 0.588 | 0.2825 |
|  | 0.645 | 0.55 |
|  | 0.6635 | 0.52 |
|  | 0.576 | 0.2535 |
|  | 0.7765 | 0.55 |
|  | 0.5745 | 0.51 |
|  | 0.513 | 0.426 |
|  | 0.4325 | 0.451 |
|  | 0.7255 | 0.227 |
|  | 0.859 | 0.3905 |
|  | 0.6435 | 0.265 |
|  | 0.5795 | 0.4295 |
|  | 0.8655 | 0.291 |
|  | 0.671 | 0.347 |
|  | 0.596 | 0.4495 |
|  | 0.662 | 0.3725 |
|  | 0.602 | 0.181 |
|  | 0.525 | 0.2725 |
|  | 0.53 | 0.426 |
|  | 0.565 | 0.1915 |
|  | 0.517 | 0.222 |
|  | 0.607 | 0.395 |
|  | 0.3705 | 0.34 |
|  | 0.397 | 0.307 |
|  | 0.4395 | 0.219 |
|  |  | 0.491 |
|  |  | 0.2265 |
|  |  | 0.2605 |
| MEAN | 0.62 | 0.33 |
| STD DEV | 0.14 | 0.10 |
| THRESHOLD VALUE |  | 0.53 |

In accordance with the first method of calculation, and as shown in FIG. 29 and in the corresponding Table 1, 26 of the 29 MS sera give a positive result (net OD greater than or equal to 0.50), indicating the presence of IgGs specifically directed against the POL2B peptide, hence against a portion of the reverse transcriptase enzyme of the MSRV-1 retrovirus encoded by its pol gene, and consequently against the MSRV-1 retrovirus. Thus, approximately 90% of the MS patients tested have reacted against an epitope carried by the POL2B peptide and possess circulating IgGs directed against the latter.

Five out of 32 blood donors in apparent good health show a positive result. Thus, it is apparent that approximately 15% of the symptomless population may have been in contact with an epitope carried by the POL2B peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at-risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus. Thus, the difference in seroprevalence between the MS and control populations is extremely significant: "chi-squared" test, p<0.001. These results hence point to an aetiopathogenic role of MSRV-1 in MS.

d) Detection of anti-MSRV-1 IgM antibodies by ELISA:

The ELISA technique with the POL2B peptide was used to test for the presence of anti-MSRV-1 IgM specific antibodies in the serum of 36 patients for whom a definite or probable diagnosis of MS was established according to the criteria of Poser (23), and of 42 healthy controls (blood donors).

Figure 30:
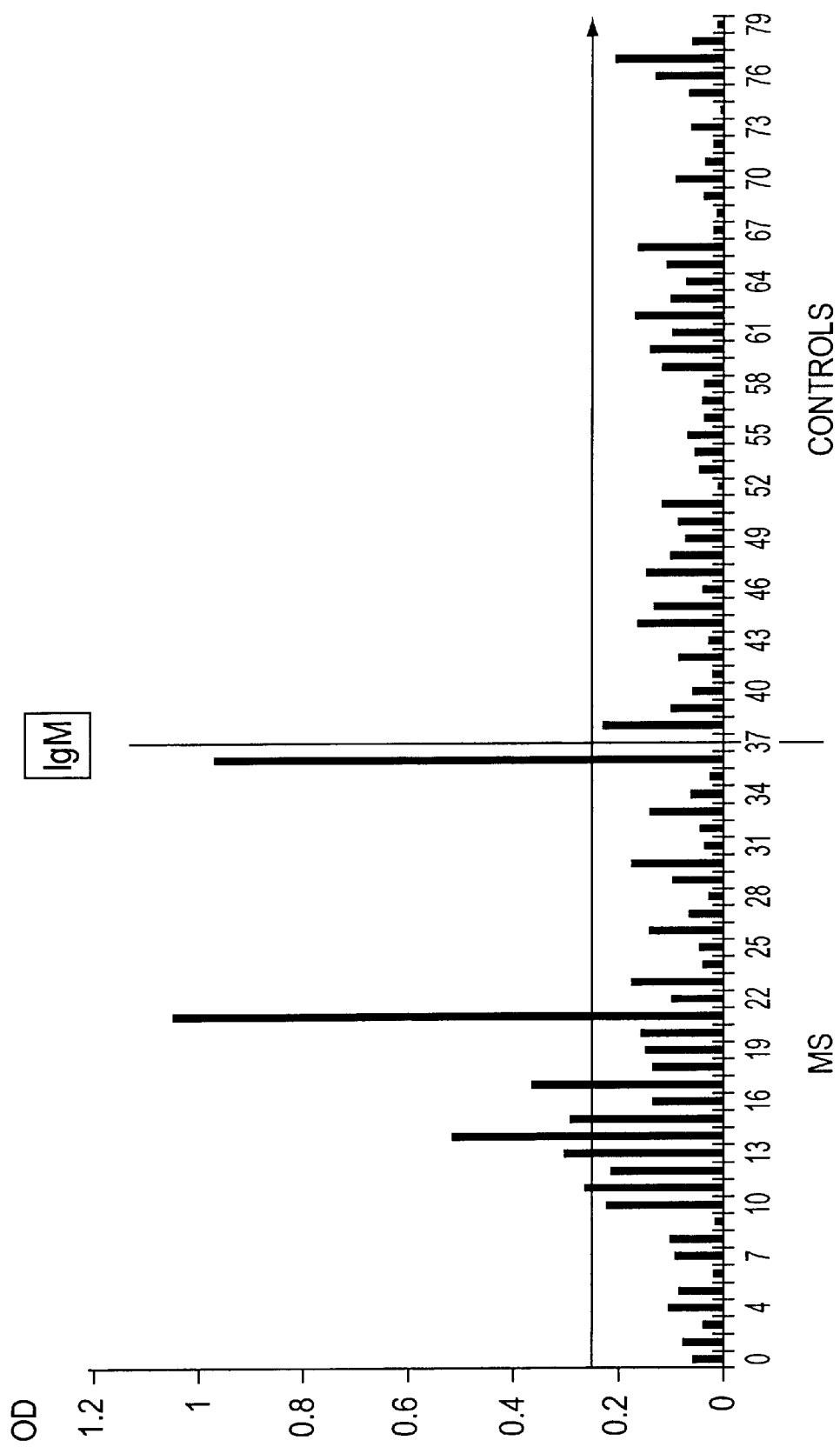
FIG. 30 shows the OD values (ELISA tests) at 492 nm obtained for 36 sera of MS patients and 42 sera of healthy controls tested with an anti-IgM antibody.

FIG. 30 shows the results for each serum tested with an anti-IgM antibody. Each vertical bar represents the net optical density (OD at 492 nm) of a serum tested. The ordinate axis gives the net OD at the top of the vertical bars. The first 36 vertical bars lying to the left of the vertical line cutting the abscissa axis represent the sera of 36 cases of MS tested, and the vertical bars lying to the right of the vertical broken line represent the sera of 42 healthy controls (blood donors). The horizontal line drawn in the middle of the diagram represents a theoretical threshold defining the boundary of the positive results (in which the top of the bar lies above) and the negative results (in which the top of the bar lies below).

The mean of the net OD values for the MS cases tested is 0.19.

The mean of the net OD values for the controls is 0.09.

The standard deviation of the negative controls is 0.05.

In view of the small difference between the mean and the standard deviation of the controls, the threshold of theoretical positivity may be calculated according to the formula:

threshold value=(mean of the net *OD* values of the seronegative controls)+(3×standard deviation of the net *OD* values of the seronegative controls).

The threshold value is hence equal to 0.09+(3×0.05)= 0.26; or, in practice, 0.25.

The negative results represent a non-specific "background" of the presence of antibodies directed specifically against an epitope of the peptide.

According to this analysis, and as shown in FIG. 30 and in the corresponding Table 2, the IgM test is specific for MS, since no control has a net OD above the threshold. Seven of the 36 MS sera produce a positive IgM result; now, a study of the clinical data reveals that these positive sera were taken during a first attack of MS or an acute attack in untreated patients. It is known that IgMs directed against pathogenic agents are produced during primary infections or during reactivations following a latency phase of the said pathogenic agent.

The difference in seroprevalence between the MS and control populations is extremely significant: "chi- squared" test, p<0.001.

These results point to an aetiopathogenic role of MSRV-1 in MS.

The detection of IgM and IgG antibodies against the POL2B peptide enables the course of an MSRV-1 infection and/or of the viral reactivation of MSRV-1 to be evaluated.

TABLE 2

| MS | CONTROLS |
|---|---|
| 0.064 | 0.243 |
| 0.087 | 0.11 |
| 0.044 | 0.098 |
| 0.115 | 0.028 |

TABLE 2-continued

| MS | CONTROLS |
|---|---|
| 0.089 | 0.094 |
| 0.025 | 0.038 |
| 0.097 | 0.176 |
| 0.108 | 0.146 |
| 0.018 | 0.049 |
| 0.234 | 0.161 |
| 0.274 | 0.113 |
| 0.225 | 0.079 |
| 0.314 | 0.093 |
| 0.522 | 0.127 |
| 0.306 | 0.02 |
| 0.143 | 0.052 |
| 0.375 | 0.062 |
| 0.142 | 0.074 |
| 0.157 | 0.043 |
| 0.168 | 0.046 |
| 1.051 | 0.041 |
| 0.104 | 0.13 |
| 0.187 | 0.153 |
| 0.044 | 0.107 |
| 0.053 | 0.178 |
| 0.153 | 0.114 |
| 0.07 | 0.078 |
| 0.033 | 0.118 |
| 0.104 | 0.177 |
| 0.187 | 0.026 |
| 0.044 | 0.024 |
| 0.053 | 0.046 |
| 0.153 | 0.116 |
| 0.07 | 0.04 |
| 0.033 | 0.028 |
| 0.973 | 0.073 |
|  | 0.008 |
|  | 0.074 |
|  | 0.141 |
|  | 0.219 |
|  | 0.047 |
|  | 0.017 |
| MEAN 0.19 | 0.09 |
| STD. DEV. 0.23 | 0.05 |
| THRESHOLD VALUE | 0.26 | e) Search for immunodominant epitopes in the POL2B peptide:

In order to reduce the non-specific background and to optimize the detection of the responses of the anti-MSRV-1 antibodies, the synthesis of octapeptides, advancing in successive one amino acid steps, covering the whole of the sequence determined by POL2B, was carried out according to the protocol described below.

The chemical synthesis of overlapping octapeptides covering the amino acid sequence 61–110 shown in the identifier SEQ ID NO:35 was carried out on an activated cellulose membrane according to the technique of BERG et al. (1989. J. Ann. Chem. Soc., 111, 8024–8026) marketed by Cambridge Research Biochemicals under the trade name Spotscan. This technique permits the simultaneous synthesis of a large number of peptides and their analysis.

The synthesis is carried out with esterified amino acids in which the α-amino group is protected with an FMOC group (Nova Biochem) and the side-chain groups with protective groups such as trityl, t-butyl ester or t-butyl ether. The esterified amino acids are solubilized in N-methylpyrrolidone (NMP) at a concentration of 300 nM, and 0.9 ml are applied to spots of deposit of bromophenol blue. After incubation for 15 minutes, a further application of amino acids is carried out according to another 15-minute incubation. If the coupling between two amino acids has taken place correctly, a coloration modification (change from blue to yellow-green) is observed. After three washes in DMF, an acetylation step is performed with acetic anhydride. Next, the terminal amino groups of the peptides in the process of synthesis are deprotected with 20% pyridine in DMF. The spots of deposit are restained with a 1% solution of bromophenol blue in DMF, washed three times with methanol and dried. This set of operations constitutes one cycle of addition of an amino acid, and this cycle is repeated until the synthesis is complete. When all the amino acids have been added, the $NH_2$-terminal group of the last amino acid is deprotected with 20% piperidine in DMF and acetylated with acetic anhydride. The groups protecting the side chain are removed with a dichloromethane/trifluoroacetic acid/triisobutylsilane (5 ml/5 ml/250 ml) mixture. The immunoreactivity of the peptides is then tested by ELISA.

Figure 31:
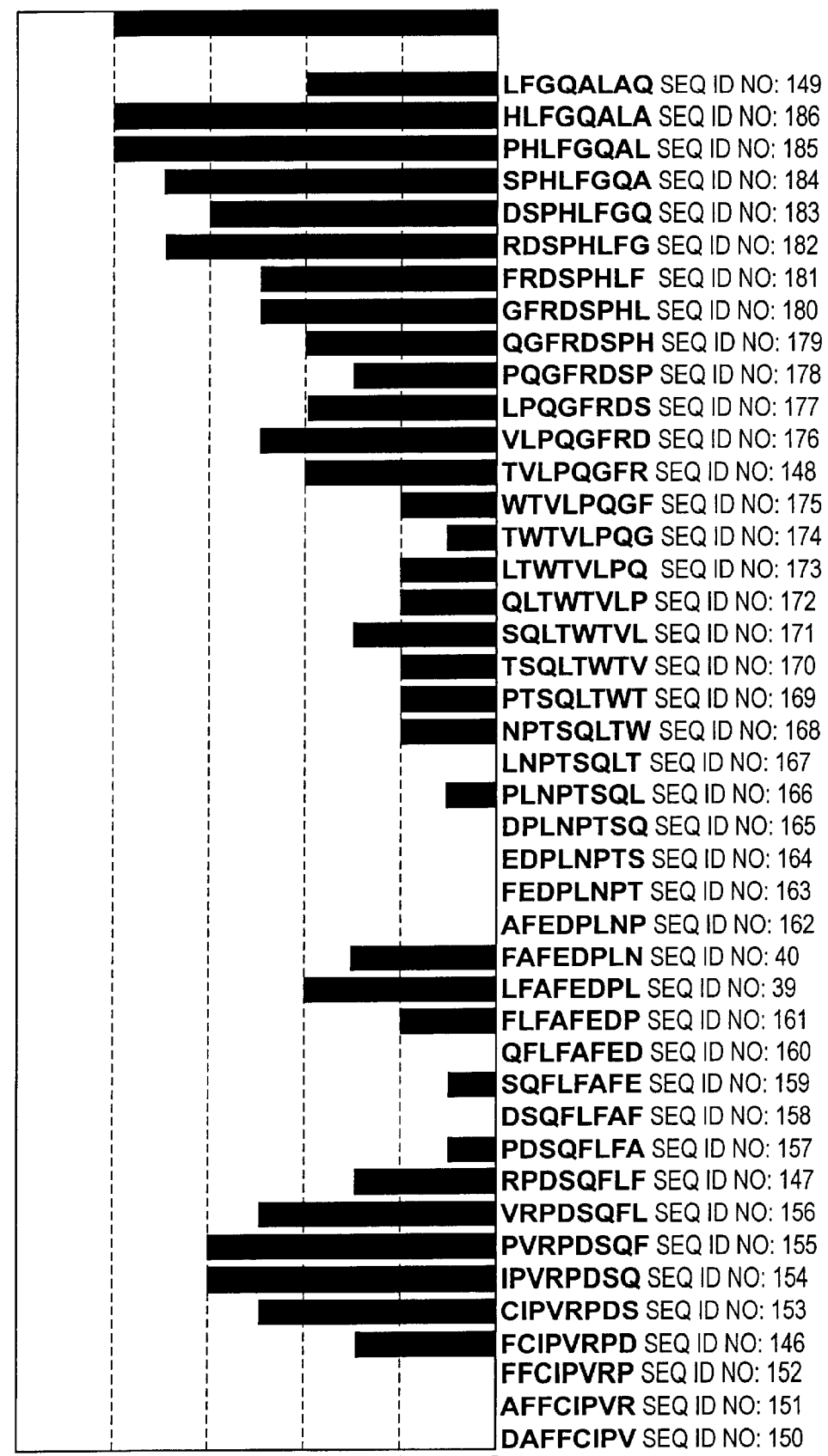
Figure 33:
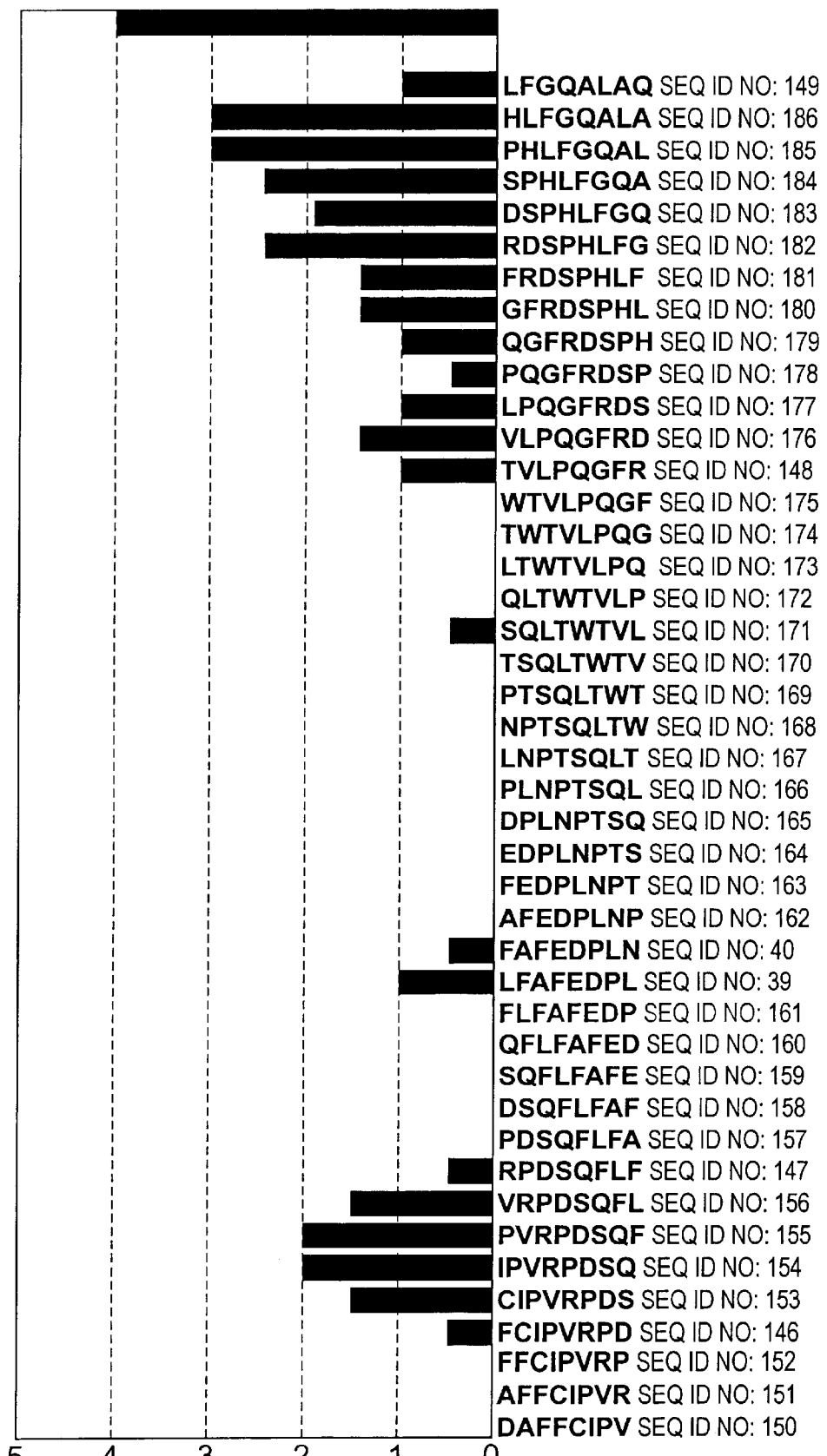

After synthesis of the different octapeptides in duplicate on two different membranes, the latter are rinsed with methanol and washed in TBS (0.1M Tris pH 7.2), then incubated overnight at room temperature in a saturation buffer. After several washes in TBS-T (0.1M Tris pH 7.2–0.05% Tween 20), one membrane is incubated with a 1/50 dilution of a reference serum originating from a patient suffering from MS, and the other membrane with a 1/50 dilution of a pool of sera of healthy controls. The membranes are incubated for 4 hours at room temperature. After washes with TBS-T, a β-galactosidase-labelled anti-human immunoglobulin conjugate (marketed by Cambridge Research Biochemicals) is added at a dilution of 1/200, and the mixture is incubated for two hours at room temperature. After washes of the membranes with 0.05% TBS-T and PBS, the immunoreactivity in the different spots is visualized by adding 5-bromo-4-chloro-3-indolyl b-D-galactopyranoside in potassium. The intensity of coloration of the spots is estimated qualitatively with a relative value from 0 to 5 as shown in the attached FIGS. 31 to 33.

In this way, it is possible to determine two immunodominant regions at each end of the POL2B peptide, corresponding, respectively, to the amino acid sequences 65–75 (SEQ ID NO:37) and 92–109 (SEQ ID NO:38), according to FIG. 34, and lying, respectively, between the octapeptides Phe-Cys-Ile-Pro-Val-Arg-Pro-Asp (FCIPVRPD) (SEQ ID NO:146) and Arg-Pro-Asp-Ser-Gln-Phe-Leu-Phe (RPDSQFLF) (SEQ ID NO:147), and Thr-Val-Leu-Pro-Gln-Gly-Phe-Arg (TVLPQGFR) (SEQ ID NO:148) and Leu-Phe-Gly-Gln-Ala-Leu-Ala-Gln (LFGQALAQ) (SEQ ID NO:149), and a region which is less reactive but apparently more specific, since it does not produce any background with the control serum, represented by the octapeptides Leu-Phe-Ala-Phe-Glu-Asp-Pro-Leu (LFAFEDPL) (SEQ ID NO:39) and Phe-Ala-Phe-Glu-Asp-Pro-Leu-Asn (FAFEDPLN) (SEQ ID NO:40).

These regions make it possible to define new peptides which are more specific and more immunoreactive according to the usual techniques.

It is thus possible, as a result of the discoveries made and the methods developed by the inventors, to carry out a diagnosis of MSRV-1 infection and/or reactivation and to evaluate a therapy in MS on the basis of its efficacy in "negativing" the detection of these agents in the patients' biological fluids. Furthermore, early detection in individuals not yet displaying neurological signs of MS could make it possible to institute a treatment which would be all the more effective with respect to the subsequent clinical course for the fact that it would precede the lesion stage which corresponds to the onset of neurological disorders. Now, at the present time, a diagnosis of MS cannot be established before a symptomatology of neurological lesions has set in, and hence no treatment is instituted before the emergence of a clinical picture suggestive of lesions of the central nervous system which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in "negativing" the detection of these agents in the patients' biological fluids.

EXAMPLE 12

Obtaining a Clone LB19 Containing a Portion of the gag Gene of the MSRV-1 Retrovirus A PCR technique derived from the technique published by Gonzalez-Quintial R et al. (19) and PLAZA et al. (25) was used. From the total RNAs extracted from a fraction of virion purified as described above, the cDNA was synthesized using a specific primer (SEQ ID No.60) at the 3' end of the genome to be amplified, using EXPAND™ REVERSE TRANSCRIPTASE (BOEHRINGER MANNHEIM).

cDNA:

AAGGGGCATG GACGAGGTGG TGGCTTATTT (SEQ ID NO:61) (antisense)

After purification, a poly(G) tail was added at the 5' end of the cDNA using the "Terminal transferases kit" marketed by the company Boehringer Mannheim, according to the manufacturer's protocol.

An anchoring PCR was carried out using the following 5' and 3' primers:

AGATCTGCAGAATTCGATATCACCCCCCCCCCCCCC (SEQ ID No. 85) (sense), and AAATGTCTGC GGCAC-CAATC TCCATGTT (SEQ ID No. 60) (antisense)

Next, a semi-nested anchoring PCR was carried out with the following 5' and 3' primers:

AGATCTGCAG AATTCGATAT CA (SEQ ID No.86) (sense), and AAATGTCTGC GGCACCAATC TCCAT-GTT (SEQ ID No.60) (antisense)

The products originating from the PCR were purified after purification on agarose gel according to conventional methods (17), and then resuspended in 10 microliters of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 µl of DNA solution were mixed with 5 µl of sterile distilled water, 1 µl of 10-fold concentrated ligation buffer "10×LIGATION BUFFER", 2 µl of "pCR™ VECTOR" (25 ng/µl ) and 1 µl of "T4 DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit™. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

PCR amplification according to the technique mentioned above was used on a cDNA synthesized from the nucleic acids of fractions of infective particles purified on a sucrose gradient, according to the technique described by H. Perron (13), from culture supernatants of B lymphocytes of a patient suffering from MS, immortalized with Epstein-Barr virus (EBV) strain B95 and expressing retroviral particles associated with reverse transcriptase activity as described by Perron et al. (3) and in French Patent Applications MS 10, 11 and 12. the clone LB 19, whose sequence, identified by SEQ ID NO:55, is presented in FIG. 35.

The clone makes it possible to define, with the clone GM3 previously sequenced and the clone G+E+A (see Example 15), a region of 690 base pairs representative of a significant portion of the gag gene of the MSRV-1 retrovirus, as presented in FIG. 36. This sequence designated SEQ ID NO:82 is reconstituted from different clones overlapping at their ends. This sequence is identified under the name MSRV-1 "gag*" region. In FIG. 36, a potential reading frame with the translation into amino acids is presented below the nucleic acid sequence.

EXAMPLE 13

Obtaining a Clone FBd13 Containing a pol Gene Region Related to the MSRV-1 Retrovirus and an Apparently Incomplete Env Region Containing a Potential Reading Frame (ORF) for a Glycoprotein Extraction of viral RNAs: The RNAs were extracted according to the method briefly described below.

A pool of culture supernatant of B lymphocytes of patients suffering from MS (650 ml) is centrifuged for 30 minutes at 10,000 g. The viral pellet obtained is resuspended in 300 microliters of PBS/10 mM $MgCl_2$. The material is treated with a DNAse (100 mg/ml)/RNAse (50 mg/ml) mixture for 30 minutes at 37° C. and then with proteinase K (50 mg/ml) for 30 minutes at 46° C.

The nucleic acids are extracted with one volume of a phenol/0.1% SDS (V/V) mixture heated to 60° C., and then re-extracted with one volume of phenol/chloroform (1:1; V/V).

Precipitation of the material is performed with 2.5 V of ethanol in the presence of 0.1 V of sodium acetate pH5.2. The pellet obtained after centrifugation is resuspended in 50 microliters of sterile DEPC water.

The sample is treated again with 50 mg/ml of "RNAse free" DNAse for 30 minutes at room temperature, extracted with one volume of phenol/chloroform and precipitated in the presence of sodium acetate and ethanol.

The RNA obtained is quantified by an OD reading at 260 nm. The presence of MSRV-1 and the absence of DNA contaminant is monitored by a PCR and an MSRV-1-specific RTPCR associated with a specific ELOSA for the MSRV-1 genome.

Synthesis of cDNA:

5 µl g of RNA are used to synthesize a cDNA primed with a poly(DT) oligonucleotide according to the instructions of the "cDNA Synthesis Module" kit (ref RPN 1256, Amersham) with a few modifications: The reverse transcription is performed at 45° C. instead of the recommended 42° C.

The synthesis product is purified by a double extraction and a double purification according to the manufacturer's instructions.

The presence of MSRV-1 is verified by an MSRV-1 PCR associated with a specific ELOSA for the MSRV-1 genome.

"Long Distance PCR": (LD-PCR)

500 ng of cDNA are used for the LD-PCR step (Expand Long Template System; Boehringer (ref.1681 842)).

Several pairs of oligonucleotides were used. Among these, the pair defined by the following primers:

5' primer: GGAGAAGAGC AGCATAAGTG G (SEQ ID NO:62)

3' primer: GTGCTGATTG GTGTATTTAC AATCC (SEQ ID NO:63).

The amplification conditions are as follows:

94° C. 10 seconds

56° C. 30 seconds

68° C. 5 minutes;

10 cycles, then 20 cycles with an increment of 20 seconds in each cycle on the elongation time. At the end of this first amplification, 2 microliters of the amplification product are subjected to a second amplification under the same conditions as before.

The LD-PCR reactions are conducted in a Perkin model 9600 PCR apparatus in thin-walled microtubes (Boehringer).

The amplification products are monitored by electrophoresis of 1/5th of the amplification volume (10 microliters) in 1% agarose gel. For the pair of primers described above, a band of approximately 1.7 kb is obtained.

Cloning of the amplified fragment:

The PCR product was purified by passage through a preparative agarose gel and then through a Costar column (Spin; D. Dutcher) according to the supplier's instructions.

2 microliters of the purified solution are joined up with 50 ng of vector PCRII according to the supplier's instructions (TA Cloning Kit; British Biotechnology)).

The recombinant vector obtained is isolated by transformation of competent DH5aF' bacteria. The bacteria are selected using their resistance to ampicillin and the loss of metabolism for Xgal (=white colonies). The molecular structure of the recombinant vector is confirmed by plasmid minipreparation and hydrolysis with the enzyme EcoR1.

FBd13, a positive clone for all these criteria, was selected. A large-scale preparation of the recombinant plasmid was performed using the Midiprep Quiagen kit (ref 12243) according to the supplier's instructions.

Sequencing of the clone FBd13 is performed by means of the Perkin Prism Ready Amplitaq FS dye terminator kit (ref. 402119) according to the manufacturer's instructions. The sequence reactions are introduced into a Perkin type 377 or 373A automatic sequencer. The sequencing strategy consists in gene walking carried out on both strands of the clone Fbd13.

The sequence of the clone FBd13 is identified by SEQ ID NO:54.

Figure 37:
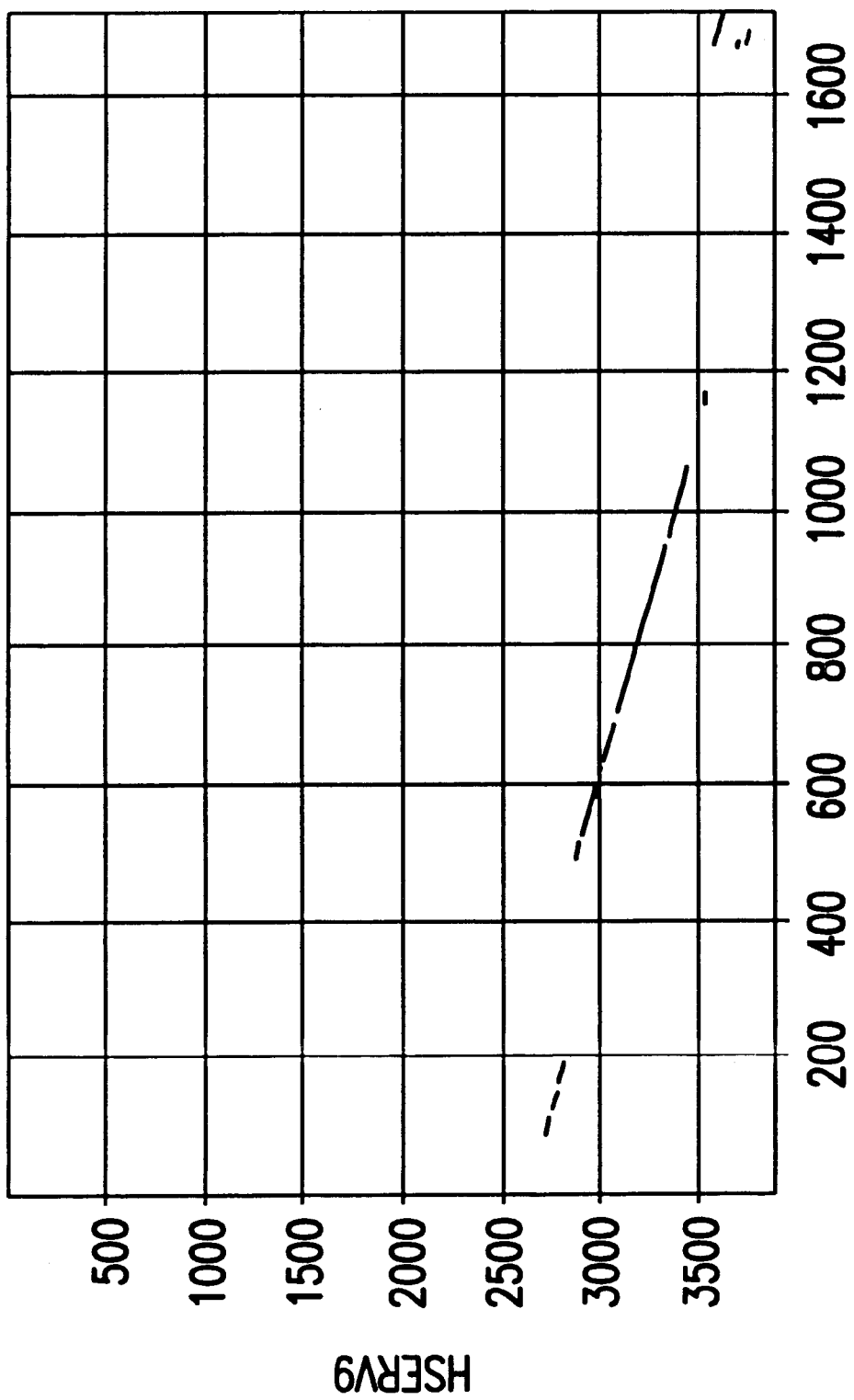
FIG. 37 shows the sequence homology between the clone FBd13 and the HSERV-9 retrovirus; according to this representation, the continuous line means a percentage homology greater than or equal to 70% and the absence of a line means a smaller percentage homology.

In FIG. 37, the sequence homology between the clone FBd13 and the HSERV-9 retrovirus is shown on the matrix chart by a continuous line for any partial homology greater than or equal to 70%. It can be seen that there are homologies in the flanking regions of the clone (with the pol gene at the 5' end and with the env gene and then the LTR at the 3' end), but that the internal region is totally divergent and does not display any homology, even weak, with the env gene of HSERV-9. Furthermore, it is apparent that the clone FBd13 contains a longer "env" region than the one which is described for the defective endogenous HSERV-9; it may thus be seen that the internal divergent region constitutes an "insert" between the regions of partial homology with the HSERV-9 defective genes.

This additional sequence determines a potential orf, designated ORF B13, which is represented by its amino acid sequence SEQ ID NO:81.

The molecular structure of the clone FBd13 was analyzed using the Gen Works® software and GenBank™ and SwissProt data banks.

5 glycosylation sites were found.

The protein does not have significant homology with already known sequences.

It is probable that this clone originates from a recombination of an endogenous retroviral element (ERV), linked to the replication of MSRV-1.

Such a phenomenon does not lack generation of the expression of polypeptides, or even of endogenous retroviral proteins which are not necessarily tolerated by the immune system. Such a scheme of aberrant expression of endogenous elements related to MSRV-1 and/or induced by the latter is liable to multiply the aberrant antigens, and hence tends to contribute to the induction of autoimmune processes such as are observed in MS. It clearly constitutes a novel element never hitherto described. In effect, interrogation of the data banks of nucleic acid sequences available in version No. 19 (1996) of the "Entrez" software (NCBI, NIH, Bethesda, USA) did not enable a known homologous sequence comprising the whole of the env region of this clone to be identified.

EXAMPLE 14
Obtaining a Clone FP6 Containing a Portion of the pol Gene, with a Region Coding for the Reverse Transcriptase Enzyme Homologous to the Clone POL* MSRV-1, and a 3' pol Region Divergent from the Equivalent Sequences Described in the Clones POL*, tpol, FBd3, JLBc1 and JLBc2

A 3' RACE was performed on total RNA extracted from plasma of a patient suffering from MS. A healthy control plasma treated under the same conditions was used as negative control. The synthesis of cDNA was carried out with the following modified oligo(dT) primer:

5' GACTCGCTGC AGATCGATTT TTTTTTTTTT TTTT 3' (SEQ ID NO:64)

and Boehringer "Expand RT" reverse transcriptase according to the conditions recommended by the company. A PCR was performed with the enzyme Klentaq (Clontech) under the following conditions: 94° C. 5 min then 93° C. 1 min, 58° C. 1 min, 68° C. 3 min for 40 cycles and 68° C. for 8 min, and with a final reaction volume of 50 µl.

Primers used for the PCR:

5' primer, identified by SEQ ID NO:65

5' GCCATCAAGC CACCCAAGAA CTCTTAACTT 3';

3' primer, identified by SEQ ID NO:64 (=the same as for the cDNA)

A second, so-called "semi-nested" PCR was carried out with a 5' primer located within the region already amplified. This second PCR was performed under the same experimental conditions as those used in the first PCR, using 10 ml of the amplification product originating from the first PCR.

Primers used for the semi-nested PCR:

5' primer, identified by SEQ ID NO:66

5' CCAATAGCCA GACCATTATA TACACTAATT 3';

3' primer, identified by SEQ ID NO:64 (=the same as for the cDNa)

Primers SEQ ID NO:65 and SEQ ID NO:66 are specific for the pol* region: position No. 403 to No. 422 and No. 641 to No. 670, respectively.

An amplification product was thus obtained from the extracellular RNA extracted from the plasma of a patient suffering from MS. The corresponding fragment was not observed for the plasma of the healthy control. This amplification product was cloned in the following manner.

The amplified DNA was inserted into a plasmid using the TA Cloning™ kit. The 2 µl of DNA solution were mixed with 5 µl of sterile distilled water, 1 µl of a 10-fold concentrated ligation buffer "10×LIGATION BUFFER", 2 µl of "pCR™ VECTOR" (25 ng/µl) and 1 µl of "TA DNA LIGASE". This mixture was incubated overnight at 12° C. The following steps were carried out according to the instructions of the TA Cloning™ kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide was selected for sequencing of the insert, after hybridization with a primer complementary to the Sp6 promoter present on the cloning plasmid of the TA cloning kit™. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

The clone obtained, designated FP6, enables a region of 467 bp which is 89% homologous to the pol* region of the MSRV-1 retrovirus and a region of 1167 bp which is 64% homologous to the pol region of ERV-9 (No. 1634 to 2856) to be defined.

The clone FP6 is represented in FIG. 38 by its nucleotide sequence identified by SEQ ID NO:57. The three potential reading frames of this clone are indicated by their amino acid sequence under the nucleotide sequence.

EXAMPLE 15
Obtaining a Region Designated G+E+A Containing an ORF for a Retroviral Protease, by PCR Amplification of the Nucleic Acid Sequence Contained Between the 5' Region Defined by the Clone "GM3" and the 3' Region Defined by the Clone POL*, from the RNA Extracted from a Pool of Plasmas of Patients Suffering from MS Oligonucleotides specific for the MSRV-1 sequences already identified by the Applicant were defined in order to amplify the retroviral RNA originating from virions present in the plasma of patients suffering from MS. Control reactions were performed so as to monitor the presence of contaminants (reaction with water). The amplification consists of a step of RT-PCR followed by a "nested" PCR. Pairs of primers were defined for amplifying three overlapping regions (designated G, E and A) on the regions defined by the sequences of the clones GM3 and pol* described above.

Semi-nested RT-PCR for amplification of the region G:

in the first RT-PCR cycle, the following primers are used:

primer 1: SEQ ID NO:67 (sense)

primer 2: SEQ ID NO:68 (antisense)

in the second PCR cycle, the following primers are used:

primer 1: SEQ ID NO:69 (sense)

primer 4: SEQ ID NO:70 (antisense)

Nested RT-PCR for amplification of the region E:

in the first RT-PCR cycle, the following primers are used:

primer 5: SEQ ID NO:71 (sense)

primer 6: SEQ ID NO:72 (antisense)

in the second PCR cycle, the following primers are used:

primer 7: SEQ ID NO:73 (sense)

primer 8: SEQ ID NO:72 (antisense)

Semi-nested RT-PCR for amplification of the region A:
in the first RT-PCR cycle, the following primers are used:
primer 9: SEQ ID NO:74 (sense)
primer 10: SEQ ID NO:75 (antisense)
in the second PCR cycle, the following primers are used:
primer 9: SEQ ID NO:74 (sense)
primer 11: SEQ ID NO:76 (antisense)
The primers and the regions G, E and A which they define are positioned as foll side-chain protective groups, simultaneously, using hydrofluoric acid (HF) in a suitable apparatus (type I cleavage apparatus, Peptide Instiute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDAC™ C18 analytical column (250×4.6 mm) at a flow rate of 1 ml/min. Fractions having the same retention time are pooled and lyophilized. The preponderant fraction is then analyzed by analytical high performance liquid chromatography with the system described above. The peptide which is considered to be of acceptable purity manifests itself in a single peak representing not less than 95% of the chromatogram.

The purified peptides are then analyzed with the object of monitoring their amino acid composition, using an Applied Biosystems 420H automatic amino acid analyzer. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated S24Q to be selected, whose sequence is identified by SEQ ID NO:59, encoded by a nucleotide sequence of the pol gene of MSRV-1 (SEQ ID NO:58).

b) Antigenic properties:

The antigenic properties of the S24Q peptide were demonstrated according to the ELISA protocol described below.

The lyophilized S24Q peptide was dissolved in 10% acetic acid at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 5 micrograms/ml. 100 microliters of this dilution are placed in each well of Nunc Maxisorb (trade name) microtitration plates. The plates are covered with a "plate-sealer" type adhesive and kept for 2 hours at +37° C. for the phase of adsorption of the peptide to the plastic. The adhesive is removed and the plates are washed three times with a volume of 300 microliters of a solution A (1×' PBS, 0.05% Tween 20r), then inverted over an absorbent tissue. The plates thus drained are filled with 250 microliters per well of a solution B (solution A+10% of goat serum), then covered with an adhesive and incubated for 1 hour at 37° C. The plates are then washed three times with the solution A as described above.

The test serum samples are diluted beforehand to 1/100 in the solution B, and 100 microliters of each dilute test serum are placed in the wells of each microtitration plate. A negative control is placed in one well of each plate, in the form of 100 microliters of buffer B. The plates covered with an adhesive are then incubated for 1 hour 30 min at 37° C. The plates are then washed three times with the solution A as described above. For the IgG response, a peroxidase-labelled goat antibody directed against human IgG (marketed by Jackson Immuno Research Inc.) is diluted in the solution B (dilution 1/10,000). 100 microliters of the appropriate dilution of the labelled antibody are then placed in each well of the microtitration plates, and the plates covered with an adhesive are incubated for 1 hour at 37° C. A further washing of the plates is then performed as described above. In parallel, the peroxidase substrate is prepared according to the directions of the bioMérieux kits. 100 microliters of substrate solution are placed in each well, and the plates are placed protected from light for 20 to 30 minutes at room temperature.

When the color reaction has stabilized, 50 microliters of Color 2 (bioMérieux trade name) are placed in each well in order to stop the reaction. The plates are placed immediately in an ELISA plate spectrophotometric reader, and the optical density (OD) of each well is read at a wavelength of 492 nm.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20x, 10% goat serum).

c) Detection of anti-MSRV-1 IgG antibodies (S24Q) by ELISA:

The technique described above was used with the S24Q peptide to test for the presence of anti-MSRV-1 specific IgG antibodies in the serum of 15 patients for whom a definite diagnosis of MS was established according to the criteria of Poser (23), and of 15 healthy controls (blood donors).

Figure 41:
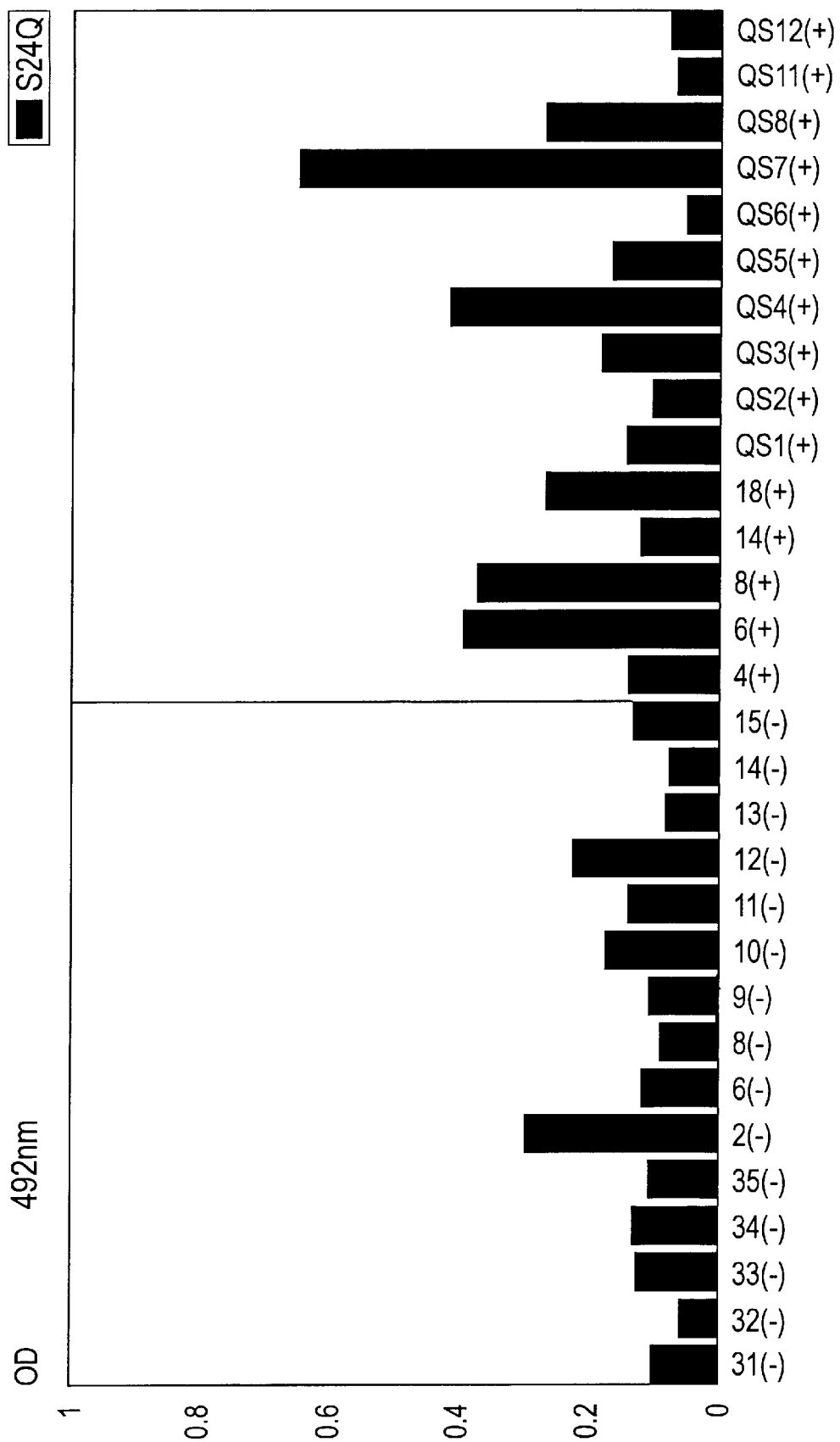
FIG. 41 shows the response of each serum of patients suffering from MS, indicated by the symbol (+), and of healthy patients, symbolised by (−), tested with an anti-IgG antibody, expressed as net optical density at 492 nm.

FIG. 41 shows the results for each serum tested with an anti-IgG antibody. Each vertical bar represents the net optical density (OD at 492 nm) of a serum tested. The ordinate axis gives the net OD at the top of the vertical bars. The first 15 vertical bars lying to the left of the vertical broken line represent the sera of 15 healthy controls (blood donors), and the 15 vertical bars lying to the right of the vertical broken line represent the sera of 15 cases of MS tested. The diagram enables 2 controls to be revealed whose OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.129 and the standard deviation is 0.06. Without the 2 controls whose OD values are greater than 0.2, the mean of the "negative" controls is 0.107 and the standard deviation is 0.03. A theoretical threshold of positivity may be calculated according to the formula:

> threshold value (mean of the net *OD* values of the negative controls)+(2 or 3' standard deviation of the net *OD* values of the negative controls).

In the first case, there are considered to be symptomless seropositives, and the threshold value is equal to 0.11+(3× 0.03)=0.20. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.13+ (3×0.06)=0.31.

According to this latter analysis, the test is specific for MS. In this respect, it is seen that the test is specific for MS, since, as shown in Table 1, no control has a net OD above this threshold. In fact, this result reflects the fact that the antibody titres in patients suffering from MS are, for the most part, higher than in healthy controls who have been in contact with MSRV-1.

In accordance with the first method of calculation, and as shown in FIG. 41 and in Table 3, 6 of the 15 MS sera give a positive result (OD greater than or equal to 0.2), indicating the presence of IgGs specifically directed against the S24Q peptide, hence against a portion of the reverse transcriptase enzyme of the MSRV-1 retrovirus encoded by its pol gene, and consequently against the MSRV-1 retrovirus.

Thus, approximately 40% of the MS patients tested have reacted against an epitope carried by the S24Q peptide and possess circulating IgGs directed against the latter.

Two out of 15 blood donors in apparent good health show a positive result. Thus, it is apparent that approximately 13% of the symptomless population may have been in contact with an epitope carried by the S24Q peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at-risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus.

Lastly, the detection of anti-S24Q antibodies in only one out of two MS cases tested here may reflect the fact that this peptide does not represent an immunodominant MSRV-1 epitope, that inter-individual strain variations may induce an immunization against a divergent peptide motif in the same region, or that the course of the disease and the treatments followed may modulate over time the antibody response against the S24Q peptide.

TABLE 3

|  | CONTROLS | MS |
|---|---|---|
|  | 0.101 | 0.136 |
|  | 0.058 | 0.391 |
|  | 0.126 | 0.37 |
|  | 0.131 | 0.119 |
|  | 0.105 | 0.267 |
|  | 0.294 | 0.141 |
|  | 0.116 | 0.102 |
|  | 0.088 | 0.18 |
|  | 0.105 | 0.411 |
|  | 0.172 | 0.164 |
|  | 0.137 | 0.049 |
|  | 0.223 | 0.644 |
|  | 0.08 | 0.268 |
|  | 0.073 | 0.065 |
|  | 0.132 | 0.074 |
| Mean | 0.129 |  |
| Std. Dev. | 0.06 |  |
| Threshold | 0.31 |  | d) Detection of anti-MSRV-1 IgM antibodies by ELISA:

The ELISA technique with the S24Q peptide was used to test for the presence of anti-MSRV-1 IgM specific antibodies in the same sera as above.

Figure 42:
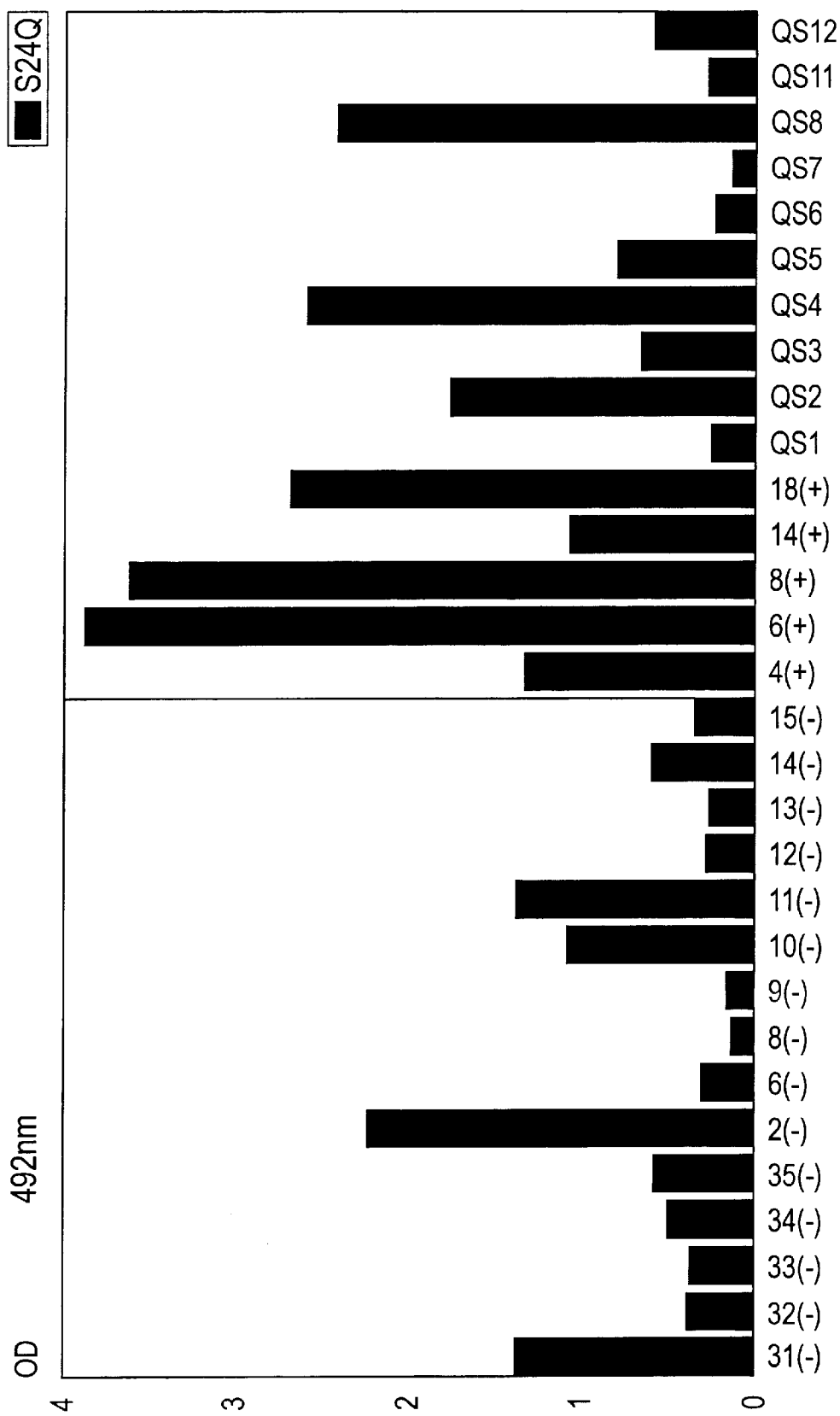
FIG. 42 shows the response of each serum of patients suffering from MS, indicated by the symbols (+) and (QS), and of healthy patients (−), tested with an anti-IgM antibody, expressed as net optical density at 492 nm.

FIG. 42 shows the results for each serum tested with an anti-IgM antibody. Each vertical bar represents the net optical density (OD at 492 nm) of a serum tested. The ordinate axis gives the net OD at the top of the vertical bars. The first 15 vertical bars lying to the left of the vertical line cutting the abscissa axis represent the sera of 15 healthy controls (blood donors), and the vertical bars lying to the right of the vertical broken line represent the sera of 15 cases of MS tested.

The mean of the OD values for the MS cases tested is 1.6.
The mean of the net OD values for the controls is 0.7.
The standard deviation of the negative controls is 0.6.
The threshold of theoretical positivity may be calculated according to the formula:

threshold value=(mean of the OD values of the negative controls)+(3×standard deviation of the OD values of the negative controls)

The threshold value is hence equal to 0.7+(3×0.6)=2.5;

The negative results represent a non-specific "background" of the presence of antibodies directed specifically against an epitope of the peptide.

According to this analysis, and as shown in FIG. 42 and in the corresponding Table 4, the IgM test is specific for MS, since no control has a net OD above the threshold. Six of the 15 MS sera produce a positive IgM result.

The difference in seroprevalence between the MS and control populations is extremely significant: "chi-squared" test, $p<0.002$.

These results point to an aetiopathogenic role of MSRV-1 in MS.

Thus, the detection of IgM and IgG antibodies against the S24Q peptide makes it possible to evaluate, alone or in combination with other MSRV-1 peptides, the course of an MSRV-1 infection and/or of the viral reactivation of MSRV-1.

TABLE 4

|  | CONTROLS | MS |
|---|---|---|
|  | 1.449 | 0.974 |
|  | 0.371 | 6.117 |
|  | 0.448 | 2.883 |
|  | 0.456 | 1.945 |
|  | 0.885 | 1.787 |
|  | 2.235 | 0.273 |
|  | 0.301 | 1.766 |
|  | 0.138 | 0.668 |
|  | 0.16 | 2.603 |
|  | 1.073 | 0.802 |
|  | 1.366 | 0.245 |
|  | 0.283 | 0.147 |
|  | 0.262 | 2.441 |
|  | 0.585 | 0.287 |
|  | 0.356 | 0.589 |
| Mean | 0.7 |  |
| Std. Dev. | 0.6 |  |
| Threshold Value | 2.5 |  |

It is possible, as a result of the new discoveries made and the new methods developed by the inventors, to permit the improved implementation of diagnostic tests for MSRV-1 infection and/or reactivation and to evaluate a therapy in MS and/or RA on the basis of its efficacy in "negativing" the detection of these agents in the patient's biological fluids.

Furthermore, early detection in individuals not yet displaying neurological signs of MS or rheumatological signs of RA could make it possible to institute a treatment which would be all the more effective with respect to the subsequent clinical course for the fact that it would precede the lesion stage which corresponds to the onset of the clinical disorders. Now, at the present time, a diagnosis of MS or RA cannot be established before a symptomatology of lesions has set in, and hence no treatment is instituted before the emergence of a clinical picture suggestive of lesions which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in "negativing" the detection of these agents in the patients' biological fluids.

EXAMPLE 18

1) Materials and Methods

Patients and clinical samples

Choroid plexus cells from MS patients and controls were obtained from the brain-cell library, Laboratoire R. Escourolles, Hôpital de la Salpêtriére, Paris, France. Non-tumoral leptomeningeal cells from controls were obtained as previously described (26). Peripheral blood from MS and control patients used for obtaining B-cell lines and plasma, were obtained from the Neurological Departments, CHU de Grenoble, and from INSERM U 134, Hôpital de la Salpêtriére, France. Clinical details and origin of the 10 MS patients and of the 10 patients with other neurological diseases who provided CSF samples are given in Table 6.

Cell cultures, virus isolation and purification

All cell-types were cultured as previously described (3, 5, 26). All cultures were regularly screened for mycoplasma contamination with an ELISA mycoplasma-detection kit (Boehringer). No cell-extract nor supernatant used contained detectable mycoplasma.

Extracellular virion purification and sucrose density gradients were performed as previously described (3, 5, 26). From each sucrose gradient 0.5–1 ml fractions were collected from the top of the tubes, with a 1000 µl Pipetman and a different sterile tip for each fraction. 60 µl were used for RT activity assay and the rest was mixed with 1 volume of buffer containing 4M guanidinium thiocyanate, 0.5% N-Lauroyl sarcosin, 25 mM EDTA, 0.2% β-mercaptoethanol adjusted at pH 5.5 with acetic acid. These mixtures were frozen at −80° C. for further RNA extraction or directly processed according to Chomzynski (20), with an overnight precipitation step at −20° C., in the presence of RNase-free glycogen (Boehringer). RNA was dissolved in 20 to 50 µl of DEPC-treated water in the presence of 1–2 µl of recombinant RNase-inhibitor (PROMEGA) and 0,1 mM DTT. 10 µl aliquots were used for each RT-PCR.

Reverse transcriptase activity

RT-activity was tested with 20 mM Mg$^{++}$ and poly-Cm or polyC templates, in virion pellets or fractions from sucrose gradients as previously described (3, 5, 26).

cDNA synthesis and 'Pan-retro' RT-PCR with degenerate primers

A total RT-activity between $10^6$–$10^7$ dpm was required in the fraction containing the peak of purified virions. The "Pan-retro" RT-PCR technique (27) was performed on virion RNA extracted by the method of Chomczynski (20) and dissolved in 20 µl RNase-free water. 5 µl RNA solution was incubated for 30 min at 37° C. with 0.3 units (3 units for CSF series) of RNase-free DNase-1 (Boehringer) in a 20 ml reaction containing 7.5 mM random hexamers, 5 mM Hepes-HCl pH 6.9, 75 mM KCl, 3 mM MgCl$_2$, 10 mM DTT, 50 mM Tris-HCl pH 7.5, 0.5 mM each dNTP, and 20 units recombinant RNase inhibitor (Promega). The DNase was then heat inactivated at 80° C. for 10 min. 20 units MoMLV RT (Pharmacia) and a further 20 units of RNase inhibitor were added to each tube in a Genesphere™ enclosure (Safetech, Ireland) and cDNA was synthesised for 90 min at 37° C. Following reverse transcription, the cDNA was boiled for 5 min then cooled rapidly on ice. The Round 1 PCR mix (final volume 25 µl per reaction; 20 mM Tris-HCl pH 8.4, 60 mM KCl, 2.5 mM MgCl$_2$, 200 ng each of primers PAN-UO and PAN-DI [see FIG. 44], 0.2 mM each dNTP) was treated with 0.3 units DNase-1 and then heat inactivated as above. 2.5 µl cDNA was added in the Genesphere™ enclosure and the tubes heated to 80° C. before adding 0.5 units Taq polymerase (Perkin Elmer) individually to each tube ("hot start"). Round 1 PCR parameters were 35 cycles of 95° C. for 1 min, 34° C. for 30 sec, 72° C. for 1 min, with a final 7 min extension at 72° C. 0.5 ml of Round 1 PCR product was transferred to the Round 2 DNase-treated PCR mix (composition as for Round 1 but containing primers PAN-UI and PAN-DI) using the "hot start" procedure. Round 2 PCR parameters were as for Round 1 but using 30 cycles only and annealing at 45° C. for 1 min.

Cloning™ of PCR products

PCR products were cloned using the TA-cloning™ kit (British Biotechnology) according to the manufacturer's recommendations.

Sequencing

Sequencing reactions were performed using the "Prism ready reaction kit dye deoxyterminator cycle sequencing kit" (Applied Biosystems). Automatic sequence analysis was performed on an automatic sequencer (Applied Biosystems, 373 A).

RT-PCR with ST1 primer sets

The first PCR round was performed directly from the cDNA reaction mixture according to the one-step RT-PCR technique described by Mallet et al. (28). This one-step RT-PCR procedure reduced the probability of airborne contamination when opening the tubes and transferring PCR reagents after an independent cDNA synthesis. RNA was extracted as previously from 2 ml of plasma (snap-frozen in liquid nitrogen and stored at −80° C.) or from a 500 ml sucrose fraction with a total RT-activity above $10^6$ dpm, and resuspended in 50 µl of RNase-free water. For each RT-PCR reaction 10 µl of RNA solution was incubated in a Perkin-Elmer 480 thermocycler, 15 min at 20° C. with 1 U of RNase-free DNASE 1 and 1.2 µl of 10×DNASE buffer (50 mM Tris, 10mM MgC12 and 0,1 mM DTT) containing 1 U/ml of RNase-inhibitor (PROMEGA), and heated at 70° C. for 10 min for DNase inactivation. The solution was placed on ice and mixed (in conditions preventing airborne dust/DNA contamination) with 88 µl of PCR mix containing: 1×taq buffer, 25 nM/tube dNTPs, 40 pM/tube of each first round primer (ST1.1 upstream primer: 5' AGGAGTAAG-GAAACCCAACGGAC 3' (SEQ ID NO:15); ST1.1 downstream primer: 5'TAAGAGTTGCACAAGTGCG 3' (SEQ ID NO:16)), 2.5 U/tube of taq (Appligene) and 10 U/tube of AMV-RT (Boehringer). Each tube was further incubated in a Perkin-Elmer 480 thermocycler for 10 min at 65° C., followed by 2 h at 42° C. for CDNA synthesis and 5 min at 95° C. for inactivation of AMV-RT and DNA denaturation. First round parameters were 40 cycles of 95° C. for 1 min, 53° C. for 2.5 min, 72° C. for 1 min, with a final extension of 10 min at 72° C. 10 µl of the first round were transferred to the second round PCR mix previously treated at 20° C. for 15 min with RNase-free DNase 1 (0.02 U/ml) followed by DNase inactivation at 70° C. for 10 min. This mix contained 1×taq buffer, 25 nM/tube dNTPs, 40 pM/tube of each second round primers [ST1.2 upstream primer: 5'TCAGGGAT-AGCCCCCATCTAT3' (SEQ ID NO:17); ST1.2 downstream primer: 5'AACCCTTTGCCACTACATCAATTT3' (SEQ ID NO: 18)] and 2.5 U/tube of taq (Appligene). Second round parameters were 30 cycles of 95° C. for 1 min, 53° C. for 1.5 min, 72° C. for 1 min, with a final extension of 8 min at 72° C. 20 ml of this nested RT-PCR product were deposited on a 0,7% agarose gel containing ethidium bromide and exposed to UV light for the visualization of amplified products.

Hybridisation analysis of PCR products: MSRV-pol detection by ELOSA

The protocol was essentially as previously described (21) but with the following modifications: Nunc Maxisorb microtiter plates were coated with 100 ng per well capture probe CpV1b (see FIG. 44) either by passive adsorption (21) or alternatively by using streptavidin coated plates and biotinylated CpV1b. Peroxidase-labelled detector probe DpV1 (see FIG. 44) was used and the assay cut-off was defined as the mean of 4 negative controls plus 0.2 $OD_{492}$ units.

RNA extraction, cDNA synthesis and PCR amplification from MS plasma samples:

Total RNA was extracted from human MS plasma by a guanidium method as described elsewhere (29). Total RNA extracted from 100 ul of plasma, were treated with RNase-free DNase I (0.1 U/ml; Boehringer Manheim, France) and reverse transcribed under the conditions recommended by the manufacturer, using Superscript reverse transcriptase (Gibco-BRL, FRANCE). The resulting cDNAs were amplified by semi-nested PCR through 35 cycles (94° C. 1 min, 55° C. 1 mn, 72° C. 1 min 30 sec) and 72° C. 8 min for a final extension.

Three different fragments in the RT region were amplified by the following specific primers:

in the protease (PRT) region, for the 1st and 2nd round of PCR, respectively, sense primer [5' TCC AGC AGC AGG ACT GAG GGT 3' (SEQ ID NO:93)] and antisense primers [5' CTG TCC GTT GGG TTT CCT TAC TCC T 3' (SEQ ID NO:72)/5' GAC AGC AAA TGG GTA TTC CTT TCC 3' (SEQ ID NO:94)]

in the fragment A of the RT region (Cf. FIG. 46), for the 1st and 2nd round of PCR, respectively, sense primer [5' AGG AGT AAG GAA ACC CAA CGG ACA G 3' (SEQ ID NO:95)] and antisense primers [5' TGT ATA TAA TGG TCT GGC TAT TGG G 3' (SEQ ID NO:96)/ 5' TTC GGC AGA AAC CTG TTA TGC CAA GG 3' (SEQ ID NO:76)]

in the fragment B of the RT region (Cf. FIG. 46), for the 1st and 2nd round of PCR, respectively, sense primers [5' GGC TCT GCT CAC AGG AGA TTA GAT AC 3' (SEQ ID NO:97)/5' AAA GGC ACC AGG GCC CTC AGT GAG GA 3' (SEQ ID NO:98)] and antisense primer 3'[5' GGT TTA AGA GTT GCA CAA GTG CGC AGT C 3' (SEQ ID NO:99)].

The amplified fragments were analyzed on ethidium bromide-stained agarose gels, cloned in the TA cloning vector (Invitrogen) and sequenced.

2) Results

Specific retroviral RNA is found in extracellular virions from MS patient-derived cell cultures and in MS patients' CSF.

Choroid plexus cells (4) (obtained post-mortem) and EBV-immortalized peripheral blood B-lymphocytes (30, 31) from MS patients gave rise to cultures expressing 100–120 nm viral particles associated with RT-activity similar to that of the original LM7 isolate (3). Similar cell-types from non-MS donors produced neither this RT-activity nor virions. All the 'infected' cultures were poorly and/or transiently productive and/or had a limited lifespan. Therefore, in order to analyze the genomic RNA present in the very limited quantity of extracellular virions, we used an RT-PCR approach to amplify, with degenerate primers, a conserved region of the pol gene present in all known retroviruses (12); the techniques based on this approach will be called "Pan-retro" RT-PCR. Extensive DNase treatment of samples and reagents was essential, because human DNA contains many endogenous retroviral elements amplifiable by this technique.

Figure 43:
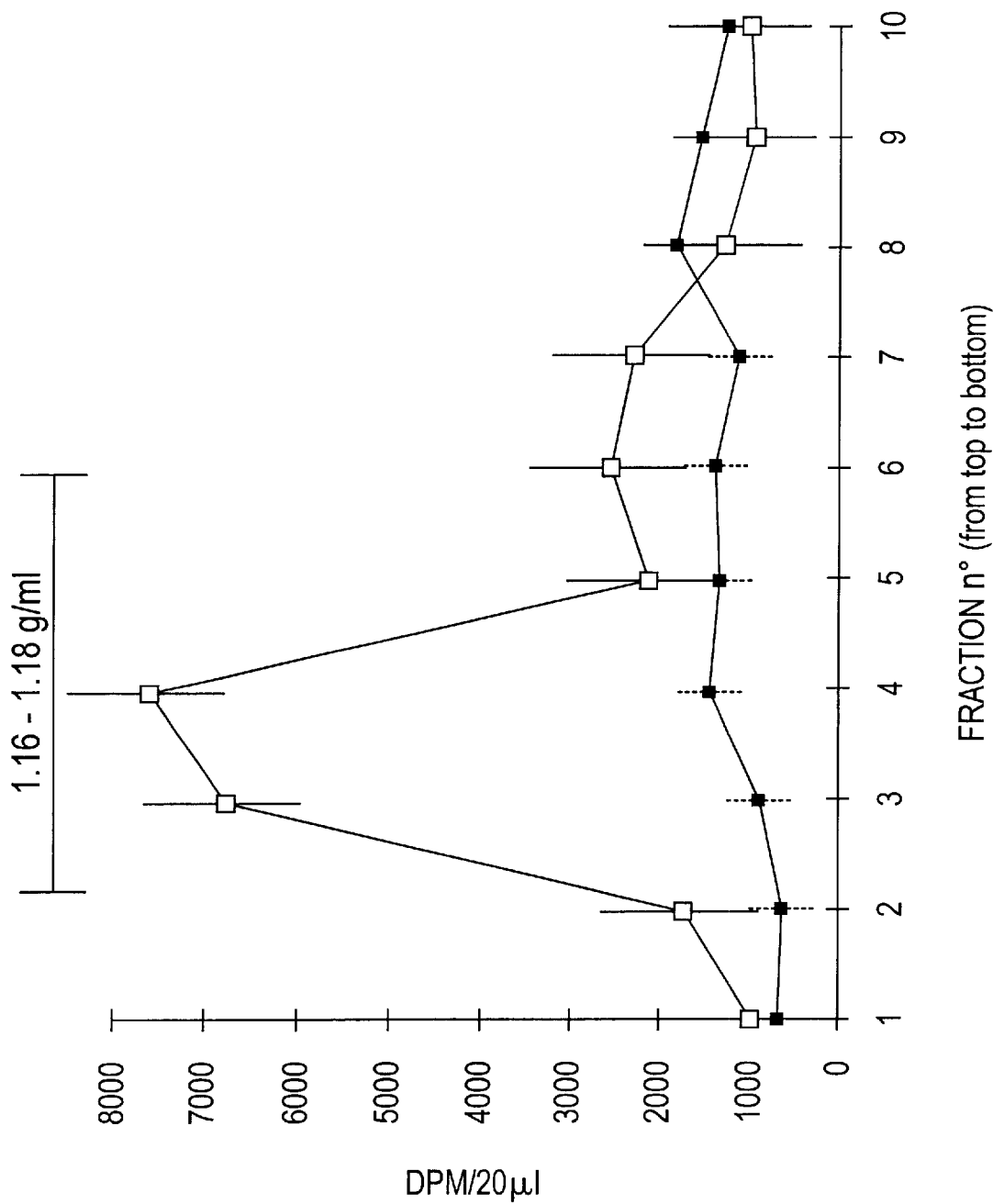
FIG. 43 shows the RT-activity profile in sucrose density gradients of pellets from B-cell line supernatants; Control B-cell line n was obtained from the relative of a patient with mitochondriopathy. MS B-Cell line o was obtained from a patient with definite MS.

"Pan-retro" RT-PCR experiments were performed on sucrose-density gradient purified virions from supernatants of different types of cell cultures and their non-infected controls: (i) choroid plexus cells sampled post-mortem from MS brain (PLI-1), (ii) choroid plexus cells from non-MS brain autopsy, infected by co-culture with irradiated LM7 cells (LM7P), and (iii) identical non-infected choroid-plexus cells. "Early" B-cell lines obtained by spontaneous in vitro transformation of two EBV-seropositive individuals, (iv) one MS patient and (v) one non-MS control, were also analysed. FIG. 43 illustrates the RT-activity in sucrose-gradient fractions obtained from the B-cell cultures. The technique described by Shih et al. (12) was modified in a semi-nested RT-PCR protocol (27) using degenerate primers (FIG. 2) and extensive DNase treatment. PCR amplifications were performed in London (Dpt of Virology, U.C.L.M.S.) on coded aliquots of the density gradient fractions. Blind and systematic cloning and sequencing of the PCR products were undertaken in an independent laboratory (bioMérieux, Lyon). After complete sequencing of 20 to 30 clones per sucrose gradient fraction, the codes were broken and results analysed in parallel with the RT-activity data.

TABLE 5

SEQUENCES GENERATED BY 'PAN-RETROVIRUS' PCR OF DENSITY GRADIENT FRACTIONS (containing the peak of RT-activity or the corresponding control fraction)

| CULTURE | MSRV c-pol | ERV9 (V) | PCR artefacts (VI) | Total clones |
|---|---|---|---|---|
| LM7P (I) | 16 | 4 | 6 | 26 |
| PLI-I (II) | 9 | 1 | 13 | 23 |
| MS B-CELL LINE (III) | 9 | 2 | 8 | 19 |
| CONTROL B-CELL LINE (IV) | 0 | 0 | 26 | 26 |

I LM7-infected choroid plexus cell culture.
II MS patient-derived choroid plexus cell culture (PLI-2).
III MS patient-derived spontaneous B-cell line (immortalized by endogenous EBV strain).
IV Non-MS control B-cell line.
V Clones with >90% homology with the GenBank sequence HSERV9 are designated ERV9 in this study.
VI PCR artefacts included primer multimers, concatemers, single primer amplifications, etc.

Table 5 presents the distribution of sequences obtained from sucrose gradient fractions containing the peak of viral RT-activity in MS-derived cultures and also the sequences amplified from the corresponding RT-activity negative fractions of uninfected cultures. The predominant sequence detected in bands of the expected size ($\cong$140 bp) amplified in all the RT-activity positive fractions (but not in the RT-activity negative fractions) was different from known retroviruses and was designated MSRV-cpol. MSRV-cpol sequences exhibited partial homology (70–75%) with ERV9, a previously described endogenous retroviral sequence (18). A few ERV9 sequences (>90% homology with ERV9) were also present but clearly represented a minority of clones. In addition to typical pol sequences, numerous PCR artefacts (primer multimers, concatemers or single-primer amplifications) related to the use of degenerate primers and low-temperature annealing, were found in all samples (Table 5).

FIG. 44 shows an alignment of a consensus sequence of MSRV-cpol with the corresponding VLPQG/YMDD region of diverse retroviruses. FIG. 45 displays a phylogenic tree based on the evolutionarily conserved amino acid sequences of both exogenous and endogenous retroviruses in this region. From this tree it can be seen that the pol gene of MSRV is phylogenically related to the C-type group of oncovirinae.

A small scale study was performed to determine the prevalence of MSRV c-pol sequences in the CSF of patients with MS. Identification of MSRV-cpol in PCR products by cloning and sequencing is both laborious and time consuming. We therefore devised an enzyme-linked oligosorbent assay (ELOSA), using a capture probe (CpV1B) and a peroxidase-labelled detector probe (DpV1), for the rapid identification of MSRV-cpol sequences in 'Pan-retrovirus' PCR products (FIG. 44). The specificity of this sandwich hybridization-based assay for HMSRV-cpol was tested with both distantly related (HIV and MoMLV) and closely related (ERV9) pol sequences. No significant cross reactivity with such targets was observed despite the ability of the ELOSA to detect as little as 0.01 ng of MSRV-cpol DNA.

to be correlated with age, sex or type of MS, but was seen in untreated patients only (5/6). No patient with immunosuppressive therapy was found positive (0/4). No correlation between MSRV-cpol detection and CSF cell count was observed.

Cloning™ and sequencing a larger region of the pol gene

An independent identification of the MSRV genomic sequence was obtained by a non-PCR approach using RNA extracted from concentrated virions derived from 2.5 liters of LM7-infected sub-cultures of choroid plexus cells. A limited number of clones was obtained by direct cloning of the cDNA, one of which (PSJ17) showed partial homology with ERV9 pol. Specific primers based on the MSRV-cpol region and on the PSJ17 clone, amplified a 740 bp fragment linking the two independent sequences in RNA extracted from purified virions. PSJ17 was localized on the 3' side of MSRV-cpol. Further sequence extension on the 5' side of MSRV-cpol and on the 3' side of PSJ17, was obtained using RT-PCR approaches on RNA from purified LM7-like virions produced in MS choroid plexus cultures (4).

In FIG. 46, the nucleotide sequence corresponding to overlapping clones obtained by sequence extension in the pol gene is represented with the amino acid translation corresponding to the putative open reading frames (ORFs) of the protease and of the reverse-transcriptase. The active site motifs of the protease (PRT) and of the reverse-transcriptase (RT) are underlined. In the C-terminal region of the RT sequence, the dispersed amino acid residues regularly present in retroviral RNase H domains, are also underlined.

Non-degenerate primers detect MSRV-specific RNA in virions associated with the peak of RT-activity and in in MS patients' plasma.

TABLE 6

DETECTION OF HMSRV IN THE CSF OF PATIENTS WITH MULTIPLE SCLEROSIS AND OTHER NEUROLOGICAL DISEASES

| Patient[1] | Age/Sex | Diagnosis | MS Type | MS Activity | MS Duration | MS Treatment at sampling | MSRV ELOSA |
|---|---|---|---|---|---|---|---|
| ITMS1 | 27 yrs/M | multiple sclerosis | 2° progressive | slow progression | 5 yrs | corticosteroids | negative |
| ITMS2 | 55 yrs/M | multiple sclerosis | 1° progressive | slow progression | 9 yrs | none | POSITIVE |
| ITMS3 | 51 yrs/F | multiple sclerosis | 1° progressive | slow progression | 2 yrs | none | negative |
| ITMS4 | 22 yrs/F | multiple sclerosis | relapsing/remitting | In remission | 8 yrs | none | POSITIVE |
| ITMS5 | 27 yrs/F | multiple sclerosis | 1° progressive | slow progression | 8 yrs | cyclophosphamide | negative |
| ITMS6 | 33 yrs/M | multiple sclerosis | 2° progressive | slow progression | 16 yrs | none (previously cycloph. + corticost.) | negative |
| ITMS7 | 33 yrs/F | multiple sclerosis | 2° progressive | slow progression | 9 yrs | none | POSITIVE |
| ITMS8 | 25 yrs/F | multiple sclerosis | relapsing/remitting | stable | 3 yrs | none | POSITIVE |
| ITMS9 | 36 yrs/F | multiple sclerosis | 2° progressive | slow progression | 3 yrs | none | POSITIVE |
| ITMS10 | 38 yrs/M | multiple sclerosis | 2° progressive | slow progression | 7 yrs | corticosteroids | negative |
| OND1 | 37 yrs/F | cerebellar atrophy | NA[2] | NA | NA | NA | negative |
| OND2 | 26 yrs/F | viral myelitis | NA | NA | NA | NA | negative |
| OND3 | 38 yrs/F | viral encephalitis | NA | NA | NA | NA | negative |
| OND4 | 28 yrs/F | viral encephalitis | NA | NA | NA | NA | negative |
| OND5 | 54 yrs/M | viral encephalitis | NA | NA | NA | NA | negative |
| OND6 | 32 yrs/M | Guillain - Barré | NA | NA | NA | NA | negative |
| OND7 | 54 yrs/F | cerebrovascular | NA | NA | NA | NA | negative |
| OND8 | 52 yrs/F | hydrocephalus | NA | NA | NA | NA | negative |
| OND9 | 25 yrs/F | 1° cerebral tumour | NA | NA | NA | NA | negative |
| OND10 | 21 yrs/M | epilepsy | NA | NA | NA | NA | negative |

[1]CSF samples from patients ITMS1–OND2 were made available by Prof. P. Ferrante, University Centre for Multiple Sclerosis, Milan, Italy.
CSF samples from patients OND3–OND10 were made available by Profs. J. Pallat and J. Perrel, Dept. of Neurology, University Hospital, Grenoble, Frances.
[2]NA = Not Applicable Cerebrospinal fluid (CSF) samples were available from 10 patients with MS and from 10 patients with other neurological disorders. Total RNA was extracted from CSF pellets, reverse transcribed and amplified as above. ELOSA analysis (Table 6) of the PCR products revealed MSRV-cpol sequences in 5 of the 10 MS patient samples but in none of the 10 samples from patients with other neurological diseases (P<0.05). The presence of MSRV-cpol did not appear PCR primers (ST1.1 primer set; positions 603–625/1732–1714, on FIG. 4) based on overlapping clones in the pol gene, amplified a 1.15 kb segment of the RT region from several different isolates obtained from different MS patients. Nested primers (ST1.2; positions 869–889/1513–1490, on FIG. 46) generated a 700 bp fragment (FIG. 47) which was more easily visualized by ethidium bromide staining than the first round product generated by ST1.1. The specificity of PCR products was confirmed by stringent hybridization with a peroxidase-labeled MSRV-cpol probe (FIG. 44), using the ELOSA technique (21).

The ST1.1 and 2 primer set was used to detect extracellular MSRV RNA in human plasma, although non-optimal for this application. FIG. 47 illustrates the results of PCR amplification of cDNA derived from 2 MS patient and 2 control plasma samples tested in parallel with cDNA from the sucrose density gradient fractions of an MS choroid plexus isolate. Taq-sequencing of the 700 bp bands confirmed the presence of MSRV sequence. A very faint 700 bp band is also visible in fraction 10 which corresponds to the bottom of the tube where aggregated particles usually sediment. Control RT-PCR for cellular aldolase transcripts on plasma-derived RNA was negative, indicating that the results were not due to cellular RNA released by cell lysis during plasma separation. It should be noted that this PCR technique was not designed for epidemiological studies since its sensitivity is impaired by the length of the cDNA required (1.15 kb).

Non-degenerate primers amplifying three fragments of the pol gene (the whole protease region, regions A and B of the reverse transcriptase; Cf. FIG. 46) were also used to confirm the presence of MSRV sequences in DNase-treated RNA from MS plasma. These fragments were amplified from the plasma of a further 4 MS patients with active disease. Sequence analysis confirmed that the PRT and RT regions were homologous (>95% and >90% respectively) to MSRV sequences previously obtained on culture virion. No such sequence were detected in plasma from healthy controls (n=4), tested in parallel with MS plasma.

3) Discussion

Phylogeny of MSRV

From the results of this study, it can be concluded that the virus previously referred to as "LM7" (3, 5, 26) possesses an RNA genome containing the MSRV pol sequences described here. The conserved RT motif of both MSRV and ERV9 is two amino acids shorter than that of other retroviruses, apart from human foamy viruses which nonetheless have a functional RT. The potential ORF encompassing the entire PRT-RT region is consistent with the virion-associated RT-activity detected in sucrose density gradients with infected culture supernatants. Moreover, since we have recently succeeded in expressing a recombinant protein from the sequence of MSRV protease cloned from MS plasma, we can confirm the reality of the potential PRT ORF. Similar cloning and expression of other sequences containing potential ORFs for MSRV proteins, is being undertaken to confirm their ability to encode enzymes and structural proteins of MSRV virions. The phylogenic tree in FIG. 45, based on the most conserved amino acid sequence in retroviruses (VLPQG . . . YXDD), shows that the MSRVpol gene is related to the C-type oncoviruses. Apart from ERV9, the closest known retroviral element is RTLV-H, a human endogenous sequence known to have a subtype with a functional pol gene (32). In the pol region, this phylogenic affiliation to C-type oncoviruses apparently contradicts our previous assumptions based on the general morphology of the particles observed by electron microscopy (EM), which were compatible with a B or D-type oncovirus (3, 5, 26). However, preliminary data on env sequences detected in MSRV virions, would suggest a greater phylogenic proximity to D-type. Such difference in phylogenies of the pol and env genes have been described in MPMV and suggest a recombinatorial origin in D-type retroviruses (33). D to C type morphological conversion is also possible since it has been reported that a single amino acid substitution in the gag protein can convert retrovirus morphology to that of a different type (34).

Is MSRV an exogenous retrovirus sharing extensive homology with a related endogenous retrovirus family or an endogenous retrovirus producing extracellular virions?

Southern blot analysis with an MSRV pol probe under stringent conditions, showed hybridisation with a multicopy endogenous family (data not presented), indicating the existence of endogenous elements more closely related to MSRV than ERV9 itself. Consequently, we were unable to look for a virion-specific provirus in MSRV-producing cells. In agreement with southern blot findings, PCR studies on genomic DNA showed multiple band amplification of MSRV-related endogenous sequences. Since pol is the most conserved retroviral gene, the sequence described here is the least suitable region to discriminate between exogenous and endogenous sequences. It is hoped that sequence information from other parts of the genome may permit such a discrimination, would it be on a tiny portion as has recently been demonstrated for the Jaagsiekte retrovirus (JSRV) of sheep (35). With such sequence data, it would then become possible to identify the MSRV-specific provirus in the genome of virion-producing cell cultures.

MSRV could represent a virion-producing exogenous member of an ERV9-like endogenous family, just as exogenous strains exist in the well-studied mouse mammary tumour virus (MMTV) and murine leukaemia virus (MuLV) retroviral families of mice, and also, in the JSRV retroviral family of sheep (36). Alternatively, it is also conceivable that the extracellular MSRV virions may be produced by a replication-competent endogenous provirus. Whether MSRV is exogenous or endogenous, conceptual similarities exist with the category of retroviruses represented by MuLV, MMTV and JSRV. Unlike defective endogenous elements, this category of agents are known to produce infectious and pathogenic virions, to cause neurological disease (37), solid tumours/leukaemias (36, 38) and to express "endogenous superantigens" (39, 40). Furthermore, in MuLV infections, the genetic endogenous retroviral background of the mouse strain can determine susceptibility or resistance to disease (39, 41). Indeed, such interactions between an infectious retrovirus and its endogenous counterpart may be relevant in the pathogenesis of MS, since endogenous retroviral genotypes are not identical in all individuals. A genetic control due to related endogenous retroviral genotypes could therefore contribute to the known hereditary susceptibility to MS (43), if MSRV does indeed play an active role in this disease. Elsewhere, the data in Table 5 suggest that ERV9 elements may be co-expressed, possibly via trans-activation in infected cells, and give rise to heterologous RNA packaging in MSRV virions. Such heterologous packaging is known to occur in other retroviral systems (42).

A role for the numerous common viruses previously evoked in MS?

Among the numerous reports of viruses putatively involved in the aetiopathogenesis of MS, a significant proportion focus on two viral families, the paramyxoviridae and the herpesviridae. Regarding the paramyxoviridae, the key observation is of a frequently increased antibody titer to measles virus in MS patients essentially directed, in CSF, against measles fusion protein (44). The existence of aminoacid similarities between conserved domains of the fusion proteins of paramyxoviridae and the transmembrane protein of retroviruses (45), may explain this observation if antigenic cross-reactivity between these two proteins occured.

With regard to the herpesvirus family, the involvement of Epstein-Barr Virus (EBV), Herpes Simplex Virus type 1

(HSV-1) and, most recently, Human Herpes Virus 6 (HHV-6) has been proposed (31, 46, 47). From our previous studies and from those of other groups, it appears that herpesviruses may play an important role in MSRV expression: we have shown that HSV-1 immediate-early ICP0 and ICP4 proteins can transactivate MSRV/LM7 in vitro (6) and Haahr et al. have proposed an important epidemiological role for EBV, as a co-factor in MS, triggering retrovirus reactivation (31). The recent description by Challoner et al. (47) showing significant expression of HHV6 proteins in MS plaques may also suggest a similar role for HHV6 in the brain.

EXAMPLE 19

MSRV Genome Detection Technique

Following 0.4 mm filtration to remove cellular debris and RNase digestion to remove residual non-encapsidated RNA, serum was processed to extract viral RNA by means of adsorption to a silica matrix. Viral RNA was subjected to DNase digestion, then a combined reverse transcription-PCR (RT-PCR) reaction was performed using primers PTpol-A (sense: 5'xxxx3', SEQ ID NO:142) and PTpol-F (antisense: 5'xxxx3', SEQ ID NO:143). A second round of amplification with nested primers PTpol-B (sense: 5'xxxx3', SEQ ID NO:144) and PTpol-E (antisense: 5'xxxx3', SEQ ID NO:145) generated a 435 bp PCR product which was identified by gel electrophoresis. The specificity of each product was confirmed by dideoxy sequencing. Control reactions without reverse transcriptase were performed to ensure that the products were derived from viral RNA. In addition, to exclude the possibility that the extracted viral RNA might be contaminated with host cell derived nucleic acids, aliquots were tested by nested PCR for the presence of pyruvate dehydrogenase (PDH) DNA and RNA. Samples which generated a signal in either the PDH or the "no-RT" PCR assays were excluded from the analysis.

Sera from patients with clinically active MS and controls were amplified by RT-PCR and sequenced. Virion associated MSRV-RNA was detected in the serum of 10 of 19 (53%) patients with MS but in only 3 of 44 controls without MS (P=0.0001). The control group consisted of 8 patients (all MSRV-RNA negative) with rheumatological disorders and 36 healthy adults. MSRV-RNA titres in both MS patients and controls were apparently low because even moderate dilution of sera (<10 fold) caused loss of signal.

In MS patients, detection of MSRV-RNA was not associated with age, sex, disease duration, or MS type, however a significant negative correlation with treatment was observed. 26 serum samples were obtained from the 19 patients; 100% of the sera from untreated patients contained detectable MSRV-RNA whereas it was detectable in only 4 of 19 samples (21%) obtained during treatment with corticosteroids and/or azathioprine (P=0.001).

The reason for the apparent loss of virion associated MSRV-RNA during immunosupressive treatment is unknown but the finding is in agreement with the previous observations on the detection of MSRV in cerebrospinal fluid.

TABLE 7

DETECTION OF VIRION ASSOCIATED MSRV-RNA IN MS UNTREATED PATIENTS & CONTROLS

|  | Positive | Negative | Total | % Positive |
|---|---|---|---|---|
| Controls without MS[a] | 3[b] | 41 | 44 | 7% |
| MS sera untreated at time of sampling | 7 | 0 | 7 | 100% |

[a]The control group consisted of 8 patients with miscellaneous non-MS disorders and 36 healthy adults.
[b]The detection of MSRV RNA in plasma of a few controls in conditions which select virion-packaged RNA, is consistent with the knowledge that a virus associated with MS should be present in a minor proportion of apparently healthy population. Indeed, such individuals can be either healthy carriers or be in the pre-clinical (or sub-clinical) phase of the disease which can last for years.

Method
Modified SNAP RNA Extraction with Filtration and RNase Digestion
(All centrifugation are at room temperature)
Up to 500 microliters of serum is filtered using 0.45 micron spin filters (Nanosep MF from Flowgen Catalogue No. U3-0126 Ref. ODM45). The serum is spun for 5 min at 130,000 g (or for further 10 min if necessary).
150 microliters of filtered serum is incubated with 10 units RNase One (Promega Catalogue No.M4261) for 30 min at 37° C.
The 150 microliters was then extracted using the SNAP RNA extraction kit (Invitrogen) as below:
  10 micrograms of poly A RNA was added to the 450 microliters of Binding Buffer to act as a carrier; this was then added to the serum and mixed by inversion 6 times; 300 microliters of propan-2-ol was then added and mixed by inversion 10 times; 500 microliters was transferred to the SNAP column and spun at 1300 g for 1 min and the flow-through discarded; the remainder was then added to the SNAP column and spun at 1300 g for 1 min and the flow-through discarded; the column was then washed with 600 microliters of Super wash and the flow-through discarded; the column was then washed with 600 microliters of 1×RNA wash and the flow-through discarded; this wash was repeated with a 2 min 1300 g spin and the flow-through discarded; the bound nucleic acid was then eluted by incubating with 135 microliters of RNase free water for 5 min and spun at 1300 g for 1 min.
  15 microliters of 10×DNAse buffer and 3 microliters (30 units) of DNase I, RNase free (Boehringer Mannheim Cat. No. 776 785) was added and incubated for 30 min at 37° C.; 450 microliters of Binding Buffer was added and mixed by inversion 6 times; 300 microliters of propan-2-ol was then added and mixed by inversion 10 times; 500 microliters was transferred to the SNAP column and spun at 1300 g for 1 min and the flow-through discarded; the remainder was then added to the SNAP column and spun at 1300 g for 1 min and the flow-through discarded; the column was then washed with 600 microliters 1×RNA wash and the flow-through discarded; this wash was repeated with a 2 min 1300 g spin and the flow-through discarded; the bound nucleic acid was then eluted by incubating with 105 microliters of RNase free water for 5 min and spun at 1300 g for 1 min.
Titan RT-PCR
RT-PCR was performed using the Titan one tube RT-PCR system (Boehringer Mannheim Cat. No. 1 855 476) 25 microliters of RNA was used in the combined RT-PCR reaction. The total reaction volume was 50 microliters. Promega rRNAsin (10 units) was the RNase inhibitor used. 170 ng of primers SEQ ID NO:142 and SEQ ID NO:143, respectively, were used. A single master mix was prepared and the sample RNA added last. This was performed at room temperature, not on ice.

The RT step consisted of two sequential 30 min incubations at 50° C. and then 60° C. This was immediately followed by the PCR which had the following steps.

Initial denaturation of template at 94° C. for 2 min, 40 cycles of 94° C. for 30 seconds; 60° C. for 30 seconds; 68° C. for 45 seconds, 1 cycle of 68° C. for 7 min.

The second round PCR was performed using the Expand long template PCR system (Boehringer Mannheim Cat. No. 1681 842). 0.5 microliters of the RT-PCR mix was added to 25 microliters of the round 2 PCR mix. Buffer No. 3 and 50 ng of primers B and E were used. The PCR had the following steps:

5 cycles of 94° C. for 30 seconds, 60° C. for 30 seconds., 68° C. for 45 seconds, 1 cycle of 68° C. for 7 min.

The PCR products were then run on a 2% agarose gel.

The no RT controls were performed using "Expand" PCR system for both rounds. The first round was 40 cycles and the second round 20 cycles.

As a positive control a DNA dilution series was used in both the RT-PCR and the "no RT" PCR. For a result to be valid the RT-PCR and "no-RT" PCRs had to have detected DNA equivalent to between 1 and 0.1 cells.

The analysis of PCR products of an approximately 435 bp fragment in the pol region is shown in Table 8.

TABLE 8

ANALYSIS OF PCR PRODUCTS WITH ORF *

| Exp | Disease | Clone | ORF | Fragment (bp) | AA-RT Motif Site |
|---|---|---|---|---|---|
| 46-7 | MS | 1 | + | 429 | YGDD |
|  |  | 5 | + | 429 | YGDD |
|  |  | 8 | + | 429 | YGDD |
| 68-1 | MS | 41 | + | 438 | YMDD |
|  |  | 42 | + | 438 | YMDD |
|  |  | 43 | + | 438 | YMDD |

* Defective RNA can also be present in circulating virions, since the fidelity of the MSRV reverse transcriptase appears to be low and since recombination events with related endogenous elements can occur. It is then obvious that the intra- and inter-patients variability can be greater than that illustrated in this example, because of these encapsidated defective MSRV RNA copies.

Table 9, which data have been determined from the alignments of FIGS. 49 to 53, shows a variability:

between the clones obtained from the same patient plasma sample in the same PCR amplification experiment; this means that the patient possesses a virion population which comprises different MSRV variants for a given time, between the sequenced variant populations from different patients; this means that the variants differ from a patient to another one patient.

TABLE 9

Degree of identity (percentage) between nucleotide sequences and between peptide sequences, by direct comparison of said sequences (see FIGS. 49–53)

| Patient | 68-1 | 46-7 |
|---|---|---|
| Nucleotide sequences | between SEQ ID NO: 128 and MSRV-pol (SEQ ID NO: 1) 90.4%[b] 93.3%[a] SEQ ID NOs: 129, 130, 131 between them 98.6%[b] 98.7%[a] | between SEQ ID NO: 135 and MSRV-pol (SEQ ID NO: 1) 82.5%[a] 84%[b] SEQ ID NOs: 136, 137, 138 between them 94.5%[a] 95.1%[b] |
| Peptide sequences | between SEQ ID NOs: 132, 133, 134 and trans of MSRV-1 81% SEQ ID NOs: 132, 133, 134 between them 97% | between SEQ ID NOs: 139, 140, 141 and trans MSRV-1 73.5% SEQ ID NOs: 139, 140, 141 between them 89% |

[a]this percentage is determined on the basis of sequences excluding the primers
[b]this percentage is determined on the basis of sequences including the primers.

From FIGS. 53A and 53B, the variability between tested patients sequences can be determined:

between SEQ ID NO:128 and SEQ ID NO:135: 16.5%[a] and 14.8%[b]

between the peptide sequences obtained from SEQ ID NO:128 and SEQ ID NO:135: 20%.

BIBLIOGRAPHY (1) Norrby E., Prog. Med. Virol., 1978; 24, 1–39.
(2) Johnson R. T., "Handbook of clinical neurology, 47 Demyelinating diseases", Vinken P. and Bruyn G. W., eds. Amsterdam, Elsevier Science Publishing, 1985, 319–336.
(3) Perron H. et al., Res. Virol. 1989, 140, 551–561.
(4) Perron H. et al., "Current concepts in multiple sclerosis" Wiethölter et al., eds. Amsterdam, Elsevier, 1991, 111–116.
(5) Perron H. et al., The Lancet 1991, 337, 862–863.
(6) Perron H. et al., J. Gen. Virol. 1993, 74, 65–72.
(7) Fields and Knipe, Fondamental Virology 1986, Rev Press N.Y.
(8) Nielsen P. E. et al., Science 1991; 254, 1497–1500.
(9) Maniatis et al., Molecular Cloning, Cold Spring Harbour, 1982.
(10) Southern. E. M., J. Mol. Biol. 1975, 98, 503.
(11) Dunn A. R. and Hassel J. A., Cell 1977, 12, 23,
(12) Shih et al., J. Virol. 1989, 63, 64–75.
(13) Perron H. et al., Res. Vir. 1992, 143, 337–350.
(14) Meyerhans et al., Cell 1989, 58, 901–910.
(15) Linial M. L. and Miller A. D., "Current topics in microbiology and immunobiology. Retroviruses, strategies of replication" vol. 157, 125–152; Swanstrom R. and Vogt P. K., editors, Springer-Verlag, Heidelberg 1990.
(16) Lori F. et al., J. Virol. 1992, 66, 5067–5074.
(17) Sambrook J., Fritsch E. F. and Maniatis T., Molecular cloning, a laboratory manual. Cold Spring Harbour Laboratory Press, 1989.
(18) La Mantia et al., Nucleic Acids Research 1991, 19, 1513–1520.
(19) Gonzales-Quintial R, Baccala R, Pope R M and Theofilopoulos N, J. Clin. Invest, Vol. 97, Number 5, pp1335–1343, 1996.
(20) Chomzynski P. and N. Sacchi, Analytical Biochemistry 1987, 162, 156–159.
(21) F. Mallet et al., Journal of Clinical Microbiology 1993; 31, 1444–1449.

(22) G. Barany and R. B. Merrifielsd, 1980, In the Peptides, 2, 1–284, Gross E and Meienhofer J, Eds., Academic Press, New York.
(23) Poser et al., Gbers G. C. eds. The diagnosis of multiple sclerosis Thieme Stratton Inc, New York 1984: 225–229.
(24) La Mantia et al., Nucleic Acid Research 1989, 17, 5913–22.
(25) PLAZA, A; KONO, D. H.; THEOFILOPOULOS, A. N. NEW HUMAN Vb GENES AND POLYMORPHIC VARIANTS. J. Imm; 147(12): 4360–4365, 1991.
(26) H. Perron, In vitro transmission and antigenicity of a retrovirus isolated from multiple sclerosis, Res. Virol. 143, 337–350 (1992).
(27) J. Garson et al., Development of a "Pan-retrovirus" detection system for multiple sclerosis studies. Acta Neurol. Scand. (in Press).
(28) F. Mallet, G. Oriol, C. Mary, B. Verrier and B. Mandrand. Continuous RT-PCR and taq DNA polymerase: Characterization and comparison to uncoupled procedures. Biotechniques 18, 678–687 (1995).
(29) R. Baccala, D. H. Kono, S. Walker, R. S. Balderas and Theophilopoulos. Genomically imposed and somatically modified human thymocyte vb gene repertoires. Proc. Natl. Acad. Sci. USA (1991) 88, 2908.
(30) Haahr S., Koch-Henriksen N., Moller-Larsen, A. Eriksen L. S. & Andersen H. M. K. Increased risk of multiple sclerosis after late Epstein-Barr virus infection: a historical prospective study. Muliple Sclerosis 1, 73–77 (1995).
(31) Haahr S et al. A putative new retrovirus associated with multiple sclerosis and the possible involvement of Epstein-Barr virus in this disease. Ann. N.Y. Acad. Science. 724, 148–156 (1994).
(32) Wilkinson D. A., Goodchild N. L., Saxton T. M., Wood S. & Mager D. L. Evidence for a functional subclass of the RTLV-H family of human endogenous retrovirus-like sequences. J. Virol. 67, 2981–2989 (1993).
(33) Sonigo P., Barker C., Hunter E. and Wain-Hobson S. Nucleotide sequence of Mason-Pfizer monkey virus: an immunosuppressive D-type retrovirus. Cell 45, 375–85 (1986).
(34) Rhee S. S., and Hunter E. A single amino acid substitution within the matrix protein of a D-type retrovirus converts its morphogenesis to that of a C-type retrovirus. Cell 63, 77–86 (1990).
(35) Bai J., Zhu R. Y., Stedman K., Cousens C., Carlson J., Sharp J. M. and DeMartini J. C. Unique long terminal repeat U3 sequences distinguish exogenous Jaagsiekte sheep retroviruses associated with ovine pulmonary carcinoma from endogenous loci in the sheep genome. J. Virol. 70, 3159–3168 (1996).
(36) Palmarini M., Cousens C., Dalziel R. G., Bai J., Stedman K., DeMartini J. C. and Sharp J. M. The exogenous form of Jaagsiekte retrovirus is specifically associated with a contagious lung cancer of sheep. J. Virol. 70, 1618–1623 (1996).
(37) Portis J. L. Wild mouse retrovirus: pathogenesis. in "Retrovirus infections of the nervous system". Oldstone M. B. A. and Koprowsky H. Eds. Current topics in microbiology and immunology, n°160, p. 11–27. (Springer-Verlag, Berlin 1990).
(38) Gardner M. B., Chivi A., Dougherty M. F., Casagrande J & Estes J. D. Congenital transmission of murine leukaemia virus from wild mice prone to development of lymphoma and paralysis. J. Natl. Cancer Inst. 62, 63–69 (1979).
(39) Marrack P., Kushnir E. & Kappler J. A maternally inherited superantigen encoded by a mammary tumor virus. Nature 349, 524–526 (1991).
(40) Hügin A. W., Vacchio M. S. & Morse H. C. A virus-encoded superantigen in a retrovirus-induced immunodeficiency syndrome of mice. Science 252, 424–427 (1991).
(41) Gardner M. B. Genetic resistance to a retroviral neurologic disease in wild mice, in "Retrovirus infections of the nervous system" Oldstone M. B. A. and Koprowsky H. Eds. Current topics in microbiology and immunology, n° 160, p. 3–10. (Springer-Verlag, Berlin 1990).
(42) Linial M. L. & Miller A. D. Retroviral RNA packaging: sequence requirements and implications, in "Retroviruses-strategies of replication" Swanstrom R. & Vogt P. K. Eds. Current topics in microbiology and immunology, n° 157, p. 125–152. (Springer-Verlag, Berlin 1990).
(43) Bell J. I. and Lathrop G. M. Multiple loci for multiple sclerosis. Nature Genetics 13, 377–78 (1996).
(44) Dhib-Jalbut S., Lewis K., Bradburn E., McFarlin D. E. and McFarland H. F. Measles virus polypeptide-specific antibody profile in multiple sclerosis. Neurology, 1990; 40: 430–435.
(45) Gonzalez-Scarano F., Waxham M. N., Ross A. M. and Hoxie J. A. Sequence similarities between human immunodeficiency virus gp41 and Paramyxovirus fusion proteins. AIDS Res. Hum. Retrov. 1987; 3: 245–252.
(46) Bergström, T., Andersen, O. & Vahlne A. (1989). Isolation of herpes virus type 1 during first attack of multiple sclerosis. Annales Neurology 26, 283–285.
(47) Challoner P. B. et al. Plaque-associated expression of human herpesvirus 6 in multiple sclerosis. Proc. Natl. Acad. Sci. USA 92, 7440–7444 (1995).
(48) A. Gessain et al; Antibodies to Human T-Lymphotrophic Virus type-I in patients with tropical spastic paraparesis. Lancet 2, 407–410 (1985).
(49) H. Perron, J. A. Garson, F. Bedin et al., Molecular identification of a novel retrovirus repeatedly isolated from patients with multiple sclerosis. Proc. Nat. Acad. Sci. USA 94:7583–7588 (1997).

We claim:

1. An isolated or purified nucleic acid selected from a group consisting of SEQ ID NO: 87 or its complementary sequence.

2. An isolated or purified nucleic acid selected from a group consisting of SEQ ID NO: 88 or its complementary sequence.

3. An isolated or purified nucleic acid coding for a peptide sequence encoded by SEQ ID NO: 87, SEQ ID NO: 88, or their complementary sequences.

4. A process for detecting, in a biological sample, a virus associated with multiple sclerosis or rheumatoid arthritis, comprising:

contacting a probe to said biological sample under stringent conditions at which said probe hybridizes to a nucleotide sequence selected from the group consisting of SEQ ID NO: 87, SEQ ID NO: 88 and their complementary sequences; and determining whether the probe hybridizes with nucleic material in the biological sample, wherein hybridization indicates the presence of said virus.

5. The process of claim 4, wherein said probe comprises:
(a) a sequence of at least 10 contiguous monomers of a nucleotide sequence selected from the group consisting of SEQ ID NO: 87, SEQ ID NO: 88 and their complementary sequences.

* * * * *

SEQUENCE LISTING (1) GENERAL INFORMATION:

(iii) NUMBER OF SEQUENCES: 210

(2) INFORMATION FOR SEQ ID NO:1:

(i) SEQUENCE CHARACTERISTICS:
      (A) LENGTH: 1158 base pairs
      (B) TYPE: nucleotide
      (C) STRANDEDNESS: single
      (D) TOPOLOGY: linear (ii) MOLECULE TYPE: cDNA (xi) SEQUENCE DESCRIPTION: SEQ ID NO:1:

| | | | | | |
|---|---|---|---|---|---|
| CCCTTTGCCA | CTACATCAAT | TTTAGGAGTA | AGGAAACCCA | ACGGACAGTG | GAGGTTAGTG | 60 |
| CAAGAACTCA | GGATTATCAA | TGAGGCTGTT | GTTCCTCTAT | ACCCAGCTGT | ACCTAACCCT | 120 |
| TATACAGTGC | TTTCCCAAAT | ACCAGAGGAA | GCAGAGTGGT | TTACAGTCCT | GGACCTTAAG | 180 |
| GATGCCTTTT | TCTGCATCCC | TGTACGTCCT | GACTCTCAAT | TCTTGTTTGC | CTTTGAAGAT | 240 |
| CCTTTGAACC | CAACGTCTCA | ACTCACCTGG | ACTGTTTTAC | CCCAAGGGTT | CAGGGATAGC | 300 |
| CCCCATCTAT | TTGGCCAGGC | ATTAGCCCAA | GACTTGAGTC | AATTCTCATA | CCTGGACACT | 360 |
| CTTGTCCTTC | AGTACATGGA | TGATTTACTT | TTAGTCGCCC | GTTCAGAAAC | CTTGTGCCAT | 420 |
| CAAGCCACCC | AAGAACTCTT | AACTTTCCTC | ACTACCTGTG | GCTACAAGGT | TTCCAAACCA | 480 |
| AAGGCTCGGC | TCTGCTCACA | GGAGATTAGA | TACTNAGGGC | TAAAATTATC | CAAAGGCACC | 540 |
| AGGGCCCTCA | GTGAGGAACG | TATCCAGCCT | ATACTGGCTT | ATCCTCATCC | CAAAACCCTA | 600 |
| AAGCAACTAA | GAGGGTTCCT | TGGCATAACA | GGTTTCTGCC | GAAAACAGAT | TCCCAGGTAC | 660 |
| ASCCCAATAG | CCAGACCATT | ATATACACTA | ATTANGGAAA | CTCAGAAAGC | CAATACCTAT | 720 |
| TTAGTAAGAT | GGACACCTAC | AGAAGTGGCT | TTCCAGGCCC | TAAAGAAGGC | CCTAACCCAA | 780 |
| GCCCCAGTGT | TCAGCTTGCC | AACAGGGCAA | GATTTTTCTT | TATATGCCAC | AGAAAAAACA | 840 |
| GGAATAGCTC | TAGGAGTCCT | TACGCAGGTC | TCAGGGATGA | GCTTGCAACC | CGTGGTATAC | 900 |
| CTGAGTAAGG | AAATTGATGT | AGTGGCAAAG | GGTTGGCCTC | ATNGTTTATG | GGTAATGGNG | 960 |
| GCAGTAGCAG | TCTNAGTATC | TGAAGCAGTT | AAAATAATAC | AGGGAAGAGA | TCTTNCTGTG | 1020 |
| TGGACATCTC | ATGATGTGAA | CGGCATACTC | ACTGCTAAAG | GAGACTTGTG | GTTGTCAGAC | 1080 |
| AACCATTTAC | TTAANTATCA | GGCTCTATTA | CTTGAAGAGC | CAGTGCTGNG | ACTGCGCACT | 1140 |
| TGTGCAACTC | TTAAACCC | | | | | 1158 |

(2) INFORMATION FOR SEQ ID NO:2:

(i) SEQUENCE CHARACTERISTICS:
        (A) LENGTH: 297 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:2:

| | | | | | |
|---|---|---|---|---|---|
| CCCTTTGCCA | CTACATCAAT | TTTAGGAGTA | AGGAAACCCA | ACGGACAGTG | GAGGTTAGTG | 60 |
| CAAGAACTCA | GGATTATCAA | TGAGGCTGTT | GTTCCTCTAT | ACCCAGCTGT | ACCTAACCCT | 120 |
| TATACAGTGC | TTTCCCAAAT | ACCAGAGGAA | GCAGAGTGGT | TTACAGTCCT | GGACCTTAAG | 180 |
| GATGCCTTTT | TCTGCATCCC | TGTACGTCCT | GACTCTCAAT | TCTTGTTTGC | CTTTGAAGAT | 240 |
| CCTTTGAACC | CAACGTCTCA | ACTCACCTGG | ACTGTTTTAC | CCCAAGGGTT | CAAGGGA | 297 |

(2) INFORMATION FOR SEQ ID NO:3:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:3:

GTTTAGGGAT ANCCCTCATC TCTTTGGTCA GGTACTGGCC CAAGATCTAG GCCACTTCTC    60

AGGTCCAGSN ACTCTGTYCC TTCAG    85

(2) INFORMATION FOR SEQ ID NO:4:

(i) SEQUENCE CHARACTERISTICS:
        (A) LENGTH: 86 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:4:

GTTCAGGGAT AGCCCCCATC TATTTGGCCA GGCACTAGCT CAATACTTGA GCCAGTTCTC    60

ATACCTGGAC AYTCTYGTCC TTCGGT    86

(2) INFORMATION FOR SEQ ID NO:5:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:5:

GTTCARRGAT AGCCCCCATC TATTTGGCCW RGYATTAGCC CAAGACTTGA GYCAATTCTC    60

ATACCTGGAC ACTCTTGTCC TTYRG    85

(2) INFORMATION FOR SEQ ID NO:6:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:6:

GTTCAGGGAT AGCTCCCATC TATTTGGCCT GGCATTAACC CGAGACTTAA GCCAGTTCTY    60

ATACGTGGAC ACTCTTGTCC TTTGG    85

(2) INFORMATION FOR SEQ ID NO:7:

(i) SEQUENCE CHARACTERISTICS:
        (A) LENGTH: 111 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:7:

GTGTTGCCAC AGGGGTTTAR RGATANCYCY CATCTMTTTG GYCWRGYAYT RRCYCRAKAY    60

YTRRGYCAVT TCTYAKRYSY RGSNAYTCTB KYCCTTYRGT ACATGGATGA C    111

(2) INFORMATION FOR SEQ ID NO:8:

(i) SEQUENCE CHARACTERISTICS:
        (A) LENGTH: 645 base pairs (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:8:

```
TCAGGGATAG CCCCCATCTA TTTGGCCAGG CATTAGCCCA AGACTTGAGT CAATTCTCAT      60
ACCTGGACAC TCTTGTCCTT CAGTACATGG ATGATTTACT TTTAGTCGCC CGTTCAGAAA     120
CCTTGTGCCA TCAAGCCACC CAAGAACTCT TAACTTTCCT CACTACCTGT GGCTACAAGG     180
TTTCCAAACC AAAGGCTCGG CTCTGCTCAC AGGAGATTAG ATACTNAGGG CTAAAATTAT     240
CCAAAGGCAC CAGGGCCCTC AGTGAGGAAC GTATCCAGCC TATACTGGCT TATCCTCATC     300
CCAAAACCCT AAAGCAACTA AGAGGGTTCC TTGGCATAAC AGGTTTCTGC CGAAAACAGA     360
TTCCCAGGTA CASCCCAATA GCCAGACCAT TATATACACT AATTANGGAA ACTCAGAAAG     420
CCAATACCTA TTTAGTAAGA TGGACACCTA CAGAAGTGGC TTTCCAGGCC CTAAAGAAGG     480
CCCTAACCCA AGCCCCAGTG TTCAGCTTGC CAACAGGGCA AGATTTTTCT TTATATGCCA     540
CAGAAAAAAC AGGAATAGCT CTAGGAGTCC TTACGCAGGT CTCAGGGATG AGCTTGCAAC     600
CCGTGGTATA CCTGAGTAAG GAAATTGATG TAGTGGCAAA GGGTT                     645
```

(2) INFORMATION FOR SEQ ID NO:9:

(i) SEQUENCE CHARACTERISTICS:
        (A) LENGTH: 741 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:9:

```
CAAGCCACCC AAGAACTCTT AAATTTCCTC ACTACCTGTG GCTACAAGGT TTCCAAACCA      60
AAGGCTCAGC TCTGCTCACA GGAGATTAGA TACTTAGGGT TAAAATTATC CAAAGGCACC     120
AGGGGCCTCA GTGAGGAACG TATCCAGCCT ATACTGGGTT ATCCTCATCC CAAAACCCTA     180
AAGCAACTAA GAGGGTTCCT TAGCATGATC AGGTTTCTGC CGAAAACAAG ATTCCCAGGT     240
ACAACCAAAA TAGCCAGACC ATTATATACA CTAATTAAGG AAACTCAGAA AGCCAATACC     300
TATTTAGTAA GATGGACACC TAAACAGAAG GCTTTCCAGG CCCTAAAGAA GGCCCTAACC     360
CAAGCCCCAG TGTTCAGCTT GCCAACAGGG CAAGATTTTT CTTTATATGG CACAGAAAAA     420
ACAGGAATCG CTCTAGGAGT CCTTACACAG GTCCGAGGGA TGAGCTTGCA ACCCGTGGCA     480
TACCTGAATA AGGAAATTGA TGTAGTGGCA AAGGGTTGGC CTCATNGTTT ATGGGTAATG     540
GNGGCAGTAG CAGTCTNAGT ATCTGAAGCA GTTAAAATAA TACAGGGAAG AGATCTTNCT     600
GTGTGGACAT CTCATGATGT GAACGGCATA CTCACTGCTA AAGGAGACTT GTGGTTGTCA     660
GACAACCATT TACTTAANTA TCAGGCTCTA TTACTTGAAG AGCCAGTGCT GNGACTGCGC     720
ACTTGTGCAA CTCTTAAACC C                                               741
```

(2) INFORMATION FOR SEQ ID NO:10:

(i) SEQUENCE CHARACTERISTICS:
        (A) LENGTH: 93 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:10:

TGGAAAGTGT TGCCACAGGG CGCTGAAGCC TATCGCGTGC AGTTGCCGGA TGCCGCCTAT    60

AGCCTCTACA TGGATGACAT CCTGCTGGCC TCC                                 93

(2) INFORMATION FOR SEQ ID NO:11:

(i) SEQUENCE CHARACTERISTICS:
        (A) LENGTH: 96 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:11:

TTGGATCCAG TGYTGCCACA GGGCGCTGAA GCCTATCGCG TGCAGTTGCC GGATGCCGCC    60

TATAGCCTCT ACGTGGATGA CCTSCTGAAG CTTGAG                              96

(2) INFORMATION FOR SEQ ID NO:12:

(i) SEQUENCE CHARACTERISTICS:
        (A) LENGTH: 748 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:12:

TGCAAGCTTC ACCGCTTGCT GGATGTAGGC CTCAGTACCG GNGTGCCCCG CGCGCTGTAG    60

TTCGATGTAG AAAGCGCCCG GAAACACGCG GGACCAATGC GTCGCCAGCT TGCGCGCCAG   120

CGCCTCGTTG CCATTGGCCA GCGCCACGCC GATATCACCC GCCATGGCGC CGGAGAGCGC   180

CAGCAGACCG GCGGCCAGCG GCGCATTCTC AACGCCGGGC TCGTCGAACC ATTCGGGGGC   240

GATTTCCGCA CGACCGCGAT GCTGGTTGGA GAGCCAGGCC CTGGCCAGCA ACTGGCACAG   300

GTTCAGGTAA CCCTGCTTGT CCCGCACCAA CAGCAGCAGG CGGGTCGGCT TGTCGCGCTC   360

GTCGTGATTG GTGATCCACA CGTCAGCCCC GACGATGGGC TTCACGCCCT TGCCACGCGC   420

TTCCTTGTAG ANGCGCACCA GCCCGAAGGC ATTGGCGAGA TCGGTCAGCG CCAAGGCGCC   480

CATGCCATCT TTGGCGGCAG CCTTGACGGC ATCGTCGAGA CGGACATTGC CATCGACGAC   540

GGAATATTCG GAGTGGAGAC GGAGGTGGAC GAAGCGCGGC GAATTCATCC GCGTATTGTA   600

ACGGGTGACA CCTTCCGCAA AGCATTCCGG ACGTGCCCGA TTGACCCGGA GCAACCCCGC   660

ACGGCTGCGC GGGCAGTTAT AATTTCGGCT TACGAATCAA CGGGTTACCC CAGGGCGCTG   720

AAGCCTATCG CGTGCAGTTG CCGGATGC                                      748

(2) INFORMATION FOR SEQ ID NO:13:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:13:

GCATCCGGCA ACTGCACG                                                  18

(2) INFORMATION FOR SEQ ID NO:14:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:14:

GTAGTTCGAT GTAGAAAGCG                                                                  20

(2) INFORMATION FOR SEQ ID NO:15:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:15:

AGGAGTAAGG AAACCCAACG GAC                                                             23

(2) INFORMATION FOR SEQ ID NO:16:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:16:

TAAGAGTTGC ACAAGTGCG                                                                 19

(2) INFORMATION FOR SEQ ID NO:17:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:17:

TCAGGGATAG CCCCCATCTA T                                                              21

(2) INFORMATION FOR SEQ ID NO:18:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:18:

AACCCTTTGC CACTACATCA ATTT                                                          24

(2) INFORMATION FOR SEQ ID NO:19:

(i) SEQUENCE CHARACTERISTICS:
        (A) LENGTH: 15 base pairs (B) TYPE: nucleotide
        (C) STRANDEDNESS: single
        (D) TOPOLOGY: linear (ii) MOLECULE TYPE: cDNA (ix) FEATURE:
        (B) LOCATION: 5, 7, 10, 13
        (D) OTHER INFORMATION: N represents inosine (i)

(xi) SEQUENCE DESCRIPTION: SEQ ID NO:19:

GGTCNTNCCN CANGG                                                    15

(2) INFORMATION FOR SEQ ID NO:20:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:20:

TTAGGGATAG CCCTCATCTC T                                             21

(2) INFORMATION FOR SEQ ID NO:21:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:21:

GCGTAAGGAC TCCTAGAGCT ATT                                           23

(2) INFORMATION FOR SEQ ID NO:22:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:22:

TCATCCATGT ACCGAAGG                                                 18

(2) INFORMATION FOR SEQ ID NO:23:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:23:

ATGGGGTTCC CAAGTTCCCT                                               20

(2) INFORMATION FOR SEQ ID NO:24:

(i) SEQUENCE CHARACTERISTICS:
        (A) LENGTH: 20 base pairs (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:24:

GCCGATATCA CCCGCCATGG                                              20

(2) INFORMATION FOR SEQ ID NO:25:

(i) SEQUENCE CHARACTERISTICS:
            (A) LENGTH: 20 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:25:

CGCGATGCTG GTTGGAGAGC                                              20

(2) INFORMATION FOR SEQ ID NO:26:

(i) SEQUENCE CHARACTERISTICS:
            (A) LENGTH: 20 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:26:

TCTCCACTCC GAATATTCCG                                              20

(2) INFORMATION FOR SEQ ID NO:27:

(i) SEQUENCE CHARACTERISTICS:
            (A) LENGTH: 26 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:27:

GATCTAGGCC ACTTCTCAGG TCCAGS                                       26

(2) INFORMATION FOR SEQ ID NO:28:

(i) SEQUENCE CHARACTERISTICS:
            (A) LENGTH: 23 base pairs
            (B) TYPE: nucleotide
            (C) STRANDEDNESS: single
            (D) TOPOLOGY: linear (ii) MOLECULE TYPE: cDNA (ix) FEATURE:
            (B) LOCATION: 6, 12, 19
            (D) OTHER INFORMATION: N represents inosine (i)

(xi) SEQUENCE DESCRIPTION: SEQ ID NO:28:

CATCTNTTTG GNCAGGCANT AGC                                          23

(2) INFORMATION FOR SEQ ID NO:29:

(i) SEQUENCE CHARACTERISTICS:
            (A) LENGTH: 24 base pairs (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:29:

CTTGAGCCAG TTCTCATACC TGGA                                              24

(2) INFORMATION FOR SEQ ID NO:30:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:30:

AGTGYTRCCM CARGGCGCTG AA                                                22

(2) INFORMATION FOR SEQ ID NO:31:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:31:

GMGGCCAGCA GSAKGTCATC CA                                                22

(2) INFORMATION FOR SEQ ID NO:32:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:32:

GGATGCCGCC TATAGCCTCT AC                                                22

(2) INFORMATION FOR SEQ ID NO:33:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:33:

AAGCCTATCG CGTGCAGTTG CC                                                22

(2) INFORMATION FOR SEQ ID NO:34:

(i) SEQUENCE CHARACTERISTICS:
            (A) LENGTH: 40 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:34:

TAAAGATCTA GAATTCGGCT ATAGGCGGCA TCCGGCAAGT          40

(2) INFORMATION FOR SEQ ID NO:35:

(i) SEQUENCE CHARACTERISTICS:
        (A) LENGTH: 50 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:35:

Asp Ala Phe Phe Cys Ile Pro Val Arg Pro Asp Ser Gln Phe Leu Phe
1               5                   10                  15

Ala Phe Glu Asp Pro Leu Asn Pro Thr Ser Gln Leu Thr Trp Thr Val
            20                  25                  30

Leu Pro Gln Gly Phe Arg Asp Ser Pro His Leu Phe Gly Gln Ala Leu
        35                  40                  45

Ala Gln
    50

(2) INFORMATION FOR SEQ ID NO:36:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

GATGCCTTTT TCTGCATCCC TGTACGTCCT GACTCTCAAT TCTTGTTTGC CTTTGAAGAT          60

CCTTTGAACC CAACGTCTCA ACTCACCTGG ACTGTTTTAC CCCAAGGGTT CAGGGATAGC         120

CCCCATCTAT TTGGCCAGGC ATTAGCCCAA                                          150

(2) INFORMATION FOR SEQ ID NO:37:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:37:

Cys Ile Pro Val Arg Pro Asp Ser Gln Phe Leu
1               5                   10

(2) INFORMATION FOR SEQ ID NO:38:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:38:

```
Val Leu Pro Gln Gly Phe Arg Asp Ser Pro His Leu Phe Gly Glu Ala
1               5                   10                  15

Leu
```

(2) INFORMATION FOR SEQ ID NO:39:

(i) SEQUENCE CHARACTERISTICS:
        (A) LENGTH: 8 amino acid
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:39:

```
Leu Phe Ala Phe Glu Asp Pro Leu
1               5
```

(2) INFORMATION FOR SEQ ID NO:40:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:40:

```
Phe Ala Phe Glu Asp Pro Leu Asn
1               5
```

(2) INFORMATION FOR SEQ ID NO:41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

```
GTGCTGATTG GTGTATTTAC AATCC                                         25
```

(2) INFORMATION FOR SEQ ID NO:42:

(i) SEQUENCE CHARACTERISTICS:
        (A) LENGTH: 1859 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
GTGCTGATTG GTGTATTTAC AATCCTTTAT CTAATCCGAA ATGCCCATGT TGCAATATGG    60

AAAGAAAGGG AGTTCCTAAC CTCTGGGGGA ACCCCCATTA AATACCACAA GTAAATCATG   120

GAGTTATTGC ACACAGTGCA AAAACTCAAG GAGGTGGAAG TCTTACACTG CCAAAGCCAT   180

CAGAAAAGGG AAGAGGGGAG AAGAGCAGCA TAAGTGGCTA CAGAGGCAAG GAAAGACTAG   240

CAGAAAGGAA AGAGAGAAAG AGACAGAAAG TCAGAGAGAG AGAGAGGAAG AGACAGAGCA   300

CAAAGAGGGA GTCAGAGAGA GAGAGAGACA GAGAGTCAGA GAGAAGGAAA GAGAGAGAGG   360

AAGAGACAAA GAATGAATCA AACAGAGAGA CAGAAAGTCA GAGAGAGAGA GAGAGAGGAA   420
```

```
GAGACAGAGA AAAAGAGGGA GTCAGAAAAA GAGAGACCAA AGAAGAAGTC CAAAGAGAAA      480

GAAAGAGAGA TGGAAGTAGT AAAGGAAAAA CAGTGTACCC TATTCCTTTA AAAGCCGGGG      540

TAAATTTAAA ACCTATAATT GATAACTGAA GGTCTTCTCT GTAACCCTGT AACACTCCAA      600

TACCACCTTG TTGTCAAGTG TAAACAAGGG CGTAGCCCAA AAGCACTGAG GCCACTAACA      660

ACCCATAGCC TTCCTATCAA AATTCCTTAA CCCAGCAGGT TTCCTAACAG GGATCTAAA      720

TCTTAATTAA TTACCATACA ATGGTCCAAC CAGACTTAGG AGGAATTCCC TTCAGGACGG      780

GAAGATAGAT GCTTCCTCCC AGGCGATTAA GGGAGAAAGA CACAATGGGT ATTCAGTAAG      840

TGCCAAGGGG AACACTTGTA GAAGCAAAGT TAGGAAAATT GCCAAATAAT TGGTTTGCTC      900

AAGAGTTGTT TGCACTCAGC CAAACCTTGA AGTACTTGCA GAATCAGAAA GGAGCCATCT      960

ATACCAATTC TAAGTTAATA TGGACTGAAG GAGGTTTTAT TAATACCAAA GAGAAATTAA     1020

AATCCCAAAC TTATAAGGTT TTCAACCAAA GTAAAGTTTG CTAAAAGTTA ACAGCGTAAC     1080

ATGTATTATC CTACTACCAC ACACTCTCAA AGGATTTCTC AGACAGTTTG CAAGAAATAA     1140

TGATATCTAT CCTTACTCTA CAATCCCAAA TAGACTCTTT GGCAGCAGTG ACTCTCCAAA     1200

ACCGTCAAGG CCTAGACCTC CTCACTGCTG AGAAAGGAGG ACTCTGCACC TTCTTAAGGG     1260

AAGAGTGTTG TCTTTACACT AACCAGTCAG GGATAGTATG AGATGCTGCC CGGCATTTAC     1320

AGAAAAAGGC TTCTGAAATC AGACAACGCC TTTCAAATTC CTATACCAAC CTCTGGAGTT     1380

GGGCAACATG GTTTCTTCCC TTTCTATGTC CCATGGCTGC CATCTTGCTA TTACTCGCCT     1440

TTGGGCCCTG TATTTTTAAC CTCCTTGTCA AATTTGTTTC TTCTAGGATC GAGGCCATCA     1500

AGCTACAGAT GGTCTTACAA ATGGAACCCC AAATGAGCTC AACTATCAAC TTCTACTGAG     1560

GACCCCTAGA CCAACCCCCT GGCCCTTTCA CTGGCCTAAA GAGTTCCCCT CTGGAGGACA     1620

CTACCACTGC AGGGCCCCAT CTTTGCCCCT ATCCAGAAGG AAGTAGCTAG AGCAGTCATT     1680

GCCCAATTCC CAAGAGCAGC TGGGGTGTCC CGTTTAGAGT GGGGATTGAG AGGTGAAGCC     1740

AGCTGGACTT CTGGGTCGGG TGGGGACTTG GAGAACTTTT GTGTCTAGCT AAAGGATTGT     1800

AAATGCAACA ATCAGTGCTC TGTGTCTAGC TAAAGGATTG TAAATACACC AATCAGCAC     1859
```

(2) INFORMATION FOR SEQ ID NO:43:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

```
TGATGTGAAC GGCATACTCA CTG                                              23
```

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

```
CCCAGAGGTT AGGAACTCCC TTTC                                             24
```

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

```
GCTAAAGGAG ACTTGTGGTT GTCAG                                          25
```

(2) INFORMATION FOR SEQ ID NO:46:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:46:

```
CAACATGGGC ATTTCGGATT AG                                             22
```

(2) INFORMATION FOR SEQ ID NO:47:

(i) SEQUENCE CHARACTERISTICS:
        (A) LENGTH: 400 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:47:

```
GGCTGCTAAA GGAGACTTGT GGTTGTCAGA CAATCGCCTA CTTAGGTACC AGGCCTTATT     60
ACTTGAGGGA CTGGTGCTTC AGATGCGCAC TTGTGCAGCT CTTAACCCAA ACTTATGCTG    120
CCCAGAAGGA TCTTTTAGAG GTCCCCTTAG CCAACCCTGA CCTCAACCTA TATATATACT    180
GATGGAAGTT CGTTTGTAGA AAAGGGATTA CAAAGGGNAG GATATNCCAT AGGTTAGTGA    240
TAAAGCAGTA CTTGAAAGTA AGCCTCTTCC CCCCAGGGAC CAGCGCCCCC GTTAGCAGAA    300
CTAGTGGCAC TGACCCCGAG CCTTAGAACT TGGAAAGGGA GGAGGATAAA TGTGTATACA    360
GATAGCAAGT ATGCTTATCT AATCCGAAAT GCCCATGTTG                          400
```

(2) INFORMATION FOR SEQ ID NO:48:

(i) SEQUENCE CHARACTERISTICS:
        (A) LENGTH: 2389 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:48:

```
TCAGGGATAG CCCCCATCTA TTTGGTCAGG CACTGGCCCA AGATCTAGGG ACATGCCACT     60
TTTAAGAGCC ATTTCTCAAG TCCAGGTACT CTGGTCCTTC GGTATGTGGA TGATTTACTT    120
TTGGCTACCA GTTCAGTAGC CTCATGCCAG CAGGCTACTC TAGATCTCTT GAACTTTCTA    180
GCTAATCAAG GGTACAAGGC ATCTAGGTTG AAGGCCCAGC TTTGCCTACA GCAGGTCAAA    240
TATCTAGGCC TAATCTTAGC CAGAGGGACC AGGGCACTCA GCAAGGAACA AATACAGCCT    300
```

```
ATACTGGCTT ATCCTCACCC TAAGACATTA AACAGTTGC GGGGGTTCCT TGGAATCACT      360

GGCTTTTTGG TGACTATGGA TTCCCAGATA CAGCAAGATT GGCAGGCCCC TCTATACTGT      420

AATCAAGGAG ACTCACGAGG GCAAGTACTC ATCTAGTAGA ATGGGAACTA GGGACAGAAA      480

CAGCCTTCAA AACCTTAAAG CAGGCCCTAG TACAATCTCC AGCTTAAGC CTTCCCACAG       540

GACAAAACTT CTCTTTATAC ATCACAGAGA GGGCAGAGAT AGCTCTTGGT GTCCTTATTC      600

AGACTCATGG GACTACCCCA CAACCAGTGG CACACCTAAG TAAGGAAATT GATGTAGTAG      660

CAAAAGGCTG GCCTCACTGT TTATGGGTAG CTGTGGTGGT GGCTGTCTTA GTGTCAGAAG      720

CTATCAAAAT AATACAAGGA AAGGATCTCA CTGTCTGGAC TACTCATGAT GTAATGGCAT      780

ACTAGGTGCC AAAAGAAGTT TATGGGTATC AGACAACCAC CTGCTTAGAT ACCAGGGACT      840

ACTCCTGGAG GATTGGGCTT CAAGTGCGTT TTTTGTGGCC TCAACCCTGC CACTTTTCCT      900

CCAGAGGATG GAGAGCCGCT TGAGCATGCT TGCCAACAGG TTGTAGGCCA GAATTATTCC      960

ACCCGAGATG ATCTCTTAGA GTACCCTTAG CTAATCCTGA CCTTAACCTA TATACCAATG     1020

GAAGTTCATT TGTGGAAAAC GGGATATGAA GGGCAGGTTA TGTCATAGTT AGTGATGTAA     1080

TCATACTTGC AAGTAAGCCT CTTACCCCAG GGGCCAGCAC TCAGTTAGCA GAACTAGTCA     1140

CACTTACCTT AACCTTAGAA CTGGGAAAGG GAAAAAGAAT AAATATGTAT ACAGATAGTA     1200

AGTATGCTTA TCTAATCCTA CATGCCCATG CTGCAATATG GAAGGAAAGG GAGTTCCTAA     1260

CCCCTGGGGG AACCCCCATT AAATACCACA AGGYAAATCA TGGAGTTATT GCACGCAGTG     1320

CAAAAACTCA AGGAGGTGGC AGTCTTACAC TGCCGAAGCY ATCAAAAAGG GGAAGGAGAG     1380

GGGAGAACAG CAGCATAAGT GGTTGGCAGA GGCAGTGAAA GACCAGCAGA GAGAAGGAGA     1440

GAGACAACGT CAACGACAGA AGGAAAGAAG AGGAGGAGAC AGAGAGGAAG AGACAGAGAG     1500

ACAGTTAGTC CAAGAGAGAG ACAGAGAGAG GAAGAGACAG ACAGAAAGTC AAGAGAGAA      1560

GGAAAGAGAG GAAGAGACCA AGGAGTCCNA GAGAGAGAAA GAGATAGAAG TAGTAAAGAA     1620

AAAACATTGT ACCCTATTCC TTTAAAAGCC GGGGTATATT TAAAACCTAT AATTGATAAT     1680

TGAGTTCTTG CACCCTCCTC CAGGGGATYG CTGGGAGGAA ACCCTCAACC GATATGTGAA     1740

AATTGTGGGT CGTCCCTATG TCTCAATTAC CAGCCAATAC CCCCTTGTTT TTAGTGTGAA     1800

CGAGGGTGTA GAGCGCAGAC AGGGAGACCT CTGACAATCC ATACCCTTCC TATCCAAAAT     1860

CCTTAACCCA GCAGGTTTTC TAAAAGGGGA TCTAAATCTT AATTAATTAC CATACAAAGG     1920

TCAAACCAGA TCTAGGAGGA ACTTCCTTCA GGACAGGATG ATAGATGGTT CCTCCCAGGC     1980

GATTAAAGAA AATAAAAAGA CACATGGGCA GCCAGTAAGT GATAAGGGAA CACTAGTAGA     2040

AGCAGTTAGG AGAAGTTGCC TAATAATTGG TCTACTCCAA ATGTGTGAGT TGTTCGCACT     2100

CAGCCCAAAT CTTAAAGTAC TTACAGAATT AGGGAGGAGC CATTTACACC AATTCTAAGT     2160

TAATATGGAC TGGATGAGGT TTTATTAATA GCGAAGGAGA ATTAAATCCT AAACTNACAA     2220

GGTTTTCAAC TAAAGTAAAT TTTACTAAAA GCTAACAGTG TAACATGCAT TATCCTACTA     2280

CAACACACTC TCANAGGATT CCTCAGACAG TTTACAAGAA ATAACAAAAT CTATCTGGTA     2340

AGGATAGTAA CTACAATCCC AAATACATTC TTTGGCAGCA GTGACTCTC                2389
```

(2) INFORMATION FOR SEQ ID NO:49:

(i) SEQUENCE CHARACTERISTICS:
        (A) LENGTH: 2448 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:49:

```
TCAGGGATAG CCCCCATCTA TTTGATCAGG CACTAGCCCA AGATCTAGGC CACTTCTGAA      60
GTCCAGGCAT TCTAGTCCTT CAGTATGTGG ATGATTTACT TTTGGCTACC AGTTTGGAAG     120
CCTCATGCCA GCAGGCTACT TGAGATCTCT TGAACTTTCT AGCTAATCAA GGGTGTATGG     180
CATCTAAATT GAAAGTCCAG CTCTGCCTAC AACAAGTCAA ATATCTAGGC CTAATCTTAG     240
ATAGAAGAAC CAGGGCCCTC AGCAAGGAAT GAATAAAGCC TATGCTGGCT TATCGGCACC     300
CTAAGACATT AAAACAATTG TGGGGGTTCC TTGGAATCAC TGGCTTTTGC CGACTATGGA     360
TCCCTGGATA GAGTGAGATA GCCAGGCCCC CTCTATTACT CTTATCAAGG AGACCCAGAG     420
GGCAAATACT TATCTAGTAT TATGGGNACC AGAGGCAGAA AAAGCCTTCC AAACCTAAAA     480
GGAGACCCTA GTACAAGCTC CAGCTTTAAG CCTTCCCACA GGACAAANCT TCTCTTTATA     540
TGTCACAGAG AGAGCAGGAA TAGCTCCTGG AGTCCTTACT CAGACTTTTG GACGACCCCA     600
CGGCCAGTGG CRTACCTAAG TAAGGAAATT GATGTAGTAG CAAAAGGCTG GCCTCACTGT     660
TTATGGGTAG TTGCGGCTGT GGCAGTCTTA CTGTCAAAGG CTATCAAAAT AATACAAGGA     720
AAGGATTTCA CTATCTGGAC TACTCATGAG GAAAATGGCA TATTAGGTGC CAAAGGAAGT     780
TTTTGGCTAT CAGACAACCA CCTGCTCAGA TTCCAGGCAC TACTGATTGA GAGACCAGTG     840
CTTTAAATAT GTATGTGTGT GTGTGGCCCT CAACCCTGCC ACTGTTCTCC CAGAAGATGG     900
AGAACCAATG AAGCATTACT GTCAACAAAT TAGAGTCCAG AGTTATGCTG CCTGAGAGGA     960
TCTCTTAGAA GTCCCCTTAG CTAATCCTGA CCTTAACCTA TATGCTGATG GAAGTTCACT    1020
TGTGGAGAAT GGGATACGAA AAGCACATTA TGCCATAGTT AGTGAGGTAA CAGTACTTGA    1080
AAGTAAGCCT ATTCCCCCAT GGACCAGAGC CCAGTTAGCA GAACTAGTGG CACTTACCCA    1140
AGCCTTAGAA CTAGGAAAGG GAAAAATAAT AAATGTGTAT ACAGATAGCA AGTATGCTTA    1200
TCTAATCCTA CATGCCCATG CTGCAGTATG GAAAGAAAGG GAGTTCCTAA CCTCTGGGGG    1260
AACCCCCATT AAATACCACA AGGCAAATCA TGGAGTTATT GCATGTAGTG CAAAACCTCA    1320
AGTAGGTGGC AGTTTTACAC TGCCTGAAGC TATGGGGAAG GAGAGAGGAG AACAGCAGCA    1380
TAAGTGGCTA GCAGAGGCAG CGAAAGACTA GCAGAGAGGA GAGGTAGGGG AAAGACAGAA    1440
AGTCAAAGAA AAGAAGTCAA AGACAGACAG AGAAAGAGAC AGAGGGAGCC AGAGAGAAAG    1500
AAAAGAGAGA ACGAAAGAGA CAGAATGTCA AGAACAGAA GAGAGAGGCA GCGCCAGAAG    1560
AGTTAAGAAA GTGAGAAAGA GAGATGGAAA TAGTAAAGAA AAAACAGTGT ACCCTATTCC    1620
TTTAAAAGCC AGGGTAAATT TAAAACGTAT AATTTTATAA TTGGAAGGTC TTCTCCATAA    1680
CCCTATAACA TTAAAATACC ACCTTGTTGT CAGTGTAAAC AAGAGCATAG CCCAAAAGCA    1740
CTGAGGCCAC TGACAACCCA TAGCCTTCCT ATCAAAAATC CTTAACTCTG CAGGTTTCCT    1800
AACAGGGGAT CTAAATCTCA ACTAATCACC ATACAATGGT CCGACCAGAC CTAGGAGCGA    1860
CTCCCCTCAG GACAGAAGGA TGGATGGTTC CTCCCAGGCC ATTAAGGGAA AGAGACACAA    1920
TGGGTATTCA GTAAGTGATA AGGGAACTCT TGTAGAAGCA GTTAGGAAGA TTGCCTAATA    1980
TTTGGTCTGC TCAAATGTGC CAGCTGTTTG CACTCAGCTA AACCTAAAT TACTTACAGA    2040
ATTAGGAAGG AGCCATCTAT ACCAATTCTG AGTTAATATG AGCTGAACAA GTTCTTATTA    2100
ATAGCAAAGA ATCATTGAAA TCTCAAACTT GCAAAGTTTT CAACAAAAGT AAAGTTTGCT    2160
GAAAGTTAGC AGTGTAACAT GTATTATCCT AACTTCTAAT CTTGTGGAAA TCAGACCCTA    2220
TCAGTGCCCC TCAAAGCTGA AGTCCATCAG CATATGGCCA TACAACTAAT ACCCCTATTT    2280
```

| | |
|---|---|
| ATAGGGTTAG GAATGGCCAC TGCTACAGGA ATGGGAGTAA CAGGTTTATC TACTTCATTA | 2340 |
| TCCTATTACC ACACACTCTT AAAGGATTTC TCAGACAGTT TACAAGAAAT AACAAAATCT | 2400 |
| ATCCTTACTC TNTARTCCCA AATAGRTTCT TTGGCAGCAG TGACTCTC | 2448 |

(2) INFORMATION FOR SEQ ID NO:50:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:50:

| | |
|---|---|
| CCTGAGTTCT TGCACTAACC C | 21 |

(2) INFORMATION FOR SEQ ID NO:51:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:51:

| | |
|---|---|
| GTCCGTTGGG TTTCCTTACT CCT | 23 |

(2) INFORMATION FOR SEQ ID NO:52:

(i) SEQUENCE CHARACTERISTICS:
        (A) LENGTH: 1196 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:52:

| | |
|---|---|
| TTCCTGAGTT CTTGCACTAA CCTCAAATGA GAGAAGTGCC GCCATAACTG CAACCCAAGA | 60 |
| GTTTGGCGAT CCCTGGTATC TCAGTCAGGT CAATGACAGG ATGACAACAG AGGAAAGATA | 120 |
| ATGATTCCCC ACAGGCCAGC AGGCAGTTCC CAGTGTAGAC CCTCATTAGG ACACAGAATC | 180 |
| AGAACATGGA GATTGGTGCC GCAGACATTT GCTAACTTGC GTGCTAGAAG GACTAAGGAA | 240 |
| AACTAGGAAG ATATGAATTA TTCAATGATG TCCACTATAA CACAGGGGAA AGGAAGAAAA | 300 |
| TCCTACTGCC TTTCTGGAGA GACTAAGGGA GGCATTGAGG AAGCATACCA GGCAAGTGGA | 360 |
| CATTGGAGGC TCTGGAAAAG GGAAAAGTTG GAAAAGTAT ATGTCTAATA GGGCTTGCTT | 420 |
| CCAGTGTGGT CTACAAGGAC ACTTTAAAAA AGATTGTCCA ATAGAAATAA GCCACCACCT | 480 |
| CGTCCATGCC CCTTATGTCA AGGGAATCAC TGGAAGGCCC ACTGCCCCAG GGGATGAAGG | 540 |
| TCCTCTGAGT CAGAAGCCAC TAACCAGATG ATCCAGCAGC AGGACTGAGG GTGCCCGGGG | 600 |
| CAAGCGCCAG CCCATGCCAT CACCCTCACA GAGCCCCAGG TATGCTTGAC CATTGAGGGT | 660 |
| CAGAAGGGTA CTGTCTCCTG GACACTGGCG GGCCTTCTCA GTCTTACTTT CCTGTCCTGG | 720 |
| ACAACTGTCC TCCAGATCTG TCACTGTCCG AGGGGTCCTA GGACAGCCAG TCACTAGATA | 780 |
| CTTCTCCCAG CCACTAAGTT GTGACTGGGG AACTTTACTC TTCCACATGC TTTTCTAATT | 840 |
| ATGCCTGAAA GCCCCACTCT CTTGTTAGGG GAGAGACATT CTAGCAAAAG CAGGGGCCAT | 900 |

```
TATACATGTG AATATAGGAG AAGGAACAAC TGTTTGTTGT CCCCTGCTTG AGGAAGGAAT    960

TAATCCTGAA GTCCGGGCAA CAGAAGGACA ATATGGACAA GCAAAGAATG CCCGTCCTGT   1020

TCAAGTTAAA CTAAAGGATT CCACCTCCTT TCCCTACCAA AGGCAGTACC CCCTCAGACC   1080

CGAGACCCAA CAAGAACTCC AAAAGATTGT AAAGGACCTA AAAGCCCAAG GCCTAGTAAA   1140

ACCAAGCAAT AGCCCTTGCA AGACTCCAAT TTTAGGAGTA AGGAAACCCA ACGGAC       1196

(2) INFORMATION FOR SEQ ID NO:53:

(i) SEQUENCE CHARACTERISTICS:
        (A) LENGTH: 2391 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:53:

ATGATCCAGC AGCAGGACNG AGGGTGCCCG GGGCAAGCGC CAGCCCATGC CATCACCCTC     60

ACAGAGCCCC AGGTATGCTT GACCATTGAG GGTCAGAAGG GTNACTGTCT CCTGGACACT    120

GGCGGNGCCT TCTCAGTCTT ACTTTCCTGT CCTGGACAAC TGTCCTCCAG ATCTGTCACT    180

GTCCGAGGGG TCCTAGGACA GCCAGTCACT AGATACTTCT CCCAGCCACT AAGTTGTGAC    240

TGGGAACTT TACTCTTCCC ACATGCTTTT CTAATTATGC CTGAAAGCCC CACTCTCTTG    300

TTGGGGAGAG ACATTCTAGC AAAAGCAGGG GCCATTATAC ATGTGAATAT AGGAGAAGGA    360

ACAACTGTTT GTTGTCCCCT GCTTGAGGAA GGAATTAATC CTGAAGTCCG GCAACAGAA    420

GGACAATATG GACAAGCAAA GAATGCCCGT CCTGTTCAAG TTAAACTAAA GGATTCCACC    480

TCCTTTCCCT ACCAAAGGCA GTACCCCCTC AGACCCGAGA CCCAACAAGA ACTCCAAAAG    540

ATTGTAAAGG ACCTAAAAGC CCAAGGCCTA GTAAACCAA GCAATAGCCC TTGCAAGACT    600

CCAATTTTAG GAGTAAGGAA ACCCAACGGA CAGTGGAGGT TAGTGCAAGA ACTCAGGATT    660

ATCAATGAGG CTGTTGTTCC TCTATACCCA GCTGTACCTA ACCCTTATAC AGTGCTTTCC    720

CAAATACCAG AGGAAGCAGA GTGGTTTACA GTCCTGGACC TTAAGGATGC CTTTTTCTGC    780

ATCCCTGTAC GTCCTGACTC TCAATTCTTG TTTGCCTTTG AAGATCCTTT GAACCCAACG    840

TCTCAACTCA CCTGGACTGT TTTACCCCAA GGGTTCAGGG ATAGCCCCCA TCTATTTGGC    900

CAGGCATTAG CCCAAGACTT GAGTCAATTC TCATACCTGG ACACTCTTGT CCTTCAGTAC    960

ATGGATGATT TACTTTTAGT CGCCCGTTCA GAAACCTTGT GCCATCAAGC CACCCAAGAA   1020

CTCTTAACTT TCCTCACTAC CTGTGGCTAC AAGGTTTCCA AACCAAAGGC TCGGCTCTGC   1080

TCACAGGAGA TTAGATACTN AGGGCTAAAA TTATCCAAAG GCACCAGGGC CCTCAGTGAG   1140

GAACGTATCC AGCCTATACT GGCTTATCCT CATCCCAAAA CCCTAAAGCA ACTAAGAGGG   1200

TTCCTTGGCA TAACAGGTTT CTGCCGAAAA CAGATTCCCA GGTACASCCC AATAGCCAGA   1260

CCATTATATA CACTAATTAN GGAAACTCAG AAAGCCAATA CCTATTTAGT AAGATGGACA   1320

CCTACAGAAG TGGCTTTCCA GGCCCTAAAG AAGGCCCTAA CCCAAGCCCC AGTGTTCAGC   1380

TTGCCAACAG GCAAGATTT TCTTTATAT GCCACAGAAA AAACAGGAAT AGCTCTAGGA   1440

GTCCTTACGC AGGTCTCAGG GATGAGCTTG CAACCCGTGG TATACCTGAG TAAGGAAATT   1500

GATGTAGTGG CAAAGGGTTG GCCTCATNGT TTATGGGTAA TGGNGGCAGT AGCAGTCTNA   1560

GTATCTGAAG CAGTTAAAAT AATACAGGGA AGAGATCTTN CTGTGTGGAC ATCTCATGAT   1620

GTGAACGGCA TACTCACTGC TAAAGGAGAC TTGTGGTTGT CAGACAACCA TTTACTTAAN   1680
```

| | | | |
|---|---|---|---|
| TATCAGGCTC | TATTACTTGA | AGAGCCAGTG | CTGNGACTGC GCACTTGTGC AACTCTTAAA | 1740 |
| CCCAAACTTA | TGCTGCCCAG | AAGGATCTTT | NTAGAGGTCC CCTTAGCCAA CCCTGACCTC | 1800 |
| AACTATATAT | ATACTGATGG | AAGTTCGTTT | GTAGAAAAGG GATTACAAAG GGNAGGATAT | 1860 |
| NCCATAGGTG | TTAGTGATAA | AGCAGTACTT | GAAAGTAAGC CTCTTCCCCC CCAGGGACCA | 1920 |
| GCGCCCCCGT | TAGCAGAACT | AGTGGCACTG | ACCCCGCGAG CCTTAGAACT TTGGAAAGGG | 1980 |
| AGGAGGATAA | ATGTGTATAC | AGATAGCAAG | TATGCTTATC TAATCCGAAA TGCCCATGTT | 2040 |
| GTTTATCTAA | TCCGAAATGC | CCATGTTGCA | ATATGGAAAG AAAGGGAGTT CCTAACCTCT | 2100 |
| GGGGGAACCC | CCATTAAATA | CCACAAGTTA | ATCATGGAGT TATTGCACAC AGTGCAAAAA | 2160 |
| CTCAAGGAGG | TGGAAGTCTT | ACACTGCCAA | AGCCATCAGA AAAGGGAAAG GGGAGAAGAG | 2220 |
| CAGCATAAGT | GGCTACAGAG | GCAAGGAAAG | ACTAGCAGAA AGGAAAGAGA GAAAGAGACA | 2280 |
| GAAAGTCAGA | GAGAGAGAGA | GGAAGAGACA | GAGCACAAAG AGGGAGTCAG AGAGAGAGAG | 2340 |
| AGACAGAGAG | TCAGAGAGAA | GGAAAGAGAG | AGAGGAAGAG ACAAAGAATG A | 2391 |

(2) INFORMATION FOR SEQ ID NO:54:

(i) SEQUENCE CHARACTERISTICS:
        (A) LENGTH: 1722 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:54:

| | | | | |
|---|---|---|---|---|
| TGGAGAATAG | CAGCATAAGT | TGGCTGGCAG | AAGTAGGGAA AGACAGCAAG AAGTAAAGAA | 60 |
| AAAAARGAGA | AAGTCAGAGA | AAGAAAAAAA | GAGAGGAAGA AACAAAGAAG AACTTGAAGA | 120 |
| GAGAAAGAAG | TAGTAAAGAA | AAAACAGTAT | ACCCTATTCC TTTAAAAGCC AGGGTAAATT | 180 |
| TCTGTCTACC | TAGCCAAGGC | ATATTCTTCT | TATGTGGAAC ATCAACCTAT ATCTGCCTCC | 240 |
| CCACTAACTG | GACAGGCACC | TGAACCTTAG | TCTTTCTAAG TCCCAACATT AACATTGCCC | 300 |
| CAGGAAATCA | GACCCTATTG | GTACCTGTCA | AAGCTAAAGT CCCGTCAGTG CAGAGCCATA | 360 |
| CAACTAATAT | CCCTATTTAT | AGGGTTAGGA | ATGGCTACTG CTACAGGAAC TGGAATAGCC | 420 |
| GGTTTATCTA | CTTCATTATC | CTACTACCAT | ACACTCTCAA AGAATTTCTC AGACAGTTTG | 480 |
| CAAGAAATAA | TGAAATCTAT | TCTTACTTTA | CAATCCCAAT TAGACTCTTT GGCAGCAATG | 540 |
| ACTCTCCAAA | ACCGCCGAGG | CCCACACCTC | CTCACTGCTG AGAAAGGAGG ACTCTGCACC | 600 |
| TTCTTAGGGG | AAGAGTGTTG | TTTTTACACT | AACCAGTCAG GGATAGTACG AGATGCCACC | 660 |
| TGGCATTTAC | AGGAAAGGGC | TTCTGATATC | AGACAATGCC TTTCAAACTC TTATACCAAC | 720 |
| CTCTGGAGTT | GGGCAACATG | GCTTCTTCCA | TTTCTAGGTC CCATGGCAGC CATCTTGCTG | 780 |
| TTACTCACCT | TTGGGCCCTG | TATTTTTAAG | CTTCTTGTCA AATTTGTTTC CTCTAGGATC | 840 |
| GAAGCCATCA | AGCTACAGAT | GGTCTTACAA | ATGGAACCCC AAATGAGTTC AACTAACAAC | 900 |
| TTCTACCAAG | GACCCCTGGA | ACGATCCACT | GGCACTTCCA CTAGCCTAGA GATTCCCCTC | 960 |
| TGGAAGACAC | TACAACTGCA | GGGCCCCTTC | TTTGCCCCTA TCCAGCAGGA AGTAGCTAGA | 1020 |
| GCGGTCATCG | GCCAAATTCC | CAACAGCAGT | TGGGGTGTCC TGTTTAGAGG GGGGATTGAA | 1080 |
| GAGGTGACAG | CCTGCTGGCA | GCCTCACAGC | CCTCGTTGGY TCTCAGTGCC TCCTCAGCCT | 1140 |
| TGGTGCCCAC | TCTGGCCGTG | CTTGAGGAGC | CCTTCAGCCT GCCACTGCAC TGTGGGAGCC | 1200 |
| TCTTTCTGGG | CTGGACAAGG | CCGGAGCCAG | CTCCCTCAGC TTGCAGGGAG GTATGGAGGG | 1260 |

```
AGAGATGCAG GCGGGAACCA GGGCTGCGCA TGGCGCTTGC GGGCCAGCAT GAGTTCCAGG    1320

TGGGCGTGGG CTCGGCGGGC CCCACACTCG GGCAGTGAGG GGCTTAGCAC CTGGGCCAGA    1380

CAGATGCTGT GCTCAACTTC TTCGCTGGGC CTTAGCTGCC TTCCCCGTGG GGCAGGGCTY    1440

CGGGAACMTG CAGCCTGCCC ATGCTTGAGC CCCCCACCCC GCCGTGGGTT CYTGCACAGC    1500

CCAAGCTTCC CGGACAAGCA CCACCCCTTA TCCACGGTGC CCAGTCCCAT CAACCACCCA    1560

AGGGTTGAGG AGTGCGGGCA CACAGCGCGG GATTGGCAGG CAGTTCCACT TGCGGCCTTG    1620

GTGCGGGATC CACTGCGTGA AGCCAGCTGG GCTCCTGAGT CTGGTGGGGA CTTGGAGAAT    1680

CTTTATGTCT AGCTAAGGGA TTGTAAATAC ACCAATCAGC AC                      1722

(2) INFORMATION FOR SEQ ID NO:55:

(i) SEQUENCE CHARACTERISTICS:
          (A) LENGTH: 495 base pairs
          (B) TYPE: nucleotide
          (C) STRANDEDNESS: single
          (D) TOPOLOGY: linear (ii) MOLECULE TYPE: cDNA (xi) SEQUENCE DESCRIPTION: SEQ ID NO:55:

CTTCCCCAAC TAATAAGGAC CCCCCTTTCA ACCCAAACAG TCCAAAAGGA CATAGACAAA      60

GGAGTAAACA ATGAACCAAA GAGTGCCAAT ATTCCCTGGT TATGCACCCT CCAAGCGGTG    120

GGAGAAGAAT TCGGCCCAGC CAGAGTGCAT GTACCTTTTT CTCTCTCACA CTTGAAGCAA    180

ATTAAAATAG ACNTAGGTNA ATTNTCAGAT AGCCCTGATG GYTATATTGA TGTTTTACAA    240

GGATTAGGAC AATCCTTTGA TCTGACATGG AGAGATATAA TATTACTGCT AAATCAGACG    300

CTAACCTCAA ATGAGAGAAG TGCTGCCATA ACTGGAGCCC GAGAGTTTGG CAATCTCTGG    360

TATCTCAGTC AGGTCAATGA TAGGATGACA ACGGAGGAAA GAGAACGATT CCCCACAGGG    420

CAGCAGGCAG TTCCCAGTGT AGCTCCTCAT TGGGACACAG AATCAGAACA TGGAGATTGG    480

TGCCGCAGAC ATTTA                                                    495

(2) INFORMATION FOR SEQ ID NO:56:

(i) SEQUENCE CHARACTERISTICS:
          (A) LENGTH: 2503 base pairs
          (B) TYPE: nucleotide
          (C) STRANDEDNESS: single
          (D) TOPOLOGY: linear (ii) MOLECULE TYPE: cDNA (xi) SEQUENCE DESCRIPTION: SEQ ID NO:56:

CCAAGAACCC ACCAATTCCG GANCACATTT TGGCGACCAC GAAGGGACTT TCGCATATCG      60

CCAAGCGGTG AGACAATAGC CGAGCGGTGA GACCTTTCCC AATCGCCAAG CAGTGAGTAC    120

CATCAGACCC CTTTCACTTG CTATTCTGTC CTATCTTTCT TTAGAATTCG GGGGCTAAAT    180

ACCGGGCATC TGTCAGCCAT TTAAAAGTGA CTAGCGGGCC GCCGGACTAA AGACACGGGT    240

GTCAAGCTTT CTGGGAAAGG GCTCTCTAAC AACCCCCAAC TCTTTGGAGT TGGGACCGTT    300

GGTTTGCCTA GAACCAGCTT CCGCTTTTCC TGTACTTCTG GGCTGAGCCG TGGGTTGACA    360

GTGAAGGAAA GCCATGCATC TCCGGGGTCT CGMCAACATG TTGGTTGACC CTGCGGCCAT    420

GAGTGGAACT CTCAAAAGCA TGTCGCCCAA GCGACACTCG CCTATCTATC CTATCTATCC    480

TGACCCTTGC CCTCTGGGTC CTAATGCCTG CCAGACAAAC TTCCTCTCGC CTCTCTTCTC    540
```

```
TGAAGCTAGA ACCGCTTCTA AAAATTGCTA CCTGGTCTCT GGTGCTTTTC CTARTTTCTC      600

CTATAAAGAA TGAWTTCTAG TATTAAACTC CAGGACTCTG TTACCTTCTT TAGGCACCCG      660

GGCTCACCAA TCAGAAAGAC ACAGTTTTTG CCCAAGGCCC CATCGTAGTG GGACTACCT       720

GGAATTTTAG GATCCCTCCT CAGACTAACA GGCCTAACAA AAGTTATTCC TGAAGCTAGG      780

ATATGGGGAG CCTCAGAAAT TGTATCCCTC CTATTCATAT AAGTGAGAAC AAAAGGTGTC      840

ACTCTTCCAA CCCTGAAGAT CCCCTCCCTC CCTCAGGGTA TGGCCCTCCA TTTCATTTTT      900

GTGGCATAAC ATCTTTATAG GATGGGGTAA AGTCCCAATA CTAACAGGAG AATGCTTAGG      960

ACTCTAACAG GTTTTTGAGA ATGCGTCAGT AAGGGCCACT AAATCTGATT TTTCTCAGTC     1020

GGTCCTCCTT GTGGTCTAGG AGGACAGGCA AGGTTGTGCA GGTTTTCGAG AATGCGTCAG     1080

TAAGGACCAC TAAATCCGAC CTTCCTCGGT CCTCCATGTG GTCTGGGAGG AAAACTAGTG     1140

TTTCTGCTGC TGCGTCGGTG AGCGCAACTA TTCAAGTCAG CAGGGTCCAG GGACCGTTGC     1200

AGGTTCTTGG GCAGGGGTTG TTTCTGCTGC TGCATTGGTG AATGCAACTA TTCTGATCAG     1260

CAGGGTCCCA GGACCATTGC AGGTCCTTGG GCAGGGAGAG AAACAAAACA AACCAAAACT     1320

GTGGGCGGTT TTGTCTTTCA TATGGGAAAC ACTCAGGCAT CAACAGGTTC ACCCTTGAAA     1380

TGCATCCTAA GCCATTGGGA CCAATTTGAC CCACAAACCC TGAAAAGAG GAGGCTCATT      1440

TTTTCCTGCA CTACGGCTTG GCCCCAATAT TCTCTTTYTG ATGGGAAAA ATGGCCACCT      1500

GAGGGAAGCA CAAATTACAA TAYTATCCTA CAGCYTGATC TTTTCTGTAA GAGGGAAGGC    1560

AAATGGAGTG AATACCTTAT GTCCAAGCTT TCTTTTCATT GAGGGAGAAT ACACAACTAT    1620

GCAAAGCTTG CAATTTACAT CCCACAGGAG GACCCTTCAG CTTACCCCCA TATCCTAGCC    1680

TCCCTATAGC TTCCCTTCCT ATTGATGATA CTCCTCCTCT AATCTCCCCT GCCCAGAAGG    1740

AAATAAGCAA AGAAATCTCC AAAGGTCCAC AAAAACCCCC GGGCTATCGG TTATGTCCCT    1800

TCAAGYTGTA GGGGGAGGGG AATTTGGCCC AACCCGGGTG CATGTCCCTT CTCCCTCTCT    1860

GATTTAAAGC AGATCAAGGC AGACCTGGGG AAGTTTTCAG ATGATCCTGA TAGGTACATA    1920

GATGTCCTAC AGGGTCTAGG GCAAACCTTT GACCTCACTT GGAGAGACGT CATGCTACTG    1980

TTAGATCAAA CCCTGGCCTT TAATGAAAAG AATGCGGCTT TAGCTGCAGC CTGAGAGTTT    2040

GGAGATACCT GGTATCCTAG TCAAGTAAAT GAAAGAATGA CAGCCGAAGA AAGGGACAAC    2100

TTCCTTACTG GTCAGCAACC CATCCCCAGT ATGGATCCCC ACTGGGACTT TGACTCAGAT    2160

CATGGGGACT GGAGTCGTAA ACATCTGTTG ATCTGTGTTC TGGAAGGACT AAGGAGAATT    2220

GGGAAAAAGC CCATGAATTA TTCAATGATA TCCACCATAA CCCAGGGAAA GGAAGAAAAT    2280

CCTTCTGCCT TCCTCGAGCG GCTACAAGAG GCCTTAAGAA AATATACTCC CCTGTCACCC    2340

GAATCACTCG AGGGTCAATT GATTCTAAAA GATAAGTTTA TTACCCAATC AGCCACAGAT    2400

ATCAGGAGAA AGCTCCAAAA GCAAGCCCTG AGCCTGAACA AAATCTAGAG ACATTATTAA    2460

ACCTGGCAAC CTTGGTGTTC TATAATAGGG ACCAAGAGGA ACA                      2503
```

(2) INFORMATION FOR SEQ ID NO:57:

(i) SEQUENCE CHARACTERISTICS:
        (A) LENGTH: 1167 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:57:

```
AAGGAAACTC AGAAAGCCAA TACCCATTTA GTAAGATGGA CACCAGAAGC AGAAGCAGCT         60

TTCCAGGCCC TAAAGAAATC CCTAACCCAA GCCCCAGTGT TAAGCTTGCC AACGGGGCAA        120

GACTTTTCTT TATATGTCAC AGAAAAACAG GAATAGCTCT AGGAGTCCTT ACACAGGTCC        180

AAGGGACAAG CTTGCAACCT GTGGCATACC TGAGTAAGGA AACTGATGTA NTGGCAAAGG        240

GTTGGCCTCA TTGTTTACAG GTAGGGCAGC AGTAGCAGTC TTAGTTTCTG AAACAGTTAA        300

AATAATACAG GGAAGAGATC TTACTGTGTG GACATCTCAT GATGTGAACG GCATACTCAC        360

TGCTAAAGAG GACTTGTGGC TGTCAGACAA CCATTTACTT AAATAGCAGG TTCTATTACT        420

TGAAGTGCCA GTGCTGCGAC TGCACATTTG TGCAACTCTT AACCCAGCCA CATTTCTTCC        480

AGACAATGAA GAAAGATAG AACATAACTG TCAACAAGTA ATTGCTCAAA CCTATGCTGC         540

TCGAGGGGAC CTTCTAGAGG TTCCCTTGAC TGATCCCGAC CTCAACTTGT ATACTGATGG        600

AAGTTCCTTG GCAGAAAAAG GACTTTGAAA AGCGGGGTAT GCAGTGATCA GTGATAATGG        660

AATACTTGAA AGTAATCGCC TCACTCCAGG AACTAGTGCT CACCTGGCAG AACTAATAGC        720

CCTCACTTGG GCACTAGAAT TAGGAGAAGG AAAAAGGGTA AATATATATT CAGACTCTAA        780

GTATGCTTAC CTAGTCCTCC ATGCCCATGC AGCAATATGG AGAGAGAGGG AATTCCTAAC        840

TTCTGAGGGA ACACCTATCA ACCATCAGGG AAGCCATTAG GAGATTATTA TTGGCTGTAC        900

AGAAACCTAA AGAGGTGGCA GTCTTACACT GCCAGGGTCA TCAGGAAGAA GAGGAAAGGG        960

AAATAGAAGG CAATCGCCAA GCGGATATTG AAGCAAAAAA AGCCGCAAGG CAGGACTCTC       1020

CATTAGAAAT GCTTATAGAA GGACCCCTAG TATGGGGTAA TCCCCTCTGG GAAACCAAGC       1080

CCCAGTACTC AGCAGGAAAA ATAGAATAGG AAACCTCACA AGGACATACT TTCCTCCCCT       1140

CCAGATGGCT AGCCACTGAG GAAGGAA                                           1167

(2) INFORMATION FOR SEQ ID NO:58:

(i) SEQUENCE CHARACTERISTICS:
        (A) LENGTH: 78 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:58:

TCCAAAGGCA CCAGGGCCCT CAGTGAGGAA CGTATCCAGC CTATACTGGC TTATCCTCAT         60

CCCAAAACCC TAAAGCAA                                                      78

(2) INFORMATION FOR SEQ ID NO:59:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:59:

Ser Lys Gly Thr Arg Ala Leu Ser Glu Glu Arg Ile Gln Pro Ile Leu
1               5                   10                  15

Ala Tyr Pro His Pro Lys Thr Leu Lys Gln
            20                  25

(2) INFORMATION FOR SEQ ID NO:60:
```

(i) SEQUENCE CHARACTERISTICS:
    (A) LENGTH: 28 base pairs
    (B) TYPE: nucleotide
    (C) STRANDEDNESS: single
    (D) TOPOLOGY: linear (ii) MOLECULE TYPE: cDNA (xi) SEQUENCE DESCRIPTION: SEQ ID NO:60:

```
AAATGTCTGC GGCACCAATC TCCATGTT                                28
```

(2) INFORMATION FOR SEQ ID NO:61:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:61:

```
AAGGGGCATG GACGAGGTGG TGGCTTATTT                              30
```

(2) INFORMATION FOR SEQ ID NO:62:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:62:

```
GGAGAAGAGC AGCATAAGTG G                                       21
```

(2) INFORMATION FOR SEQ ID NO:63:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:63:

```
GTGCTGATTG GTGTATTTAC AATCC                                   25
```

(2) INFORMATION FOR SEQ ID NO:64:

(i) SEQUENCE CHARACTERISTICS:
        (A) LENGTH: 34 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:64:

```
GACTCGCTGC AGATCGATTT TTTTTTTTTT TTTT                         34
```

(2) INFORMATION FOR SEQ ID NO:65:

(i) SEQUENCE CHARACTERISTICS:
        (A) LENGTH: 30 base pairs
        (B) TYPE: nucleotide
        (C) STRANDEDNESS: single (D) TOPOLOGY: linear (ii) MOLECULE TYPE: cDNA (xi) SEQUENCE DESCRIPTION: SEQ ID NO:65:

GCCATCAAGC CACCCAAGAA CTCTTAACTT                                    30

(2) INFORMATION FOR SEQ ID NO:66:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:66:

CCAATAGCCA GACCATTATA TACACTAATT                                    30

(2) INFORMATION FOR SEQ ID NO:67:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:67:

GCCATAACTG CAACCCAAGA GTT                                           23

(2) INFORMATION FOR SEQ ID NO:68:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:68:

GGACGAGGTG GTGGCTTATT TCT                                           23

(2) INFORMATION FOR SEQ ID NO:69:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:69:

AACTTGCGTG CTAGAAGGAC TAAGG                                         25

(2) INFORMATION FOR SEQ ID NO:70:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:70:

AACTTTTCCC TTTTCCAGAT CCTC                                         24

(2) INFORMATION FOR SEQ ID NO:71:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:71:

GCATACCAGG CAAGTGGACA TT                                           22

(2) INFORMATION FOR SEQ ID NO:72:

(i) SEQUENCE CHARACTERISTICS:
            (A) LENGTH: 25 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:72:

CTGTCCGTTG GGTTTCCTTA CTCCT                                        25

(2) INFORMATION FOR SEQ ID NO:73:

(i) SEQUENCE CHARACTERISTICS:
            (A) LENGTH: 24 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:73:

GAGGCTCTGG AAAAGGGAAA AGTT                                         24

(2) INFORMATION FOR SEQ ID NO:74:

(i) SEQUENCE CHARACTERISTICS:
            (A) LENGTH: 25 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:74:

AGGAGTAAGG AAACCCAACG GACAG                                        25

(2) INFORMATION FOR SEQ ID NO:75:

(i) SEQUENCE CHARACTERISTICS:
            (A) LENGTH: 25 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO:75:

TGTATATAAT GGTCTGGCTA TTGGG                                        25

(2) INFORMATION FOR SEQ ID NO:76:

(i) SEQUENCE CHARACTERISTICS:
        (A) LENGTH: 26 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:76:

TTCGGCAGAA ACCTGTTATG CCAAGG                                   26

(2) INFORMATION FOR SEQ ID NO:77:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:77:

CTCGATTTCT TGCTGGGCCT TA                                      22

(2) INFORMATION FOR SEQ ID NO:78:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:78:

GTTGATTCCC TCCTCAAGCA                                        20

(2) INFORMATION FOR SEQ ID NO:79:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:79:

CTCTACCAAT CAGCATGTGG                                        20

(2) INFORMATION FOR SEQ ID NO:80:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:80:

TGTTCCTCTT GGTCCCTAT                                          19

(2) INFORMATION FOR SEQ ID NO:81:

(i) SEQUENCE CHARACTERISTICS:

(A) LENGTH: 433 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:81:

```
Met Ala Thr Ala Thr Gly Thr Gly Ile Ala Gly Leu Ser Thr Ser Leu
 1               5                  10                  15

Ser Tyr Tyr His Thr Leu Ser Lys Asn Phe Ser Asp Ser Leu Gln Glu
            20                  25                  30

Ile Met Lys Ser Ile Leu Thr Leu Gln Ser Gln Leu Asp Ser Leu Ala
        35                  40                  45

Ala Met Thr Leu Gln Asn Arg Arg Gly Pro His Leu Leu Thr Ala Glu
    50                  55                  60

Lys Gly Gly Leu Cys Thr Phe Leu Gly Glu Glu Cys Cys Phe Tyr Thr
65                  70                  75                  80

Asn Gln Ser Gly Ile Val Arg Asp Ala Thr Trp His Leu Gln Glu Arg
                85                  90                  95

Ala Ser Asp Ile Arg Gln Cys Leu Ser Asn Ser Tyr Thr Asn Leu Trp
            100                 105                 110

Ser Trp Ala Thr Trp Leu Leu Pro Phe Leu Gly Pro Met Ala Ala Ile
        115                 120                 125

Leu Leu Leu Leu Thr Phe Gly Pro Cys Ile Phe Lys Leu Leu Val Lys
    130                 135                 140

Phe Val Ser Ser Arg Ile Glu Ala Ile Lys Leu Gln Met Val Leu Gln
145                 150                 155                 160

Met Glu Pro Gln Met Ser Ser Thr Asn Asn Phe Tyr Gln Gly Pro Leu
                165                 170                 175

Glu Arg Ser Thr Gly Thr Ser Thr Ser Leu Glu Ile Pro Leu Trp Lys
            180                 185                 190

Thr Leu Gln Leu Gln Gly Pro Phe Phe Ala Pro Ile Gln Gln Glu Val
        195                 200                 205

Ala Arg Ala Val Ile Gly Gln Ile Pro Asn Ser Ser Trp Gly Val Leu
    210                 215                 220

Phe Arg Gly Gly Ile Glu Glu Val Thr Ala Cys Trp Gln Pro His Ser
225                 230                 235                 240

Pro Arg Trp Xaa Ser Val Pro Pro Gln Pro Trp Cys Pro Leu Trp Pro
                245                 250                 255

Cys Leu Arg Ser Pro Ser Ala Cys His Cys Thr Val Gly Ala Ser Phe
            260                 265                 270

Trp Ala Gly Gln Gly Arg Ser Gln Leu Pro Gln Leu Ala Gly Arg Tyr
        275                 280                 285

Gly Gly Arg Asp Ala Gly Gly Asn Gln Gly Cys Ala Trp Arg Leu Arg
    290                 295                 300

Ala Ser Met Ser Ser Arg Trp Ala Trp Ala Arg Arg Ala Pro His Ser
305                 310                 315                 320

Gly Ser Glu Gly Leu Ser Thr Trp Ala Arg Gln Met Leu Cys Ser Thr
                325                 330                 335

Ser Ser Leu Gly Leu Ser Cys Leu Pro Arg Gly Ala Gly Leu Arg Glu
            340                 345                 350

Xaa Ala Ala Cys Pro Cys Leu Ser Pro Pro Arg Arg Gly Phe Leu
        355                 360                 365

His Ser Pro Ser Phe Pro Asp Lys His His Pro Leu Ser Thr Val Pro
```

-continued

```
            370                  375                  380
Ser Pro Ile Asn His Pro Arg Val Glu Glu Cys Gly His Thr Ala Arg
385                 390                  395                 400

Asp Trp Gln Ala Val Pro Leu Ala Ala Leu Val Arg Asp Pro Leu Arg
                405                  410                 415

Glu Ala Ser Trp Ala Pro Glu Ser Gly Gly Asp Leu Glu Asn Leu Tyr
                420                  425                 430

Val
```

(2) INFORMATION FOR SEQ ID NO:82:

(i) SEQUENCE CHARACTERISTICS:
        (A) LENGTH: 693 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:82:

```
CTTCCCCAAC TAATAAGGAC CCCCCTTTCA ACCCAAACAG TCCAAAAGGA CATAGACAAA    60
GGAGTAAACA ATGAACCAAA GAGTGCCAAT ATTCCCTGGT TATGCACCCT CCAAGCGGTG   120
GGAGAAGAAT TCGGCCCAGC CAGAGTGCAT GTACCTTTTT CTCTCTCACA CTTGAAGCAA   180
ATTAAAATAG ACNTAGGTNA ATTNTCAGAT AGCCCTGATG GYTATATTGA TGTTTTACAA   240
GGATTAGGAC AATCCTTTGA TCTGACATGG AGAGATATAA TATTACTGCT AAATCAGACG   300
CTAACCTCAA ATGAGAGAAG TGCTGCCATA ACTGGAGCCC GAGAGTTTGG CAATCTCTGG   360
TATCTCAGTC AGGTCAATGA TAGGATGACA ACGGAGGAAA GAGAACGATT CCCCACAGGG   420
CAGCAGGCAG TTCCCAGTGT AGCTCCTCAT TGGGACACAG AATCAGAACA TGGAGATTGG   480
TGCCGCAGAC ATTTACTAAC TTGCGTGCTA GAAGGACTAA GGAAAACTAG GAAGACTATG   540
AATTATTCAA TGATGTCCAC TATAACACAG GGGAAGGAA GAAAATCCTA CTGCCTTTCT   600
GGAGAGACTA AGGGAGGCAT TGAGGAAGCA TACCAGGCA GTGGACATTG GAGGCTCTGG   660
AAAAGGGAAA AGTTGGGCAA ATTGAATGCC TAA                                693
```

(2) INFORMATION FOR SEQ ID NO:83:

(i) SEQUENCE CHARACTERISTICS:
        (A) LENGTH: 1577 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:83:

```
AACTTGCGTG CTAGAAGGAC TAAGGAAAAC TAGGAAGACT ATGAATTATT CAATGATGTC    60
CACTATAACA CAGGGGAAAG GAAGAAAATC CTACTGCCTT TCTGGAGAGA CTAAGGGAGG   120
CATTGAGGAA GCATACCAGG CAAGTGGACA TTGGAGGCTC TGGAAAAGGG AAAAGTTGGG   180
CAAATTGAAT GCCTAATAGG GCTTGCTTCC AGTGCAGTCT ACAAGGACGC TTTAGAAAAG   240
ATTGTCCAAG TAGAAATAAG CCGCCCCTCG TCCATGCCCC TTATGTCAAG GAATCACTG   300
GAAGGCCTAC TGCCCCAGGG GACGAAGGTC CTCTGAGTCA GAAGCCACTA ACCTGATGAT   360
CCAGCAGCAG GACTGAGGGT GCCCGGGGCA AGTGCCAGCC CATGCCATCA CCCTCAGAGC   420
CCCGGGTATG TTTGACCATT GAGAGCCAGG AAGTTAACTG TCTCCTGGAC ACTGGCGCAG   480
```

-continued

```
CCTTCTCAGT CTTACTTTCC TGTCCCAGAC AATTGTCCTC CAGATCTGTC ACTATCCGAG    540

GGGTCCTAAG ACAGCCAGTC ACTACATACT TCTCTCAGCC ACTAAGTTGT GACTGGGGAA    600

CTTTACTCTT TTCACATGCT TTTCTAATTA TGCCTGAAAG CCCCACTCCC TTGTTAGGGA    660

GAGACATTTT AGCAAAAGCA GGGGCCATTA TACACCTGAA CATAGGAAAA GGAATACCCA    720

TTTGCTGTCC CCTGCTTGAG GAAGGAATTA ATCCTGAAGT CTGGGCAATA GAAGGACAAT    780

ATGGACAAGC AAAGAATGCC CGTCCTGTTC AAGTTAAACT AAAGGATTCT GCCTCCTTTC    840

CCTACCAAAG GAAGTACCCT CTTAGACCCG AGGCCCTACA AGGACTCAAA AGATTGTTAA    900

GGACCTAAAA GCCCAAGGCC TAGTAAAACC ATGCAGTAGC CCCTGCAATA CTCCAATTTT    960

AGGAGTAAGG AAACCCAACG GACAGTGGAG GTTAGTGCAA GATCTCAGGA TTATTAATGA   1020

GGCTGTTTTT CCTCTATACC CAGCTGTATC TAGCCCTTAT ACTCTGCTTT CCCTAATACC   1080

AGAGGAAGCA GAGTAGTTTA CAGTCCTGGA CCTTAAGGAT GCCTCTTTCT GCATCCCTGT   1140

ACATCCTGAT TCTCAATTCT TGTTTGTCTT TGAAGATCCT TTGAACCCAA TGTCTCAATT   1200

CACCTGGACT GTTTTACCCC AGGGGTTCCG GGATAGCCCC CATCTATTTG GCCAGGCATT   1260

AGCCCAAGAC TTGAGCCAAT TCTCATACCT GGACATCTTG TCCTTCGGTA TGGGATGATT   1320

TAATTTTAGC CACCCGTTCA GAAACCTTGT GCCATCAAGC CACCCAAGCG TTCTTAAATT   1380

TCCTCACTCC GTGTGGCTAC AAGGTTTCCA AACCAAAGGC TCAGCTCTGC TCACAGCAGG   1440

TTAAATACTT AGGGTTAAAA TTATCCAAAG GCACCAGGGC CCTCTGTGAG GAATGTATCC   1500

AACCTGTACT GGCTTATCTT CATCCCAAAA CCCTAAAGCA ACTAAGAAGG TCCTTGGCAT   1560

AACAGGTTTC TGCCGAA                                                  1577
```

(2) INFORMATION FOR SEQ ID NO:84:

(i) SEQUENCE CHARACTERISTICS:
        (A) LENGTH: 182 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:84:

```
Ser Ser Ser Arg Thr Glu Gly Ala Arg Gly Lys Cys Gln Pro Met Pro
 1               5                  10                  15

Ser Pro Ser Glu Pro Arg Val Cys Leu Thr Ile Glu Ser Gln Glu Val
            20                  25                  30

Asn Cys Leu Leu Asp Thr Gly Ala Ala Phe Ser Val Leu Leu Ser Cys
        35                  40                  45

Pro Arg Gln Leu Ser Ser Arg Ser Val Thr Ile Arg Gly Val Leu Arg
    50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
            100                 105                 110

Leu Asn Ile Gly Lys Gly Ile Pro Ile Cys Cys Pro Leu Leu Glu Glu
        115                 120                 125

Gly Ile Asn Pro Glu Val Trp Ala Ile Glu Gly Gln Tyr Gly Gln Ala
    130                 135                 140

Lys Asn Ala Arg Pro Val Gln Val Lys Leu Lys Asp Ser Ala Ser Phe
```

-continued

```
                145                 150                 155                 160
            Pro Tyr Gln Arg Lys Tyr Pro Leu Arg Pro Glu Ala Leu Gln Gly Leu
                            165                 170                 175

Lys Arg Leu Leu Arg Thr
                        180
```

(2) INFORMATION FOR SEQ ID NO:85:

(i) SEQUENCE CHARACTERISTICS:
        (A) LENGTH: 36 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:85:

```
AGATCTGCAG AATTCGATAT CACCCCCCCC CCCCCC                                    36
```

(2) INFORMATION FOR SEQ ID NO:86:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO:86:

```
AGATCTGCAG AATTCGATAT CA                                                   22
```

(2) INFORMATION FOR SEQ ID NO:87:

(i) SEQUENCE CHARACTERISTICS:
        (A) LENGTH: 2304 base pairs
        (B) TYPE: nucleotide
        (C) STRANDEDNESS: single
        (D) TOPOLOGY: linear (xi) SEQUENCE DESCRIPTION: SEQ ID NO:87:

```
TCCAGCAGCA GGACTGAGGG TGCCCGGGGC AAGTGCCAGC CCATGCCATC ACCCTCAGAG           60
CCCCGGGTAT GTTTGACCAT TGAGAGCCAG GAAGTTAACT GTCTCCTGGA CACTGGCGCA          120
GCCTTCTCAG TCTTACTTTC CTGTCCCAGA CAATTGTCCT CCAGATCTGT CACTATCCGA          180
GGGGTCCTAG GACAGCCAGT CACTACATAC TTCTCTCAGC CACTAAGTTG TGACTGGGGA          240
ACTTTACTCT TTTCACATGC TTTTCTAATT ATGCCTGAAA GCCCCACTCC CTTGTTAGGG          300
AGAGACATTT TAGCAAAAGC AGGGGCCATT ATACACCTGA ACATAGGAAA AGGAATACCC          360
ATTTGCTGTC CCCTGCTTGA GGAAGGAATT AATCCTGAAG TCTGGGCAAT AGAAGGACAA          420
TATGGACAAG CAAAGAATGC CCGTCCTGTT CAAGTTAAAC TAAAGGATTC TGCCTCCTTT          480
CCCTACCAAA GGAAGTACCC TCTTAGACCC GAGGCCCTAC AAGGANCTCA AAAGATTGTT          540
AAGGACCTAA AAGCCCAAGG CCTAGTAAAA CCATGCAGTA GCCCCTGCAA TACTCCAATT          600
TTAGGAGTAA GGAAACCCAA CGGACAGTGG AGGTTAGTGC AAGATCTCAG GATTATTAAT          660
GAGGCTGTTT TTCCTCTATA CCCAGCTGTA TCTAGCCCTT ATACTCTGCT TTCCCTAATA          720
CCAGAGGAAG CAGAGTGGTT TACAGTCCTG GACCTTAAGG ATGCCTTTTT CTGCATCCCT          780
GTACGTCCTG ACTCTCAATT CTTGTTTGCC TTTGAAGATC CTTTGAACCC AACGTCTCAA          840
CTCACCTGGA CTGTTTTACC CCAAGGGTTC AGGGATAGCC CCCATCTATT TGGCCAGGCA          900
```

| | |
|---|---|
| TTAGCCCAAG ACTTGAGTCA ATTCTCATAC CTGGACACTC TTGTCCTTCA GTACGTGGAT | 960 |
| GATTTACTTT TAGTCGCCCG TTCAGAAACC TTGTGCCATC AAGCCACCCA AGAACTCTTA | 1020 |
| ACTTTCCTCA CTACCTGTGG CTACAAGGTT TCCAAACCAA AGGCTCGGCT CTGCTCACAG | 1080 |
| GAGATTAGAT ACTTAGGGCT AAAATTATCC AAAGGCACCA GGGCCCTCAG TGAGGAACGT | 1140 |
| ATCCAGCCTA TACTGGCTTA TCCTCATCCC AAAACCCTAA AGCAACTAAG AGGGTTCCTT | 1200 |
| GGCATAACAG GTTTCTGCCG AAAACAGATT CCCAGGTACA CCCCAATAGC CAGACCATTA | 1260 |
| TATACACTAA TTAGGGAAAC TCAGAAAGCC AATACCTATT TAGTAAGATG GACACCTACA | 1320 |
| GAAGTGGCTT TCCAGGCCCT AAAGAAGGCC CTAACCCAAG CCCCAGTGTT CAGCTTGCCA | 1380 |
| ACAGGGCAAG ATTTTTCTTT ATATGCCACA GAAAAAACAG GAATAGCTCT AGGAGTCCTT | 1440 |
| ACGCAGGTCT CAGGGATGAG CTTGCAACCC GTGGTATACC TGAGTAAGGA AATTGATGTA | 1500 |
| GTGGCAAAGG GTTGGCCTCA TTGTTTATGG GTAATGGCGG CAGTAGCAGT CTTAGTATCT | 1560 |
| GAAGCAGTTA AAATAATACA GGGAAGAGAT CTTACTGTGT GGACATCTCA TGATGTGAAC | 1620 |
| GGCATACTCA CTGCTAAAGG AGACTTGTGG TTGTCAGACA ACCATTTACT TAATTATCAG | 1680 |
| GCTCTATTAC TTGAAGAGCC AGTGCTGAGA CTGCGCACTT GTGCAACTCT TAAACCCGCC | 1740 |
| ACATTTCTTC CAGACAATGA AGAAAAGATA GAACATAACT GTCAACAAGT AATTGCTCAA | 1800 |
| ACCTATGCTG CTCGAGGGGA CCTTCTAGAG GTTCCCTTGA CTGATCCCGA CCTCAACTTG | 1860 |
| TATACTGATG GAAGTTCCTT GGCAGAAAAA GGACTTCGAA AAGCGGGGTA TGCAGTGATC | 1920 |
| AGTGATAATG GAATACTTGA AAGTAATCGC CTCACTCCAG GAACTAGTGC TCACCTGGCA | 1980 |
| GAACTAATAG CCCTCACTTG GGCACTAGAA TTAGGAGAAG GAAAAAGGGT AAATATATAT | 2040 |
| TCAGACTCTA AGTATGCTTA CCTAGTCCTC CATGCCCATG CAGCAATATG GAGAGAGAGG | 2100 |
| GAATTCCTAA CTTCTGAGGG AACACCTATC AACCATCAGG AAGCCATTAG GAGATTATTA | 2160 |
| TTGGCTGTAC AGAAACCTAA AGAGGTGGCA GTCTTACACT GCCAGGGTCA TCAGGAAGAA | 2220 |
| GAGGAAAGGG AAATAGAAGG CAATCGCCAA GCGGATATTG AAGCAAAAAA AGCCGCAAGG | 2280 |
| CAGGACTCTC CATTAGAAAT GCTT | 2304 |

(2) INFORMATION FOR SEQ ID NO:88:

(i) SEQUENCE CHARACTERISTICS:
        (A) LENGTH: 2365 base pairs
        (B) TYPE: nucleotide
        (C) STRANDEDNESS: single
        (D) TOPOLOGY: linear (xi) SEQUENCE DESCRIPTION: SEQ ID NO:88:

| | |
|---|---|
| ATGATCCAGC AGCAGGACNG AGGGTGCCCG GGGCAAGCGC CAGCCCATGC CATCACCCTC | 60 |
| ACAGAGCCCC AGGTATGCTT GACCATTGAG GGTCAGAAGG GTNACTGTCT CCTGGACACT | 120 |
| GGCGGNGCCT TCTCAGTCTT ACTTTCCTGT CCTGGACAAC TGTCCTCCAG ATCTGTCACT | 180 |
| GTCCGAGGGG TCCTAGGACA GCCAGTCACT AGATACTTCT CCCAGCCACT AAGTTGTGAC | 240 |
| TGGGGAACTT TACTCTTCCC ACATGCTTTT CTAATTATGC CTGAAAGCCC CACTCTCTTG | 300 |
| TTGGGGAGAG ACATTCTAGC AAAAGCAGGG GCCATTATAC ATGTGAATAT AGGAGAAGGA | 360 |
| ACAACTGTTT GTTGTCCCCT GCTTGAGGAA GGAATTAATC CTGAAGTCCG GCAACAGAA | 420 |
| GGACAATATG GACAAGCAAA GAATGCCCGT CCTGTTCAAG TTAAACTAAA GGATTCCACC | 480 |
| TCCTTTCCCT ACCAAAGGCA GTACCCCCTC AGACCCGAGA CCCAACAAGA ACTCCAAAAG | 540 |
| ATTGTAAAGG ACCTAAAAGC CCAAGGCCTA GTAAAACCAA GCAATAGCCC TTGCAAGACT | 600 |

```
CCAATTTTAG GAGTAAGGAA ACCCAACGGA CAGTGGAGGT TAGTGCAAGA ACTCAGGATT      660

ATCAATGAGG CTGTTGTTCC TCTATACCCA GCTGTACCTA ACCCTTATAC AGTGCTTTCC      720

CAAATACCAG AGGAAGCAGA GTGGTTTACA GTCCTGGACC TTAAGGATGC CTTTTTCTGC      780

ATCCCTGTAC GTCCTGACTC TCAATTCTTG TTTGCCTTTG AAGATCCTTT GAACCCAACG      840

TCTCAACTCA CCTGGACTGT TTTACCCCAA GGGTTCAGGG ATAGCCCCCA TCTATTTGGC      900

CAGGCATTAG CCCAAGACTT GAGTCAATTC TCATACCTGG ACACTCTTGT CCTTCAGTAC      960

ATGGATGATT TACTTTTAGT CGCCCGTTCA GAAACCTTGT GCCATCAAGC CACCCAAGAA     1020

CTCTTAACTT TCCTCACTAC CTGTGGCTAC AAGGTTTCCA AACCAAAGGC TCGGCTCTGC     1080

TCACAGGAGA TTAGATACTN AGGGCTAAAA TTATCCAAAG GCACCAGGGC CCTCAGTGAG     1140

GAACGTATCC AGCCTATACT GGCTTATCCT CATCCCAAAA CCCTAAAGCA ACTAAGAGGG     1200

TTCCTTGGCA TAACAGGTTT CTGCCGAAAA CAGATTCCCA GGTACASCCC AATAGCCAGA     1260

CCATTATATA CACTAATTAN GGAAACTCAG AAAGCCAATA CCTATTTAGT AAGATGGACA     1320

CCTACAGAAG TGGCTTTCCA GGCCCTAAAG AAGGCCCTAA CCCAAGCCCC AGTGTTCAGC     1380

TTGCCAACAG GGCAAGATTT TTCTTTATAT GCCACAGAAA AAACAGGAAT AGCTCTAGGA     1440

GTCCTTACGC AGGTCTCAGG GATGAGCTTG CAACCCGTGG TATACCTGAG TAAGGAAATT     1500

GATGTAGTGG CAAAGGGTTG GCCTCATNGT TTATGGGTAA TGGNGGCAGT AGCAGTCTNA     1560

GTATCTGAAG CAGTTAAAAT AATACAGGGA AGAGATCTTN CTGTGTGGAC ATCTCATGAT     1620

GTGAACGGCA TACTSRCTGC TAAAGGAGAC TTGTGGTTGT CAGACAACCA TTTACTTAAN     1680

TAYCAGGCYY TATTACTTGA AGAGCCAGTG CTGNGACTGC GCACTTGTCC AACTCTTAAA     1740

CCCAAACTTA TGCTGCCCAG AAGGATCTTT NTAGAGGTCC CCTTAGCCAA CCCTGACCTC     1800

AACTATATAT ATACTGATGG AAGTTCGTTT GTAGAAAAGG GATTACAAAG GGNAGGATAT     1860

NCCATAGGTG TTAGTGATAA AGCAGTACTT GAAAGTAAGC CTCTTCCCCC CCAGGGACCA     1920

GCGCCCCCGT TAGCAGAACT AGTGGCACTG ACCCCGCGAG CCTTAGAACT TTGGAAAGGG     1980

AGGAGGATAA ATGTGTATAC AGATAGCAAG TATGCTTATC TAATCCGAAA TGCCCATGTT     2040

GCAATATGGA AGAAAGGGA GTTCCTAACC TCTGGGGAA CCCCCATTAA ATACCACAAG      2100

TTAATCATGG AGTTATTGCA CACAGTGCAA AAACTCAAGG AGGTGGAAGT CTTACACTGC     2160

CAAAGCCATC AGAAAAGGGA AAGAGGGGAA GAGCAGCATA AGTGGCTACA GAGGCAAGGA     2220

AAGACTAGCA GAAAGGAAAG AGAGAAAGAG ACAGAAAGTC AGAGAGAGAG AGAGGAAGAG     2280

ACAGAGCACA AAGAGGGAGT CAGAGAGAGA GAGAGACAGA GAGTCAGAGA GAAGGAAAGA     2340

GAGAGAGGAA GAGACAAAGA ATGA                                           2365
```

(2) INFORMATION FOR SEQ ID NO:89:

(i) SEQUENCE CHARACTERISTICS:
        (A) LENGTH: 768 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:89:

```
Ser Ser Ser Arg Thr Glu Gly Ala Arg Gly Lys Cys Gln Pro Met Pro
1               5                  10                  15

Ser Pro Ser Glu Pro Arg Val Cys Leu Thr Ile Glu Ser Gln Glu Val
            20                  25                  30
```

```
Asn Cys Leu Leu Asp Thr Gly Ala Ala Phe Ser Val Leu Leu Ser Cys
         35                  40                  45

Pro Arg Gln Leu Ser Ser Arg Ser Val Thr Ile Arg Gly Val Leu Gly
         50                  55                  60

Gln Pro Val Thr Thr Tyr Phe Ser Gln Pro Leu Ser Cys Asp Trp Gly
 65                  70                  75                  80

Thr Leu Leu Phe Ser His Ala Phe Leu Ile Met Pro Glu Ser Pro Thr
                 85                  90                  95

Pro Leu Leu Gly Arg Asp Ile Leu Ala Lys Ala Gly Ala Ile Ile His
                100                 105                 110

Leu Asn Ile Gly Lys Gly Ile Pro Ile Cys Cys Pro Leu Leu Glu Glu
        115                 120                 125

Gly Ile Asn Pro Glu Val Trp Ala Ile Glu Gly Gln Tyr Gly Gln Ala
        130                 135                 140

Lys Asn Ala Arg Pro Val Gln Val Lys Leu Lys Asp Ser Ala Ser Phe
145                 150                 155                 160

Pro Tyr Gln Arg Lys Tyr Pro Leu Arg Pro Glu Ala Leu Gln Gly Xaa
                165                 170                 175

Gln Lys Ile Val Lys Asp Leu Lys Ala Gln Gly Leu Val Lys Pro Cys
                180                 185                 190

Ser Ser Pro Cys Asn Thr Pro Ile Leu Gly Val Arg Lys Pro Asn Gly
        195                 200                 205

Gln Trp Arg Leu Val Gln Asp Leu Arg Ile Ile Asn Glu Ala Val Phe
        210                 215                 220

Pro Leu Tyr Pro Ala Val Ser Ser Pro Tyr Thr Leu Leu Ser Leu Ile
225                 230                 235                 240

Pro Glu Glu Ala Glu Trp Phe Thr Val Leu Asp Leu Lys Asp Ala Phe
                245                 250                 255

Phe Cys Ile Pro Val Arg Pro Asp Ser Gln Phe Leu Phe Ala Phe Glu
                260                 265                 270

Asp Pro Leu Asn Pro Thr Ser Gln Leu Thr Trp Thr Val Leu Pro Gln
        275                 280                 285

Gly Phe Arg Asp Ser Pro His Leu Phe Gly Gln Ala Leu Ala Gln Asp
        290                 295                 300

Leu Ser Gln Phe Ser Tyr Leu Asp Thr Leu Val Leu Gln Tyr Val Asp
305                 310                 315                 320

Asp Leu Leu Leu Val Ala Arg Ser Glu Thr Leu Cys His Gln Ala Thr
                325                 330                 335

Gln Glu Leu Leu Thr Phe Leu Thr Thr Cys Gly Tyr Lys Val Ser Lys
                340                 345                 350

Pro Lys Ala Arg Leu Cys Ser Gln Glu Ile Arg Tyr Leu Gly Leu Lys
        355                 360                 365

Leu Ser Lys Gly Thr Arg Ala Leu Ser Glu Glu Arg Ile Gln Pro Ile
        370                 375                 380

Leu Ala Tyr Pro His Pro Lys Thr Leu Lys Gln Leu Arg Gly Phe Leu
385                 390                 395                 400

Gly Ile Thr Gly Phe Cys Arg Lys Gln Ile Pro Arg Tyr Thr Pro Ile
                405                 410                 415

Ala Arg Pro Leu Tyr Thr Leu Ile Arg Glu Thr Gln Lys Ala Asn Thr
                420                 425                 430

Tyr Leu Val Arg Trp Thr Pro Thr Glu Val Ala Phe Gln Ala Leu Lys
        435                 440                 445

Lys Ala Leu Thr Gln Ala Pro Val Phe Ser Leu Pro Thr Gly Gln Asp
```

```
            450                 455                 460
Phe Ser Leu Tyr Ala Thr Glu Lys Thr Gly Ile Ala Leu Gly Val Leu
465                 470                 475                 480

Thr Gln Val Ser Gly Met Ser Leu Gln Pro Val Val Tyr Leu Ser Lys
                485                 490                 495

Glu Ile Asp Val Val Ala Lys Gly Trp Pro His Cys Leu Trp Val Met
            500                 505                 510

Ala Ala Val Ala Val Leu Val Ser Glu Ala Val Lys Ile Ile Gln Gly
        515                 520                 525

Arg Asp Leu Thr Val Trp Thr Ser His Asp Val Asn Gly Ile Leu Thr
    530                 535                 540

Ala Lys Gly Asp Leu Trp Leu Ser Asp Asn His Leu Leu Asn Tyr Gln
545                 550                 555                 560

Ala Leu Leu Leu Glu Glu Pro Val Leu Arg Leu Arg Thr Cys Ala Thr
                565                 570                 575

Leu Lys Pro Ala Thr Phe Leu Pro Asp Asn Glu Glu Lys Ile Glu His
            580                 585                 590

Asn Cys Gln Gln Val Ile Ala Gln Thr Tyr Ala Ala Arg Gly Asp Leu
        595                 600                 605

Leu Glu Val Pro Leu Thr Asp Pro Asp Leu Asn Leu Tyr Thr Asp Gly
    610                 615                 620

Ser Ser Leu Ala Glu Lys Gly Leu Arg Lys Ala Gly Tyr Ala Val Ile
625                 630                 635                 640

Ser Asp Asn Gly Ile Leu Glu Ser Asn Arg Leu Thr Pro Gly Thr Ser
                645                 650                 655

Ala His Leu Ala Glu Leu Ile Ala Leu Thr Trp Ala Leu Glu Leu Gly
            660                 665                 670

Glu Gly Lys Arg Val Asn Ile Tyr Ser Asp Ser Lys Tyr Ala Tyr Leu
        675                 680                 685

Val Leu His Ala His Ala Ala Ile Trp Arg Glu Arg Glu Phe Leu Thr
    690                 695                 700

Ser Glu Gly Thr Pro Ile Asn His Gln Glu Ala Ile Arg Arg Leu Leu
705                 710                 715                 720

Leu Ala Val Gln Lys Pro Lys Glu Val Ala Val Leu His Cys Gln Gly
                725                 730                 735

His Gln Glu Glu Glu Glu Arg Glu Ile Glu Gly Asn Arg Gln Ala Asp
            740                 745                 750

Ile Glu Ala Lys Lys Ala Ala Arg Gln Asp Ser Pro Leu Glu Met Leu
        755                 760                 765

(2) INFORMATION FOR SEQ ID NO:90:

(i) SEQUENCE CHARACTERISTICS:
        (A) LENGTH: 114 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:90:

Ser Ser Ser Arg Thr Glu Gly Ala Arg Gly Lys Cys Gln Pro Met Pro
1               5                   10                  15

Ser Pro Ser Glu Pro Arg Val Cys Leu Thr Ile Glu Ser Gln Glu Val
                20                  25                  30

Asn Cys Leu Leu Asp Thr Gly Ala Ala Phe Ser Val Leu Leu Ser Cys
```

```
                35                  40                  45
Pro Arg Gln Leu Ser Ser Arg Ser Val Thr Ile Arg Gly Val Leu Gly
        50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
               100                 105                 110

Leu Asn
```

(2) INFORMATION FOR SEQ ID NO:91:

(i) SEQUENCE CHARACTERISTICS:
      (A) LENGTH: 654 amino acids
      (B) TYPE: amino acid
      (C) STRANDEDNESS: Not Relevant
      (D) TOPOLOGY: linear (ii) MOLECULE TYPE: peptide (xi) SEQUENCE DESCRIPTION: SEQ ID NO:91:

```
Ile Gly Lys Gly Ile Pro Ile Cys Cys Pro Leu Leu Glu Glu Gly Ile
1               5                   10                  15

Asn Pro Glu Val Trp Ala Ile Glu Gly Gln Tyr Gly Gln Ala Lys Asn
                20                  25                  30

Ala Arg Pro Val Gln Val Lys Leu Lys Asp Ser Ala Ser Phe Pro Tyr
                35                  40                  45

Gln Arg Lys Tyr Pro Leu Arg Pro Glu Ala Leu Gln Gly Xaa Gln Lys
        50                  55                  60

Ile Val Lys Asp Leu Lys Ala Gln Gly Leu Val Lys Pro Cys Ser Ser
65                  70                  75                  80

Pro Cys Asn Thr Pro Ile Leu Gly Val Arg Lys Pro Asn Gly Gln Trp
                85                  90                  95

Arg Leu Val Gln Asp Leu Arg Ile Ile Asn Glu Ala Val Phe Pro Leu
               100                 105                 110

Tyr Pro Ala Val Ser Ser Pro Tyr Thr Leu Leu Ser Leu Ile Pro Glu
               115                 120                 125

Glu Ala Glu Trp Phe Thr Val Leu Asp Leu Lys Asp Ala Phe Phe Cys
        130                 135                 140

Ile Pro Val Arg Pro Asp Ser Gln Phe Leu Phe Ala Phe Glu Asp Pro
145                 150                 155                 160

Leu Asn Pro Thr Ser Gln Leu Thr Trp Thr Val Leu Pro Gln Gly Phe
                165                 170                 175

Arg Asp Ser Pro His Leu Phe Gly Gln Ala Leu Ala Gln Asp Leu Ser
                180                 185                 190

Gln Phe Ser Tyr Leu Asp Thr Leu Val Leu Gln Tyr Val Asp Asp Leu
        195                 200                 205

Leu Leu Val Ala Arg Ser Glu Thr Leu Cys His Gln Ala Thr Gln Glu
        210                 215                 220

Leu Leu Thr Phe Leu Thr Thr Cys Gly Tyr Lys Val Ser Lys Pro Lys
225                 230                 235                 240

Ala Arg Leu Cys Ser Gln Glu Ile Arg Tyr Leu Gly Leu Lys Leu Ser
                245                 250                 255

Lys Gly Thr Arg Ala Leu Ser Glu Glu Arg Ile Gln Pro Ile Leu Ala
                260                 265                 270
```

-continued

```
Tyr Pro His Pro Lys Thr Leu Lys Gln Leu Arg Gly Phe Leu Gly Ile
            275                 280                 285

Thr Gly Phe Cys Arg Lys Gln Ile Pro Arg Tyr Thr Pro Ile Ala Arg
        290                 295                 300

Pro Leu Tyr Thr Leu Ile Arg Glu Thr Gln Lys Ala Asn Thr Tyr Leu
305                 310                 315                 320

Val Arg Trp Thr Pro Thr Glu Val Ala Phe Gln Ala Leu Lys Lys Ala
                325                 330                 335

Leu Thr Gln Ala Pro Val Phe Ser Leu Pro Thr Gly Gln Asp Phe Ser
            340                 345                 350

Leu Tyr Ala Thr Glu Lys Thr Gly Ile Ala Leu Gly Val Leu Thr Gln
        355                 360                 365

Val Ser Gly Met Ser Leu Gln Pro Val Val Tyr Leu Ser Lys Glu Ile
    370                 375                 380

Asp Val Val Ala Lys Gly Trp Pro His Cys Leu Trp Val Met Ala Ala
385                 390                 395                 400

Val Ala Val Leu Val Ser Glu Ala Val Lys Ile Ile Gln Gly Arg Asp
                405                 410                 415

Leu Thr Val Trp Thr Ser His Asp Val Asn Gly Ile Leu Thr Ala Lys
            420                 425                 430

Gly Asp Leu Trp Leu Ser Asp Asn His Leu Leu Asn Tyr Gln Ala Leu
        435                 440                 445

Leu Leu Glu Glu Pro Val Leu Arg Leu Arg Thr Cys Ala Thr Leu Lys
    450                 455                 460

Pro Ala Thr Phe Leu Pro Asp Asn Glu Glu Lys Ile Glu His Asn Cys
465                 470                 475                 480

Gln Gln Val Ile Ala Gln Thr Tyr Ala Ala Arg Gly Asp Leu Leu Glu
                485                 490                 495

Val Pro Leu Thr Asp Pro Asp Leu Asn Leu Tyr Thr Asp Gly Ser Ser
            500                 505                 510

Leu Ala Glu Lys Gly Leu Arg Lys Ala Gly Tyr Ala Val Ile Ser Asp
        515                 520                 525

Asn Gly Ile Leu Glu Ser Asn Arg Leu Thr Pro Gly Thr Ser Ala His
    530                 535                 540

Leu Ala Glu Leu Ile Ala Leu Thr Trp Ala Leu Glu Leu Gly Glu Gly
545                 550                 555                 560

Lys Arg Val Asn Ile Tyr Ser Asp Ser Lys Tyr Ala Tyr Leu Val Leu
                565                 570                 575

His Ala His Ala Ala Ile Trp Arg Glu Arg Glu Phe Leu Thr Ser Glu
            580                 585                 590

Gly Thr Pro Ile Asn His Gln Glu Ala Ile Arg Arg Leu Leu Leu Ala
        595                 600                 605

Val Gln Lys Pro Lys Glu Val Ala Val Leu His Cys Gln Gly His Gln
    610                 615                 620

Glu Glu Glu Glu Arg Glu Ile Glu Gly Asn Arg Gln Ala Asp Ile Glu
625                 630                 635                 640

Ala Lys Lys Ala Ala Arg Gln Asp Ser Pro Leu Glu Met Leu
                645                 650
```

(2) INFORMATION FOR SEQ ID NO:92:

(i) SEQUENCE CHARACTERISTICS:
        (A) LENGTH: 149 amino acids
        (B) TYPE: amino acid (C) STRANDEDNESS: Not Relevant
        (D) TOPOLOGY: linear (ii) MOLECULE TYPE: peptide (xi) SEQUENCE DESCRIPTION: SEQ ID NO:92:

Leu Tyr Thr Asp Gly Ser Ser Leu Ala Glu Lys Gly Leu Arg Lys Ala
1               5                   10                  15

Gly Tyr Ala Val Ile Ser Asp Asn Gly Ile Leu Glu Ser Asn Arg Leu
            20                  25                  30

Thr Pro Gly Thr Ser Ala His Leu Ala Glu Leu Ile Ala Leu Thr Trp
        35                  40                  45

Ala Leu Glu Leu Gly Glu Gly Lys Arg Val Asn Ile Tyr Ser Asp Ser
50                  55                  60

Lys Tyr Ala Tyr Leu Val Leu His Ala His Ala Ala Ile Trp Arg Glu
65                  70                  75                  80

Arg Glu Phe Leu Thr Ser Glu Gly Thr Pro Ile Asn His Gln Glu Ala
            85                  90                  95

Ile Arg Arg Leu Leu Leu Ala Val Gln Lys Pro Lys Glu Val Ala Val
            100                 105                 110

Leu His Cys Gln Gly His Gln Glu Glu Glu Arg Glu Ile Glu Gly
            115                 120                 125

Asn Arg Gln Ala Asp Ile Glu Ala Lys Lys Ala Ala Arg Gln Asp Ser
130                 135                 140

Pro Leu Glu Met Leu
145

(2) INFORMATION FOR SEQ ID NO:93:

(i) SEQUENCE CHARACTERISTICS:
        (A) LENGTH: 21 base pairs
        (B) TYPE: nucleotide
        (C) STRANDEDNESS: single
        (D) TOPOLOGY: linear (xi) SEQUENCE DESCRIPTION: SEQ ID NO:93:

TCCAGCAGCA GGACTGAGGG T                                                21

(2) INFORMATION FOR SEQ ID NO:94:

(i) SEQUENCE CHARACTERISTICS:
        (A) LENGTH: 24 base pairs
        (B) TYPE: nucleotide
        (C) STRANDEDNESS: single
        (D) TOPOLOGY: linear (xi) SEQUENCE DESCRIPTION: SEQ ID NO:94:

GACAGCAAAT GGGTATTCCT TTCC                                             24

(2) INFORMATION FOR SEQ ID NO:95:

(i) SEQUENCE CHARACTERISTICS:
        (A) LENGTH: 25 base pairs
        (B) TYPE: nucleotide
        (C) STRANDEDNESS: single
        (D) TOPOLOGY: linear (xi) SEQUENCE DESCRIPTION: SEQ ID NO:95:

AGGAGTAAGG AAACCCAACG GACAG                                            25

(2) INFORMATION FOR SEQ ID NO:96:

```
        (i) SEQUENCE CHARACTERISTICS:
            (A) LENGTH: 25 base pairs
            (B) TYPE: nucleotide
            (C) STRANDEDNESS: single
            (D) TOPOLOGY: linear (xi) SEQUENCE DESCRIPTION: SEQ ID NO:96:

TGTATATAAT GGTCTGGCTA TTGGG                                             25

(2) INFORMATION FOR SEQ ID NO:97:

(i) SEQUENCE CHARACTERISTICS:
            (A) LENGTH: 26 base pairs
            (B) TYPE: nucleotide
            (C) STRANDEDNESS: single
            (D) TOPOLOGY: linear (xi) SEQUENCE DESCRIPTION: SEQ ID NO:97:

GGCTCTGCTC ACAGGAGATT AGATAC                                            26

(2) INFORMATION FOR SEQ ID NO:98:

(i) SEQUENCE CHARACTERISTICS:
            (A) LENGTH: 26 base pairs
            (B) TYPE: nucleotide
            (C) STRANDEDNESS: single
            (D) TOPOLOGY: linear (xi) SEQUENCE DESCRIPTION: SEQ ID NO:98:

AAAGGCACCA GGGCCCTCAG TGAGGA                                            26

(2) INFORMATION FOR SEQ ID NO:99:

(i) SEQUENCE CHARACTERISTICS:
            (A) LENGTH: 28 base pairs
            (B) TYPE: nucleotide
            (C) STRANDEDNESS: single
            (D) TOPOLOGY: linear (xi) SEQUENCE DESCRIPTION: SEQ ID NO:99:

GGTTTAAGAG TTGCACAAGT GCGCAGTC                                          28

(2) INFORMATION FOR SEQ ID NO:100:

(i) SEQUENCE CHARACTERISTICS:
            (A) LENGTH: 310 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:100:

GCTTATAGAA GGACCCCTAG TATGGGGTAA TCCCCTCTGG GAAACCAAGC CCCAGTACTC        60

AGCAGGAAAA ATAGAATAGG AAACCTCACA AGGACATACT TTCCTCCCCT CCAGATGGCT       120

AGCCACTGAG GAAGGAAAAA TACTTTCACC TGCAGCTAAC CAACAGAAAT TACTTAAAAC       180

CCTTCACCAA ACCTTCCACT TAGGCATTGA TAGCACCCAT CAGATGGCCA AATTATTATT       240

TACTGGACCA GGCCTTTTCA AAACTATCAA GAAGATAGTC AGGGGCTGTG AAGTGTGCCA       300

AAGAAATAAT                                                             310

(2) INFORMATION FOR SEQ ID NO:101:

(i) SEQUENCE CHARACTERISTICS:
            (A) LENGTH: 103 amino acids
```

(B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

Leu Ile Glu Gly Pro Leu Val Trp Gly Asn Pro Leu Trp Glu Thr Lys
1               5                   10                  15

Pro Gln Tyr Ser Ala Gly Lys Ile Glu Xaa Glu Thr Ser Gln Gly His
            20                  25                  30

Thr Phe Leu Pro Ser Arg Trp Leu Ala Thr Glu Glu Gly Lys Ile Leu
        35                  40                  45

Ser Pro Ala Ala Asn Gln Gln Lys Leu Leu Lys Thr Leu His Gln Thr
    50                  55                  60

Phe His Leu Gly Ile Asp Ser Thr His Gln Met Ala Lys Leu Leu Phe
65                  70                  75                  80

Thr Gly Pro Gly Leu Phe Lys Thr Ile Lys Lys Ile Val Arg Gly Cys
                85                  90                  95

Glu Val Cys Gln Arg Asn Asn
            100

(2) INFORMATION FOR SEQ ID NO:102:

(i) SEQUENCE CHARACTERISTICS:
        (A) LENGTH: 635 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

CCCTGTATCT TTAACCTCCT TGTTAAGTTT GTCTCTTCCA GAATCAAAAC TGTAAAACTA        60

CAAATTGTTC TTCAAATGGA GCACCAGATG GAGTCCATGA CTAAGATCCA CCGTGGACCC       120

CTGGACCGGC CTGCTAGCCC ATGCTCCGAT GTTAATGACA TTGAAGGCAC CCCTCCCGAG       180

GAAATCTCAA CTGCACAACC CCTACTATGC CCCAATTCAG CGGGAAGCAG TTAGAGCGGT       240

CATCAGCCAA CCTCCCCAAC AGCACTTGGG TTTTCCTGTT GAGAGGGGGG ACTGAGAGAC       300

AGGACTAGCT GGATTTCCTA GGCCAACGAA GAATCCCTAA GCCTAGCTGG AAGGTGACT        360

GCATCCACCT CTAAACATGG GCTTGCAAC TTAGCTCACA CCCGACCAAT CAGAGAGCTC       420

ACTAAAATGC TAATTAGGCA AAAATAGGAG GTAAAGAAAT AGCCAATCAT CTATTGCCTG      480

AGAGCACAGC GGGAGGGACA AGGATCGGGA TATAAACCCA GGCATTCGAG CCGGCAACGG      540

CAACCCCCTT TGGGTCCCCT CCCTTTGTAT GGGCGCTCTG TTTTCACTCT ATTTCACTCT     600

ATTAAATCTT GCAACTGAAA AAAAAAAAA AAAAA                                 635

(2) INFORMATION FOR SEQ ID NO:103:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Pro Cys Ile Phe Asn Leu Leu Val Lys Phe Val Ser Ser Arg Ile Lys
1               5                   10                  15

```
Thr Val Lys Leu Gln Ile Val Leu Gln Met Glu His Gln Met Glu Ser
            20                  25                  30

Met Thr Lys Ile His Arg Gly Pro Leu Asp Arg Pro Ala Ser Pro Cys
            35                  40                  45

Ser Asp Val Asn Asp Ile Glu Gly Thr Pro Pro Glu Glu Ile Ser Thr
            50                  55                  60

Ala Gln Pro Leu Leu Cys Pro Asn Ser Ala Gly Ser Ser
 65              70                  75
```

(2) INFORMATION FOR SEQ ID NO:104:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:104:

```
TGGGGTTCCA TTTGTAAGAC CATCTGTAGC TT                            32
```

(2) INFORMATION FOR SEQ ID NO:105:

(i) SEQUENCE CHARACTERISTICS:
        (A) LENGTH: 1481 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

```
ATGGCCCTCC CTTATCATAC TTTTCTCTTT ACTGTTCTCT TACCCCCTTT CGCTCTCACT     60

GCACCCCCTC CATGCTGCTG TACAACCAGT AGCTCCCCTT ACCAAGAGTT CTATGAAGA     120

ACGCGGCTTC CTGGAAATAT TGATGCCCCA TCATATAGGA GTTTATCTAA GGGAAACTCC   180

ACCTTCACTG CCCACACCCA TATGCCCCGC AACTGCTATA ACTCTGCCAC TCTTTGCATG   240

CATGCAAATA CTCATTATTG GACAGGGAAA ATGATTAATC CTAGTTGTCC TGGAGGACTT   300

GGAGCCACTG TCTGTTGGAC TTACTTCACC CATACCAGTA TGTCTGATGG GGGTGGAATT   360

CAAGGTCAGG CAAGAGAAAA ACAAGTAAAG GAAGCAATCT CCCAACTGAC CCGGGGACAT   420

AGCACCCCTA GCCCCTACAA AGGACTAGTT CTCTCAAAAC TACATGAAAC CCTCCGTACC   480

CATACTCGCC TGGTGAGCCT ATTTAATACC ACCCTCACTC GGCTCCATGA GGTCTCAGCC   540

CAAAACCCTA CTAACTGTTG GATGTGCCTC CCCCTGCACT TCAGGCCATA CATTTCAATC   600

CCTGTTCCTG AACAATGGAA CAACTTCAGC ACAGAAATAA ACACCACTTC CGTTTTAGTA   660

GGACCTCTTG TTTCCAATCT GGAAATAACC CATACCTCAA ACCTCACCTG TGTAAAATTT   720

AGCAATACTA TAGACACAAC CAGCTCCCAA TGCATCAGGT GGGTAACACC TCCCACACGA   780

ATAGTCTGCC TACCCTCAGG AATATTTTTT GTCTGTGGTA CCTCAGCCTA TCATTGTTTG   840

AATGGCTCTT CAGAATCTAT GTGCTTCCTC TCATTCTTAG TGCCCCCTAT GACCATCTAC   900

ACTGAACAAG ATTTATACAA TCATGTCGTA CCTAAGCCCC ACAACAAAAG AGTACCCATT   960

CTTCCTTTTG TTATCAGAGC AGGAGTGCTA GGCAGACTAG GTACTGGCAT TGGCAGTATC  1020

ACAACCTCTA CTCAGTTCTA CTACAAACTA TCTCAAGAAA TAAATGGTGA CATGGAACAG  1080

GTCACTGACT CCCTGGTCAC CTTGCAAGAT CAACTTAACT CCCTAGCAGC AGTAGTCCTT  1140
```

-continued

```
CAAAATCGAA GAGCTTTAGA CTTGCTAACC GCCAAAAGAG GGGGAACCTG TTTATTTTTA    1200

GGAGAAGAAC GCTGTTATTA TGTTAATCAA TCCAGAATTG TCACTGAGAA AGTTAAAGAA    1260

ATTCGAGATC GAATACAATG TAGAGCAGAG GAGCTTCAAA ACACCGAACG CTGGGGCCTC    1320

CTCAGCCAAT GGATGCCCTG GGTTCTCCCC TTCTTAGGAC CTCTAGCAGC TCTAATATTG    1380

TTACTCCTCT TTGGACCCTG TATCTTTAAC CTCCTTGTTA AGTTTGTCTC TTCCAGAATT    1440

GAAGCTGTAA AGCTACAGAT GGTCTTACAA ATGGAACCCC A                        1481
```

(2) INFORMATION FOR SEQ ID NO:106:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

```
Met Ala Leu Pro Tyr His Thr Phe Leu Phe Thr Val Leu Leu Pro Pro
1               5                   10                  15

Phe Ala Leu Thr Ala Pro Pro Cys Cys Cys Thr Thr Ser Ser Ser
            20                  25                  30

Pro Tyr Gln Glu Phe Leu Xaa Arg Thr Arg Leu Pro Gly Asn Ile Asp
            35                  40                  45

Ala Pro Ser Tyr Arg Ser Leu Ser Lys Gly Asn Ser Thr Phe Thr Ala
        50                  55                  60

His Thr His Met Pro Arg Asn Cys Tyr Asn Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Ala Thr Val Cys Trp Thr Tyr Phe Thr His Thr
            100                 105                 110

Ser Met Ser Asp Gly Gly Gly Ile Gln Gly Gln Ala Arg Glu Lys Gln
        115                 120                 125

Val Lys Glu Ala Ile Ser Gln Leu Thr Arg Gly His Ser Thr Pro Ser
130                 135                 140

Pro Tyr Lys Gly Leu Val Leu Ser Lys Leu His Glu Thr Leu Arg Thr
145                 150                 155                 160

His Thr Arg Leu Val Ser Leu Phe Asn Thr Thr Leu Thr Arg Leu His
                165                 170                 175

Glu Val Ser Ala Gln Asn Pro Thr Asn Cys Trp Met Cys Leu Pro Leu
            180                 185                 190

His Phe Arg Pro Tyr Ile Ser Ile Pro Val Pro Glu Gln Trp Asn Asn
        195                 200                 205

Phe Ser Thr Glu Ile Asn Thr Thr Ser Val Leu Val Gly Pro Leu Val
        210                 215                 220

Ser Asn Leu Glu Ile Thr His Thr Ser Asn Leu Thr Cys Val Lys Phe
225                 230                 235                 240

Ser Asn Thr Ile Asp Thr Thr Ser Ser Gln Cys Ile Arg Trp Val Thr
                245                 250                 255

Pro Pro Thr Arg Ile Val Cys Leu Pro Ser Gly Ile Phe Phe Val Cys
            260                 265                 270

Gly Thr Ser Ala Tyr His Cys Leu Asn Gly Ser Ser Glu Ser Met Cys
        275                 280                 285
```

```
Phe Leu Ser Phe Leu Val Pro Pro Met Thr Ile Tyr Thr Glu Gln Asp
    290                 295                 300
Leu Tyr Asn His Val Val Pro Lys Pro His Asn Lys Arg Val Pro Ile
305                 310                 315                 320
Leu Pro Phe Val Ile Arg Ala Gly Val Leu Gly Arg Leu Gly Thr Gly
                325                 330                 335
Ile Gly Ser Ile Thr Thr Ser Thr Gln Phe Tyr Tyr Lys Leu Ser Gln
            340                 345                 350
Glu Ile Asn Gly Asp Met Glu Gln Val Thr Asp Ser Leu Val Thr Leu
            355                 360                 365
Gln Asp Gln Leu Asn Ser Leu Ala Ala Val Val Leu Gln Asn Arg Arg
370                 375                 380
Ala Leu Asp Leu Leu Thr Ala Lys Arg Gly Gly Thr Cys Leu Phe Leu
385                 390                 395                 400
Gly Glu Glu Arg Cys Tyr Tyr Val Asn Gln Ser Arg Ile Val Thr Glu
                405                 410                 415
Lys Val Lys Glu Ile Arg Asp Arg Ile Gln Cys Arg Ala Glu Glu Leu
                420                 425                 430
Gln Asn Thr Glu Arg Trp Gly Leu Leu Ser Gln Trp Met Pro Trp Val
            435                 440                 445
Leu Pro Phe Leu Gly Pro Leu Ala Ala Leu Ile Leu Leu Leu Leu Phe
        450                 455                 460
Gly Pro Cys Ile Phe Asn Leu Leu Val Lys Phe Val Ser Ser Arg Ile
465                 470                 475                 480
Glu Ala Val Lys Leu Gln Met Val Leu Gln Met Glu Pro
                485                 490

(2) INFORMATION FOR SEQ ID NO:107:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:107:

TCAAAATCGA AGAGCTTTAG ACTTGCTAAC CG                                    32

(2) INFORMATION FOR SEQ ID NO:108:

(i) SEQUENCE CHARACTERISTICS:
        (A) LENGTH: 1329 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

TCAAAATCGA AGAGCTTTAG ACTTGCTAAC CGCCAAAAGA GGGGGAACCT GTTTATTTTT    60

AGGGGAAGAA TGCTGTTAGT ATGTTAATCA ATCTGGAATC ATTACTGAGA AAGTTAAAGA   120

AATTTGAGAT CGAATATAAT GTAGAGCAGA GGACCTTCAA AACACTGCAC CCTGGGGCCT   180

CCTCAGCCAA TGGATGCCCT GGACTCTCCC CTTCTTAGGA CCTCTAGCAG CTATAATATT   240

TTTACTCCTC TTTGGACCCT GTATCTTCAA CTTCCTTGTT AAGTTTGTCT CTTCCAGAAT   300

TGAAGCTGTA AAGCTACAAA TAGTTCTTCA AATGGAACCC CAGATGCAGT CCATGACTAA   360
```

-continued

```
AATCTACCGT GGACCCCTGG ACCGGCCTGC TAGACTATGC TCTGATGTTA ATGACATTGA      420

AGTCACCCCT CCCGAGGAAA TCTCAACTGC ACAACCCCTA CTACACTCCA ATTCAGTAGG      480

AAGCAGTTAG AGCAGTTGTC AGCCAACCTC CCCAACAGTA CTTGGGTTTT CCTGTTGAGA      540

GGGTGGACTG AGAGACAGGA CTAGCTGGAT TTCCTAGGCT GACTAAGAAT CCCNAAGCCT      600

ANCTGGGAAG GTGACCGCAT CCATCTTTAA ACATGGGGCT TGCAACTTAG CTCACACCCG      660

ACCAATCAGA GAGCTCACTA AAATGCTAAT CAGGCAAAAA CAGGAGGTAA AGCAATAGCC      720

AATCATCTAT TGCCTGAGAG CACAGCGGGA AGGACAAGGA TTGGGATATA AACTCAGGCA      780

TTCAAGCCAG CAACAGCAAC CCCCTTTGGG TCCCCTCCCA TTGTATGGGA GCTCTGTTTT      840

CACTCTATTT CACTCTATTA AATCATGCAA CTGCACTCTT CTGGTCCGTG TTTTTTATGG      900

CTCAAGCTGA GCTTTTGTTC GCCATCCACC ACTGCTGTTT GCCACCGTCA CAGACCCGCT      960

GCTGACTTCC ATCCCTTTGG ATCCAGCAGA GTGTCCACTG TGCTCCTGAT CCAGCGAGGT     1020

ACCCATTGCC ACTCCCGATC AGGCTAAAGG CTTGCCATTG TTCCTGCATG GCTAAGTGCC     1080

TGGGTTTGTC CTAATAGAAC TGAACACTGG TCACTGGGTT CCATGGTTCT CTTCCATGAC     1140

CCACGGCTTC TAATAGAGCT ATAACACTCA CCGCATGGCC CAAGATTCCA TTCCTTGGTA     1200

TCTGTGAGGC CAAGAACCCC AGGTCAGAGA ANGTGAGGCT TGCCACCATT TGGGAAGTGG     1260

CCCACTGCCA TTTTGGTAGC GGCCCACCAC CATCTTGGGA GCTGTGGGAG CAAGGATCCC     1320

CCAGTAACA                                                             1329
```

(2) INFORMATION FOR SEQ ID NO:109:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

```
Gln Asn Arg Arg Ala Leu Asp Leu Leu Thr Ala Lys Arg Gly Gly Thr
1               5                  10                  15

Cys Leu Phe Leu Gly Glu Glu Cys Cys Xaa Tyr Val Asn Gln Ser Gly
                20                  25                  30

Ile Ile Thr Glu Lys Val Lys Glu Ile Xaa Asp Arg Ile Xaa Cys Arg
            35                  40                  45

Ala Glu Asp Leu Gln Asn Thr Ala Pro Trp Gly Leu Leu Ser Gln Trp
        50                  55                  60

Met Pro Trp Thr Leu Pro Phe Leu Gly Pro Leu Ala Ala Ile Ile Phe
65                  70                  75                  80

Leu Leu Leu Phe Gly Pro Cys Ile Phe Asn Phe Leu Val Lys Phe Val
                85                  90                  95

Ser Ser Arg Ile Glu Ala Val Lys Leu Gln Ile Val Leu Gln Met Glu
                100                 105                 110

Pro Gln Met Gln Ser Met Thr Lys Ile Tyr Arg Gly Pro Leu Asp Arg
            115                 120                 125

Pro Ala Arg Leu Cys Ser Asp Val Asn Asp Ile Glu Val Thr Pro Pro
        130                 135                 140

Glu Glu Ile Ser Thr Ala Gln Pro Leu Leu His Ser Asn Ser Val Gly
145                 150                 155                 160

Ser Ser
```

(2) INFORMATION FOR SEQ ID NO:110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:110:

```
GGCATTGATA GCACCCATCA G                                          21
```

(2) INFORMATION FOR SEQ ID NO:111:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:111:

```
CATGTCACCA GGGTGGAATA G                                          21
```

(2) INFORMATION FOR SEQ ID NO:112:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:112:

```
GGCATTGATA GCACCCATCA GATGGCCAAA TCATTATTTA CTGGACCAGG CCTTTTCAAA    60
ACTATCAAGC AGATAGGGCC CGTGAAGCAT GCCAAAGAAA TAATCCCCTG CCTTATCGCC   120
ATGTTCCTTC AGGAGAACAA AGAACAGGCC ATTACCCAGG GGAAGACTGG CAACTAGATT   180
TTACCCACAT GGCCAAATGT CAGGGATTTC AGCATCTACT AGTCTGGGCA GATACTTTCA   240
CTGGTTGGGT GGAGTCTTCT CCTTGTAGGA CAGAAAAGAC CCAAGAGGTA ATAAAGGCAC   300
TAATGAAATA ATTCCCAGAT TTGGACTTCC CCCAGGATTA CAGGGTGACA ATGGCCCCGC   360
TTTCAAGGCT GCAGTAACCC AGGGAGTATC CCAGGTGTTA GGCATACAAT ATCACTTACA   420
CTGTGCCTGG AGGCCACAAT CCTCCAGAAA AGTCAAGAAA ATGAATGAAA CACTCAAAGA   480
TCTAAAAAAG CTAACCCAAG AAACCCACAT TGCATGACCT GTTCTGTTGC CTATAACCTT   540
ACTAAGAATC CATAACTATC CCCCAAAAAG CAGGACTTAG CCCATACGAG ATGCTATATG   600
GATGGCCTTT CCTAACCAAT GACCTTGTGC TTGACTGAGA AATGGCCAAC TTAGTTGCAG   660
ACATCACCTC CTTAGCCAAA TATCAACAAG TTCTTAAAAC ATCACAGGGA ACCTGTCCCC   720
GAGAGGAGGG AAAGGAACTA TTCCACCCTG GTGACATG                          758
```

(2) INFORMATION FOR SEQ ID NO:113:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:113:

CGGACATCCA AAGTGATGGG AAACG                                                  25

(2) INFORMATION FOR SEQ ID NO:114:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:114:

GGACAGGAAA GTAAGACTGA GAAGGC                                                 26

(2) INFORMATION FOR SEQ ID NO:115:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:115:

CCTAGAACGT ATTCTGGAGA ATTGGG                                                 26

(2) INFORMATION FOR SEQ ID NO:116:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:116:

TGGCTCTCAA TGGTCAAACA TACCCG                                                 26

(2) INFORMATION FOR SEQ ID NO:117:

(i) SEQUENCE CHARACTERISTICS:
        (A) LENGTH: 1511 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:117:

CCTAGAACGT ATTCTGGAGA ATTGGGACCA ATGTGACACT CAGACGCTAA GAAAGAAACG            60

ATTTATATTC TTCTGCAGTA CCGCCTGGCC ACAATATCCT CTTCAAGGGA GAGAAACCTG           120

GCTTCCTGAG GGAAGTATAA ATTATAACAT CATCTTACAG CTAGACCTCT TCTGTAGAAA           180

GGAGGGCAAA TGGAGTGAAG TGCCATATGT GCAAACTTTC TTTTCATTAA GAGACAACTC           240

ACAATTATGT AAAAGTGTG GTTTATGCCC TACAGGAAGC CCTCAGAGTC CACCTCCCTA            300

CCCCAGCGTC CCCTCCCCGA CTCCTTCCTC AACTAATAAG GACCCCCCTT TAACCCAAAC           360

GGTCCAAAAG GAGATAGACA AAGGGGTAAA CAATGAACCA AAGAGTGCCA ATATTCCCCG           420

ATTATGCCCC CTCCAAGCAG TGAGAGGAGG AGAATTCGGC CCAGCCAGAG TGCCTGTACC           480

```
TTTTTCTCTC TCAGACTTAA AGCAAATTAA AATAGACCTA GGTAAATTCT CAGATAACCC      540

TGACGGCTAT ATTGATGTTT TACAAGGGTT AGGACAATCC TTTGATCTGA CATGGAGAGA      600

TATAATGTTA CTACTAAATC AGACACTAAC CCCAAATGAG AGAAGTGCCG CTGTAACTGC      660

AGCCCGAGAG TTTGGCGATC TTTGGTATCT CAGTCAGGCC AACAATAGGA TGACAACAGA      720

GGAAAGAACA ACTCCCACAG GCCAGCAGGC AGTTCCCAGT GTAGACCCTC ATTGGGACAC      780

AGAATCAGAA CATGGAGATT GGTGCCACAA ACATTTGCTA ACTTGCGTGC TAGAAGGACT      840

GAGGAAAACT AGGAAGAAGC CTATGAATTA CTCAATGATG TCCACTATAA CACAGGGAAA      900

GGAAGAAAAT CTTACTGCTT TTCTGGACAG ACTAAGGGAG GCATTGAGGA AGCATACCTC      960

CCTGTCACCT GACTCTATTG AAGGCCAACT AATCTTAAAG GATAAGTTTA TCACTCAGTC     1020

AGCTGCAGAC ATTAGAAAAA ACTTCAAAAG TCTGCCTTAG GCCCGGAGCA GAACTTAGAA     1080

ACCCTATTTA ACTTGGCATC CTCAGTTTTT TATAATAGAG ATCAGGAGGA GCAGGCGAAA     1140

CGGGACAAAC GGGATAAAAA AAAAAGGGGG GGTCCACTAC TTTAGTCATG GCCCTCAGGC     1200

AAGCAGACTT TGGAGGCTCT GCAAAAGGGA AAAGCTGGGC AAATCAAATG CCTAATAGGG     1260

CTGGCTTCCA GTGCGGTCTA CAAGGACACT TTAAAAAAGA TTATCCAAGT AGAAATAAGC     1320

CGCCCCCTTG TCCATGCCCC TTACGTCAAG GGAATCACTG GAAGGCCCAC TGCCCCAGGG     1380

GATGAAGATA CTCTGAGTCA GAAGCCATTA ACCAGATGAT CCAGCAGCAG GACTGAGGGT     1440

GCCCGGGGCG AGCGCCAGCC CATGCCATCA CCCTCACAGA GCCCCGGGTA TGTTTGACCA     1500

TTGAGAGCCA A                                                         1511
```

(2) INFORMATION FOR SEQ ID NO:118:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:118:

```
Leu Glu Arg Ile Leu Glu Asn Trp Asp Gln Cys Asp Thr Gln Thr Leu
1               5                   10                  15

Arg Lys Lys Arg Phe Ile Phe Phe Cys Ser Thr Ala Trp Pro Gln Tyr
            20                  25                  30

Pro Leu Gln Gly Arg Glu Thr Trp Leu Pro Glu Gly Ser Ile Asn Tyr
        35                  40                  45

Asn Ile Ile Leu Gln Leu Asp Leu Phe Cys Arg Lys Glu Gly Lys Trp
    50                  55                  60

Ser Glu Val Pro Tyr Val Gln Thr Phe Phe Ser Leu Arg Asp Asn Ser
65                  70                  75                  80

Gln Leu Cys Lys Lys Cys Gly Leu Cys Pro Thr Gly Ser Pro Gln Ser
                85                  90                  95

Pro Pro Pro Tyr Pro Ser Val Pro Ser Pro Thr Pro Ser Ser Thr Asn
            100                 105                 110

Lys Asp Pro Pro Leu Thr Gln Thr Val Gln Lys Glu Ile Asp Lys Gly
        115                 120                 125

Val Asn Asn Glu Pro Lys Ser Ala Asn Ile Pro Arg Leu Cys Pro Leu
    130                 135                 140

Gln Ala Val Arg Gly Gly Glu Phe Gly Pro Ala Arg Val Pro Val Pro
145                 150                 155                 160
```

```
Phe Ser Leu Ser Asp Leu Lys Gln Ile Lys Ile Asp Leu Gly Lys Phe
            165                 170                 175
Ser Asp Asn Pro Asp Gly Tyr Ile Asp Val Leu Gln Gly Leu Gly Gln
            180                 185                 190
Ser Phe Asp Leu Thr Trp Arg Asp Ile Met Leu Leu Leu Asn Gln Thr
            195                 200                 205
Leu Thr Pro Asn Glu Arg Ser Ala Ala Val Thr Ala Ala Arg Glu Phe
            210                 215                 220
Gly Asp Leu Trp Tyr Leu Ser Gln Ala Asn Asn Arg Met Thr Thr Glu
225                 230                 235                 240
Glu Arg Thr Thr Pro Thr Gly Gln Gln Ala Val Pro Ser Val Asp Pro
            245                 250                 255
His Trp Asp Thr Glu Ser Glu His Gly Asp Trp Cys His Lys His Leu
            260                 265                 270
Leu Thr Cys Val Leu Glu Gly Leu Arg Lys Thr Arg Lys Lys Pro Met
            275                 280                 285
Asn Tyr Ser Met Met Ser Thr Ile Thr Gln Gly Lys Glu Glu Asn Leu
            290                 295                 300
Thr Ala Phe Leu Asp Arg Leu Arg Glu Ala Leu Arg Lys His Thr Ser
305                 310                 315                 320
Leu Ser Pro Asp Ser Ile Glu Gly Gln Leu Ile Leu Lys Asp Lys Phe
            325                 330                 335
Ile Thr Gln Ser Ala Ala Asp Ile Arg Lys Asn Phe Lys Ser Leu Pro
            340                 345                 350
```

(2) INFORMATION FOR SEQ ID NO:119:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:119:

TGCTGGAATT CGGGATCCTA GAACGTATTC                      30

(2) INFORMATION FOR SEQ ID NO:120:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:120:

AGTTCTGCTC CGAAGCTTAG GCAGACTTTT                      30

(2) INFORMATION FOR SEQ ID NO:121:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:121:

```
Met Gly Ser Ser His His His His Ser Ser Gly Leu Val Pro
1               5                   10                  15

Arg Gly Ser His Met Ala Ser Met Thr Gly Gln Gln Met Gly Arg
                20              25              30

Ile Leu Glu Arg Ile Leu Glu Asn Trp Asp Gln Cys Asp Thr Gln Thr
            35              40              45

Leu Arg Lys Lys Arg Phe Ile Phe Phe Cys Ser Thr Ala Trp Pro Gln
    50              55              60

Tyr Pro Leu Gln Gly Arg Glu Thr Trp Leu Pro Glu Gly Ser Ile Asn
65              70              75                      80

Tyr Asn Ile Ile Leu Gln Leu Asp Leu Phe Cys Arg Lys Glu Gly Lys
                85              90              95

Trp Ser Glu Val Pro Tyr Val Gln Thr Phe Phe Ser Leu Arg Asp Asn
            100             105             110

Ser Gln Leu Cys Lys Lys Cys Gly Leu Cys Pro Thr Gly Ser Pro Gln
        115             120             125

Ser Pro Pro Tyr Pro Ser Val Pro Ser Pro Thr Pro Ser Ser Thr
130             135             140

Asn Lys Asp Pro Pro Leu Thr Gln Thr Val Gln Lys Glu Ile Asp Lys
145             150             155             160

Gly Val Asn Asn Glu Pro Lys Ser Ala Asn Ile Pro Arg Leu Cys Pro
                165             170             175

Leu Gln Ala Val Arg Gly Gly Glu Phe Gly Pro Ala Arg Val Pro Val
        180             185             190

Pro Phe Ser Leu Ser Asp Leu Lys Gln Ile Lys Ile Asp Leu Gly Lys
        195             200             205

Phe Ser Asp Asn Pro Asp Gly Tyr Ile Asp Val Leu Gln Gly Leu Gly
    210             215             220

Gln Ser Phe Asp Leu Thr Trp Arg Asp Ile Met Leu Leu Asn Gln
225             230             235             240

Thr Leu Thr Pro Asn Glu Arg Ser Ala Ala Val Thr Ala Ala Arg Glu
            245             250             255

Phe Gly Asp Leu Trp Tyr Leu Ser Gln Ala Asn Asn Arg Met Thr Thr
            260             265             270

Glu Glu Arg Thr Thr Pro Thr Gly Gln Gln Ala Val Pro Ser Val Asp
        275             280             285

Pro His Trp Asp Thr Glu Ser Glu His Gly Asp Trp Cys His Lys His
    290             295             300

Leu Leu Thr Cys Val Leu Glu Gly Leu Arg Lys Thr Arg Lys Lys Pro
305             310             315             320

Met Asn Tyr Ser Met Met Ser Thr Ile Thr Gln Gly Lys Glu Glu Asn
                325             330             335

Leu Thr Ala Phe Leu Asp Arg Leu Arg Glu Ala Leu Arg Lys His Thr
            340             345             350

Ser Leu Ser Pro Asp Ser Ile Glu Gly Gln Leu Ile Leu Lys Asp Lys
        355             360             365

Phe Ile Thr Gln Ser Ala Ala Asp Ile Arg Lys Asn Phe Lys Ser Leu
    370             375             380

Pro Lys Leu Ala Ala Ala Leu Glu His His His His His
385             390             395
```

(2) INFORMATION FOR SEQ ID NO:122:

(i) SEQUENCE CHARACTERISTICS:

(A) LENGTH: 378 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

Met Ala Ser Met Thr Gly Gly Gln Gln Met Gly Arg Ile Leu Glu Arg
1               5                   10                  15

Ile Leu Glu Asn Trp Asp Gln Cys Asp Thr Gln Thr Leu Arg Lys Lys
            20                  25                  30

Arg Phe Ile Phe Phe Cys Ser Thr Ala Trp Pro Gln Tyr Pro Leu Gln
        35                  40                  45

Gly Arg Glu Thr Trp Leu Pro Glu Gly Ser Ile Asn Tyr Asn Ile Ile
    50                  55                  60

Leu Gln Leu Asp Leu Phe Cys Arg Lys Glu Gly Lys Trp Ser Glu Val
65                  70                  75                  80

Pro Tyr Val Gln Thr Phe Phe Ser Leu Arg Asp Asn Ser Gln Leu Cys
                85                  90                  95

Lys Lys Cys Gly Leu Cys Pro Thr Gly Ser Pro Gln Ser Pro Pro Pro
            100                 105                 110

Tyr Pro Ser Val Pro Ser Pro Thr Pro Ser Ser Thr Asn Lys Asp Pro
            115                 120                 125

Pro Leu Thr Gln Thr Val Gln Lys Glu Ile Asp Lys Gly Val Asn Asn
        130                 135                 140

Glu Pro Lys Ser Ala Asn Ile Pro Arg Leu Cys Pro Leu Gln Ala Val
145                 150                 155                 160

Arg Gly Gly Glu Phe Gly Pro Ala Arg Val Pro Val Pro Phe Ser Leu
                165                 170                 175

Ser Asp Leu Lys Gln Ile Lys Ile Asp Leu Gly Lys Phe Ser Asp Asn
            180                 185                 190

Pro Asp Gly Tyr Ile Asp Val Leu Gln Gly Leu Gly Gln Ser Phe Asp
        195                 200                 205

Leu Thr Trp Arg Asp Ile Met Leu Leu Leu Asn Gln Thr Leu Thr Pro
210                 215                 220

Asn Glu Arg Ser Ala Ala Val Thr Ala Ala Arg Glu Phe Gly Asp Leu
225                 230                 235                 240

Trp Tyr Leu Ser Gln Ala Asn Asn Arg Met Thr Thr Glu Glu Arg Thr
            245                 250                 255

Thr Pro Thr Gly Gln Gln Ala Val Pro Ser Val Asp Pro His Trp Asp
                260                 265                 270

Thr Glu Ser Glu His Gly Asp Trp Cys His Lys His Leu Leu Thr Cys
            275                 280                 285

Val Leu Glu Gly Leu Arg Lys Thr Arg Lys Lys Pro Met Asn Tyr Ser
        290                 295                 300

Met Met Ser Thr Ile Thr Gln Gly Lys Glu Glu Asn Leu Thr Ala Phe
305                 310                 315                 320

Leu Asp Arg Leu Arg Glu Ala Leu Arg Lys His Thr Ser Leu Ser Pro
                325                 330                 335

Asp Ser Ile Glu Gly Gln Leu Ile Leu Lys Asp Lys Phe Ile Thr Gln
            340                 345                 350

Ser Ala Ala Asp Ile Arg Lys Asn Phe Lys Ser Leu Pro Lys Leu Ala
        355                 360                 365

Ala Ala Leu Glu His His His His His His (2) INFORMATION FOR SEQ ID NO:123:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:123:

| | |
|---|---|
| CTTGGAGGGT GCATAACCAG GGAAT | 25 |

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:124:

| | |
|---|---|
| TGTCCGCTGT GCTCCTGATC | 20 |

(2) INFORMATION FOR SEQ ID NO:125:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:125:

| | |
|---|---|
| CTATGTCCTT TTGGACTGTT TGGGT | 25 |

(2) INFORMATION FOR SEQ ID NO:126:

(i) SEQUENCE CHARACTERISTICS:
        (A) LENGTH: 764 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:126:

| | |
|---|---|
| TGTCCGCTGT GCTCCTGATC CAGCACAGGC GCCCATTGCC TCTCCCAATT GGGCTAAAGG | 60 |
| CTTGCCATTG TTCCTGCACA GCTAAGTGCC TGGGTTCATC CTAATCGAGC TGAACACTAG | 120 |
| TCACTGGGTT CCACGGTTCT CTTCCATGAC CCATGGCTTC TAATAGAGCT ATAACACTCA | 180 |
| CTGCATGGTC CAAGATTCCA TTCCTTGGAA TCCGTGAGAC CAAGAACCCC AGGTCAGAGA | 240 |
| ACACAAGGCT TGCCACCATG TTGGAAGCAG CCCACCACCA TTTTGGAAGC AGCCCGCCAC | 300 |
| TATCTTGGGA GCTCTGGGAG CAAGGACCCC AGGTAACAAT TGGTGACCA CGAAGGGACC | 360 |
| TGAATCCGCA ACCATGAAGG GATCTCCAAA GCAATTGGAA ATGTTCCTCC CAAGGCAAAA | 420 |
| ATGCCCCTAA GATGTATTCT GGAGAATTGG GACCAATTTG ACCCTCAGAC AGTAAGAAAA | 480 |
| AAATGACTTA TATTCTTCTG CAGTACCGCC CTGGCCACGA TATCCTCTTC AAGGGGGAGA | 540 |
| AACCTGGCCT CCTGAGGGAA GTATAAAATTA TAACACCATC TTACAGCTAG ACCTGTTTTG | 600 |

| TAGAAAAGGA GGCAAATGGA GTGAAGTGCC ATATTTACAA ACTTTCTTTT CATTAAAAGA | 660 |
| CAACTCGCAA TTATGTTAAC AGTGTGATTT GTGTTCCTAC ACGGAAGCCC TCAGATTCTA | 720 |
| CTCCCCACCC CCGGCATCTC CCCTGAATCC CTCCCCAACT TATT | 764 |

(2) INFORMATION FOR SEQ ID NO:127:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:127:

| TGTCCGCTGT GCTCCTGATC CAGCACAGGC GCCCATTGCC TCTCCCAATT GGGCTAAAGG | 60 |
| CTTGCCATTG TTCCTGCACA GCTAAGTGCC TGGGTTCATC CTAATCGAGC TGAACACTAG | 120 |
| TCACTGGGTT CCACGGTTCT CTTCCATGAC CCATGGCTTC TAATAGAGCT ATAACACTCA | 180 |
| CTGCATGGTC CAAGATTCCA TTCCTTGGAA TCCGTGAGAC CAAGAACCCC AGGTCAGAGA | 240 |
| ACACAAGGCT TGCCACCATG TTGGAAGCAG CCCACCACCA TTTTGGAAGC GGCCCGCCAC | 300 |
| TATCTTGGGA GCTCTGGGAG CAAGGACCCC CAGGTAACAA TTTGGTGACC ACGAAGGGAC | 360 |
| CTGAATCCGC AACCATGAAG GGATCTCCAA AGCAATTGGA AATGTTCCTC CCAAGGCAAA | 420 |
| AATGCCCCTA AGATGTATTC TGGAGAATTG GACCAATCT GACCCTCAGA CAGTAAGAAA | 480 |
| AAAAATGACT TATATTCTTC TGCAGTACCG CCTGGCCACG GATATCCTCT TCAAGGGGA | 540 |
| GAAACCTGGC CTCCTGAGGG AAGTATAAAT TATAACACCA TCTTACAGCT AGACCTGTTT | 600 |
| TGTAGAAAAG GAGGCAAATG GAGTGAAGTG CCATATTTAC AAACTTTCTT TTCATTAAAA | 660 |
| GACAACTCGC AATTATGTAA ACAGTGTGAT TTGTGTCCTA CAGGAAGCCC TCAGATCTAC | 720 |
| CTCCCTACCC CGGCATCTCC CTGACTCCTT CCCCAACTAA TAAGGACCCA CTTCAGCCCA | 780 |
| AACAGTCCAA AAGGACATAG | 800 |

(2) INFORMATION FOR SEQ ID NO:128:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:128:

| GACTTGAGCC AGTCYTCATA CCTGGACAYT CTTGTCCTTC GGTACATGGA TGATTTACTT | 60 |
| TTAGCCACCC ATTCAGAAAC CTTGTGCCAT CAAGCCACCC AAGCACTCTT AAATTTCCTT | 120 |
| GCTACCTGTG GCTACAAGGT TTCCAAACCA AAGGCTCAGC TCTGCTCACA GCAGGTTAAA | 180 |
| TACTTAGGGC TAAAATTATC CAAAGGCACC AGAACCCTCA GTGAGGAACG TATCCAGCCT | 240 |
| ATACTGGGTT ATCCTCATCC CAAAACCCTA AAGCAACTAA CAGCGTTCCT TGGCATAACA | 300 |
| GGTTTCTGCC AAATATGGAT TCCCAGGTAC AGCAARRTAG CCAGACCATT AAATACACGA | 360 |
| ATTAAGGAAA CTCAAAAAGC CARTACCCAT TTAGTAAGAT GGACAYCTGA AGCAGAAGTG | 420 |
| GCTTTCCAGG CCCTAAAG | 438 |

(2) INFORMATION FOR SEQ ID NO:129:

(i) SEQUENCE CHARACTERISTICS:
            (A) LENGTH: 438 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:129:

| | |
|---|---|
| GACTTGAGCC AGTCCTCATA CCTGGACACT CTTGTCCTTC GGTACATGGA TGATTTACTT | 60 |
| TTAGCCACCC ATTCAGAAAC CTTGTGCCAT CAAGCCACCC AAGCACTCTT AAATTTCCTT | 120 |
| GCTACCTGTG GCTACAAGGT TTCCAAACCA AAGGCTCAGC TCTGCTCACA GCAGGTTAAA | 180 |
| TACTTAGGGC TAAAATTATC CAAAGGCACC AGAACCCTCA GTGAGGAACG TATCCAGCCT | 240 |
| ATACTGGGTT ATCCTCATCC CAAAACCCTA AAGCAACTAA CAGCGTTCCT TGGCATAACA | 300 |
| GGTTTCTGCC AAATATGGAT TCCCAGGTAC AGCAAGATAG CCAGACCATT AAATACACGA | 360 |
| ATTAAGGAAA CTCAAAAAGC CAATACCCAT TTAGTAAGAT GGACACCTGA AGCAGAAGTG | 420 |
| GCTTTCCAGG CCCTAAAG | 438 |

(2) INFORMATION FOR SEQ ID NO:130:

(i) SEQUENCE CHARACTERISTICS:
            (A) LENGTH: 438 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:130:

| | |
|---|---|
| GACTTGAGCC AGTCCTCATA CCTGGACACT CTTGTCCTTC GGTACATGGA TGATTTACTT | 60 |
| TTAGCCACCC ATTCAGAAAC CTTGTGCCAT CAAGCCACCC AAGCACTCTT AAATTTCCTT | 120 |
| GCTACCTGTG GCTACAAGGT TTCCAAACCA AAGGCTCAGC TCTGCTCACA GCAGGTTAAA | 180 |
| TACTTAGGGC TAAAATTATC CAAAGGCACC AGAACCCTCA GTGAGGAACG TATCCAGCCT | 240 |
| ATACTGGGTT ATCCTCATCC CAAAACCCTA AAGCAACTAA CAGCGTTCCT TGGCATAACA | 300 |
| GGTTTCTGCC AAATATGGAT TCCCAGGTAC AGCAAAGTAG CCAGACCATT AAATACACGA | 360 |
| ATTAAGGAAA CTCAAAAAGC CAGTACCCAT TTAGTAAGAT GGACACCTGA AGCAGAAGTG | 420 |
| GCTTTCCAGG CCCTAAAG | 438 |

(2) INFORMATION FOR SEQ ID NO:131:

(i) SEQUENCE CHARACTERISTICS:
            (A) LENGTH: 438 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:131:

| | |
|---|---|
| GACTTGAGCC AGTCYTCATA CCTGGACAYT CTTGTCCTTC GGTACATGGA TGATTTACTT | 60 |
| TTAGCCACCC ATTCAGAAAC CTTGTGCCAT CAAGCCACCC AAGCACTCTT AAATTTCCTT | 120 |
| GCTACCTGTG GCTACAAGGT TTCCAAACCA AAGGCTCAGC TCTGCTCACA GCAGGTTAAA | 180 |
| TACTTAGGGC TAAAATTATC CAAAGGCACC AGAACCCTCA GTGAGGAACG TATCCAGCCT | 240 |
| ATACTGGGTT ATCCTCATCC CAAAACCCTA AAGCAACTAA CAGCGTTCCT TGGCATAACA | 300 |

```
GGTTTCTGCC AAATATGGAT TCCCAGGTAC AGCAAAATAG CCAGACCATT AAATACACGA    360

ATTAAGGAAA CTCAAAAAGC CAATACCCAT TTAGTAAGAT GGACATCTGA AGCAGAAGTG    420

GCTTTCCAGG CCCTAAAG                                                  438
```

(2) INFORMATION FOR SEQ ID NO:132:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:132:

```
Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Ile Ala Arg Pro Leu Asn Thr Arg Ile Lys Glu Thr Gln Lys Ala Asn
        115                 120                 125

Thr His Leu Val Arg Trp Thr Pro Glu Ala Glu Val Ala Phe Gln Ala
    130                 135                 140

Leu Lys
145
```

(2) INFORMATION FOR SEQ ID NO:133:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:133:

```
Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95
```

Leu Gly Ile Thr Gly Phe Cys Gln Ile Trp Ile Pro Arg Tyr Ser Lys
            100                 105                 110

Val Ala Arg Pro Leu Asn Thr Arg Ile Lys Glu Thr Gln Lys Ala Ser
        115                 120                 125

Thr His Leu Val Arg Trp Thr Pro Glu Ala Glu Val Ala Phe Gln Ala
    130                 135                 140

Leu Lys
145

(2) INFORMATION FOR SEQ ID NO:134:

(i) SEQUENCE CHARACTERISTICS:
       (A) LENGTH: 146 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:134:

Asp Leu Ser Gln Ser Ser Tyr Leu Asp Xaa Leu Val Leu Arg Tyr Met
1               5                   10                  15

Asp Asp Leu Leu Leu Ala Thr His Ser Glu Thr Leu Cys His Gln Ala
            20                  25                  30

Thr Gln Ala Leu Leu Asn Phe Leu Ala Thr Cys Gly Tyr Lys Val Ser
        35                  40                  45

Lys Pro Lys Ala Gln Leu Cys Ser Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
            100                 105                 110

Ile Ala Arg Pro Leu Asn Thr Arg Ile Lys Glu Thr Gln Lys Ala Asn
        115                 120                 125

Thr His Leu Val Arg Trp Thr Ser Glu Ala Glu Val Ala Phe Gln Ala
    130                 135                 140

Leu Lys
145

(2) INFORMATION FOR SEQ ID NO:135:

(i) SEQUENCE CHARACTERISTICS:
       (A) LENGTH: 429 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:135:

GACTTGAGCC AGTCCTCATA CCTGGACATT CTTGTTCTTC AGTATGGGGA TGAYTTRATT    60

ATAGCCACCC ATTCAGAAAC CTTGTGGCAY CAAGCCACCC AAGYGCTCTT AAATTTCCTY   120

GCTACCTGTG GCTCCAAACA AAARGCTCAY CTCTGCTCAC AYCAGGTTAA ATACTTAGGG   180

CTAAAATTAT CCAAAGTCRC CAGGGCCCTC AGAGAGGAAC GTATCCAGCG TATACTGGRT   240

TATCCYCATC CCAYAACCRT AAAGCAACTA AGARGGTTCC TTGGCATAYC AGCCTTCTGC   300

```
CGAATATGGA TTCCCRGATA CAGYGAAATA GCCAGGCCAT TATGTACATT ARYTAAGGAA    360

ACTCAGAAAG CCAATACCCA TATAGTAAGA TGGACACCTG AAACAGAAGT GGCTTTCCAG    420

GCCCTAAAG                                                            429
```

(2) INFORMATION FOR SEQ ID NO:136:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:136:

```
GACTTGAGCC AGTCCTCATA CCTGGACATT CTTGTTCTTC AGTATGGGGA TGACTTAATT     60

ATAGCCACCC ATTCAGAAAC CTTGTGGCAT CAAGCCACCC AAGCGCTCTT AAATTTCCTT    120

GCTACCTGTG GCTCCAAACA AAAGGCTCAC CTCTGCTCAC ACCAGGTTAA ATACTTAGGG    180

CTAAAATTAT CCAAAGTCAC CAGGGCCCTC AGAGAGGAAC GTATCCAGCG TATACTGGCT    240

TATCCTCATC CCATAACCCT AAAGCAACTA AGAGGGTTCC TTGGCATATC AGCCTTCTGC    300

CGAATATGGA TTCCCGGATA CAGTGAAATA GCCAGGCCAT TATGTACATT AATTAAGGAA    360

ACTCAGAAAG CCAATACCCA TATAGTAAGA TGGACACCTG AAACAGAAGT GGCTTTCCAG    420

GCCCTAAAG                                                            429
```

(2) INFORMATION FOR SEQ ID NO:137:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:137:

```
GACTTGAGCC AGTCCTCATA CCTGGACATT CTTGTTCTTC AGTATGGGGA TGACTTAATT     60

ATAGCCACCC ATTCAGAAAC CTTGTGGCAT CAAGCCACCC AAGTGCTCTT AAATTTCCTC    120

GCTACCTGTG GCTCCAAACA AAAGGCTCAC CTCTGCTCAC AGCAGGTTAA ATACTTAGGG    180

CTAAAATTAT CCAAAGTCGC CAGGGCCCTC AGAGAGGAAC GTATCCAGCG TATACTGGAT    240

TATCCTCATC CCAAAACCAT AAAGCAACTA AGAGGGTTCC TTGGCATAAC AGCCTTCTGC    300

CGAATATGGA TTCCCCGATA CAGTGAAATA GCCAGGCCAT TATGTACATT AGTTAAGGAA    360

ACTCAGAAAG CCAATACCCA TATAGTAAGA TGGACACCTG AGACAGAAGT GGCTTTCCAG    420

GCCCTAAAG                                                            429
```

(2) INFORMATION FOR SEQ ID NO:138:

(i) SEQUENCE CHARACTERISTICS:
        (A) LENGTH: 429 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:138:

```
GACTTGAGCC AGTCCTCATA CCTGGACATT CTTGTTCCTC AGTATGGGGA TGATTTAATT     60
```

```
ATAGCCACCC ATTCAGAAAC CTTGTGGCAC CAAGCCACCC AAGCGCTCTT AAATTTCCTC      120

GCTACCTGTG GCTCCAAACA AAAGGCTCAG CTCTGCTCAC AGCAGGTTAA ATACTTAGGG      180

CTAAAATTAT CCAAAGTCAC CAGGGCCCTC AGAGAGGAAC GTATCCAGCG TATACTGGCT      240

TATCCCCATC CCAAAACCCT AAAGCAACTA AGARGGTTCC TTGGCATAAC AGCCTTCTGC      300

CGAATATGGA TTCCCAGATA CAGCGAAATA GCCAGGCCAT TATGTACATT ATCTAAGGAA      360

ACTCAGAAAG CCAATACCCA TATAGTAAGA TGGACACCTG AAACAGAAGT GGCTTTCCAG      420

GCCCTAAAG                                                             429
```

(2) INFORMATION FOR SEQ ID NO:139:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

```
Asp Leu Ser Gln Ser Ser Tyr Leu Asp Ile Leu Val Leu Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala His Leu Cys Ser His Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Ile Thr Leu Lys Gln Leu Arg Gly Phe Leu Gly Ile
                85                  90                  95

Ser Ala Phe Cys Arg Ile Trp Ile Pro Gly Tyr Ser Glu Ile Ala Arg
            100                 105                 110

Pro Leu Cys Thr Leu Ile Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140
```

(2) INFORMATION FOR SEQ ID NO:140:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

```
Asp Leu Ser Gln Ser Ser Tyr Leu Asp Ile Leu Val Leu Gln Tyr Arg
1               5                   10                  15

Asp Asp Leu Ile Ile Ala Thr His Ser Glu Thr Leu Trp His Gln Ala
            20                  25                  30

Thr Gln Val Leu Leu Asn Phe Leu Ala Thr Cys Gly Ser Lys Gln Arg
        35                  40                  45

Ala Gln Leu Cys Ser Gln Gln Val Lys Tyr Leu Gly Leu Lys Leu Ser
    50                  55                  60
```

```
Lys Val Ala Arg Ala Leu Arg Glu Glu Arg Ile Gln Arg Ile Leu Asp
 65                  70                  75                  80

Tyr Pro His Pro Lys Thr Ile Lys Gln Leu Arg Gly Phe Leu Gly Ile
                 85                  90                  95

Thr Ala Phe Cys Arg Ile Trp Ile Pro Arg Tyr Ser Glu Ile Ala Arg
                100                 105                 110

Pro Leu Cys Thr Leu Val Lys Glu Thr Gln Lys Ala Asn Thr His Ile
                115                 120                 125

Val Arg Trp Thr Pro Glu Thr Glu Val Ala Phe Gln Ala Leu Lys
                130                 135                 140
```

(2) INFORMATION FOR SEQ ID NO:141:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

```
Asp Leu Ser Gln Ser Ser Tyr Leu Asp Ile Leu Val Pro Gln Tyr Gly
 1               5                  10                  15

Asp Asp Leu Ile Ile Ala Thr His Ser Glu Thr Leu Trp His Gln Ala
                 20                  25                  30

Thr Gln Ala Leu Leu Asn Phe Leu Ala Thr Cys Gly Ser Lys Gln Lys
                 35                  40                  45

Ala Gln Leu Cys Ser Gln Gln Val Lys Tyr Leu Gly Leu Lys Leu Ser
                 50                  55                  60

Lys Val Thr Arg Ala Leu Arg Glu Glu Arg Ile Gln Arg Ile Leu Ala
 65                  70                  75                  80

Tyr Pro His Pro Lys Thr Leu Lys Gln Leu Arg Xaa Phe Leu Gly Ile
                 85                  90                  95

Thr Ala Phe Cys Arg Ile Trp Ile Pro Arg Tyr Ser Glu Ile Ala Arg
                100                 105                 110

Pro Leu Cys Thr Leu Ser Lys Glu Thr Gln Lys Ala Asn Thr His Ile
                115                 120                 125

Val Arg Trp Thr Pro Glu Thr Glu Val Ala Phe Gln Ala Leu Lys
                130                 135                 140
```

(2) INFORMATION FOR SEQ ID NO:142:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:142:

GGCCAGGCAT CAGCCCAAGA CTTGA                                        25

(2) INFORMATION FOR SEQ ID NO:143:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:143:

TGCAAGCTCA TCCCTSRGAC CT                                              22

(2) INFORMATION FOR SEQ ID NO:144:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:144:

GACTTGAGCC AGTCCTCATA CCT                                             23

(2) INFORMATION FOR SEQ ID NO:145:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:145:

CTTTAGGGCC TGGAAAGCCA CT                                              22

(2) INFORMATION FOR SEQ ID NO:146:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:146:

Phe Cys Ile Pro Val Arg Pro Asp
1               5

(2) INFORMATION FOR SEQ ID NO:147:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:147:

Arg Pro Asp Ser Gln Phe Leu Phe
1               5

(2) INFORMATION FOR SEQ ID NO:148:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide

```
        (xi) SEQUENCE DESCRIPTION: SEQ ID NO:148:

Thr Val Leu Pro Gln Gly Phe Arg
1               5

(2) INFORMATION FOR SEQ ID NO:149:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:149:

Leu Phe Gly Gln Ala Leu Ala Gln
1               5

(2) INFORMATION FOR SEQ ID NO:150:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:150:

Asp Ala Phe Phe Cys Ile Pro Val
1               5

(2) INFORMATION FOR SEQ ID NO:151:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:151:

Ala Phe Phe Cys Ile Pro Val Arg
1               5

(2) INFORMATION FOR SEQ ID NO:152:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:152:

Phe Phe Cys Ile Pro Val Arg Pro
1               5

(2) INFORMATION FOR SEQ ID NO:153:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide
```

(xi) SEQUENCE DESCRIPTION: SEQ ID NO:153:

Cys Ile Pro Val Arg Pro Asp Ser
1               5

(2) INFORMATION FOR SEQ ID NO:154:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:154:

Ile Pro Val Arg Pro Asp Ser Gln
1               5

(2) INFORMATION FOR SEQ ID NO:155:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:155:

Pro Val Arg Pro Asp Ser Gln Phe
1               5

(2) INFORMATION FOR SEQ ID NO:156:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:156:

Val Arg Pro Asp Ser Gln Phe Leu
1               5

(2) INFORMATION FOR SEQ ID NO:157:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:157:

Pro Asp Ser Gln Phe Leu Phe Ala
1               5

(2) INFORMATION FOR SEQ ID NO:158:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO:158:

Asp Ser Gln Phe Leu Phe Ala Phe
1               5

(2) INFORMATION FOR SEQ ID NO:159:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:159:

Ser Gln Phe Leu Phe Ala Phe Glu
1               5

(2) INFORMATION FOR SEQ ID NO:160:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:160:

Gln Phe Leu Phe Ala Phe Glu Asp
1               5

(2) INFORMATION FOR SEQ ID NO:161:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:161:

Phe Leu Phe Ala Phe Glu Asp Pro
1               5

(2) INFORMATION FOR SEQ ID NO:162:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:162:

Ala Phe Glu Asp Pro Leu Asn Pro
1               5

(2) INFORMATION FOR SEQ ID NO:163:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:163:

Phe Glu Asp Pro Leu Asn Pro Thr
1               5

(2) INFORMATION FOR SEQ ID NO:164:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:164:

Glu Asp Pro Leu Asn Pro Thr Ser
1               5

(2) INFORMATION FOR SEQ ID NO:165:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:165:

Asp Pro Leu Asn Pro Thr Ser Gln
1               5

(2) INFORMATION FOR SEQ ID NO:166:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:166:

Pro Leu Asn Pro Thr Ser Gln Leu
1               5

(2) INFORMATION FOR SEQ ID NO:167:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:167:

Leu Asn Pro Thr Ser Gln Leu Thr
1               5

(2) INFORMATION FOR SEQ ID NO:168:

(i) SEQUENCE CHARACTERISTICS:
            (A) LENGTH: 8 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:168:

Asn Pro Thr Ser Gln Leu Thr Trp
1               5

(2) INFORMATION FOR SEQ ID NO:169:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:169:

Pro Thr Ser Gln Leu Thr Trp Thr
1               5

(2) INFORMATION FOR SEQ ID NO:170:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:170:

Thr Ser Gln Leu Thr Trp Thr Val
1               5

(2) INFORMATION FOR SEQ ID NO:171:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:171:

Ser Gln Leu Thr Trp Thr Val Leu
1               5

(2) INFORMATION FOR SEQ ID NO:172:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:172:

Gln Leu Thr Trp Thr Val Leu Pro
1               5

(2) INFORMATION FOR SEQ ID NO:173:

(i) SEQUENCE CHARACTERISTICS:
        (A) LENGTH: 8 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:173:

Leu Thr Trp Thr Val Leu Pro Gln
1               5

(2) INFORMATION FOR SEQ ID NO:174:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:174:

Thr Trp Thr Val Leu Pro Gln Gly
1               5

(2) INFORMATION FOR SEQ ID NO:175:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:175:

Trp Thr Val Leu Pro Gln Gly Phe
1               5

(2) INFORMATION FOR SEQ ID NO:176:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:176:

Val Leu Pro Gln Gly Phe Arg Asp
1               5

(2) INFORMATION FOR SEQ ID NO:177:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:177:

Leu Pro Gln Gly Phe Arg Asp Ser
1               5

(2) INFORMATION FOR SEQ ID NO:178:

(i) SEQUENCE CHARACTERISTICS:
            (A) LENGTH: 8 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:178:

Pro Gln Gly Phe Arg Asp Ser Pro
1               5

(2) INFORMATION FOR SEQ ID NO:179:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:179:

Gln Gly Phe Arg Asp Ser Pro His
1               5

(2) INFORMATION FOR SEQ ID NO:180:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:180:

Gly Phe Arg Asp Ser Pro His Leu
1               5

(2) INFORMATION FOR SEQ ID NO:181:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:181:

Phe Arg Asp Ser Pro His Leu Phe
1               5

(2) INFORMATION FOR SEQ ID NO:182:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:182:

Arg Asp Ser Pro His Leu Phe Gln
1               5

(2) INFORMATION FOR SEQ ID NO:183:

(i) SEQUENCE CHARACTERISTICS:

```
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:183:

Asp Ser Pro His Leu Phe Gly Gln
1               5

(2) INFORMATION FOR SEQ ID NO:184:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:184:

Ser Pro His Leu Phe Gly Gln Ala
1               5

(2) INFORMATION FOR SEQ ID NO:185:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:185:

Pro His Leu Phe Gly Gln Ala Leu
1               5

(2) INFORMATION FOR SEQ ID NO:186:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:186:

His Leu Phe Gly Gln Ala Leu Ala
1               5

(2) INFORMATION FOR SEQ ID NO:187:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:187:

TGGAAAGTGT TACCCC                                                     16

(2) INFORMATION FOR SEQ ID NO:188:

(i) SEQUENCE CHARACTERISTICS:
```

(A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:188:

AGTGTTACCC CAAGG                                                            15

(2) INFORMATION FOR SEQ ID NO:189:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:189:

ATGTACCTAC TGTACGAC                                                         18

(2) INFORMATION FOR SEQ ID NO:190:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:190:

TGGAAAGTAC TACCCCAAGG GTTTAAAAAT AGTCCCACCC TGTTCGAAAT GCAGCTGGCC            60

CATATCCTGC AGCCCATTCG GCAAGCTTTC CCCCAATGCA CTATTCTTCA GTACATGGAT          120

GACATTCTC                                                                  129

(2) INFORMATION FOR SEQ ID NO:191:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:191:

TACAATGTGC TTCCACAGGG ATGGAAAGGA TCACCAGCAA TATTCCAAAG TAGCATGACA            60

AAAATCTTAG AGCCTTTTAA AAAACAAAAT CCAGACATAG TTATCTATCA ATACATGGAT          120

GATTTGTAT                                                                  129

(2) INFORMATION FOR SEQ ID NO:192:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:192:

TGGACCAGAC TCCCACAGGG TTTCAAAAAC AGTCCCACCC TGTTTGATGA GGCACTGCAC            60

```
AGAGACCTAG CAGACTTCCG GATCCAGCAC CCAGACTTGA TCCTGCTACA GTACGTGGAT      120

GACTTACTG                                                              129
```

(2) INFORMATION FOR SEQ ID NO:193:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:193:

```
TGGAAGGTTT TACCACAAGG TATGGCCAAC AGTCCTACCT TATGTCAAAA ATATGTGGCC      60

ACAGCCATAC ATAAGGTTAG ACATGCCTGG AAACAAATGT ATATTATACA TTACATGGAT     120

GACATCCTA                                                             129
```

(2) INFORMATION FOR SEQ ID NO:194:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:194:

```
TGGATGGTCT TGCCCCAAGG GTTTAGGGAT AGCCCTCATC TGTTTGGTCA GGCCCTAGCC      60

AAAGATCTAG GCCACTTCTC AAGTCCAGGC ACTCTGGTCC TTCAATATGT GGATGATTTA     120

CTT                                                                   123
```

(2) INFORMATION FOR SEQ ID NO:195:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:195:

```
GTTCAGGGAT AGCCCCCATC TATTTGGCCA GGCATTAGCC CAAGACTTGA GCCAATTCTC      60

ATACCTGGAC ACTCTTGTCC TTCAG                                            85
```

(2) INFORMATION FOR SEQ ID NO:196:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:196:

```
CATCTNTTTG GNCAGGCANT AGC                                              23
```

(2) INFORMATION FOR SEQ ID NO:197:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:197:

CTTGAGCCAG TTCTCATACC TGGA                                              24

(2) INFORMATION FOR SEQ ID NO:198:

(i) SEQUENCE CHARACTERISTICS:
        (A) LENGTH: 683 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:198:

Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
        195                 200                 205

Gly Gln Ala Leu Ala Gln Asp Leu Ser Gln Pro Ser Tyr Leu Asp Ile
    210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
                245                 250                 255

Cys Gly Tyr Lys Val Ser Lys Pro Lys Ala Arg Leu Cys Ser Gln Glu
            260                 265                 270

Ile Arg Tyr Leu Gly Leu Lys Leu Ser Lys Gly Thr Arg Ala Leu Ser
        275                 280                 285

Glu Glu Arg Ile Gln Pro Ile Leu Ala Tyr Pro His Pro Lys Thr Leu
    290                 295                 300

```
Lys Gln Leu Arg Gly Phe Leu Gly Ile Thr Gly Phe Cys Arg Lys Gln
305                 310                 315                 320

Ile Pro Arg Tyr Thr Pro Ile Ala Arg Pro Leu Tyr Thr Leu Ile Arg
                325                 330                 335

Glu Thr Gln Lys Ala Asn Thr Tyr Leu Val Arg Trp Thr Pro Thr Glu
                340                 345                 350

Val Ala Phe Gln Ala Leu Lys Lys Ala Leu Thr Gln Ala Pro Val Phe
            355                 360                 365

Ser Leu Pro Thr Gly Gln Asp Phe Ser Leu Tyr Ala Thr Glu Lys Thr
370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
                405                 410                 415

Pro His Cys Leu Trp Val Met Ala Ala Val Ala Val Leu Val Ser Glu
                420                 425                 430

Ala Val Lys Ile Ile Gln Gly Arg Asp Leu Thr Val Trp Thr Ser His
            435                 440                 445

Asp Val Asn Gly Ile Leu Thr Ala Lys Gly Asp Leu Trp Leu Ser Asp
450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Gln Ile Glu His Asn Cys Gln Gln Val Ile Ala Gln Thr
                500                 505                 510

Tyr Ala Ala Arg Gly Asp Leu Leu Glu Val Pro Leu Thr Asp Pro Asp
            515                 520                 525

Leu Asn Leu Tyr Thr Asp Gly Ser Ser Leu Ala Glu Lys Gly Leu Arg
530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
                565                 570                 575

Thr Trp Ala Leu Glu Leu Gly Glu Gly Lys Arg Val Asn Ile Tyr Ser
                580                 585                 590

Asp Ser Lys Tyr Ala Tyr Leu Val Leu His Ala His Ala Ala Ile Trp
            595                 600                 605

Arg Glu Arg Glu Phe Leu Thr Ser Glu Gly Thr Pro Ile Asn His Gln
610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Arg Glu Ile
                645                 650                 655

Glu Gly Asn Arg Gln Ala Asp Ile Glu Ala Lys Lys Ala Ala Arg Gln
                660                 665                 670

Asp Ser Pro Leu Glu Met Leu Ile Glu Gly Pro
            675                 680

(2) INFORMATION FOR SEQ ID NO:199:

(i) SEQUENCE CHARACTERISTICS:
        (A) LENGTH: 143 amino acids
        (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO:199:

Asp Leu Ser Gln Ser Ser Tyr Leu Asp Ile Leu Val Leu Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala Gln Leu Cys Ser Gln Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Lys Thr Leu Lys Gln Leu Arg Gly Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Xaa Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140

(2) INFORMATION FOR SEQ ID NO:200:

(i) SEQUENCE CHARACTERISTICS:
        (A) LENGTH: 683 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:200:

Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

Glu Gly Gln Tyr Gly Gln Ala Lys Asn Ala Arg Pro Val Gln Val Lys
    50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
        115                 120                 125

Ile Ile Asn Glu Ala Val Phe Pro Leu Tyr Pro Ala Val Ser Ser Pro
    130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
                165                 170                 175

-continued

```
Gln Phe Leu Phe Ala Phe Glu Asp Pro Leu Asn Pro Thr Ser Gln Leu
            180                 185                 190
Thr Trp Thr Val Leu Pro Gln Gly Phe Arg Asp Ser Pro His Leu Phe
        195                 200                 205
Gly Gln Ala Leu Ala Gln Asp Leu Ser Gln Pro Ser Tyr Leu Asp Ile
        210                 215                 220
Leu Val Leu Gln Tyr Val Asp Asp Leu Leu Val Ala Arg Ser Glu
225                 230                 235                 240
Thr Leu Cys His Gln Ala Thr Gln Glu Leu Leu Ile Phe Leu Thr Thr
                245                 250                 255
Cys Gly Tyr Lys Val Ser Lys Pro Lys Ala Arg Leu Cys Ser Gln Glu
                260                 265                 270
Ile Arg Tyr Leu Gly Leu Lys Leu Ser Lys Gly Thr Arg Ala Leu Ser
            275                 280                 285
Glu Glu Arg Ile Gln Pro Ile Leu Ala Tyr Pro His Pro Lys Thr Leu
            290                 295                 300
Lys Gln Leu Arg Gly Phe Leu Gly Ile Thr Gly Phe Cys Arg Lys Gln
305                 310                 315                 320
Ile Pro Arg Tyr Thr Pro Ile Ala Arg Pro Leu Tyr Thr Leu Ile Arg
                325                 330                 335
Glu Thr Gln Lys Ala Asn Thr Tyr Leu Val Arg Trp Thr Pro Thr Glu
                340                 345                 350
Val Ala Phe Gln Ala Leu Lys Lys Ala Leu Thr Gln Ala Pro Val Phe
            355                 360                 365
Ser Leu Pro Thr Gly Gln Asp Phe Ser Leu Tyr Ala Thr Glu Lys Thr
        370                 375                 380
Gly Ile Ala Leu Gly Val Leu Thr Gln Val Ser Gly Met Ser Leu Gln
385                 390                 395                 400
Pro Val Val Tyr Leu Ser Lys Glu Ile Asp Val Val Ala Lys Gly Trp
                405                 410                 415
Pro His Cys Leu Trp Val Met Ala Ala Val Ala Val Leu Val Ser Glu
                420                 425                 430
Ala Val Lys Ile Ile Gln Gly Arg Asp Leu Thr Val Trp Thr Ser His
            435                 440                 445
Asp Val Asn Gly Ile Leu Thr Ala Lys Gly Asp Leu Trp Leu Ser Asp
        450                 455                 460
Asn His Leu Leu Asn Tyr Gln Ala Leu Leu Glu Glu Pro Val Leu
465                 470                 475                 480
Arg Leu Arg Thr Cys Ala Thr Leu Gln Pro Ala Thr Phe Leu Pro Asp
                485                 490                 495
Asn Glu Glu Gln Ile Glu His Asn Cys Gln Gln Val Ile Ala Gln Thr
                500                 505                 510
Tyr Ala Ala Arg Gly Asp Leu Leu Glu Val Pro Leu Thr Asp Pro Asp
            515                 520                 525
Leu Asn Leu Tyr Thr Asp Gly Ser Ser Leu Ala Glu Lys Gly Leu Arg
        530                 535                 540
Lys Ala Gly Tyr Ala Val Ile Ser Asp Asn Gly Ile Leu Glu Ser Asn
545                 550                 555                 560
Arg Leu Thr Pro Gly Thr Ser Ala His Leu Ala Glu Leu Ile Ala Leu
                565                 570                 575
Thr Trp Ala Leu Glu Leu Gly Glu Gly Lys Arg Val Asn Ile Tyr Ser
            580                 585                 590
```

```
Asp Ser Lys Tyr Ala Tyr Leu Val Leu His Ala His Ala Ala Ile Trp
        595                 600                 605

Arg Glu Arg Glu Phe Leu Thr Ser Glu Gly Thr Pro Ile Asn His Gln
        610                 615                 620

Glu Ala Ile Arg Arg Leu Leu Ala Val Gln Lys Pro Lys Glu Val
625                 630                 635                 640

Ala Val Leu His Cys Gln Gly His Gln Glu Glu Glu Arg Glu Ile
                645                 650                 655

Glu Gly Asn Arg Gln Ala Asp Ile Glu Ala Lys Lys Ala Ala Arg Gln
                660                 665                 670

Asp Ser Pro Leu Glu Met Leu Ile Glu Gly Pro
        675                 680
```

(2) INFORMATION FOR SEQ ID NO:201:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:201:

```
GACTTGAGCC AGTCYTCATA CCTGGACAYT CTTGTYCYTC RGTAYRKGGA TGAYTTAMTT    60
WTAGCCACCC ATTCAGAAAC CTTGTGSCAY CAAGCCACCC AAGYRCTCTT AAATTTCCTY   120
GCTACCTGTG GCTACAAGGT TTCCAAACMA ARGGCTCASC TCTGCTCACA SCAGGTTAAA   180
TACTTAGGGC TAAAATTATC CAAAGKCRCC AGRRCCCTCA GWGAGGAACG TATCCAGCST   240
ATACTGGVTT ATCCYCATCC CAWAACCMTA AAGCAACTAA SARSGTTCCT TGGCATAWCA   300
GSYTTCTGCC RAATATGGAT TCCCVGRTAC AGYRARRTAG CCAGRCCATT AWRTACAYKA   360
DYTAAGGAAA CTCARAAAGC CARTACCCAT WTAGTAAGAT GGACAYCTGA RRCAGAAGTG   420
GCTTTCCAGG CCCTAAAG                                                 438
```

(2) INFORMATION FOR SEQ ID NO:202:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:202:

```
Asp Leu Ser Gln Ser Ser Tyr Leu Asp Thr Leu Val Leu Arg Tyr Met
1               5                   10                  15

Asp Asp Leu Leu Leu Ala Thr His Ser Glu Thr Leu Cys His Gln Ala
                20                  25                  30

Thr Gln Ala Leu Leu Asn Phe Leu Ala Thr Cys Gly Tyr Lys Val Ser
            35                  40                  45

Lys Pro Lys Ala Gln Leu Cys Ser Gln Gln Val Lys Tyr Leu Gly Leu
    50                  55                  60

Lys Leu Ser Lys Gly Thr Arg Thr Leu Ser Glu Glu Arg Ile Gln Pro
65                  70                  75                  80

Ile Leu Gly Tyr Pro His Pro Lys Thr Leu Lys Gln Leu Thr Ala Phe
                85                  90                  95

Leu Gly Ile Thr Gly Phe Cys Gln Ile Trp Ile Pro Arg Tyr Ser Lys
```

-continued

```
                    100                 105                 110
Ile Ala Arg Pro Leu Asn Thr Arg Ile Lys Glu Thr Gln Lys Ala Asn
            115                 120                 125
Thr His Leu Val Arg Trp Thr Pro Glu Ala Glu Val Ala Phe Gln Ala
    130                 135                 140
Leu Lys
145

(2) INFORMATION FOR SEQ ID NO:203:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:203:

Asp Leu Ser Gln Ser Ser Tyr Leu Asp Ile Leu Val Leu Gln Tyr Gly
1               5                   10                  15

Asp Asp Leu Ile Ile Ala Thr His Ser Glu Thr Leu Trp His Gln Ala
            20                  25                  30

Thr Gln Ala Leu Leu Asn Phe Leu Ala Thr Cys Gly Ser Lys Gln Lys
        35                  40                  45

Ala Gln Leu Cys Ser Gln Gln Val Lys Tyr Leu Gly Leu Lys Leu Ser
    50                  55                  60

Lys Val Thr Arg Ala Leu Arg Glu Glu Arg Ile Gln Arg Ile Leu Ala
65                  70                  75                  80

Tyr Pro His Pro Lys Thr Leu Lys Gln Leu Arg Gly Phe Leu Gly Ile
                85                  90                  95

Thr Ala Phe Cys Arg Ile Trp Ile Pro Arg Tyr Ser Glu Ile Ala Arg
            100                 105                 110

Pro Leu Cys Thr Leu Xaa Lys Glu Thr Gln Lys Ala Asn Thr His Ile
        115                 120                 125

Val Arg Trp Thr Pro Glu Thr Glu Val Ala Phe Gln Ala Leu Lys
    130                 135                 140

(2) INFORMATION FOR SEQ ID NO:204:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:204:

Asp Leu Ser Gln Ser Ser Tyr Leu Asp Xaa Leu Val Leu Xaa Tyr Xaa
1               5                   10                  15

Asp Asp Leu Xaa Xaa Ala Thr His Ser Glu Thr Leu Xaa His Gln Ala
            20                  25                  30

Thr Gln Ala Leu Leu Asn Phe Leu Ala Thr Cys Gly Xaa Lys Xaa Xaa
        35                  40                  45

Xaa Xaa Lys Ala Gln Leu Cys Ser Gln Gln Val Lys Tyr Leu Gly Leu
    50                  55                  60

Lys Leu Ser Lys Xaa Thr Arg Xaa Leu Xaa Glu Glu Arg Ile Gln Xaa
65                  70                  75                  80
```

```
Ile Leu Xaa Tyr Pro His Pro Lys Thr Leu Lys Gln Leu Xaa Xaa Phe
            85              90                  95

Leu Gly Ile Thr Xaa Phe Cys Xaa Ile Trp Ile Pro Arg Tyr Ser Xaa
            100             105             110

Ile Ala Arg Pro Leu Xaa Thr Xaa Xaa Lys Glu Thr Gln Lys Ala Asn
            115             120             125

Thr His Xaa Val Arg Trp Thr Pro Glu Xaa Glu Val Ala Phe Gln Ala
            130             135             140

Leu Lys
145

(2) INFORMATION FOR SEQ ID NO:205:

(i) SEQUENCE CHARACTERISTICS:
        (A) LENGTH: 1597 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:205:
```

| | | | | | |
|---|---|---|---|---|---|
| ATTATGCCTG | AAAGCCCCAC | TCCCTTGTTA | GGGAGAGACA | TTTTAGCAAA | AGCAGGGGCC | 60 |
| ATTATACACC | TGAACATAGG | AAAAGGAATA | CCCATTTGCT | GTCCCCTGCT | TGAGGAAGGA | 120 |
| ATTAATCCTG | AAGTCTGGGC | AATAGAAGGA | CAATATGGAC | AAGCAAAGAA | TGCCCGTCCT | 180 |
| GTTCAAGTTA | AACTAAAGGA | TTCTGCCTCC | TTTCCCTACC | AAAGGAAGTA | CCCTCTTAGA | 240 |
| CCCGAGGCCC | TACAAGGANC | TCAAAAGATT | GTTAAGGACC | TAAAAGCCCA | AGGCCTAGTA | 300 |
| AAACCATGCA | GTAGCCCCTG | CAATACTCCA | ATTTTAGGAG | TAAGGAAACC | CAACGGACAG | 360 |
| TGGAGGTTAG | TGCAAGAACT | CAGGATTATC | AATGAGGCTG | TTGTTCCTCT | ATACCCAGCT | 420 |
| GTACCTAACC | CTTATACAGT | GCTTTCCCAA | ATACCAGAGG | AAGCAGAGTG | GTTTACAGTC | 480 |
| CTGGACCTTA | AGGATGCCTT | TTTCTGCATC | CCTGTACGTC | CTGACTCTCA | ATTCTTGTTT | 540 |
| GCCTTTGAAG | ATCCTTTGAA | CCCAACGTCT | CAACTCACCT | GGACTGTTTT | ACCCCAAGGG | 600 |
| TTCAGGGATA | GCCCCCATCT | ATTTGGCCAG | GCATTAGCCC | AAGACTTGAG | TCAATTCTCA | 660 |
| TACCTGGACA | CTCTTGTCCT | TCAGTACATG | GATGATTTAC | TTTTAGTCGC | CCGTTCAGAA | 720 |
| ACCTTGTGCC | ATCAAGCCAC | CCAAGAACTC | TTAACTTTCC | TCACTACCTG | TGGCTACAAG | 780 |
| GTTTCCAAAC | CAAAGGCTCG | GCTCTGCTCA | CAGGAGATTA | GATACTNAGG | CTAAAATTA | 840 |
| TCCAAAGGCA | CCAGGGCCCT | CAGTGAGGAA | CGTATCCAGC | CTATACTGGC | TTATCCTCAT | 900 |
| CCCAAAACCC | TAAAGCAACT | AAGAGGGTTC | CTTGGCATAA | CAGGTTTCTG | CCGAAAACAG | 960 |
| ATTCCCAGGT | ACASCCCAAT | AGCCAGACCA | TTATATACAC | TAATTANGGA | AACTCAGAAA | 1020 |
| GCCAATACCT | ATTTAGTAAG | ATGGACACCT | ACAGAAGTGG | CTTTCCAGGC | CCTAAAGAAG | 1080 |
| GCCCTAACCC | AAGCCCAGT | GTTCAGCTTG | CCAACAGGGC | AAGATTTTTC | TTTATATGCC | 1140 |
| ACAGAAAAAA | CAGGAATAGC | TCTAGGAGTC | CTTACGCAGG | TCTCAGGGAT | GAGCTTGCAA | 1200 |
| CCCGTGGTAT | ACCTGAGTAA | GGAAATTGAT | GTAGTGGCAA | AGGGTTGGCC | TCATNGTTTA | 1260 |
| TGGGTAATGG | NGGCAGTAGC | AGTCTNAGTA | TCTGAAGCAG | TTAAAATAAT | ACAGGGAAGA | 1320 |
| GATCTTNCTG | TGTGGACATC | TCATGATGTG | AACGGCATAC | TCACTGCTAA | AGGAGACTTG | 1380 |
| TGGTTGTCAG | ACAACCATTT | ACTTAANTAT | CAGGCTCTAT | TACTTGAAGA | GCCAGTGCTG | 1440 |
| NGACTGCGCA | CTTGTGCAAC | TCTTAAACCC | GCCACATTTC | TTCCAGACAA | TGAAGAAAAG | 1500 |
| ATAGAACATA | ACTGTCAACA | AGTAATTGCT | CAAACCTATG | CTGCTCGAGG | GGACCTTCTA | 1560 |

GAGGTTCCCT TGACTGATCC CGACCTCAAC TTGTATA                               1597

(2) INFORMATION FOR SEQ ID NO:206:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:206:

ATTATGCCTG AAAGCCCCAC TCCCTTGTTA GGGAGAGACA TTTTAGCAAA AGCAGGGGCC        60

ATTATACACC TGAACATAGG AAAAGGAATA CCCATTTGCT GTCCCCTGCT TGAGGAAGGA       120

ATTAATCCTG AAGTCTGGGC AATAGAAGGA CAATATGGAC AAGCAAAGAA TGCCCGTCCT       180

GTTCAAGTTA AACTAAAGGA TTCTGCCTCC TTTCCCTACC AAAGGAAGTA CCCTCTTAGA       240

CCCGAGGCCC TACAAGGANC TCAAAAGATT GTTAAGGACC TAAAAGCCCA AGGCCTAGTA       300

AAACCATGCA GTAGCCCCTG CAATACTCCA ATTTTAGGAG TAAGGAAACC CAACGGACAG       360

TGGAGGTTAG TGCAAGAACT CAGGATTATC AATGAGGCTG TTGTTCCTCT ATACCCAGCT       420

GTACCTAACC CTTATACAGT GCTTTCCCAA ATACCAGAGG AAGCAGAGTG GTTTACAGTC       480

CTGGACCTTA AGGATGCCTT TTTCTGCATC CCTGTACGTC CTGACTCTCA ATTCTTGTTT       540

GCCTTTGAAG ATCCTTTGAA CCCAACGTCT CAACTCACCT GGACTGTTTT ACCCCAAGGG       600

TTCAGGGATA GCCCCCATCT ATTTGGCCAG GCATTAGCCC AAGACTTGAG YCARTYCTCA       660

TACCTGGACA YTCTTGTYCY TCAGTAYRKG GATGAYTTAM TTWTAGYCRC CCRTTCAGAA       720

ACCTTGTGSC AMCAAGCCAC CCAAGHRCTC TTAAMTTTCC TYRCTACCTG TGGCTACAAG       780

GTTTCCAAAC MAARGGCTCR SCTCTGCTCA CASSAGRTTA RATACTNAGG GCTAAAATTA       840

TCCAAAGKCR CCAGGGCCCT CAGWGAGGAA CGTATCCAGC STATACTGGM TTATCCMCAT       900

CCCAWAACCM TAAAGCAACT AAGARGGTTC CTTGGCATAW CAGSYTTCTG CCGAAWAYRG       960

ATTCCCVGRT ACASYSMAAT AGCCAGRCCA TTATRTACAY TADYTARGGA AACTCAGAAA      1020

GCCAATACCY ATWTAGTAAG ATGGACACCT GARACAGAAG TGGCTTTCCA GGCCCTAAAG      1080

AAGGCCCTAA CCCAAGCCCC AGTGTTCAGC TTGCCAACAG GGCAAGATTT TCTTTATAT       1140

GCCACAGAAA AAACAGGAAT AGCTCTAGGA GTCCTTACGC AGGTCTCAGG GATGAGCTTG      1200

CAACCCGTGG TATACCTGAG TAAGGAAATT GATGTAGTGG CAAAGGGTTG GCCTCATNGT      1260

TTATGGGTAA TGGNGGCAGT AGCAGTCTNA GTATCTGAAG CAGTTAAAAT AATACAGGGA      1320

AGAGATCTTN CTGTGTGGAC ATCTCATGAT GTGAACGGCA TACTCACTGC TAAAGGAGAC      1380

TTGTGGTTGT CAGACAACCA TTTACTTAAN TATCAGGCTC TATTACTTGA AGAGCCAGTG      1440

CTGNGACTGC GCACTTGTGC AACTCTTAAA CCCGCCACAT TTCTTCCAGA CAATGAAGAA      1500

AAGATAGAAC ATAACTGTCA ACAAGTAATT GCTCAAACCT ATGCTGCTCG AGGGGACCTT      1560

CTAGAGGTTC CCTTGACTGA TCCCGACCTC AACTTGTATA                           1600

(2) INFORMATION FOR SEQ ID NO:207:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:207:

| | | | | | |
|---|---|---|---|---|---|
| ATTATGCCTG | AAAGCCCCAC | TCCCTTGTTA | GGGAGAGACA | TTTTAGCAAA | AGCAGGGGCC | 60 |
| ATTATACACC | TGAACATAGG | AAAAGGAATA | CCCATTTGCT | GTCCCCTGCT | TGAGGAAGGA | 120 |
| ATTAATCCTG | AAGTCTGGGC | AATAGAAGGA | CAATATGGAC | AAGCAAAGAA | TGCCCGTCCT | 180 |
| GTTCAAGTTA | AACTAAAGGA | TTCTGCCTCC | TTTCCCTACC | AAAGGAAGTA | CCCTCTTAGA | 240 |
| CCCGAGGCCC | TACAAGGANC | TCAAAAGATT | GTTAAGGACC | TAAAAGCCCA | AGGCCTAGTA | 300 |
| AAACCATGCA | GTAGCCCCTG | CAATACTCCA | ATTTTAGGAG | TAAGGAAACC | CAACGGACAG | 360 |
| TGGAGGTTAG | TGCAAGAACT | CAGGATTATC | AATGAGGCTG | TTGTTCCTCT | ATACCCAGCT | 420 |
| GTACCTAACC | CTTATACAGT | GCTTTCCCAA | ATACCAGAGG | AAGCAGAGTG | GTTTACAGTC | 480 |
| CTGGACCTTA | AGGATGCCTT | TTTCTGCATC | CCTGTACGTC | CTGACTCTCA | ATTCTTGTTT | 540 |
| GCCTTTGAAG | ATCCTTTGAA | CCCAACGTCT | CAACTCACCT | GGACTGTTTT | ACCCCAAGGG | 600 |
| TTCAGGGATA | GCCCCCATCT | ATTTGGCCAG | GCATTAGCCC | AAGACTTGAG | YCARTYYTCA | 660 |
| TACCTGGACA | YTCTTGTYCY | TCRGTACRTG | GATGATTTAC | TTTTAGYCRC | CCRTTCAGAA | 720 |
| ACCTTGTGCC | ATCAAGCCAC | CCAAGMACTC | TTAAMTTTCC | TYRCTACCTG | TGGCTACAAG | 780 |
| GTTTCCAAAC | CAAAGGCTCR | GCTCTGCTCA | CAGSAGRTTA | RATACTTAGG | GCTAAAATTA | 840 |
| TCCAAAGGCA | CCAGRRCCCT | CAGTGAGGAA | CGTATCCAGC | CTATACTGGS | TTATCCTCAT | 900 |
| CCCAAAACCC | TAAAGCAACT | AASAGSGTTC | CTTGGCATAA | CAGGTTTCTG | CCRAAWAYRG | 960 |
| ATTCCCAGGT | ACASCMMRRT | AGCCAGACCA | TTAWATACAC | KAATTARGGA | AACTCARAAA | 1020 |
| GCCARTACCY | ATTTAGTAAG | ATGGACAYCT | GAAGCAGAAG | TGGCTTTCCA | GGCCCTAAAG | 1080 |
| AAGGCCCTAA | CCCAAGCCCC | AGTGTTCAGC | TTGCCAACAG | GGCAAGATTT | TTCTTTATAT | 1140 |
| GCCACAGAAA | AAACAGGAAT | AGCTCTAGGA | GTCCTTACGC | AGGTCTCAGG | GATGAGCTTG | 1200 |
| CAACCCGTGG | TATACCTGAG | TAAGGAAATT | GATGTAGTGG | CAAAGGGTTG | GCCTCATNGT | 1260 |
| TTATGGGTAA | TGGNGGCAGT | AGCAGTCTNA | GTATCTGAAG | CAGTTAAAAT | AATACAGGGA | 1320 |
| AGAGATCTTN | CTGTGTGGAC | ATCTCATGAT | GTGAACGGCA | TACTCACTGC | TAAAGGAGAC | 1380 |
| TTGTGGTTGT | CAGACAACCA | TTTACTTAAN | TATCAGGCTC | TATTACTTGA | AGAGCCAGTG | 1440 |
| CTGNGACTGC | GCACTTGTGC | AACTCTTAAA | CCCGCCACAT | TCTTCCAGA | CAATGAAGAA | 1500 |
| AAGATAGAAC | ATAACTGTCA | ACAAGTAATT | GCTCAAACCT | ATGCTGCTCG | AGGGGACCTT | 1560 |
| CTAGAGGTTC | CCTTGACTGA | TCCCGACCTC | AACTTGTATA | | | 1600 |

(2) INFORMATION FOR SEQ ID NO:208:

(i) SEQUENCE CHARACTERISTICS:
        (A) LENGTH: 683 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:208:

Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
        35                  40                  45

-continued

```
Glu Gly Gln Tyr Gly Gln Ala Lys Asn Ala Arg Pro Val Gln Val Lys
 50                  55                  60
Leu Lys Asp Ser Ala Ser Phe Pro Tyr Gln Arg Lys Tyr Pro Leu Arg
 65                  70                  75                  80
Pro Glu Ala Leu Gln Gly Xaa Gln Lys Ile Val Lys Asp Leu Lys Ala
                     85                  90                  95
Gln Gly Leu Val Lys Pro Cys Ser Ser Pro Cys Asn Thr Pro Ile Leu
                100                 105                 110
Gly Val Arg Lys Pro Asn Gly Gln Trp Arg Leu Val Gln Asp Leu Arg
                115                 120                 125
Ile Ile Asn Glu Ala Val Phe Pro Leu Tyr Pro Ala Val Ser Ser Pro
130                 135                 140
Tyr Thr Leu Leu Ser Leu Ile Pro Glu Glu Ala Glu Trp Phe Thr Val
145                 150                 155                 160
Leu Asp Leu Lys Asp Ala Phe Phe Cys Ile Pro Val Arg Pro Asp Ser
                165                 170                 175
Gln Phe Leu Phe Ala Phe Glu Asp Pro Leu Asn Pro Thr Ser Gln Leu
                180                 185                 190
Thr Trp Thr Val Leu Pro Gln Gly Phe Arg Asp Ser Pro His Leu Phe
                195                 200                 205
Gly Gln Ala Leu Ala Gln Asp Leu Ser Gln Pro Ser Tyr Leu Asp Thr
210                 215                 220
Leu Val Leu Gln Tyr Val Asp Asp Leu Leu Val Ala Arg Ser Glu
225                 230                 235                 240
Thr Leu Cys His Gln Ala Thr Gln Glu Leu Leu Ile Phe Leu Thr Thr
                245                 250                 255
Cys Gly Tyr Lys Val Ser Lys Pro Lys Ala Arg Leu Cys Ser Gln Glu
                260                 265                 270
Ile Arg Tyr Leu Gly Leu Lys Leu Ser Lys Gly Thr Arg Ala Leu Ser
                275                 280                 285
Glu Glu Arg Ile Gln Pro Ile Leu Ala Tyr Pro His Pro Lys Thr Leu
290                 295                 300
Lys Gln Leu Arg Gly Phe Leu Gly Ile Thr Gly Phe Cys Arg Lys Gln
305                 310                 315                 320
Ile Pro Arg Tyr Thr Pro Ile Ala Arg Pro Leu Tyr Thr Leu Ile Arg
                325                 330                 335
Glu Thr Gln Lys Ala Asn Thr Tyr Leu Val Arg Trp Thr Pro Thr Glu
                340                 345                 350
Val Ala Phe Gln Ala Leu Lys Lys Ala Leu Thr Gln Ala Pro Val Phe
                355                 360                 365
Ser Leu Pro Thr Gly Gln Asp Phe Ser Leu Tyr Ala Thr Glu Lys Thr
                370                 375                 380
Gly Ile Ala Leu Gly Val Leu Thr Gln Val Ser Gly Met Ser Leu Gln
385                 390                 395                 400
Pro Val Val Tyr Leu Ser Lys Glu Ile Asp Val Ala Lys Gly Trp
                405                 410                 415
Pro His Cys Leu Trp Val Met Ala Ala Val Ala Val Leu Val Ser Glu
                420                 425                 430
Ala Val Lys Ile Ile Gln Gly Arg Asp Leu Thr Val Trp Thr Ser His
                435                 440                 445
Asp Val Asn Gly Ile Leu Thr Ala Lys Gly Asp Leu Trp Leu Ser Asp
450                 455                 460
```

-continued

```
Asn His Leu Leu Asn Tyr Gln Ala Leu Leu Glu Glu Pro Val Leu
465                 470                 475                 480

Arg Leu Arg Thr Cys Ala Thr Leu Gln Pro Ala Thr Phe Leu Pro Asp
                485                 490                 495

Asn Glu Glu Lys Ile Glu His Asn Cys Gln Gln Val Ile Ala Gln Thr
                500                 505                 510

Tyr Ala Ala Arg Gly Asp Leu Leu Glu Val Pro Leu Thr Asp Pro Asp
                515                 520                 525

Leu Asn Leu Tyr Thr Asp Gly Ser Ser Leu Ala Glu Lys Gly Leu Arg
530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
                565                 570                 575

Thr Trp Ala Leu Glu Leu Gly Glu Gly Lys Arg Val Asn Ile Tyr Ser
                580                 585                 590

Asp Ser Lys Tyr Ala Tyr Leu Val Leu His Ala His Ala Ala Ile Trp
            595                 600                 605

Arg Glu Arg Glu Phe Leu Thr Ser Glu Gly Thr Pro Ile Asn His Gln
610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Arg Glu Ile
                645                 650                 655

Glu Gly Asn Arg Gln Ala Asp Ile Glu Ala Lys Lys Ala Ala Arg Gln
                660                 665                 670

Asp Ser Pro Leu Glu Met Leu Ile Glu Gly Pro
            675                 680
```

(2) INFORMATION FOR SEQ ID NO:209:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:209:

```
Asp Leu Ser Gln Ser Ser Tyr Leu Asp Ile Leu Val Leu Arg Tyr Met
1               5                   10                  15

Asp Asp Leu Leu Leu Ala Thr His Ser Glu Thr Leu Cys His Gln Ala
                20                  25                  30

Thr Gln Ala Leu Leu Asn Phe Leu Ala Thr Cys Gly Tyr Lys Val Ser
            35                  40                  45

Lys Pro Lys Ala Gln Leu Cys Ser Gln Gln Val Lys Tyr Leu Gly Leu
50                  55                  60

Lys Leu Ser Lys Gly Thr Arg Ile Leu Ser Glu Glu Arg Ile Gln Pro
65                  70                  75                  80

Ile Leu Gly Tyr Pro His Pro Lys Thr Leu Lys Gln Leu Thr Ala Phe
            85                  90                  95

Leu Gly Ile Thr Gly Phe Cys Gln Ile Trp Ile Pro Arg Tyr Ser Lys
                100                 105                 110

Ile Ala Arg Pro Leu Asn Thr Arg Ile Lys Glu Thr Gln Lys Ala Asn
            115                 120                 125
```

```
Thr His Leu Val Arg Trp Thr Pro Glu Ala Glu Val Ala Phe Gln Ala
    130                 135                 140

Leu Lys
145
```

(2) INFORMATION FOR SEQ ID NO:210:

(i) SEQUENCE CHARACTERISTICS:
        (A) LENGTH: 683 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:210:

```
Ile Met Pro Glu Ser Pro Thr Pro Leu Leu Gly Arg Asp Ile Leu Ala
1               5                   10                  15

Lys Ala Gly Ala Ile Ile His Leu Asn Ile Gly Lys Gly Ile Pro Ile
            20                  25                  30

Cys Cys Pro Leu Leu Glu Glu Gly Ile Asn Pro Glu Val Trp Ala Ile
            35                  40                  45

Glu Gly Gln Tyr Gly Gln Ala Lys Asn Ala Arg Pro Val Gln Val Lys
        50                  55                  60

Leu Lys Asp Ser Ala Ser Phe Pro Tyr Gln Arg Lys Tyr Pro Leu Arg
65                  70                  75                  80

Pro Glu Ala Leu Gln Gly Xaa Gln Lys Ile Val Lys Asp Leu Lys Ala
                85                  90                  95

Gln Gly Leu Val Lys Pro Cys Ser Ser Pro Cys Asn Thr Pro Ile Leu
            100                 105                 110

Gly Val Arg Lys Pro Asn Gly Gln Trp Arg Leu Val Gln Asp Leu Arg
            115                 120                 125

Ile Ile Asn Glu Ala Val Phe Pro Leu Tyr Pro Ala Val Ser Ser Pro
130                 135                 140

Tyr Thr Leu Leu Ser Leu Ile Pro Glu Glu Ala Glu Trp Phe Thr Val
145                 150                 155                 160

Leu Asp Leu Lys Asp Ala Phe Phe Cys Ile Pro Val Arg Pro Asp Ser
            165                 170                 175

Gln Phe Leu Phe Ala Phe Glu Asp Pro Leu Asn Pro Thr Ser Gln Leu
            180                 185                 190

Thr Trp Thr Val Leu Pro Gln Gly Phe Arg Asp Ser Pro His Leu Phe
            195                 200                 205

Gly Gln Ala Leu Ala Gln Asp Leu Ser Gln Pro Ser Tyr Leu Asp Thr
210                 215                 220

Leu Val Leu Gln Tyr Val Asp Asp Leu Leu Leu Val Ala Arg Ser Glu
225                 230                 235                 240

Thr Leu Cys His Gln Ala Thr Gln Glu Leu Leu Ile Phe Leu Thr Thr
            245                 250                 255

Cys Gly Tyr Lys Val Ser Lys Pro Lys Ala Arg Leu Cys Ser Gln Glu
            260                 265                 270

Ile Arg Tyr Leu Gly Leu Lys Leu Ser Lys Gly Thr Arg Ala Leu Ser
            275                 280                 285

Glu Glu Arg Ile Gln Pro Ile Leu Ala Tyr Pro His Pro Lys Thr Leu
            290                 295                 300

Lys Gln Leu Arg Gly Phe Leu Gly Ile Thr Gly Phe Cys Arg Lys Gln
305                 310                 315                 320
```

-continued

```
Ile Pro Arg Tyr Thr Pro Ile Ala Arg Pro Leu Tyr Thr Leu Ile Arg
            325                 330                 335

Glu Thr Gln Lys Ala Asn Thr Tyr Leu Val Arg Trp Thr Pro Thr Glu
            340                 345                 350

Val Ala Phe Gln Ala Leu Lys Lys Ala Leu Thr Gln Ala Pro Val Phe
            355                 360                 365

Ser Leu Pro Thr Gly Gln Asp Phe Ser Leu Tyr Ala Thr Glu Lys Thr
    370                 375                 380

Gly Ile Ala Leu Gly Val Leu Thr Gln Val Ser Gly Met Ser Leu Gln
385                 390                 395                 400

Pro Val Val Tyr Leu Ser Lys Glu Ile Asp Val Val Ala Lys Gly Trp
            405                 410                 415

Pro His Cys Leu Trp Val Met Ala Ala Val Ala Val Leu Val Ser Glu
            420                 425                 430

Ala Val Lys Ile Ile Gln Gly Arg Asp Leu Thr Val Trp Thr Ser His
            435                 440                 445

Asp Val Asn Gly Ile Leu Thr Ala Lys Gly Asp Leu Trp Leu Ser Asp
    450                 455                 460

Asn His Leu Leu Asn Tyr Gln Ala Leu Leu Leu Glu Glu Pro Val Leu
465                 470                 475                 480

Arg Leu Arg Thr Cys Ala Thr Leu Gln Pro Ala Thr Phe Leu Pro Asp
            485                 490                 495

Asn Glu Glu Lys Ile Glu His Asn Cys Gln Gln Val Ile Ala Gln Thr
            500                 505                 510

Tyr Ala Ala Arg Gly Asp Leu Leu Glu Val Pro Leu Thr Asp Pro Asp
            515                 520                 525

Leu Asn Leu Tyr Thr Asp Gly Ser Ser Leu Ala Glu Lys Gly Leu Arg
    530                 535                 540

Lys Ala Gly Tyr Ala Val Ile Ser Asp Asn Gly Ile Leu Glu Ser Asn
545                 550                 555                 560

Arg Leu Thr Pro Gly Thr Ser Ala His Leu Ala Glu Leu Ile Ala Leu
            565                 570                 575

Thr Trp Ala Leu Glu Leu Gly Glu Gly Lys Arg Val Asn Ile Tyr Ser
            580                 585                 590

Asp Ser Lys Tyr Ala Tyr Leu Val Leu His Ala His Ala Ala Ile Trp
    595                 600                 605

Arg Glu Arg Glu Phe Leu Thr Ser Glu Gly Thr Pro Ile Asn His Gln
    610                 615                 620

Glu Ala Ile Arg Arg Leu Leu Leu Ala Val Gln Lys Pro Lys Glu Val
625                 630                 635                 640

Ala Val Leu His Cys Gln Gly His Gln Glu Glu Glu Glu Arg Glu Ile
            645                 650                 655

Glu Gly Asn Arg Gln Ala Asp Ile Glu Ala Lys Lys Ala Ala Arg Gln
            660                 665                 670

Asp Ser Pro Leu Glu Met Leu Ile Glu Gly Pro
    675                 680
```